(12) United States Patent
Boes et al.

(10) Patent No.: US 10,131,697 B2
(45) Date of Patent: Nov. 20, 2018

(54) VACCINES AGAINST APICOMPLEXAN PATHOGENS

(71) Applicant: Fraunhofer-Gesellschaft zur Foerderung der angewandten Forschung e.V, Munich (DE)

(72) Inventors: Alexander Boes, Cologne (DE); Holger Spiegel, Aachen (DE); Gueven Edgue, Aachen (DE); Veronique Beiss, Aachen (DE); Markus Sack, Alsdorf (DE); Andreas Reimann, Krefeld (DE); Rainer Fischer, Indianapolis, IN (US)

(73) Assignee: Fraunhofer-Gesellschaft zur Foerderung der angewandten Forschung E.V., Munich (DE)

(*) Notice: Subject to any disclaimer, the term of this patent is extended or adjusted under 35 U.S.C. 154(b) by 0 days.

(21) Appl. No.: 14/786,509

(22) PCT Filed: Apr. 24, 2014

(86) PCT No.: PCT/EP2014/058409
§ 371 (c)(1),
(2) Date: Oct. 22, 2015

(87) PCT Pub. No.: WO2014/174054
PCT Pub. Date: Oct. 30, 2014

(65) Prior Publication Data
US 2016/0083439 A1    Mar. 24, 2016

Related U.S. Application Data

(60) Provisional application No. 61/815,486, filed on Apr. 24, 2013.

(30) Foreign Application Priority Data

Apr. 24, 2013    (EP) .................................. 13165161

(51) Int. Cl.
A61K 39/002    (2006.01)
A61K 39/015    (2006.01)
(Continued)

(52) U.S. Cl.
CPC .......... C07K 14/445 (2013.01); *A61K 39/002* (2013.01); *A61K 39/015* (2013.01);
(Continued)

(58) Field of Classification Search
CPC .... A61K 39/385; A61K 48/00; A61K 39/015; A61K 39/002; A61P 33/06; C12N 15/00;
(Continued)

(56) References Cited

U.S. PATENT DOCUMENTS

2011/0243982 A1* 10/2011 Burns, Jr. ............ A61K 39/015
424/193.1

FOREIGN PATENT DOCUMENTS

WO    2007027860 A2    3/2007
WO    2012047679 A2    4/2012
WO    WO 2012/047679    *    4/2012    ............. A61K 48/00

OTHER PUBLICATIONS

Mahajan et al., (Infect. and Immun. 2010. 78(11):4613-4624).*
(Continued)

*Primary Examiner* — Jana A Hines
(74) *Attorney, Agent, or Firm* — Wagenknecht IP Law Group PC

(57) ABSTRACT

The technology provided herein generally relates to novel fusion proteins suitable as human and/or animal vaccines against parasites or pathogens of the phylum Apicomplexa. In particular, the present disclosure relates to novel fusion proteins as a basis for vaccines against *Plasmodium* parasites, including *P. falciparum, P. vivax, P. malariae, P. ovale* and *P. knowlesi*. Nucleic acid molecules encoding said fusion proteins, vectors, host cells containing the nucleic
(Continued)

acids and methods for preparation and producing such fusion proteins; antibodies induced or generated by the use of said fusion proteins or said nucleic acid molecules encoding said fusion proteins and the use of such antibodies or recombinant derivatives for passive immunotherapy; methods for producing such fusion proteins; compositions and methods for using such fusion proteins for the prevention and treatment of malaria are also encompassed by the present disclosure.

16 Claims, 9 Drawing Sheets

Specification includes a Sequence Listing.

(51) Int. Cl.
C07K 14/445 (2006.01)
C12N 15/62 (2006.01)
(52) U.S. Cl.
CPC .......... *C12N 15/62* (2013.01); *C07K 2319/00* (2013.01); *C07K 2319/40* (2013.01)
(58) Field of Classification Search
CPC .. C12N 15/62; C07K 14/445; C07K 2319/00; C07K 2319/40

USPC .......... 424/191.1, 192.1, 193.1, 194.1, 269.1
See application file for complete search history.

(56) References Cited

OTHER PUBLICATIONS

PCT/EP2014/058409 International Search Report dated Jul. 17, 2014.
Mahajan et al. "Multiple Antigen Peptide Vaccines against Plasmodium Falciparum Malaria." Infection and Immunity, Nov. 1, 2010, 78(11):4613-4624.
Kumar et al. "A Multilateral Effort to Develop DNA Vaccines Against Falciparum Malaria." Trends in Parasitology, Mar. 1, 2002, 18(3):129-135, Elsevier Current Trends, GB.
Schwartz et al. "A Review of Malaria Vaccine Clinical Projects Based on the WHO Rainbow Table." Malaria Journal, Jan. 9, 2012, 11(1): 5-8, 11.
Stowers et al. "Structural conformers produced during malaria vaccine production in yeast." Yeast, Jan. 30, 2001, 18(2):137-150.
Chen and Kristensen. "Opportunities and Challenges of Developing Thermostable Vaccines." Expert Rev. Vaccines, 2009, 8(5)547-557.
EP14719741.2 Communication Pursuant to Article 94(3) EPC dated Jun. 7, 2017.

* cited by examiner

Figure 2

| Species | Definitive host | Intermediate host | Preferred host environment |
|---|---|---|---|
| *Plasmodium falciparum* | Mosquito | Human | Erythrocyte (red blood cell) |
| *Plasmodium vivax* | Mosquito | Human | Erythrocyte |
| *Plasmodium berghei* | Mosquito | Rat | Erythrocyte |
| *Plasmodium yoelii* | Mosquito | Rat | Erythrocyte |
| *Theileria annulata* | Tick | Bovine | Leukocyte (white blood cell) |
| *Theileria parva* | Tick | Bovine | Leukocyte |
| *Eimeria tenella* | Poultry | None | Intestinal tract |
| *Sarcocystis falcatula* | Opossum | Avian | Leukocyte |
| *Sarcocystis neurona* | Opossum | Equine | Leukocyte |
| *Toxoplasma gondii* | Feline | Warm-blooded animals | Broad range |
| *Neospora hughesi* | Unknown | Equine | Broad range |
| *Neospora caninum* | Dogs | Bovine/Equine/Ovine | Broad range |
| *Gregarina niphandrodes* | Arthropods, nematodes and annelids | None | Intestinal track |
| *Cryptosporidium hominis* | Human | None | Intestinal track |
| *Cryptosporidium parvum* | Mammal | None | Intestinal track |

Figure 4

EGF9_PfRipr: short R9 (SEQ ID NO.16)

```
Pf_3D7              KCVHN-KKCS------ENSICVN-VMKEPICVCTYNYYK--------K----
Pv_Sal-1            MCRSDQNKCS------ENSICVNQVNKEPLCICLFNYVK--------SRSGD
Pk_H                MCRTDQNKCS------ENSICVNQVNKEPLCICLFNYEK--------SIAGL
tgon|TGME49_067680  SCIDR-DECEIEGACDENADCTN-LPGSFSCTCRAGYRQEGELCVKMNLCAD
tgon|TGME49_002400  RCDDI-DECIDPTLHGCDHICIN-LPGTYSCQCRPGYR--------LSLE--
ncan|NCLIV_022530   RCDDI-NECLDPSLHGCEQLCVN-LPGTYSCQCRQGYR--------PSVE--
ncan|NCLIV_069310   SCVDV-DECQIQGACDENADCTN-MPGSYTCTCREGYRQEGELCVKMNLCTE
cpar|cgd3_1860      ACEDI-DECSNGDSK-CDQLCFN-TIGGYKCGCYKGFR--------LNLTGP
cmur|CMU_001710     ICEDI-NECKNGEAH-CEQICIN-TLGGYKCDCFPGFK--------YKVERL
chom|Chro.30220     ACEDI-DECSNGDSK-CDQLCFN-TIGGYRCGCYKGFR--------LNLTGP
                       *    .:*           :  * *       * *   .:         .

Pf_3D7              ------DG--VCL--------------------
Pv_Sal-1            SP----EGGQTCV--------------------
Pk_H                ST----QGAHTCV--------------------
tgon|TGME49_067680  DENGGCSPHADCEHLDKIVCTCRPGYEGDGITCT
tgon|TGME49_002400  -------KKGACV--------------------
ncan|NCLIV_022530   -------KRGACV--------------------
ncan|NCLIV_069310   AEN-PCSPNAFCESLDKVVCTCKPGFEGDGITCA
cpar|cgd3_1860      EENRLDVQSRVCI--------------------
cmur|CMU_001710     DNELSSGTRGICI--------------------
chom|Chro.30220     EENRLDVKSRVCI--------------------
                                 *
```

| | |
|---|---|
| Pf_3D7 | *Plasmodium falciparum* Strain 3D7 |
| Pv_Sal-1 | *Plasmodium vivax* Strain Sal-1 |
| P_H | *Plasmodium knowlesi* Strain H |
| tgon | *Toxoplasma gondii* |
| ncan | *Neospara caninum* |
| cpar | *Cryptosporidium parvum* |
| cmur | *Cryptosporidium muris* |
| chom | *Cryptosporidium hominis* |

Figure 7
A) Sporozoite
B) Schizont
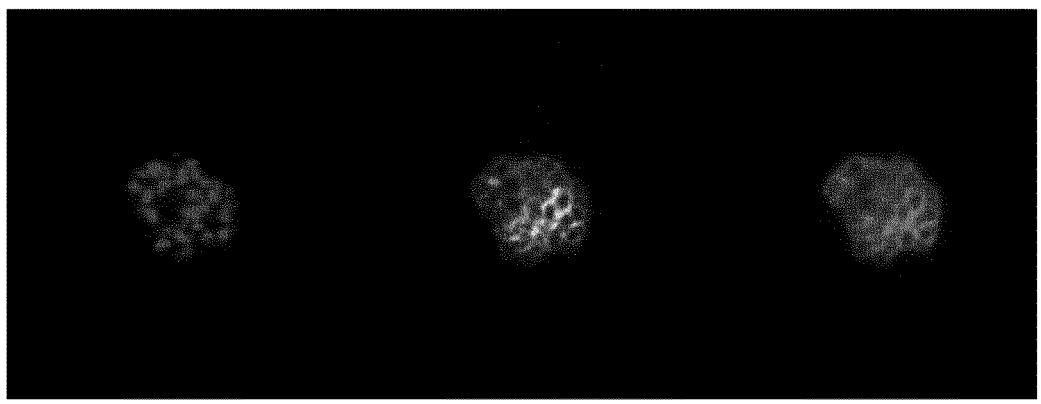
C) Makrogamete/Zygote
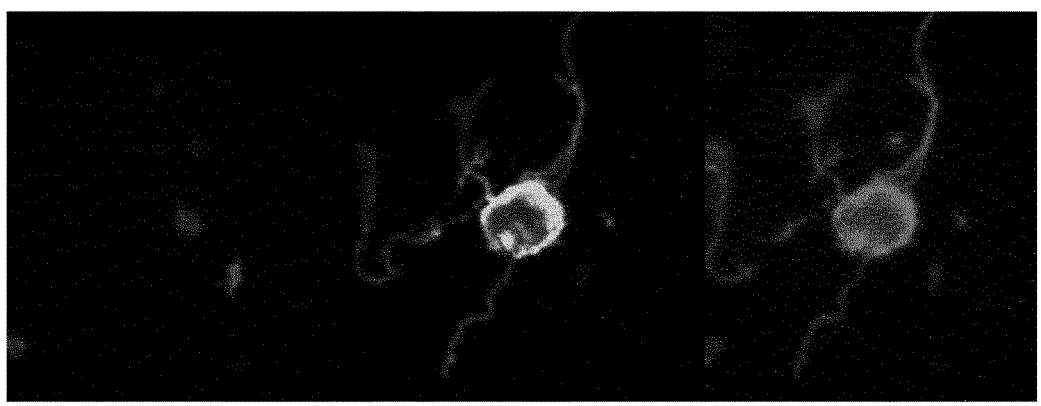

VACCINES AGAINST APICOMPLEXAN PATHOGENS

CROSS-REFERENCE TO RELATED APPLICATIONS

This application is a U.S. National stage of PCT/EP2014/058409 filed on Apr. 24, 2014, which claims priority from U.S. Provisional Application Ser. No. 61/815,486 filed on Apr. 24, 2013 and EP Application Serial No. 13165161.4 filed on Apr. 24, 2013, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCT_EP2014_058409_SEQID" created on 20 Oct. 2015 and having a size of 199 Kilobytes. The sequence listing contained in this ASCII formatted document forms part of the specification and is herein incorporated by reference in its entirety.

FIELD OF THE DISCLOSURE

The technology provided herein generally relates to novel fusion proteins suitable as human and/or animal vaccines against parasites or pathogens of the phylum Apicomplexa. In particular, the present disclosure relates to novel fusion proteins as a basis for vaccines against *Plasmodium* parasites, including *P. falciparum, P. vivax, P. malariae, P. ovale* and *P. knowlesi*. Nucleic acid molecules encoding said recombinant fusion proteins, vectors, host cells containing the nucleic acids and methods for preparation and producing such fusion proteins; antibodies induced or generated by the use of said fusion proteins or said nucleic acid molecules encoding said fusion proteins and the use of such antibodies or recombinant derivatives for passive immunotherapy; methods for producing such fusion proteins; compositions and methods for using such fusion proteins for the prevention and treatment of malaria are also encompassed by the present disclosure.

BACKGROUND

The Apicomplexa are an eukaryotic protozoan phylum of around 5000 species including parasites which belong to the most successful and devastating pathogens today, infecting a wide range of animals from mollusks to mammals. Many species of Apicomplexa cause diseases of medical and veterinary importance and represent a significant economic burden and global healthcare challenge. Members of the phylum include:

*Plasmodium*, the etiological agent of malaria, afflicting 10-40% of world population and accounting for one-in-five deaths among children under the age of five in Africa

*Toxoplasma gondii*, the causative agent of toxoplasmosis. From one-third to half of the world's human population is estimated to carry a *Toxoplasma* infection. It is a major pathogen to humans with a weakened immune system, such as AIDS patients or pregnant women

*Cryptosporidium*, a waterborne pathogen which typically does not cause serious illness in healthy people, but is a big health problem for immuno-compromised people, and the agricultural parasites *Eimeria* (infects poultry and causes annual losses in revenue totaling nearly a billion dollars), *Neospora* (an important pathogen in cattle and dogs), *Babesia* (thought to be the second most common blood parasites of mammals with a major health impact on domestic animals) and *Theileria* (causative agent of theileriosis a disease of cattle, sheep and goats).

The apicomplexan life cycle is complex and can be divided into three main stages wherein the first two serve for the asexual replication of the pathogen (more precise of the invasive stages of these protists called sporozoites and merozoites) and the third stage defines the sexual reproduction of the parasite. While the general life cycle is common to the Apicomplexa phylum, there are striking differences between species.

FIG. 1 shows the apicomplexan life cycles. As mentioned above, the members of Apicomplexa share a generalized life cycle, even though each species has its own specializations. *Plasmodium* spp. and *Theileria* spp. are transmitted and undergo sexual recombination in an insect vector, the *Anopheles* mosquito and *Rhipicephalus* tick, respectively. *Cryptosporidium* is able to autoinfect its host; the oocyst can sporulate and excyst in the same host, maintaining the infection for months to years. The Coccidian parasites are represented in this figure by *Toxoplasma*, which is able to infect the majority of warm-blooded animals. The differentiation of *Toxoplasma* tachyzoites into gametocytes is triggered only when members of the cat family (Felidae) are infected (Wasmuth et al., 2009).

Some Apicomplexa require a single host (e.g. *Cryptosporidium*), whereas others are more complex, requiring sexual reproduction in the vector species for transmission (e.g. *Theileria* and *Plasmodium*; see FIG. 2).

Although members of the Apicomplexa infect different host and cell types, they have a similar number of defining organelles involved in host cell attachment, invasion, and the establishment of an intracellular parasitophorous vacuole within the host cell. The arsenal of organelles varies between species, but typically includes rhoptries, micronemes, and dense granules. To develop novel antiparasitic compounds and increase the understanding of apicomplexan biology, several large-scale-sequencing projects were initiated and the availability of genomic data sets for 15 species opened the way for the identification of conserved protein families and their functions within the phylum and in the above mentioned processes. Domain analysis also identified both the taxonomic distribution of apicomplexan domains as well as domain architectures specific to the Apicomplexa.

Malaria is a disease caused by infection with parasites of the phylum Apicomplexa protozoan, namely parasites of the genus *Plasmodium*, globally causing more than 200 million new infections and 700 thousand deaths every year. Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum, P. vivax, P. ovale, P. malariae* and *P. knowlesi*, wherein the most prevalent being *Plasmodium falciparum* and *Plasmodium vivax*. Malaria caused by *Plasmodium falciparum* (also called malignantor malaria, *falciparum* malaria or malaria tropica) is the most dangerous form of malaria, with the highest rates of complications and mortality. Almost all malarial deaths are caused by *P. falciparum*.

Briefly, the plasmodial life cycle in man starts with the inoculation of a few sporozoites through the bite of an *Anopheles* mosquito. Within minutes, sporozoites invade the hepatocyte and start their development, multiplying by schizogony. In the case of *P. vivax* and *P. ovale*, some sporozoites may differentiate into hypnozoites, responsible for late relapses of the infection. After a period of 5-14 days—depending on the plasmodial species—schizonts develop into thousands of merozoites that are freed into the bloodstream and invade the red blood cells (RBCs). In the RBC, each merozoite develops into a trophozoite that matures and divides, generating a schizont that, after fully matured, gives rise to up to 32 merozoites within 42-72 h, depending on the plasmodial species. The merozoites, released into the bloodstream, will invade other RBC, maintaining the cycle. Some merozoites, after invading a RBC, develop into sexual forms—the male or female gametocytes which also enter the bloodstream after maturation and erythrocyte rupture. When a female *Anopheles* mosquito takes its blood meal and ingests the gametocytes, it will become infected. In the mosquito gut, the male gametocyte fuses with the female gametocyte, forming the ookinete, which binds to and passes through the gut wall, remains attached to its external face and transforms into the oocyst. The oocyst will divide by sporogony, giving rise to thousands of sporozoites that are released in the body cavity of the mosquito and eventually migrate to its salivary gland, where they will maturate, becoming capable of starting a new infection in humans when the mosquito bites the host for a blood meal.

Resistance of *Plasmodium falciparum* to the existing anti-malarial drug chloroquine emerged in the sixties and has been spreading since then. In addition, the malaria parasite has developed resistance to most other anti-malarial drugs over the past decades. This poses a major threat to public health in tropical countries and to travellers. There is every reason to believe that the prevalence and degree of anti-malarial drug resistance will continue to increase. The growing number of insecticide resistant vectors and drug resistant parasites further increases the demand for an effective malaria vaccine. Malaria vaccines are not limited to a single mode of action and hold the potential to dramatically alleviate the burden of malaria.

Some of the difficulties to develop a malaria vaccine result from the multi-stage life cycle of the parasite and its host as mentioned above. Each stage of the parasite development is characterized by different sets of surface antigens, eliciting different types of immune responses. Despite the large variety of displayed surface antigens, the immune response against them is often ineffective. One of the reasons is the extensive sequence polymorphism of plasmodial antigens, which facilitates the immune evasion of the different isolates.

Some of the most prominent blood-stage vaccine candidates MSP1, MSP2, AMA1, and RESA have primarily been selected for clinical testing because of their ability to induce growth-inhibitory antibodies in pre-clinical animal models. However, despite these promising initial data, they have in general proved poorly immunogenic in human volunteers and the induced antibodies were predominantly unable to inhibit the in vitro growth of *P. falciparum*.

A pre-erythrocytic vaccine would protect against the infectious form (sporozoite) injected by a mosquito and/or inhibit parasite development in the liver. In a previously unexposed individual, if a few parasites were to escape the immune defences induced by a pre-erythrocytic vaccine, they would eventually enter the blood-stage, multiply within the erythrocytes and establish a full-blown disease.

An erythrocytic or asexual blood-stage vaccine would inhibit the invasion and multiplication of the parasite in the red blood cells, thus preventing (or diminishing) severe disease symptoms during the blood infection. However, it would not prevent the transmission of the parasite.

A sexual-stage vaccine would not protect the person being vaccinated, but instead interrupt the cycle of transmission by inhibiting the development of parasites once they are ingested by the mosquito along with antibodies produced in response to the vaccine. Transmission-blocking vaccines could be part of a multi-faceted strategy directed towards parasite elimination and reduction of overall resistance to anti pre-erythrocytic or erythrocytic treatment.

The before mentioned multi-stage life cycle of malaria parasites presents unique challenges for a synergistic vaccine approach. Immunity against malaria parasites is stage dependent and species dependent. Many malaria researchers and textbook descriptions believe and conclude that a single-antigen vaccine representing only one stage of the life cycle will not be sufficient and that a multi-antigen, multi-stage vaccine that targets different stages of parasite development is necessary to induce effective immunity (Mahajan, Berzofsky et al. 2010). The construction of a multi-antigen vaccine (with the aim of increasing the breadth of the vaccine-induced immune responses to try to circumvent potential *P. falciparum* escape mutants) can be achieved by either genetically linking (full-size) antigens together, by a mixture of recombinant proteins or by synthetic-peptide-based (15-25-mer), chemically synthesized vaccines containing several peptides derived from different parasite proteins and stages.

A poly-protein approach being comprised of several different antigens or several different alleles of a single antigen (to induce antibodies with synergistic activities against the parasite) is hindered by antigenic diversity and the capacity of *P. falciparum* for immune evasion (Richards, Beeson, 2009). A large number of antigens have been evaluated as potential vaccine candidates, but most clinical trials have not shown significant impact on preventing clinical malaria although some of them have shown to reduce parasite growth. The size of the resulting fusion protein/vaccine candidate is another limiting factor allowing only the combination of a few selected antigens, not excluding that the chosen antigens are not targets of natural immunity and/or exhibit significant genetic polymorphism. Highly variable antigens with multiple alleles are obviously targets of the immune response under natural challenge, and vaccine studies of AMA1 and MSP2 suggest that allele-specific effects can be achieved (Schwartz, 2012). Practical considerations argue against multi-stage vaccines, particularly the associated increased manufacturing cost of a multicomponent vaccine including several antigens unless these can be encompassed by a single production step and single delivery technology (Hill, 2011). Currently only combination vaccines (being comprised of CSP and AMA1) are undergoing clinical trials that target the pre-erythrocytic and asexual blood stage of *P. falciparum* (Schwartz, 2012). A multi-antigen vaccine candidate targeting all three life cycle main stages of *Plasmodium* (including the sexual stage in *Anopheles* mosquitos and thus blocking parasite transmission) is still not tested in clinical trials.

The so-called SPf66 vaccine was the pioneer multi-epitope, multi-stage peptide-based malaria vaccine. It was first formulated and tested in Colombia (Patarroyo, 1988) and later also manufactured in the USA. SPf66 consists of epitopes of merozoite surface protein 1 (MSP1) linked by a peptide derived from the NANP repeat sequence of the circumsporozoite protein (CSP) adjuvanted with alum, and more recently tested with QS-21 (Schwartz, 2012). Since then, a number of synthetic peptide vaccines have been produced for both murine (*P. berghei* and *P. yoelii*) and human (*P. falciparum* and *P. vivax*) malarias and tested for immunogenicity or immunogenicity and efficacy. However, in spite of the early momentum, several theoretical considerations and technological hurdles have slowed the progress of this vaccine development approach. A major disadvantage of the peptide-based vaccine approach lies in its limitation to short linear epitopes that lack the surrounding sequence context often required for three-dimensional protein structures (e.g. folded domains) and complex conformational epitopes.

Therefore the availability of novel and improved multi-stage vaccines against parasites of the phylum Apicomplexa would be highly advantageous.

SUMMARY OF THE DISCLOSURE

The present disclosure relates to novel fusion proteins, in particular recombinant fusion proteins suitable as human and/or animal vaccines against a parasite of the phylum Apicomplexa, in particular against *Plasmodium falciparum* comprising a plurality of isolated heat stable fragments derived from at least two different Apicomplexa surface proteins presented on the surface of the parasite in at least two different life cycle main stages of the parasite, wherein each fragment contains at least one folded domain.

In one aspect, embodiments of the disclosure provide methods of producing and/or purifying recombinant fusion proteins according to the present disclosure comprising the steps of:
a) providing a nucleic acid construct comprising a nucleic acid encoding a fusion protein according to the present disclosure,
b) introducing the nucleic acid construct into a host cell, and
c) maintaining the host cell under conditions permitting expression of the fusion protein,
d) purifying the fusion protein from the host cell comprising a heat-treatment of the cell culture supernatant or extract, and
e) optionally further processing of the fusion protein.

In a further aspect, embodiments of this disclosure relate to methods of preparing a biologically active, therapeutic agent substantially free of active virus, wherein a source for a given fusion protein and/or vaccine according to the present disclosure is subjected to a viral inactivation step under conditions sufficient to inactivate any virus present, in particular via a heat treatment and/or an acidic-treatment.

In another aspect, embodiments of this disclosure relate to methods for purifying a recombinant fusion protein according to the present disclosure, comprising
a) suspending host cells expressing said fusion protein at a pH<8 and incubating said suspension at a temperature of between 55-70. ° C.,
b) separating, and
c) collecting the soluble fraction of the suspension, containing the recombinant fusion protein, and
d) purifying and optionally further processing said recombinant fusion protein.

In another aspect, embodiments of this disclosure relate to methods for purifying a recombinant fusion protein according to the present disclosure, comprising a) harvesting a cell culture of host cells expressing said fusion protein,
b) resuspending said host cells at a pH<8 and incubating said suspension at a temperature of between 55-70. ° C.
c) separating, and
d) collecting the soluble fraction of the suspension, containing the recombinant fusion protein, and
e) purifying and optionally further processing said recombinant fusion protein.

In a further aspect, embodiments of this disclosure relate to antibody compositions comprising isolated antibodies or fragments thereof binding to one or more recombinant fusion protein(s) according to the present disclosure.

In another aspect, embodiments of this disclosure relate to compositions comprising a recombinant fusion protein according to the present disclosure and/or an amino acid sequence selected from the group consisting of SEQ ID NO.193 to SEQ ID NO.195, SEQ ID NO.202 and SEQ ID NO.205, or homologous polypeptides thereof, wherein the composition is preferably a pharmaceutical and/or diagnostic composition.

A further aspect of the present disclosure pertains to pharmaceutical compositions comprising the recombinant fusion protein according to the present disclosure and/or an amino acid sequence selected from the group consisting of SEQ ID NO.193 to SEQ ID NO.195, SEQ ID NO.202 and SEQ ID NO.205, or homologous polypeptides thereof, and a pharmaceutically acceptable carrier.

In another aspect, embodiments of this disclosure relate to pharmaceutical and/or diagnostic compositions comprising a recombinant fusion protein according to the present disclosure.

In a further aspect, embodiments of this disclosure relate to vaccine compositions for immunizing a susceptible mammal against malaria comprising as an active ingredient the recombinant fusion protein according to the present disclosure and a carrier in a physiologically acceptable medium.

In still another aspect, embodiments of this disclosure relate to vaccine compositions for immunizing a susceptible mammal against a parasite of the phylum Apicomplexa comprising as an active ingredient a recombinant fusion protein according to the present disclosure and/or an amino acid sequence selected from the group consisting of SEQ ID NO.193 to SEQ ID NO.195, SEQ ID NO.202 and SEQ ID NO.205, or homologous polypeptides thereof, and a carrier in a physiologically acceptable medium.

In still another aspect, embodiments of this disclosure provide nucleic acids encoding said recombinant fusion protein, as well as vectors and host cells comprising such nucleic acids.

In other aspects, this disclosure relates to use of recombinant fusion protein according to the present disclosure in the prevention of malaria tropica.

Furthermore, methods of immunizing humans against an Apicomplexa infection, in particular against *Plasmodium falciparum*, comprising administering an effective amount of a fusion protein of the present disclosure, a composition comprising the recombinant fusion protein the present disclosure or a vaccine composition according to the present disclosure are disclosed.

In another important aspect, the present disclosure relates to vaccine compositions suitable as human and/or animal vaccine against a parasite of the phylum Apicomplexa comprising a plurality, in particular at least four isolated heat stable fragments derived from at least two different Apicomplexa surface proteins presented on the surface of the parasite in at least two different stages in the life cycle of the parasite, wherein each fragment contains at least one folded domain.

In yet another aspect, embodiments of this disclosure relate to methods for purifying a recombinant fusion protein according to the present disclosure from a eukaryotic expression host by means of a heat-treatment of the cell culture supernatant or extract.

In a further aspect, embodiments of this disclosure relate to viral inactivation of the recombinant protein product during downstream processing by heat-treatment.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural reference unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 2 is a summary of intermediate and definitive hosts for different apicomplexan parasites (Wasmuth et al., 2009).

FIG. 4 shows an exemplary sequence alignment of *P. falciparum* EGF9_Ripr (SEQ ID NO.16) and its orthologs in different apicomplexan species.

FIG. 7 shows the results of immunofluorescence assays of different *P. falciparum* stages using purified polyclonal rabbit antibodies raised against a multi-stage, multi-fragment vaccine candidate (SEQ ID NO.197) according to the present disclosure.

DETAILED DESCRIPTION OF THIS DISCLOSURE

Figure 1:
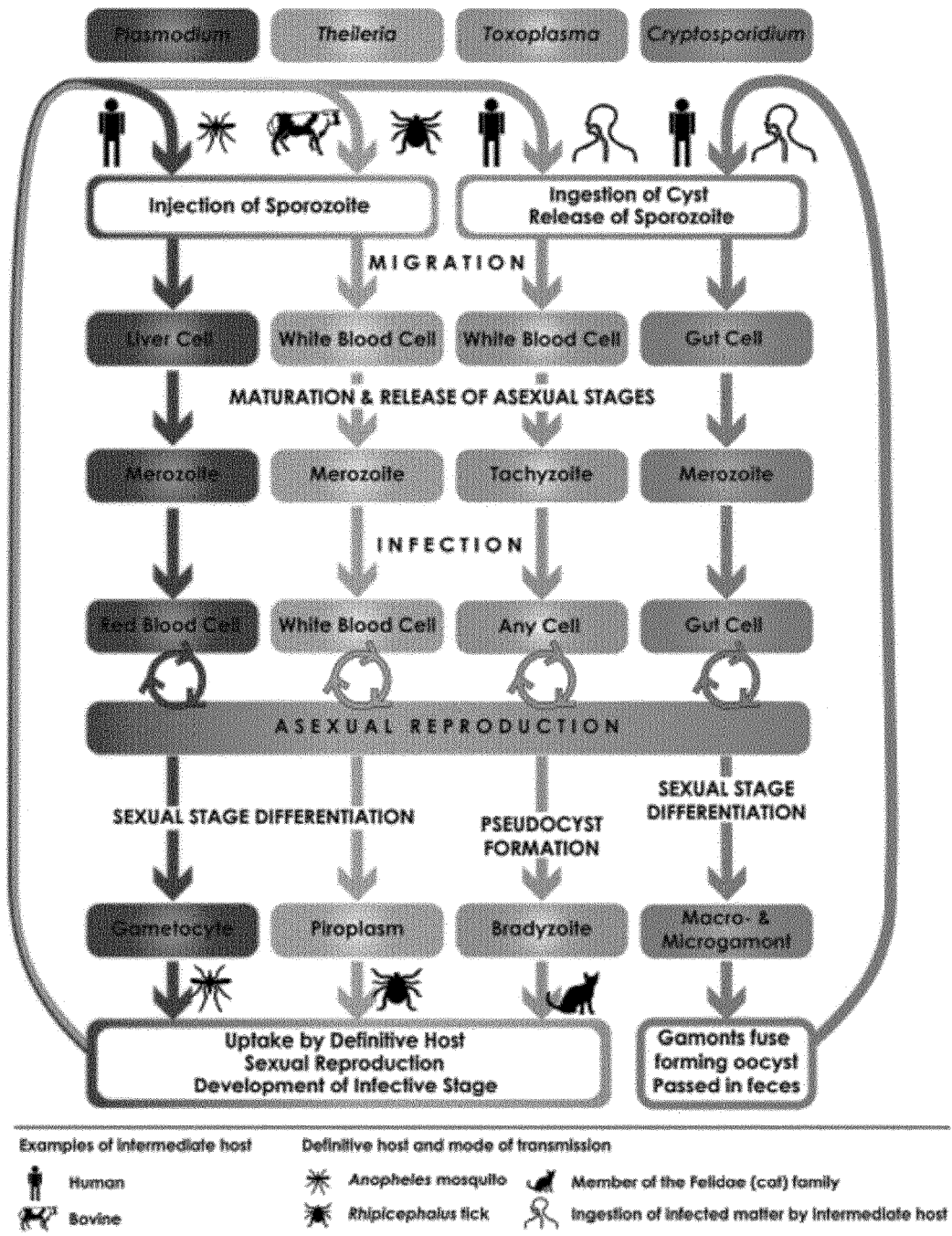
FIG. 1 is a scheme of the general life cycle of different apicomplexan parasites (Wasmuth et al., 2009).

The present disclosure pertains to therapeutically and diagnostic fusion proteins, compositions and antibodies suitable as human and/or animal vaccines against parasites of the phylum Apicomplexa, in particular against parasites of the genus *Plasmodium* like *Plasmodium falciparum*.

In advantageous embodiments, the recombinant fusion proteins and compositions according to the present disclosure combine heat stable fragments from different Apicomplexa surface proteins from different stages of the parasite development, wherein each heat stable fragment comprises at least one folded domain.

One advantage of using heat stable fragments with folded domains in place of full-length antigen proteins is to circumvent the limitation of the protein size, to allow better fusion protein heat stability and to improve the protein expression capacity.

Surprisingly, the inventors found that using isolated heat stable fragments with folded domains as building blocks for the manufacture of vaccines has several advantages:

For example, the heat stability of the fusion proteins enables an efficient purification step by heating up the cell culture supernatant or cell extract. Many host cell proteins are denatured during that step and precipitate (see FIG. 3). They can thus be easily removed by centrifugation or filtration. Moreover, many host cell proteases are thermally inactivated, resulting in increased stability of the target recombinant fusion protein during downstream processing.

Further, heat stability is moreover an extremely useful property for viral inactivation steps during downstream processing in vaccine manufacturing. Such steps are mandatory for ensuring product safety, but may not always be compatible with the activity of the target protein. In such cases expensive ultra/nano-filtration procedures have to be employed, including tedious and expensive process validation. By being able to employ simple heat treatment of the product, the overall process becomes cheaper and more efficient and results in a safer product. These properties are highly important for generating a vaccine that is particularly useful and applicable for developing countries.

Furthermore, heat stability is an important feature during the formulation (e.g. lyophilisation) of the product and the storage. In particular, vaccines destined for developing countries in sub-Saharan Africa generally cannot rely on a cold chain, thus rendering many potentially promising vaccines completely useless.

The heat stability of the fusion proteins according to this disclosure also results in longer shelf-life of the vaccine, thereby further reducing total costs for health systems.

Surprisingly, the inventors found that also the immune responses directed against such heat stable fragments with a folded domain are more robust, especially resulting in balanced immune responses against all represented components. Immuno-dominant and immuno-silent regions have not been found, even for candidates comprising a high number of different domains.

Furthermore, the inventors found that the selection of these heat stable fragments enables different (virtually all) combinations, i.e. the domains can generally be combined freely, resulting in recombinant fusion proteins comprising the same components but in a different order (e.g. A-B-C vs. B-C-A). Again, the induced immune responses are balanced, irrespective of the actual order of heat stable fragments. This possibility has tremendous advantages for (i) developing specific candidates with increased productivity and (ii) enables prime-boost regimens or (iii) combination vaccines where immune responses against the domain junctions are minimized or prevented.

The desire for a vaccine candidate composed of a single polypeptide is mainly driven by practical, technical and economical demands for reproducible, robust and cost-efficient production. However, to those skilled in the art, it is also clear, that there is a size limitation for recombinant expressed proteins. Although protein specific differences have to be taken into account as well, there is a strong decrease of expression levels and yields with increasing length of the polypeptide. Multiple challenges increase over-proportionally with size and the overall properties of large proteins are significantly less amenable to optimization than those of smaller proteins, domains or fragments. All these problems have so far been significant bottlenecks for the development of efficient vaccines against apicomplexan parasites and have resulted in an overwhelming number of sub-optimal vaccine candidates that comprise only multiple linear epitopes, one or two antigens from a one or two life cycle stages. As alternative, chemically or genetically attenuated or inactivated life-vaccines are proposed (e.g. irradiated sporozoites), but such approaches have to deal with batch-to-batch consistency, scaled-up production and most importantly product safety.

It is therefore an extremely important aspect of the present disclosure, that the heat stable fragments can be combined as building blocks e.g. in a recombinant fusion protein comprising several (in particular 4) heat stable fragments from different Apicomplexa surface proteins from the same but preferably from different life-cycle stages and can be efficiently produced. In an advantageous embodiment, the recombinant fusion proteins according to the present disclosure comprise at least four, in particular at least six heat stable fragments. It also has to be emphasized that the heat stable building blocks comprise folded protein domains that are fundamentally different from isolated small linear epitopes. Such linear epitopes are highly efficient for T-cell responses but are generally not suited as immunogens for inducing neutralizing antibodies. Quite contrary, apicomplexan parasites and in particular parasites of the genus *Plasmodium* have many proteins containing repetitive linear sequences, and their role is to divert the humoral immune response. It is therefore another particular aspect that the fusion proteins according to this disclosure do not comprise only these repetitive linear peptide epitopes.

Importantly, the fusion proteins according to the present disclosure (i) comprise domains derived from different Apicomplexa surface proteins and (ii) were designed using building blocks (domains) that have been experimentally identified and verified as heat stable (temperature tolerant).

In summary, the recombinant fusion proteins of the present disclosure can be well expressed in different expression systems, are heat stable, have a high immunological relevance and have an improved immunogenicity. In advantageous embodiments, the recombinant fusion proteins of the present disclosure used as vaccines have the ability to elicit protective immunity that blocks infection as well as prevents pathology and interrupts transmission of parasites, and would most likely be a combination vaccine composed of subunits from different parasite stages.

As mentioned above, the isolated heat stable fragments have the advantage that they are small protein fragments with a conserved stable protein fold (like the Epidermal growth factor-like domain (EGF) and the Thrombospondin type 1 repeats (TSR) domain) in contrast e.g. to specifically selected *Plasmodium* linear T/B-cell epitopes used in the prior art. Using larger, folded protein domains instead of known linear B-, and T-cell epitope sequences enables the presentation of a larger number of conformational and overlapping B-cell epitopes as well as a larger number of T-cell epitopes thereby enhancing the chances to elicit a broader and more sustained immune response.

Parts/Fragments of an antigen that are recognized by the immune system, more specifically by antibodies, B cells, or T cells are defined as epitopes or antigenic determinants. Such protein structures that are composed of amino acids that have been brought together in three-dimensional structure (e.g. in a folded domain) are known as conformational epitopes. In contrast, a single peptide chain lacking secondary structure is termed a linear epitope. Most B cell epitopes are conformational even though some antibodies bind linear peptide fragments of antigens. T cell epitopes are linear peptides presented on the surface of an antigen-presenting cell, where they are bound to MHC molecules. T cell epitopes presented by MHC class I molecules are typically peptides between 8 and 11 amino acids in length, whereas MHC class II molecules are at least 13 amino acids long, but can be much longer. The clusters of conserved residues that bind the two ends of a peptide in MHC class I molecules are not found in MHC class II molecules, and the ends of the peptides are not bound. Instead, the peptide lies in an extended conformation along the MHC class II peptide-binding pocket. By comparing the sequences of known binding peptides it is usually possible to detect a pattern of permissive amino acids for each of the different alleles of MHC class II molecules, and to model how the amino acids of this peptide sequence motif will interact with the amino acids that make up the binding pocket.

Currently, a reasonably large database of unique B-cell and T-cell epitopes from *Plasmodium* proteins, including those from human *P. falciparum* and *P. vivax* malarias, has become available. By conducting a comprehensive meta-analysis of available data for *Plasmodium* immune epitopes, Vaughan et al. have identified more than 5,000 unique B-cell and T-cell epitopes for malaria parasites. Several of the *P. falciparum* and *P. vivax* epitopes were identified in extensive field studies conducted over the last 2 decades and by computer-based predictions of immune epitopes by analysis of genomic and proteomic databases; some of these predictions were validated in HLA-peptide binding studies (T cell epitopes) and in in vitro immunological studies (B cell epitopes).

Advantageous embodiments of the present disclosure pertains to recombinant fusion proteins suitable as human and/or animal vaccines against a parasite of the phylum Apicomplexa comprising a plurality of isolated heat stable fragments from at least two different Apicomplexa surface proteins, wherein each fragment contains at least one folded domain, wherein the isolated heat stable fragments are derived from Apicomplexa surface proteins presented on the surface of the parasite in at least two different stages in the life cycle of the parasite.

The terms "recombinant fusion protein" and "fusion protein" are used herein interchangeably to refer for example to a protein produced by recombinant technology which comprises segments i.e. amino acid sequences, from heterologous sources, such as different proteins or different organisms. The segments are joined either directly or indirectly to each other via peptide bonds. By indirect joining it is meant that an intervening amino acid sequence, such as a peptide linker is juxtaposed between segments forming the fusion protein. A recombinant fusion protein is encoded by a nucleotide sequence, which is obtained by genetically joining nucleotide sequences derived from different regions of one gene and/or by joining nucleotide sequences derived from two or more separate genes. These nucleotide sequences can be derived from a parasite of the phylum Apicomplexa and in particular derived from *P. falciparum*, but they may also be derived from other organisms, the plasmids used for the cloning procedures or from other nucleotide sequences.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

A recombinant fusion protein comprising a heat stable fragment from a Apicomplexa surface protein, in particular from a *Plasmodium* surface protein can be a recombinant product prepared using recombinant DNA methodology and expression in a suitable host cell, as is known in the art (see for example Sambrook et al., (2001) Molecular Cloning, Cold Spring Harbor Laboratory Press, Cold Spring Harbor, N.Y.). Nucleotide sequences encoding specific isolated protein domain may be conveniently prepared, for example by polymerase chain reaction using appropriate oligonucleotide primers corresponding to the 5' and 3' regions of the domain required for isolation, and a full length coding of the isolated protein domain sequence as template. The source of the full length coding protein sequence may be for example, DNA extracted from parasite cells or a plasmid vector containing a cloned full-length gene. Alternatively, the protein coding sequence may partially or completely be synthesized in vitro or a combination of different approaches may be used. Non-limiting examples of properties of the fusion proteins according to the present disclosure are heat stability and pH stability. Especially the thermal performance of the fusion proteins in combination with the improved immunogenicity via using heat stable fragments comprising a folded domain is considered an important characteristic of the fusion proteins according to the present disclosure. The heat stability for example may be determined as described in Example 4.

The Apicomplexa (also referred to as Apicomplexia) are a large group of protists, most of which possess a unique organelle called apicoplast and an apical complex structure involved in penetrating a host's cell. They are a diverse group including organisms such as coccidia, gregarines, piroplasms, haemogregarines, and plasmodia (*Plasmodium falciparum, Plasmodium vivax, Plasmodium ovale, Plasmodium malariae, Plasmodium knowlesi*). Diseases caused by apicomplexan organisms include, but are not limited to Babesiosis (*Babesia*), Malaria (*Plasmodium*), Coccidian diseases including Cryptosporidiosis (*Cryptosporidium parvum*), Cyclosporiasis (*Cyclospora cayetanensis*), Isosporiasis (*Isospora belli*) and Toxoplasmosis (*Toxoplasma gondii*).

In advantageous embodiments, the recombinant fusion proteins as well as the compositions according to the present disclosure are suitable as human and/or animal vaccines against a parasite of the genus *Plasmodium* including *Plasmodium falciparum, Plasmodium vivax, Plasmodium malariae* and/or *Plasmodium ovale*. In an advantageous embodiment, the parasite is *Plasmodium falciparum*.

Apicomplexa surface proteins are preferably membrane-bound or associated proteins or proteins known to be secreted. These proteins can e.g. be identified by analyzing the Genome or known genes for the presence of an N-terminal Signal peptid, the presence of a PEXEL motif, the presence of a GPI anchor motif, or the presence of one or more transmembrane domains using generally available software tools. These proteins and their homologues e.g. include but are not limited to:

CelTOS (cell traversal protein for ookinetes and sporozoites), Antigen 2 (PfAg2, PvAg2, PoAg2, etc.)
CSP (circumsporozoite protein)
EBA175 (Erythrocyte binding antigen 175)
EXP1 (Exported Protein 1); synonyms: CRA1 (Circumsporozoite-Related Antigen-1/Cross-Reactive Antigen-1), AG 5.1 (Exported antigen 5.1), QF119
MSP1 (Merozoite surface protein 1); synonyms: MSA1 (Merozoite surface antigen 1), PMMSA, p190, p195, gp190, gp195
MSP3 (Merozoite surface protein 3); synonym: SPAM (secreted polymorphic antigen associated with the merozoite)
MSP4 (Merozoite surface protein 4)
MSP8 (Merozoite surface protein 8)
MSP10 (Merozoite surface protein 10)
MTRAP (merozoite TRAP homologue, merozoite TRAP homolog, merozoite TRAP-like protein)
Pf38; synonym: 6-cysteine protein
PfRh2a, Rh2a (Reticulocyte binding protein 2 homolog a, Reticulocyte binding protein 2 homologue a)
PfRh2b, Rh2b (Reticulocyte binding protein 2 homolog b, Reticulocyte binding protein 2 homologue b)
PfRh4, Rh4 (Reticulocyte binding protein homolog 4, Reticulocyte binding protein homologue 4)
PfRh5, Rh5 (Reticulocyte binding protein homolog 5, Reticulocyte binding protein homologue 5)
PfRipr, Ripr (Rh5 interacting protein)
Pfs25 (25 kDa ookinete surface antigen, Sexual stage antigen pfs25)
Pfs230, S230 (Transmission-blocking target antigen Pfs230, Transmission-blocking target antigen S230)
Pfs48/45 (45/48 kDa doublet proteins on *Plasmodium* gametes and gametocytes)
Ron2 (rhoptry neck protein 2)
TRAMP (thrombospondin-related apical membrane protein); synonym: PTRAMP
TRAP (Thrombospondin-related anonymous protein); synonym: SSP2 (Sporozoite Surface Protein 2)

Heat stable fragments in the recombinant fusion protein or in the vaccine compositions according to the present disclosure may be from the same Apicomplexa surface protein, in particular from the same *Plasmodium* surface protein or preferably from different Apicomplexa surface proteins.

In an advantageous embodiment, the fusion proteins or the vaccine compositions according to the present disclosure comprise a plurality of isolated heat stable fragments from at least two different Apicomplexa surface proteins, wherein each fragment contains at least one folded domain.

In some advantageous embodiments, the fusion proteins or the compositions according to the present disclosure comprise more than one, in particular at least three, more particular at least four isolated heat stable fragments from different Apicomplexa surface proteins. In an advantageous embodiment, the recombinant fusion proteins comprise at least four different isolated heat stable fragments. Preferably, the Apicomplexa surface proteins are presented on the surface of the parasite in at least two different stages in the life cycle of the parasite.

In an advantageous embodiment, the fusion proteins or the vaccine compositions according to the present disclosure comprise at least four different isolated heat stable fragments from at least two different Apicomplexa surface proteins presented on the surface of the parasite in at least two different stages in the life cycle of the parasite. Since Apicomplexa parasites are able to use alternative antigens of a single life stage for their invasion process it is an advantage that a vaccine candidate covers at least two different antigen fragments per life stage. To further increase the vaccine efficacy more than one parasite life stage should be targeted. This would equal four antigen fragments and two life stages per minimal vaccine.

However, in an advantageous embodiment the number of covered antigens and life stages may be less for one vaccine if it is used as a composition with a complementary vaccine so that the sum of both vaccines equals at least four antigen fragments and two life stages.

Therefore, the present disclosure is also directed to vaccine compositions suitable as human and/or animal vaccine against a parasite of the phylum Apicomplexa comprising a plurality, in particular at least four isolated heat stable fragments derived from at least two different Apicomplexa surface proteins presented on the surface of the parasite in at least two different stages in the life cycle of the parasite, wherein each fragment contains at least one folded domain.

In some embodiments, the isolated heat stable fragments in the vaccine compositions according to the present disclosure are comprised in at least two different recombinant fusion proteins, wherein in an advantageous embodiment one recombinant fusion protein comprises two or more heat stable fragments derived from at least one Apicomplexa surface protein presented on the surface of the parasite in a single stage of the life cycle of the parasite and wherein the other recombinant fusion protein comprises two or more heat stable fragments derived from at least one Apicomplexa surface protein presented on the surface of the parasite in a different stage of the life cycle.

In other words, the vaccine compositions according to the present disclosure may comprise different fusion proteins having heat stable fragments derived from different Apicomplexa surface proteins for directing the parasite in more than one stages of the life cycle of the parasite.

In further embodiments of the present disclosure, one or more heat stable fragments derived from at least one Apicomplexa surface protein presented on the surface of the parasite in at least one stage of the life cycle of the parasite are repeated several times within the fusion proteins according to the present disclosure. The repeated fragments may be 100% identical, e.g. to increase the valence, or the repeated fragments may represent the same region of the full-length surface protein but actually comprise sequences derived from different strains, different species or different genera.

The term "fragment" as used herein refers to a continuous part of a natural full-length protein, with or without mutations, which is separate from and not in the context of a full length Apicomplexa surface protein. It may be a structural/topographical or functional subunit of a full length or complete protein. The term "fragments" expressly excludes polypeptides corresponding to full-length amino acid sequences of an Apicomplexa surface protein but also excludes short peptides from Apicomplexa surface proteins, not folding into domains. For example, in some embodiments of the present disclosure fragments having an amino acid sequence of less than 90% of the parent full-length surface protein are used.

In an advantageous embodiment, the heat stable fragments are isolated heat stable fragments. The term "isolated" when used in relation to a nucleic acid or protein (e.g. an protein domain), refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

The term "heat stable" as used herein refers in particular to the ability of the protein fragments or fusion proteins to withstand a temperature treatment of at least 50° C. for 5 minutes, preferably of 60° C. for 5 minutes, more preferably of 65° C. for 5 minutes, most preferably of 70° C. for 5 minutes while retaining a binding activity of at least 60%, preferably 70%, more preferably 80% and most preferably 90% to at least one antibody recognizing a conformational epitope and having a recovery rate of at least 70%. In advantageous embodiments, the protein fragments or fusion proteins according to the present disclosure are able to withstand a temperature treatment of at least 80° C. for 5 minutes while retaining a binding activity of at least 60%, preferably 70%, more preferably 80% and most preferably 90% to at least one antibody recognizing a conformational epitope and having a recovery rate of at least 60%. In another advantageous embodiment, the protein fragments or fusion proteins according to the present disclosure are able to withstand a temperature treatment of at least 90° C. for 5 minutes while retaining a binding activity of at least 60%, preferably 70%, more preferably 80% and most preferably 90% to at least one antibody recognizing a conformational epitope and having a recovery rate of at least 50%.

Figure 3:
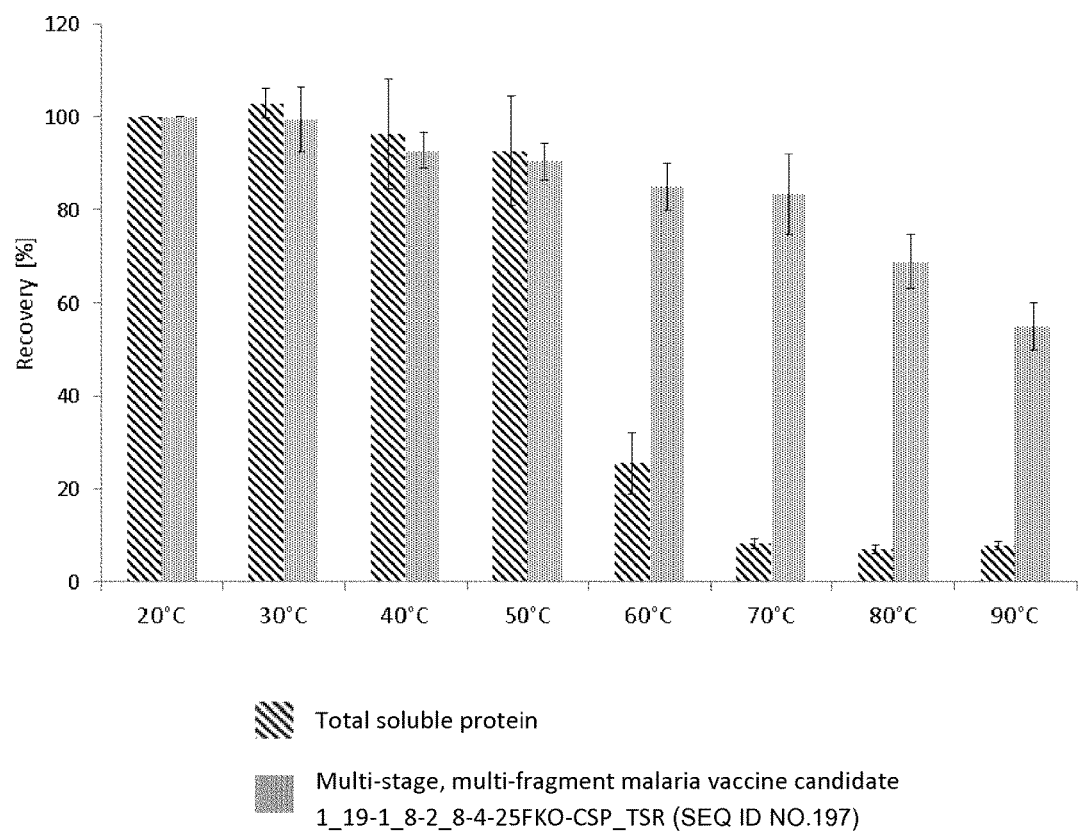
FIG. 3 is a diagram showing a time-controlled heat-treatment of an advantageous embodiment of a heat stable fusion protein according to the present disclosure.

Such heat stable protein fragments or fusion proteins have a wide range of applications, as they are more robust than other proteins. As one of these applications, the heat precipitation is exemplary described in point 4 of the Methods and Examples part in the present description. Further, FIG. 3 illustrates a time-controlled heat-treatment according to the present disclosure.

Furthermore, the term "pH stable" as used herein refers in particular to the ability of the protein fragments or fusion proteins to withstand incubation for at least 5 minutes at low and/or high pH, at least below a pH of 5 and/or above a pH of 8, preferably below a pH of 4 and/or above a pH of 9 and more preferably below a pH of 3 and/or above a pH of 10, where at least 50%, preferably at least 60%, more preferably at least 70% and most preferably at least 80% of the protein fragments or fusion proteins remain in solution and where a binding activity of at least 60%, preferably 70%, more preferably 80% and most preferably 90% to at least one antibody recognizing a conformational epitope is retained. The underlying pH stability is exemplary described for the immunoaffinity chromatography (IAC) in point 9 of the Methods and Examples part in the present description.

The term "conformational epitope" as used herein refers to an epitope of the protein fragments or fusion proteins that is characterized by a loss of the binding activity to a corresponding antibody or a reduction of the binding activity of at least 50%, preferably 70% and more preferably 90% to a corresponding antibody after reduction of disulfide bridges or by treating the protein fragment or fusion protein with reagents known to denature proteins, e.g. 8 M urea, 6 M guanidinium chloride or 1% SDS.

The term "binding activity" as used herein refers to an assay, where the protein fragments or fusion proteins are incubated with an antibody or another ligand (e.g. native interacting protein) recognizing a conformational epitope or binding region and where a quantitative readout is generated. The generated readout is proportional to the amount of protein fragments or fusion proteins that have bound to the antibody or other ligand or vice versa. Suitable methods include but are not limited to immune-assays such as ELISA, RIA, surface plasmon resonance spectroscopy based assays, electrophoretic mobility shift assays, size-exclusion chromatography based shift assays, spectroscopic techniques such as fluorescence polarization, light scattering, fluorescence resonance energy transfer (FRET) and affinity chromatography.

According to the present disclosure, the different heat stable fragments are linked to each other. "Linked" refers to non-covalent or covalent bonding between two or more molecules. Linking may be direct or indirect. Two molecules are indirectly linked when the two molecules are linked via a connecting molecule (linker). Two molecules are directly linked when there is no intervening molecule linking them. As mentioned above, the isolated protein domains are linked either directly or indirectly to each other, preferably via peptide bonds or disulfide bonds. An example of indirect covalent linking is that an intervening amino acid sequence, such as a peptide linker is juxtaposed between segments forming the fusion protein.

In some embodiments, the heat stable fragments are directly linked to each other. In other embodiments, the heat stable fragments are indirectly linked to each other via a linker, wherein in some examples the linker is a polypeptide with a size of less or equal twenty amino acids, in particular 2 to 6 amino acids.

In some advantageous embodiments, each heat stable fragment contains at least one folded domain.

The term "folded domain" as used herein refers to a protein sequence that is known or predicted to adapt a structurally distinct three dimensional structure of known structural class, fold or superfamily comprising at least one conformational epitope. Therefore, a folded domain is part of a structural/topographical or functional subunit of a full length or complete protein. It may be kept within the context of the full length or complete protein, or may be separated therefrom, as in an isolated domain. Domains corresponding to structural/topographical subunits include for example, a cytoplasmic domain, an extracellular domain or a transmembrane domain. Domains corresponding to functional subunits include for example, a receptor binding domain or in particular an antibody binding domain.

In contrast to e.g. small linear peptides, the folded domains according to this invention exhibit a higher structural order. Further, the folded domains according to this invention are characterized by the existence of at least one peptide, protein or monoclonal antibody that binds to a conformational epitope within the folded domain under physiological conditions (e.g. PBS pH 7.4). Moreover, treatment of the protein fragments or fusion proteins comprising such a folded domain with 8 M urea, 6 M guanidinium chloride or 1% SDS, or reducing conditions, either alone or in combination, results in loss of the binding activity or reduction of the binding activity of at least 50%, preferably 70% and more preferably 90% of the peptide, protein or monoclonal antibody recognizing a conformational epitope within the folded domain.

In some advantageous embodiments, the folded domain is an "EGF-like domain" which is an EGF-like motif that may be found in a variety of proteins, as well as EGF and Notch and Notch ligands, including those involved in the blood clotting cascade (Furie and Furie, 1988, Cell 53: 505-518). For example, this motif has been found in extracellular proteins such as the blood clotting factors IX and X (Rees et al., 1988, EMBO J. 7:2053-2061; Furie and Furie, 1988, Cell 53: 505-518), in other *Drosophila* genes (Knust et al., 1987 EMBO J. 761-766; Rothberg et al., 1988, Cell 55:1047-1059), and in some cell-surface receptor proteins, such as thrombomodulin (Suzuki et al., 1987, EMBO J. 6:1891-1897) and LDL receptor (Sudhof et al., 1985, Science 228:815-822). A protein binding site has been mapped to the EGF repeat domain in thrombomodulin and urokinase (Kurosawa et al., 1988, J. Biol. Chem 263:5993-5996; Appella et al., 1987, J. Biol. Chem. 262:4437-4440).

Figure 9:
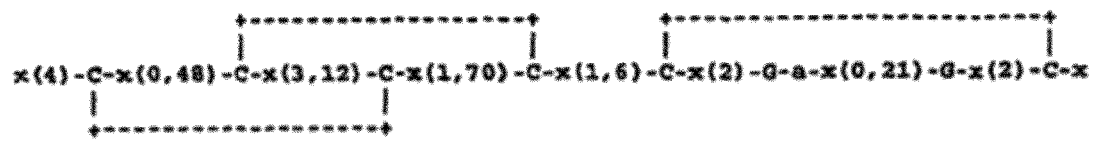
FIG. 9 shows the sequence of a typical EGF domain.

As reported by PROSITE a typical EGF domain may include six cysteine residues which have been shown (in EGF) to be involved in disulfide bonds. The main structure is proposed, but not necessarily required, to be a two-stranded beta-sheet followed by a loop to a C-terminal short two-stranded sheet. Subdomains between the conserved cysteines strongly vary in length as shown in FIG. 9, wherein "C" represents conserved cysteine involved in a disulfide bond, "G" represents often-conserved glycine, "a" represents often conserved aromatic amino acid and "x" represents any residue.

The region between the 5th and 6th cysteine contains two conserved glycines of which at least one is normally present in most EGF-like domains and force the assembly of several well-defined discontinuous epitopes (Farley and Long, 1995, Exp. Parasitol. 80, 328-332; McBride and Heidrich, 1987, supra; Uthaipibull et al, 2001, J. Mol. Biol. 307, 1381 1394).

The EGF-like domain used in the recombinant fusion proteins or compositions according to the present disclosure may be derived from any suitable Apicomplexa surface protein, expressed in any life cycle stage, including for example the pre-erythrocytic stage, the blood stage and the sexual stage. The surface proteins may occur on the different forms of the apicomplexan parasite, in particular of *Plasmodium falciparum*.

Preferably the EGF-like domains are derived from *Plasmodium vivax* and/or *Plasmodium falciparum*. The term "EGF-like domain" as used herein includes sequence variants, fragments, derivatives and mimetics having activity corresponding to naturally occurring domains.

A "TSR domain" is a small about 60-residue domain found in extracellular proteins or in the extracellular part of transmembrane proteins that are involved in immunity, cell adhesion, cell-cell-interactions and neuronal development (Tucker, 2004). Structures of TSR domains from thrombospondin-1 (TSP-1; Tan et al. 2002) and F-spondin (PDB codes 1SZL and 1VEX) have been solved. These show that a TSR domain has an elongated structure consisting of an antiparallel three-stranded β-sheet. The domain core is formed by a stacked array of side chains of conserved tryptophans, arginines, and cysteines. TSRs of several proteins have been reported to mediate glycosaminoglycan (GAG) binding. For example, the *plasmodium* surface proteins *plasmodium* CS and TRAP both contain an adhesive thrombospondin type 1 domain, TSR.

In an advantageous embodiment, the recombinant fusion proteins and the vaccine compositions according to the present disclosure comprise at least two folded domains from at least two different Apicomplexa surface proteins, wherein the first folded protein domain is an isolated EGF-like domain and the second domain is an isolated EGF-like domain or an isolated TSR domain.

In another embodiment, the heat stable isolated fragments in the recombinant fusion proteins or vaccine compositions may comprise one or more further folded domains. In advantageous embodiments, the heat stable isolated fragments may comprise 2 to 12 different folded protein domains, in particular 4 to 10, in particular 6 to 8 different folded domains, wherein at least one folded domain is an EGF-like domain.

As mentioned above, EGF-like domains as well as TSR domains show a high cysteine content. In a further embodiment, the recombinant fusion protein according to the present disclosure has a cysteine content of at least 5%, in particular of at least 7.5%, more particular of at least 10%.

It is one further advantage of the present invention that also non-heat stable isolated fragments which are for example highly immunogenic can be embedded into a fusion protein having a plurality of isolated heat stable fragments, wherein the entire fusion protein is still heat stable. Therefore, in some embodiments, recombinant fusion proteins according to the present disclosure may comprise at least one non-heat stable isolated fragment derived from an Apicomplexa surface protein, wherein the entire fusion protein is heat stable.

In some advantageous embodiments, the folded domains of the fragments in the fusion proteins and the vaccines according to the present disclosure comprise at least one conformational epitope.

The term "epitope" as used herein refers to a region of a protein molecule to which an antibody can bind. In particular, an "epitope" may be defined as an array of 3-20 amino acids aligned along the surface of a protein. In a linear epitope, the amino acids are joined sequentially and follow the primary structure of the protein. In a "conformational epitope" the amino acids are arranged in a specific three-dimensional structure in a context-dependent manner (e.g. a folded domain). With respect to conformational epitopes, the length of the epitope-defining sequence can be subject to wide variations. The portions of the primary structure of the antigen between the residues defining the epitope may not be critical to the structure of the conformational epitope. For example, deletion or substitution of these intervening sequences may not necessarily affect the conformational epitope provided sequences critical to epitope conformation are maintained (e.g. cysteines involved in disulfide bonding, glycosylation sites, etc.). A conformational epitope may also be formed by association of 2 or more subunits into homo- or hetero-oligomers. A conformational epitope may be a folded domain or an accessible part thereof that is recognized by the immune system and capable of eliciting an immune response.

As mentioned above, one of the advantages of the recombinant fusion proteins according to the present disclosure is the relatively small protein size in relation to the number of folded domains from different Apicomplexa surface proteins in contrast to vaccine constructs comprising full length surface proteins, in particular if the fusion protein is directed to surface proteins from different life cycle stages. Therefore, in some embodiments the fusion protein of the present disclosure has a molecular weight of less or equal 160 kDa if the fusion protein comprises heat stable fragments derived from a plurality of Apicomplexa surface proteins presented on the surface of the parasite in all stages of the *plasmodium* life cycle or if the fusion protein comprises heat stable fragments derived from Apicomplexa surface proteins from selected stages of less or equal 120 kDa.

The recombinant fusion proteins and/or vaccine compositions suitable as human and/or animal vaccine against a parasite of the phylum Apicomplexa may combine heat stable fragments from different stages of the parasite development, inducing several mechanisms of protection. In one embodiment, the recombinant fusion proteins and/or vaccine compositions of the present disclosure comprises heat stable fragments for pre-erythrocytic and blood stage coverage and can be used for prophylactic and/or therapeutic vaccines. In another advantageous embodiment, the recombinant fusion proteins and/or vaccine compositions of the present disclosure comprises heat stable fragments for pre-erythrocytic and blood stage coverage as well as heat stable fragments for sexual stage coverage.

As mentioned above, in some embodiments the heat stable fragments are derived from different Apicomplexa surface proteins which are expressed in the same stage of the Apicomplexa life cycle, in particular in the blood stage. In an advantageous embodiment, the heat stable fragments are from different Apicomplexa surface proteins which are expressed in different stages of the Apicomplexa life cycle, in particular in the blood stage and in the pre-erythrocyte stage. In a further embodiment, the heat stable fragments are from different Apicomplexa surface protein antigens which are expressed in different stages of the Apicomplexa life cycle, in particular the blood stage, the sexual stage and the pre-erythrocyte stage.

In advantageous embodiments the heat stable fragments are derived from different *Plasmodium falciparum* surface proteins which are expressed in the same stage of the *Plasmodium* life cycle, in particular in the blood stage. In an advantageous embodiment, the heat stable fragments are from different *Plasmodium falciparum* surface proteins which are expressed in different stages of the *Plasmodium falciparum* life cycle, in particular in the blood stage and in the pre-erythrocyte stage. In a further embodiment, the heat stable fragments are from different *Plasmodium falciparum* surface protein antigens which are expressed in different stages of the *Plasmodium falciparum* life cycle, in particular the blood stage, the sexual stage and the pre-erythrocyte stage.

Furthermore, the isolated heat stable fragments may be from different *Plasmodium* surface proteins, which are expressed in the different *Plasmodium* life cycle main stages:

The Pre-Erythrocytic Main Stage:
a) Sporozoite

The sporozoite remains in the bloodstream for a very short period of time before invading a hepatocyte. Examples for *Plasmodium* protein antigens expressed in the sporozoite are the circumsporozoite protein (CSP), the major constituent of the outer membrane of the sporozoite (Nussenzweig et al., 1989). Induced antibodies may be able to block the binding and the entrance of the sporozoite into the hepatocyte.

b) Liver Stage

During this stage, immunity is mostly mediated by cellular-dependent mechanisms involving CD8+ T cells, CD4+ T cells, natural killer (NK) cells and y6 T cells. CSP is expressed both in the sporozoite and during the liver stage. So, much of the research involving CSP has switched from the immunodominant repeats inducing humoral response to regions that are able to induce cytotoxic T-cell responses. Other identified liver-stage antigens include liver-stage antigen-1 (LSA-1), LSA-2, LSA-3, SALSA and STARP, among others (Hoffman et al., 1996;).

The Asexual Blood Main Stage:
c) Merozoite

Besides the sporozoite, the merozoite is the only stage in the human host in which the malaria parasite is extracellular. In contrast to the sporozoite, several cycles of merozoite release will occur during a malaria infection, making them often available. A major ligand in *P. falciparum* is the erythrocyte-binding antigen-175 (EBA-175), located in the microneme (Chitnis et al., 1994). Several merozoite surface proteins (MSPs) have been identified, but for most of them their function still has to be further elucidated. In the case of the major MSP, named MSP-1, a role has been postulated in merozoite binding to the RBC and in the subsequent biochemical mechanisms involved in invasion. This protein is synthesized as a precursor of 185-210 kDa in the late schizont stage and is processed to generate several polypeptides of varied molecular weights. A 42 kDa polypeptide (MSP1-42) is kept attached to the merozoite membrane, and it is further processed to generate a 19 kDa polypeptide (MSP1-19), which goes into the host cell. Besides MSP-1, at least eight other MSPs have been described in *P. falciparum*: MSP-2, MSP-3, MSP-4, MSP-5, MSP-6, MSP-7, MSP-8 and MSP-10. Another merozoite surface-associated antigen is the acidic-basic repeat antigen (ABRA). Proteins located in merozoite apical organelles have also been identified (e.g. the rhoptry proteins apical membrane antigen-1 (AMA-1), rhoptry-associated protein-1 (RAP-1) and RAP-2).

d) Infected RBC

Once it has invaded the RBC, the parasite is supposed to have found a safer place to stay. One of the most studied molecules is the ring erythrocyte surface antigen (RESA).

In an advantageous embodiment, each of the heat stable fragments are from different *Plasmodium* surface proteins expressed in at least two different stages of the *Plasmodium* life cycle.

In advantageous embodiments, the heat stable fragments are selected from the group consisting of heat stable fragments comprising an EGF-like domain from MSP1, MSP4, MSP8, MSP10, PfRipr and Pfs25.

In further advantageous embodiments, the heat stable fragments are selected from the group consisting of heat stable fragments comprising a TSR domain is selected from CSP, mTRAP, TRAP and TRAMP.

In other advantageous embodiments, the heat stable fragments are selected from the group consisting of heat stable fragments from Pfs230, Pfs45/48, CelTos and Ron2, MSP3 and EXP1.

In advantageous embodiments, the heat stable fragments comprised in the recombinant fusion protein and/or vaccine compositions according to the present disclosure are selected from the group listed in Table 1.

TABLE 1

Examples of heat stable fragments.

| Name | Amino acid | PlasmoDB | Strain | Reference |
|---|---|---|---|---|
| CelTos | $F^{25}$-$D^{182}$ | PFL0800c | 3D7 | (Bergmann-Leitner et al. 2010) |
| CSP1_TSR | $P^{293}$-$S^{365}$ | PFC0210c | 3D7 | (Plassmeyer et al. 2009) |
| EXP1 | $E^{23}$-$S^{79}$, $N^{102}$-$H^{162}$ | PF1121600 | 3D7 | (Simmons et al. 1987) |
| EGF1_MSP1-19 | $I^{1589}$-$V^{1629}$ | PFI1475w | 3D7 | (Blackman et al. 1991) |
| MSP3aGKO | $K^{26}$-$K^{157}$ | PF1035400 | 3D7 | |
| EGF_MSP4 | $L^{201}$-$L^{247}$ | PFB0310c | 3D7 | (Marshall et al.1997) |
| EGF1_MSP8 | $N^{464}$-$D^{508}$ | PFE0120c | 3D7 | (Black et al. 2001) |
| EGF2_MSP8 | $D^{509}$-$S^{551}$ | PFE0120c | 3D7 | (Black et al. 2001) |
| EGF1_MSP10 | $V^{388}$-$P^{432}$ | PFF0995c | 3D7 | (Black et al. 2003) |
| EGF2_MSP10aglyc | $K^{434}$-$K^{475}$ | PFF0995c | 3D7 | (Black et al. 2003) |
| mTRAP_TSR | $T^{3}$-$E^{76}$ | PF10_0281 | 3D7 | (Uchime et al. 2012) |
| EGF1_PfRipr | $R^{268}$-$E^{302}$ | PFC1045c | 3D7 | (Chen et al. 2011) |
| EGF2_PfRipr | $L^{306}$-$Y^{343}$ | PFC1045c | 3D7 | |
| EGF3_PfRipr | $S^{617}$-$E^{656}$ | PFC1045c | 3D7 | |
| EGF4_PfRipr | $D^{660}$-$N^{696}$ | PFC1045c | 3D7 | |
| EGF5_PfRipr | $K^{700}$-$I^{734}$ | PFC1045c | 3D7 | |
| EGF6_PfRipr | $K^{752}$-$I^{795}$ | PFC1045c | 3D7 | |
| EGF7_PfRipr | $Y^{799}$-$I^{835}$ | PFC1045c | 3D7 | |
| EGF8_PfRipr | $S^{839}$-$V^{878}$ | PFC1045c | 3D7 | |
| EGF9_PfRipr | $K^{882}$-$L^{919}$ | PFC1045c | 3D7 | |
| EGF10_PfRipr | $P^{923}$-$V^{960}$ | PFC1045c | 3D7 | |
| Pfs230_C0 | $E^{423}$-$N^{566}$ | PFB0405w | 3D7 | (Tachibana et al. 2011) |
| Pfs25FKO | $V^{2}$-$T^{171}$ | PF10_0303 | 3D7 | (Kaslow et al. 1988) |
| Pfs45/48 | $N^{28}$-$S^{427}$ | PF1346700 | 3D7 | |
| Ron2L | $M^{2020}$-$K^{2067}$ | PF14_0495 | 3D7 | (Srinivasan et al. 2011) |
| TRAMP | $F^{244}$-$K^{309}$ | PF1218000 | 3D7 | |
| TRAP_TSR | $E^{214}$-$K^{264}$ | PF13_0201 | 3D7 | (Tossavainen et al. 2006) |

Further, the serine-rich protein (SERP or SERA) is a soluble protein expressed in the schizont stage and secreted in the parasitophorous vacuole. Other proteins that are located on the RBC membrane are the erythrocyte membrane protein-1 (EMP-1), EMP-2 and EMP-3. PfEMP-1, which binds to the receptors such as CD36 in the endothelium, is a family of proteins encoded by the so-called var genes.

The Sexual Main Stage:

e) Sporogonic Cycle

Other *Plasmodium* protein antigens are expressed in sexually differentiated parasite stages such as Ps25, Ps28, Ps48/45 or Ps230. Antibodies against these sexual stage proteins may block the development of the parasite in mosquitoes.

The abbreviations used in table 1 are as follows: Aglyc/GKO: aglycosylated/glycosylation site knock-out, FKO: full glycosylation site knock-out.

In further advantageous embodiments, the heat stable fragments comprised in the recombinant fusion protein and/or vaccine compositions according to the present disclosure are selected from the group listed in Table 2.

Table 2 shows sequences of *Plasmodium falciparum* antigens and their orthologs in other Apicomplexa like *Toxoplasma*, *Theileria*, *Neospora*, *Babesia* and *Cryptosporidium*. Exemplary use and combination of these antigen fragment sequences for the generation of various fusion proteins as a basis for Apicomplexa vaccine candidates are shown in Table 3. In an advantageous embodiment, the heat stable fragments of surface proteins from one member, preferably from one strain of an Apicomplexa are used in a fusion protein according to the present disclosure. However, in some embodiments heat stable fragments of surface proteins from different members, also from different strains are used in a fusion protein according to the present disclosure useful as general vaccines.

Several online-tools were used for sequence retrieval, such as http://plasmodb.org (*Plasmodium falciparum/vivax/knowlesi* (Pf 3D7/Pv Sal-1/Pk H)), http://www.ncbi.nlm.nih.gov and http://uniprot.org (*Plasmodium malariae/ovale* (Pm/Pol/CDC)) as well as http://orthomcl.org (*Toxoplasma gondii* (Tgon), *Theileria annulata/parva* (Tann/Tpar), *Neospora caninum* (Ncan), *Babesia bovis* (Bbov) and *Cryptosporidium hominis/parvum/muris* (Chom/Cpar/Cmur)).

The abbreviations used in table 2 are as follows:
Pf 3D7 *Plasmodium falciparum* Strain 3D7
Pv Sal-1 *Plasmodium vivax* Strain Sal-1
Pk H *Plasmodium knowlesi* Strain H
Pol/CDC *Plasmodium ovale* Strain I/CDC
Pm *Plasmodium malariae*
Tgon *Toxoplasma gondii*
Ncan *Neospora caninum*
Cpar *Cryptosporidium parvum*
Cmur *Cryptosporidium muris*
Chom *Cryptosporidium hominis*
Bbov *Babesia bovis*
Tann *Theileria annulata*
Tpar *Theileria parva*
Aglyc/GKO: aglycosylated/glycosylation site knock-out
FKO: full glycosylation site knock-out

TABLE 2

Exemplary fragment sequences for the generation of novel Apicomplexa vaccine candidates.

| SEQ ID | Name | Sequence |
|---|---|---|
| 1. | Pf_3D7 EGF1_MSP119\|PF3D7_0930300 EGF1 of MSP1$_{19}$: short 1_19 | ISQHQCVKKQCPENSGCFRHLDEREECKCLLNYK QEGDKCV |
| 2. | Pf_3D7 EGF1_MSP8\|PF3D7_0502400 EGF1 of MSP8: short 1_8 | GNNKVCENTKCPLNSNCYVIDDEETCRCLPGFNNI KIDDEMNCVRD |
| 3. | Pf_3D7 EGF2_MSP8\|PF3D7_0502400 EGF2 of MSP8: short 2_8 | GDTLDCSRNNGGCDIHAKCSFINKQIVCECKDKFE GDGIYCSYS |
| 4. | Pf_3D7 EGF_MSP4\|PF3D7_0207000 EGF of MSP4: short 4 | GLEDEDLCKHNNGGCGDDKLCEYVGNRRVKCKC KEGYKLEGIECVELL |
| 5. | Pf_3D7 EGF_MSP5\|PF3D7_0206900.1 EGF of MSP5: short 5 | NRKSCAINNGGCSDDQICININNIGVKCICKDGYLL GTKCII |
| 6. | Pf_3D7 EGF1_MSP10\|PF3D7_0620400 EGF1 of MSP10: short 1_10 | VNYICEYSKCGPNSRCYIVEKDKEQCRCQPNYIVD MSVNYFKCIP |
| 7. | Pf_3D7 EGF2_MSP10aglyc\| PF3D7_0620400 EGF2 of MSP10aglyc (point mutation in bold): short 2_10a | KDMACSKNNGGCDVNAECTIVEGAVKCQCSHLYF GDGVFCVK |
| 8. | Pf_3D7 EGF1_PfRipr\|PF3D7_0323400 EGF1 of PfRipr: short R1 | RCTQDICSVNQFCDGENEACTCKTSLLPSAKNNCE |
| 9. | Pf_3D7 EGF2_PfRipr\|PF3D7_0323400 EGF2 of PfRipr: short R2 | LCTVLNCPENSACEQIGNGKKAECKCENGKYYHN NKCY |
| 10. | Pf_3D7 EGF3_PfRipr\|PF3D7_0323400 EGF3 of PfRipr: short R3 | SCSNLNKCHNNAACYGNRFNYDCFCDNPYISKYG NKLCE |

TABLE 2-continued

Exemplary fragment sequences for the generation of novel Apicomplexa vaccine candidates.

| SEQ ID | Name | Sequence |
|---|---|---|
| 11. | Pf_3D7 EGF4_PfRipr\|PF3D7_0323400 EGF4 of PfRipr: short R4 | DCESVLCSQNQVCQILPNDKLICQCEEGYKNVKG KCV |
| 12. | Pf_3D7 EGF5_PfRipr\|PF3D7_0323400 EGF5 of PfRipr: short R5 | KCDLSCPSNKVCVIENGKQTCKCSERFVLENGVCI |
| 13. | Pf_3D7 EGF6_PfRipr\|PF3D7_0323400 EGF6 of PfRipr: short R6 | KCKRKEYENICTNPNEMCAYNEETDIVKCECKEHY YRSSRGECI |
| 14. | Pf_3D7 EGF7_PfRipr\|PF3D7_0323400 EGF7 of PfRipr: short R7 | GYCKDINCKENEECSIVNFKPECVCKENLKKNNKG ECI |
| 15. | Pf_3D7 EGF8_PfRipr\|PF3D7_0323400 EGF8 of PfRipr: short R8 | SCLINEGNCPKDSKCIYREYKPHECVCNKQGHVA VNGKCV |
| 16. | Pf_3D7 EGF9_PfRipr\|PF3D7_0323400 EGF9 of PfRipr: short R9 | KCVHNKKCSENSICVNVMKEPICVCTYNYYKKDG VCL |
| 17. | Pf_3D7 EGF10_PfRipr\|PF3D7_0323400 EGF10 of PfRipr: short R10 | PCLKDNGGCSRNSECTFKYSKINCACKENYKNKD DSCV |
| 18. | Pf_3D7 Pfs25FKO\|PF3D7_1031000 Pfs25 (1x N missing, with knocked-out glycosites: 25FKO | VTVDTVCKRGFLIQMSGHLECKCENDLVLVNEETC EEKVLKCDEKTVNKPCGDFSKCIKIDGNPVSYACK CNLGYDMVNNVCIPNECKNVTCGNGKCILDTSNP VKTGVCSCNIGKVPNVQDQNKCSKDGETKCSLKC LKENETCKAVDGIYKCDCKDGFIIDNESSICTA |
| 19. | Pf_3D7 fullCSP_TSR\|PF3D7_0304600 TSR-domain of fullCSP_TSR: short fCSP_TSR | PSDKHIEGYLKKIQNSLSTEWSPCSVTCGNGIQVRI KPGSANKPKDELDYENDIEKKICKMEKCSSVFNVV NS |
| 20. | Pf_3D7 shortCSP_TSR\|PF3D7_0304600 Shortened TSR-domain of CSP (shortCSP_TSR): short CSP_TSR (only domain with an potential N-glycosylation site, marked in bold) | YLKKIQNSLSTEWSPCSVTCGNGIQVRIKPGSANK PKDELDYENDIEKKICKMEKCSSVFNVVNSS |
| 21. | Pf_3D7 mTRAP_TSR\|PF3D7_1028700 TSR-domain of mTRAP: short mTRAP_TSR | THDTCDEWSEWSACTHGISTRKCLSDSSIKDETLV CTKCDKWGEWSECKDGRMHRKVLNCPFIKEEQE CDVNNE |
| 22. | Pf_3D7 TRAP_TSR\|PF3D7_1335900 TSR-domain of TRAP: short TRAP_TSR | EKTASCGVWDEWSPCSVTCGKGTRSRKREILHE GCTSELQEQCEEERCLPK |

TABLE 2-continued

Exemplary fragment sequences for the generation of novel Apicomplexa vaccine candidates.

| SEQ ID | Name | Sequence |
|---|---|---|
| 23. | Pf_3D7 TRAMP_TSR\|PF3D7_1218000 TSR-domain of TRAMP: short TRAMP_TSR | FYSEWGEWSNCAMDCDHPDNVQIREREC IHPSG DCFKGDLKESRPCIIPLPPCNELFSHKDNSAFK |
| 24. | Pf_3D7 EBA175_F2 domain\|PF3D7_0731500 EBA175 F2 domain: short EBA175_F2 | MADKNSVDTNTKVWECKKPYKLSTKDVCVPPRR QELCLGNIDRIYDKNLLMIKEHILAIAIYESRILKRKY KNKDDKEVCKIINKAFADIRDIIGGTDYWNDLSNRK LVGKINTNSNYVHRNKQNDKLFRDEWWKVIKKDV WNVISWVFKDKTVCKEDDIENIPQFFRWFSEWGD DYCQDKTKMIETLKVECKEKPCEDDNCKRKCNSY KEWISKKKEEYNKQAKQYQEYQKGNNYKMYSEF KSIKPEVYLKKYSEKCSNLNFEDEFKEELHSDYKN KCTMCPEV |
| 25. | Pf_3D7 EBA140 EBS1\|PF3D7_1301600 EBA140 erythrocyte bindin sequence 1: short EBA140 EBA1 | MARQDESSDISRVNSPELNNNHKTNIYDSDYEDV NNKLINSFVENKSVKKKRSLSFINNKTKSYDIIPPSY SYRNDKFNSLSENEDNSGNTNSNNFANTSEISIGK DNKQYTFIQKRTHL |
| 26. | Pf_3D7 EBA140 EBS2\|PF3D7_1301600 EBA140 erythrocyte binding sequence 2: short EBA140 EBS2 | MKKSKTQMEVLTNLYKKKNSGVDKNNFLNDLFKK NNKNDLDDFFKNEKEYDDLCDCRYTATIIKSFLNG PAKNDVDIASQINVNDLRGFGCNYKSNNEKSWNC TGTFTNKFPGTCEPPRRQTLCLGRTYLLHRGHE |
| 27. | Pf_3D7 EBL1 EBS\|PF3D7_1371600 EBL erythrocyte binding sequence: short EBL1 EBS | MACNAILGSYADIGDIVRGLDVWRDINTNKLSEKF QKIFMGGGNSRKKQNDNNERNKWWEKQRNLIWS SMV |
| 28. | Pf_3D7 GAMA EBS\|PF3D7_0828800 GAMA erythrocyte binding sequence: short GAMA EBS | KDIIKLLKDLIKYLHIVKFENNEPTTNIDEEGIRKLLE NSFFDLNDDILIVRLLLKPQTVILTVIQSFMLMTPSP SRDAKAYCKKALINDQLVPTNDANILSEENELVNN FATKYVLIYEKMKLQELKEMEESKLKMKYSKTNLA ALQVTNPQNNKDKNDASNKNNNPNNAATPLIAVV TDLSGEKTEDIIN |
| 29. | Pf_3D7 Pfs230_C0\|PF3D7_0209000 Pfs230 part C0: short Pfs230_C0 | MAEYVDEKERQGEIYPFGDEEEKDEGGESFTYEK SEVDKTDLFKFIEGGEGDDVYKVDGSKVLLDDDTI SRVSKKHTARDGEYGEYGEAVEDGENVIKIIRSVL QSGALPSVGVDELDKIDLSYETTESGDTAVSEDSY DKYASNN |
| 30. | Pf_3D7 CelTos\|PF3D7_1216600 CelTos: short C | FRGNNGHDSSSSLYGGSQFIEQLDNSFTSAFLES QSMNKIGDDLAETISNELVSVLQKNSPTFLESSFDI KSEVKKHAKSMLKELIKVGLPSFENLVAENVKPPK VDPATYGIIVPVLTSLFNKVETAVGAKVSDEIWNYN SPDVSESEESLSDDFFD |
| 31. | Pf_3D7 Ron2L\|PF3D7_1452000 Ron2L | MDITQQAKDIGAGPVASCFTTRMSPPQQICLNSVV NTALSTSTQSAMK |
| 32. | Pf_3D7 EXP1\|PF3D7_1121600 EXP1 | EKTNKGTGSGVSSKKKNKKGSGEPLIDVHDLISDM IKKEEELVEVNKRKSKYKLATSNTEKGRHPFKIGSS DPADNANPDADSESNGEPNAGPQVTAQDVTPEQ PQGDDNNLVSGTEH |
| 33. | Pf_3D7 MSP3aGKO\|PF3D7_1035400 MSP3aGKO | KEIVKKYNLNLRNAILNNNAQIENEENVNTAITGND FSGGEFLWPGYTEELKAKKASEDAEKAANDAENA AKEAEEAAKEAVNLKESDKSYTKAKEAATAASKAK KAVETALKAKDDAEKSSKADSISTKTK |

TABLE 2-continued

Exemplary fragment sequences for the generation of novel Apicomplexa vaccine candidates.

| SEQ ID | Name | Sequence |
|---|---|---|
| 34. | Pf_D7 Pfs4845\|PF3D7_1346700 Pfs4845 | NNDFCKPSSLNSEISGFIGYKCNFSNEGVHNLKPD MRERRSIFCTIHSYFIYDKIRLIIPKKSSSPEFKILPE KCFQKVYTDYENRVETDISELGLIEYEIEENDTNPN YNERTITISPFSPKDIEFFCFCDNTEKVISSIEGRSA MVHVRVLKYPHNILFTNLTNDLFTYLPKTYNESNFV SNVLEVELNDGELFVLACELINKKCFQEGKEKALY KSNKIIYHKNLTIFKAPFYVTSKDVNTECTCKFKNN NYKIVLKPKYEKKVIHGCNFSSNVSSKHTFTDSLDI SLVDDSAHISCNVHLSEPKYNHLVGLNCPGDIIPDC FFQVYQPESEELEPSNIVYLDSQINIGDIEYYEDAE GDDKIKLFGIVGSIPKTTSFTCICKKDKKSAYMTVTI DS |
| 35. | Pv_Sal-1 EGF1_MSP119\|PVX_099980 Homolog of EGF1 of MSP1_19 | SSEHTCIDTNVPDNAACYRYLDGTEEWRCLLTFKE EGGKCV |
| 36. | Pv_Sal-1 EGF1_MSP8\|PVX_097625 EGF1 of MSP8: short 1_8 | QKNNVCEHKKCPLNSNCYVINGEEVCRCLPGFSD VKIDNVMNCVRD |
| 37. | Pv_Sal-1 EGF2_MSP8\|PVX_097625 EGF2 of MSP8: short 2_8 | DDTLDCSNNNGGCDVNATCTLIDKKIVCECKDNFE GDGIYCSYS |
| 38. | Pv_Sal-1 EGF_MSP4\|PVX_003775 EGF of MSP4: short 4 | VDENANLCLDNNGGCGDDKICENLGKGIVKCLCK PGYKLVGTECVESS |
| 39. | Pv_Sal-1 EGF_MSP5\|PVX_003770 EGF of MSP5: short 5 | NAKSCSVDNGGCADDQICIRIDNIGIKCICKEGHLF GDKCIL |
| 40. | Pv_Sal-1 EGF1_MSP10\|PVX_114145 EGF1 of MSP10: short 1_10 | VNHICEYSKCGANARCYIVEKDKEECRCRANYMP DDSVDYFKCIP |
| 41. | Pv_Sal-1 EGF2_MSP10\|PVX_114145 EGF2 of MSP10 | VEKDCSKENGNCDVNAECSIDKNKDIKCQCKFNYI GDGIFCVM |
| 42. | Pv_Sal-1 EGF1_PfRipr\|PVX_095055 EGF1 of PfRipr: short R1 | TCNSRVCSVNQFCDEATESCVCKTSLLPVEKTHCL |
| 43. | Pv_Sal-1 EGF2_PfRipr\|PVX_095055 EGF2 of PfRipr: short R2 | VCDAIKCPEDATCVVERNSKKAECRCDEGKYLHK NECY |
| 44. | Pv_Sal-1 EGF3_PfRipr\|PVX_095055 EGF3 of PfRipr: short R3 | TCEDLCKTCGPNSSCYGNKYKHKCLCNSPFESKK NHSICE |
| 45. | Pv_Sal-1 EGF4_PfRipr\|PVX_095055 EGF4 of PfRipr: short R4 | SCDAQVCGKNQICKMVDA-KATCTCADKYQNVNGVCL |
| 46. | Pv_Sal-1 EGF5_PfRipr\|PVX_095055 EGF5 of PfRipr: short R5 | KCDLLCPSNKSCLLENGKKICKCINGLTLQNGECV |

TABLE 2-continued

Exemplary fragment sequences for the generation of novel Apicomplexa vaccine candidates.

| SEQ ID | Name | Sequence |
|---|---|---|
| 47. | Pv_Sal-1 EGF6_PfRipr\|PVX_095055 EGF6 of PfRipr: short R6 | KCKRKEYQQLCTNEKEHCVYDEQTDIVRCDCVDH FKRNERGICI |
| 48. | Pv_Sal-1 EGF7_PfRipr\|PVX_095055 EGF7 of PfRipr: short R7 | GICIPVDYCKNVTCKENEICKVVNNTPTCECKENLK RNSNNECV |
| 49. | Pv_Sal-1 EGF8_PfRipr\|PVX_095055 EGF8 of PfRipr: short R8 | MCLVNKGNCPIDSECIYHEKKRHQCLCHKKGLVAI NGKCV |
| 50. | Pv_Sal-1 EGF9_PfRipr\|PVX_095055 EGF9 of PfRipr: short R9 | MCRSDQNKCSENSICVNQVNKEPLCICLFNYVKS RSGDSPEGGQTCV |
| 51. | Pv_Sal-1 EGF10_PfRipr\|PVX_095055 EGF10 of PfRipr: short R10 | PCLAHNGGCSPNEVCTFKNGKVSCACGENYRPR GKDSPTGQAVKRGEATKRGDAGQPGQAHSANEN ACL |
| 52. | Pv_Sal-1 Pvs25\|PVX_111175 Pvs25 | VTVDTICKNGQLVQMSNHFKCMCNEGLVHLSENT CEEKNECKKETLGKACGEFGQCIENPDPAQVNMY KCGCIEGYTLKEDTCVLDVCQYKNCGESGECIVEY LSEIQSAGCSCAIGKVPNPEDEKKCTKTGETACQL KCNTDNEVCKNVEGVYKCQCMEGFTFDKEKNVC LS |
| 53. | Pv_Sal-1 fullCSP_TSR\|PVX_119355 TSR-domain of fullCSP_TSR: short fCSP_TSR | PNEKSVKEYLDKVRATVGTEWTPCSVTCGVGVRV RRRVNAANKKPEDLTLNDLETDVCTMDKCAGIFN VVSN |
| 54. | Pv_Sal-1 shortCSP_TSR Shortened TSR-domain of CSP (shortCSP_TSR): short CSP_TSR | YLDKVRATVGTEWTPCSVTCGVGVRVRRRVNAA NKKPEDLTLNDLETDVCTMDKCAGIFNVVSNS |
| 55. | Pv_Sal-1 mTRAP_TSR\|PVX_111290 TSR-domain of mTRAP: short mTRAP_TSR | IGKRKCEQWDSWSACKDGISTRVCLTNKSVTDKM TCKACNIWGDWSACKNGKRHRKVVNCPFIREEQ DCDPNKS |
| 56. | Pv_Sal-1 TRAP_TSR\|PVX_082735 TSR-domain of TRAP: short TRAP_TSR | ERVANCGPWDPWTACSVTCGRGTHSRSRPSLHE KCTTHMVSECEEGECPVE |
| 57. | Pv_Sal-1 TRAMP_TSR\|PVX_123575 TSR-domain of TRAMP: short TRAMP_TSR | FYTEWGEWSQCSMECDHPDNVQIRERKCADPSG NCFKGDLKETRPCQVPLPPCNSLFEHKESSTFK |
| 58. | Pv_Sal-1 EBA175_F2 domain\|PVX_110810 EBA175 F2 domain | KNCNYKRKRRERDWDCNTKKDVCIPDRRYQLCM KELTNLVNNTDTNFHRDITFRKLYLKRKLIYDAAVE GDLLLKLNNYRYNKDFCKDIRWSLGDFGDIIMGTD MEGIGYSKVVENNLRSIFGTDEKAQQRRKQWWN ESKAQIWTAMMYSVKKRLKGNFIWICKLNVAVNIE PQIYRWIREWGRDYVSELPTEVQKLKEKCDGKINY TDKKVCKVPPCQNACKSYDQWITRKKNQWDVLS NKFISVKNAEKVQTAGIVTPYDILKQELDEFNEVAF ENEINKRDGAYIELCVCSVEE |

TABLE 2-continued

Exemplary fragment sequences for the generation of novel Apicomplexa vaccine candidates.

| SEQ ID | Name | Sequence |
|---|---|---|
| 59. | Pv_Sal-1 EBA140 EBS1\|PVX_110810 EBA140 erythrocyte bindin sequence 1: short EBA140 EBS1 | ERWLQGTNERRSEENIKYKYVTELKIKYAQMNGK RSSRILKESIYGAHNFGGNSYMEGKDGGDKTGEE KDGGEHKTDSKTDNGKGANNLVMLDYET |
| 60. | Pv_Sal-1 EBA140 EBS2\|PVX_110810 EBA140 erythrocyte binding sequence 2: short EBA140 EBS2 | MYSVKKRLKGNFIWICKLNVAVNIEPQIYRWIREW GRDYVSELPTEVQKLKEKCDGKINYTDKKVCKVPP CQNACKSYDQWITRKKNQWDVLSNKFISVKNAEK VQTAGIVTPYDILKQELDEFNEVAFENEINK |
| 61. | Pv_Sal-1 EBL1 EBS\|PVX_110810 EBL erythrocyte binding sequence: short EBL1 EBS | DFCKDIRWSLGDFGDIIMGTDMEGIGYSKVVENNL RSIFGTDEKAQQRRKQWWNESKAQIWTAMM |
| 62. | Pv_Sal-1 GAMA EBS\|PVX_088910 Homolog of GAMA erythrocyte binding sequence: short GAMA EBS | KDVAVLVRDLLKNTNIIKFENNEPTSQMDDEEIKKLI ESSFFDLSDNTMLRLLIKPQAAILLIIESFIMMTPS PTRDAKTYCKKALVNGQLIETSDLNAATEEDDLINE FSSRYNLFYERLKLEELREIEQNRKALKNSKGTLS VLEVANSQNAPDGKGVNGSGNAANANAANANAA NANAANANAANGNLANANLANANAANADAANANA ANANAANANAANANLANANLANANLANANLANAN LANANLANANAANANAANANAANGNAPNSNNGS GSPLIVVVGADLGEKTEDIIKNNVDVAALTADVEQA FKNLELQSG |
| 63. | Pv_Sal-1 Pvs230_C0\|PVX_003905 Pfs230 part C0: short Pfs230_C0 | LAEEDDGDDEDGDVDDDDGNDDEGTHTQPQVK GMDDEDLEGPPGEDDCFVLPEAGASDGVFDKVD EAFETTIKGDGNVLQASDPEVETFASSNTNKEYVC DFVKHITMKEASKKVVICEMKIQEPLVKVKILCPTK YADVIKYGSMEFF |
| 64. | Pv_Sal-1 CelTos\|PVX_123510 CelTos: short C | LRGKSGSTASSSLEGGSEFSERIGNSLSSFLSESA SLEVIGNELADNIANEIVSSLQKDSASFLQSGFDVK TQLKATAKKVLVEALKAALEPTEKIVASTIKPPRVS EDAYFLLGPVVKTLFNKVEDVLHKPIPDTIWEYESK GSLEEEEAEDEFSDELLD |
| 65. | Pv_Sal-1 Ron2L\|PVX_117880 Homolog of Ron2L | MDISQHATDIGMGPATSCYTSTIPPPKQVCIQQAV KATLTSSTQACMK |
| 66. | Pv_Sal-1 Exp1\|PVX_091700 EXP1 | GDNVNGLGAGNPKKKSPKSKSPEPLIDVHELISEIV RKEEELVNMTKKKSNYKLATTVLASALSAVLLGGA NAGNGRHPFSLGGGKGGDAAPTEPTPAPTAPSAT GLNDDGSSSGTES |
| 67. | Pv_Sal-1 Pvs4845\|PVX_083235 Pvs4845 | HTQMAKGEVKYVPPEELNKDVSGFFGFKCNFSSK GVHNLEPILTEKRSLVCSIYSYFIYDKIKLTIPKKIPG SKFKMLPEKCFQTVYTNYEKRTEEKIENMGLVEYE VKEDDSNSEYTEKILTISPFNTKDVEFFCICDNSEN VISNVKGRVALVQVNVLKYPHKITSINLTKEPYSYL PNQVDKTSFKSHKLDLELQDGELVVLACEKVDDK CFKKGKDTSPLSLYKSKKIVYHKNLSI FKAPVYVKS ADVTAECSCNVDSTIYTLSLKPVYTKKLIHGCNFSS DKSTHNFTNHVDMAELGENAQITCSIELVDTSYNH LIGMSCPGEVLPECFFQVYQRESPELEPSKIVYLD AQLNIGNVEYFEDSKGENIVKIFGLVGSIPKTTSFT CICRKGKKIGYMSVKIAA |
| 68. | Pk_H EGF1_MSP19\|PKH_072850 Homolog of EGF1 of MSP119: short 1_19 | SSAHKCIDTNVPENAACYRYLDGTEEWRCLLGFK EVGGKCV |

TABLE 2-continued

Exemplary fragment sequences for the generation of novel Apicomplexa vaccine candidates.

| SEQ ID | Name | Sequence |
|---|---|---|
| 69. | Pk_H EGF1_MSP8\|PKH_103110 EGF1 of MSP8: short 1_8 | EKNNVCEHKKCPLNSNCYVIDGEEVCRCLPGFSD VKIDNVMNCVRD |
| 70. | Pk_H EGF2_MSP8\|PKH_103110 EGF2 of MSP8: short 2_8 | DDTVDCNNNNGGCDVNATCTLIDKKIVCECKDNF QGDGIYCSYS |
| 71. | Pk_H EGF_MSP4\|PKH_041300 EGF of MSP4: short 4 | KDHNENLCSENNGGCGNDKICENIGDGIVKCLCKP GYKLVGTECVEAS |
| 72. | Pk_H EGF_MSP5\|PKH_041310 EGF of MSP5: short 5 | NTKSCSVNNGGCADDQICIRINNMGIKCICKEGHLF GGKCIL |
| 73. | Pk_H EGF1_MSP10\|PKH_112880 EGF1 of MSP10: short 1_10 | VNHICEYSKCGPNARCYIVEKDKEECRCIANYMPD NSVDYFKCIP |
| 74. | Pk_H EGF2_MSP10\|PKH_112880 EGF2 of MSP10 | TVKDCSKENGNCDVNAECSIDKKENIKCQCNHGYI GDGIFCVL |
| 75. | Pk_H EGF1_PfRipr\|PKH_081690 EGF1 of PfRipr: short R1 | KCKSRICSVNEFCDELTESCVCKTSLLPVEKTQCS |
| 76. | Pk_H EGF2_PfRipr\|PKH_081690 EGF2 of PfRipr: short R2 | VCDAIKCPTNSTCVVDENTKKGECRCEDDKYLYK NKCY |
| 77. | Pk_H EGF3_PfRipr\|PKH_081690 EGF3 of PfRipr: short R3 | TCVDLCTRCGPNSSCYGNKHKYKCFCNSPYVNK NNNSNCE |
| 78. | Pk_H EGF4_PfRipr\|PKH_081690 EGF4 of PfRipr: short R4 | TCNSQVCGKNQTCKMINNKPTCICADKYQDVNGV CV |
| 79. | Pk_H EGF5_PfRipr\|PKH_081690 EGF5 of PfRipr: short R5 | KCDLLCPSNKSCLIENGKKICKCINGLTLENGVCI |
| 80. | Pk_H EGF6_PfRipr\|PKH_081690 EGF6 of PfRipr: short R6 | KCKRKEYQNACTNEKEQCVYDEQKDIVRCDCVDH FQRNDRGICV |
| 81. | Pk_H EGF7_PfRipr\|PKH_081690 EGF7 of PfRipr: short R7 | GICVPVEYCKNVTCKENEICKVINNTPTCECKENLK RNNKNECI |
| 82. | Pk_H EGF8_PfRipr\|PKH_081690 EGF8 of PfRipr: short R8 | MCLVNKGNCPPDSECIYHEKKKHECLCHKKGLVAI NGKCV |
| 83. | Pk_H EGF9_PfRipr\|PKH_081690 EGF9 of PfRipr: short R9 | MCRTDQNKCSENSICVNQVNKEPLCICLFNYEKSI AGLSTQGAHTCV |

TABLE 2-continued

Exemplary fragment sequences for the generation of novel Apicomplexa vaccine candidates.

| SEQ ID | Name | Sequence |
|---|---|---|
| 84. | Pk_H EGF10_PfRipr\|PKH_081690 EGF10 of PfRipr: short R10 | PCLTNNGGCSPNEICTLKNRKVVCSCGENYRPKG KESQLGPMAQRGQLGKLGQLGQLGQLGQLGOLG KRGKLGQLGNPPTPEDNACI |
| 85. | Pk_H Pks25\|PKH_061530 Pks25 | VTVDTLCKNGHLAQMSHHFKCICNDGLVHISENEC GEKTECKEENLGKTCGDFGICRKGPDAAQQSTYK CDCIKEYTLKDGTCVVDVCLYKDCGQSGECIGEFL TEVKSAACSCSIGKVPNPEDEKKCTKDGETTCQLK CNTENEVCKAVQGVYKCQCMEGFKFDKEKKECIS |
| 86. | Pk_H fullCSP_TSR\|PKH_083560 TSR-domain of fullCSP_TSR: short fCSP_TSR | PNEKVVNDYLHKIRSSVTTEWTPCSVTCGNGVRIR RKAHAGNKKAEDLTMDDLEVEACVMDKCAGIFNV VSN |
| 87. | Pk_H shortCSP_TSR\|PKH_083560 Shortened TSR-domain of CSP (shortCSP_TSR): short CSP_TSR | YLHKIRSSVTTEWTPCSVTCGNGVRIRRKAHAGN KKAEDLTMDDLEVEACVMDKCAGIFNVVSNS |
| 88. | Pk_H mTRAP_TSR\|PKH_061300 TSR-domain of mTRAP: short mTRAP_TSR | IRDKRCEQWDSWSPCKNGISTRICLTDKSVTDKM TCTMCNIWGEWSACQNGKRHRKIVNCPFIREDQD CDPNNS |
| 89. | Pk_H TRAP_TSR\|PKH_121770 TSR-domain of TRAP: short TRAP_TSR | ERIAKCGPWDDWTPCSVTCGKGTHSRSRPLLHA GCTTHMVKECEMDECPVE |
| 90. | Pk_H TRAMP_TSR\|PKH_143510 TSR-domain of TRAMP: short TRAMP_TSR | FYTEWGEWSKCSMECDHPDNVQIRERKCANTSG DCFKGDLKETRPCQVPLPPCNSLFELKESSTFK |
| 91. | Pk H EBA175_F2 domain\|PKH_000490 EBA175 F2 domain | RRCNNKRKRGARDWDCPTKKDVCIPDRRYQLCM KELTNLVNNTKTHSHNDITFLKLNLKEKLTYDAAVE GDLLLLKKYNNVYSEDLCKDIKWSLEDFGDIIMGTD MEGIGYSQVVENNLRSIFGTGTSAQLDRKKWWN HKKYIWEATILSVKKKLNGYSAWNCKEDVQINVEP QIYRWIREWGMDYMSELPKEQRKIKEKCDRKLYY TNLRICTMSPCNDSCKLYDQWITRKKKQWDVLST KFSSVKKGQIIETENITTAYDILKQELNGFNEVMFE NEINKRDNVYIDICLCAADE |
| 92. | Pk H EBA175_F2 domain\|PKH_062300 EBA175 F2 domain | DKCNDKRKRGERDWDCPAEKDICISDRRYQLCMK ELTNLVNNTRTHSHNDITFLKLNLKRKLMYDAAVE GDLLLLKKNNYQYNKEFCKDIRWGLGDFGDIIMGTN MEGIGYSQVVENNLRSIFGTDEKAKQDRKQWWN ESKEHIWRAMMFSIRSRLKEKFVWICKKDVTLKVE PQIYRWIREWGRDYMSELPKEQGKLNEKCASKLY YNNMAICMLPLCHDACKSYDQWITRKKKQWDVLS TKFSSVKKTQKIGTENIATAYDILKQELNGFKEATF ENEINKRDNLYNHLCPCVVEE |
| 93. | Pk H EBA175_F2 domain\|PKH_134580 EBA175 F2 domain | DKCNDKRKRGERDWDCPTEKDVCIPDRRYQLCM MEITNLVDNTNTHFHSDIIFRKSYFERRLIYDVGAE GDLLLLKKYNNVYSEDLCKDIKWSLQDFGDIIMGTD MEGIGYSLVVENNLRSIFGTGTSAELDRKKWWND HKKDIWKAMILSVKEKNRYSAWNCKEDVQINVEP QIYRWIREWGRDYMSEFREQRRKLNEKCEDKLYY STMLICTLPPCNNACKSYDEWITGKKKQWDVLSTK FSSVKKAQKIETENIARAYDILKQELNGFNEVTFEN EINKRDKLYNYFCVCIVQE |

TABLE 2-continued

Exemplary fragment sequences for the generation of novel Apicomplexa vaccine candidates.

| SEQ ID | Name | Sequence |
|---|---|---|
| 94. | Pk H EBA140EBS1\|PKH_000490 EBA140 erythrocyte bindin sequence 1: short EBA140 EBS1 | LLECENEYVKNENGYKLATGHHYMDNDQIERWLQ GTDRSRRVKIEENVKYKYNVEELNTKYEQTKGKRI NRILKESTYEAQNVADNNYIDDKANGEYKTDNKTN KGEGARNMVMLDYDI |
| 95. | Pk H EBA140EBS1\|PKH_062300 EBA140 erythrocyte bindin sequence 1: short EBA140 EBS1 | LLECENEYVKNENGYKLATGHHYMDNDQIEQWLQ GTDRSRRVKIEENVKYKYNVEELNTKYEQMKGKRI NRILKESTYEAQNVADNNYIDDKANGEHKTDNKTN KGEGARNMVMLDYDI |
| 96. | Pk H EBA140EBS1\|PKH_134580 EBA140 erythrocyte bindin sequence 1: short EBA140 EBS1 | LLECENEYVKNENGYKLATGHHYMDNDQIERWLQ GTDRSRRVKIEENVKYKYNVEELNTKYEQMKGKRI NRILKESTYEAQNVADNNYIDDKANGEYKTDNKTN KGEGARNMVMLDYDI |
| 97. | Pk H EBA140EBS2\|PKH_000490 EBA140 erythrocyte binding sequence 2: short EBA140 EBS2 | ILSVKKKLNGYSAWNCKEDVQINVEPQIYRWIREW GMDYMSELPKEQRKIKEKCDRKLYYTNLRICTMSP CNDSCKLYDQWITRKKKQWDVLSTKFSSVKKGQII ETENITTAYDILKQELNGFNEVMFENEINK |
| 98. | Pk H EBA140EBS2\|PKH_062300 EBA140 erythrocyte binding sequence 2: short EBA140 EBS2 | MFSIRSRLKEKFVWICKKDVTLKVEPQIYRWIREW GRDYMSELPKEQGKLNEKCASKLYYNNMAICMLP LCHDACKSYDQWITRKKKQWDVLSTKFSSVKKTQ KIGTENIATAYDILKQELNGFKEATFENEINK |
| 99. | Pk H EBA140EBS2\|PKH_134580 EBA140 erythrocyte binding sequence 2: short EBA140 EBS2 | ILSVKEKNRYSAWNCKEDVQINVEPQIYRWIREWG RDYMSEFREQRRKLNEKCEDKLYYSTMLICTLPPC NNACKSYDEWITGKKKQWDVLSTKFSSVKKAQKI ETENIARAYDILKQELNGFNEVTFENEINK |
| 100. | Pk H EBL1EBS1\|PKH_000490 EBL erythrocyte binding sequence: short EBL1 EBS | DLCKDIKWSLEDFGDIIMGTDMEGIGYSQVVENNL RSIFGTGTSAQLDRKKWWNDHKKYIWEATI |
| 101. | Pk H EBL1EBS1\|PKH_062300 EBL erythrocyte binding sequence: short EBL1 EBS | EFCKDIRWGLGDFGDIIMGTNMEGIGYSQVVENNL RSIFGTDEKAKQDRKQWWNESKEHIWRAMM |
| 102. | Pk H EBL1EBS1\|PKH_134580 EBL erythrocyte binding sequence: short EBL1 EBS | DLCKDIKWSLQDFGDIIMGTDMEGIGYSLVVENNL RSIFGTGTSAELDRKKWWNDHKKDIWKAMI |
| 103. | Pk_H GAMAEBS\|PKH_050210 GAMA erythrocyte binding sequence: short GAMA EBS | KDVVVLVRDLLKDTNIIKFEKNEPTSQIDDEGIKKLI ESSFFDLSDNTMLMRLIIKPQASILFIIQSFIMMTPSP TRDARMYCKKKLVNGQLIENNDLKAETEEEDMINE FSSKYNLFYERLKMEELREIEQDRKSLKNSKGNLS VLEVRNSQNGPDGKEVNGSGDAANGNNMNGGN NGSASSLIVVVRDDLAEKTDDIIKNNVDLESLKADV EQAFRNFEYQSG |

TABLE 2-continued

Exemplary fragment sequences for the generation of novel Apicomplexa vaccine candidates.

| SEQ ID | Name | Sequence |
|---|---|---|
| 104. | Pk_H Pks230_C0\|PKH_041100 Pfs230 part C0: short Pfs230_C0 | DEEEEEDNDGESISYGDMDQDEEQDENYQMKGM DLEEDEDDVLDSDVFLPLVDSDASDGTFDAVDDD FQTTIKKDGEELEQSDSTVEIFASSNTNKEYVCDF EKGKILKETTKKTKICEMKIQEPLVKVKIVCPTKYSD VSADGSMGFI |
| 105. | Pk_H CelTos\|PKH_143380 CelTos: short C | LRGKSGLTASSSLEGGSEFSERIGNTLSSFLSESA SLEVIGNELADNIANEIVGSLQNDSASFLQSEFDVK AQLKATAKKVLTEALKAALEPTEKIVASTIKPPRIKE DIYFLLSPVVRSLFNKVEDVLHKPVSDDIWNYESR GSSSEEEDEVDSDEDFLD |
| 106. | Pk_H Ron2L\|PKH_125430 Ron2L | MDITQHASDIGMGPVTSCYTSTIPPPKQVCIQQAV KVTLTNSTQACMK |
| 107. | Pk H EXP1\| PKH_091900 EXP1 | GNNINHSGPHHPKKKTPKSKAPEPLIDVHELIGEM VRKEEELINVTKKKSYKLATTVLASALSAVLLGGA NAGNGRHPFSLGGGKGGEAAPAESAPTVDEPATK |
| 108. | Pk H Pks4845\|PKH_120750 Pks4845 | HTQMAKGEVKYVPPEELNKDVSGFFGFKCNFSSK GVHNLEPILTEKRSLVCSIYSYFIYDKIKLTIPKKIPG SKFKMLPEKCFQTVYTNYEKRTEEKIENMGLVEYE VKEDDSNSEYTEKILTISPFNTKDVEFFCICDNSEN VISNVKGRVALVQVNVLKYPHKITSINLTKEPYSYL PNQVDKTSFKSHKLDLELQDGELVVLACEKVDDK CFKKGKDTSPLSLYKSKKIVYHKNLSIFKAPVYVKS ADVTAECSCNVDSTIYTLSLKPVYTKKLIHGCNFSS DKSTHNFTNHVDMAELGENAQITCSIELVDTSYNH LIGMSCPGEVLPECFFQVYQRESPELEPSKIVYLD AQLNIGNVEYFEDSKGENIVKIFGLVGSIPKTTSFT CICRKGKKIGYMSVKIAA |
| 109. | Pol/CDC EGF1_MSP19\|FJ824670.1 Homolog of EGF1 of MSP119: short 1_19 | GSKHKCIDITYPDNAGCYRFSDGREEWRCLLNFK KVGETCV |
| 110. | Pol/CDC Pos25\|Q969A0 Pos25 | VTVDTNCKNGTLVQMSNHLECKCNENFVHVSEDI CEEKFECNDKMVNNPCGDYSTCIKNVDQEIEKYIC TCISGFEYDNKVCVPAECKGISCVNGKCIVNPSPD NKEGRCSCNIGKVCPNPEDNNNCTKDGDTECKLKC TKENEICKNVEGLFECNCQDGFIM DLEQNLCKA |
| 111. | Pm EGF1_MSP19\|FJ824669.1 Homolog of EGF1 of MSP119: short 1_19 | SAKHACTETKYPENAGCYRYEDGKEVWRCLLNYK LVDGGCV |
| 112. | Pm fullCSP_TSR\|CAA04809.1 Homolog of TSR-domain of fullCSP_TSR: short fCSP_TSR | PSEEHIKNYLESIRNSITEEWSPCSVTCGSGIRARR KVGAKNKKPAELVLSDLETEICSLDKCSSIFNVVSN |
| 113. | Pm shortCSP_TSR\|CAA04809.1 Homolog of shortened TSR-domain of CSP (shortCSP_TSR): short CSP_TSR | YLESIRNSITEEWSPCSVTCGSGIRARRKVGAKNK KPAELVLSDLETEICSLDKCSSIFNVVSNS |
| 114. | Tgon\|TGME49_067680 Ortholog of EGF1_PfRipr short R1 | ECALNTDNCDSHATCENTDGSYHCACGSGFTGD GFTCE |
| 115. | Tgon\|TGME49_002400 Ortholog of EGF1_PfRipr short R1 | ECAENPELCEFGCKNLPGAYECTCPPDSKQRADK RGCE |

TABLE 2-continued

Exemplary fragment sequences for the generation of novel Apicomplexa vaccine candidates.

| SEQ ID | Name | Sequence |
|---|---|---|
| 116. | Tgon\|TGME49_067680 Ortholog of EGF2_PfRipr short R2 | VCTNTMGSYTCSCLPGYTPSDDGRVCTDIDECAT ENGGCSEHSQCRNLPGSYECVCDAGYEKVEGSE HLCQ |
| 117. | Tgon\|TGME49_002400 Ortholog of EGF2_PfRipr short R2 | VCVNTPGTFFCDCAAGFVLGQDGRSCTDIDECAL DENICEHKCENLPGAFQCRCNSGYKRSVDDPRKCV |
| 118. | Tgon\|TGME49_067680 Ortholog of EGF3_PfRipr short R3 | VCTNTMGSYTCSCLPGYTPSDDGRVCTDIDECAT ENGGCSEHSQCRNLPGSYECVCDAGYEKVEGSE HLCQDIDECAAGTATIPNNSNCVNTAGSYEFACKP GFEHKDNACSKIDYCGRGGCNSLATCEETADGTD YVCTCPKGFVTQNEGRGADGCTDVDECAENGCA AYGSEGVICENTPGSFNCSCANGYLLNNGVCEEID ECAGS |
| 119. | Tgon\|TGME49_002400 Ortholog of EGF3_PfRipr short R3 | QCLNLMGKYECGCYPGFVLQPDGRCDDIDECIDP TLHGCDHICINLPGTYSCQCRPGYRLSLEKKGACV DIDECAENPELCEFGCKNLPGAYECTCPPDSKQR ADKRGCEPNLSCKEDPSQCQGDHVCR |
| 120. | Tgon\|TGME49_067680 Ortholog of EGF4_PfRipr short R4 | DCENTSGSYICKCKAGFEMRDNQCVDIDECATNT NECHNHRGRCINTHGSYTCECIAGFIGDGKICINKN ECQSGDFECGPNSHCVDTEGSYKCDCNSGYKQD PENPDSCI |
| 121. | Tgon\|TGME49_002400 Ortholog of EGF4_PfRipr short R4 | NSEGQGVTPAVRIQQQRELQGGKLLPGRPALCDQ QCLNLMGKYECGCYPGFVLQPDGRCDDIDECIDP TLHGCDHICINLPGTYSCQCRPGYRLSLEKKGACV |
| 122. | Tgon\|TGME49_067680 Ortholog of EGF5_PfRipr short R5 | ECQSGDFECGPNSHCVDTEGSYKCDCNSGYKQD PENPDSCIDRDECEIEGACDENADCTNLPGSFSCT CRAGYRQEGELCVKMNLCADDENGGCSPHADCE HLDKIVCTCRPGYEGDGITCT |
| 123. | Tgon\|TGME49_002400 Ortholog of EGF5_PfRipr short R5 | GKLLPGRPALCDQQCLNLMGKYECGCYPGFVLQ PDGRCDDIDECIDPTLHGCDHICINLPGTYSCQCR PGYRLSLEKKGACV |
| 124. | Tgon\|TGME49_067680 Ortholog of EGF6_PfRipr short R6 | ECTEGVDTCPRQGGRCVNTPGSYRCECEEGYTY TTKEDGTVECVDINECGVSEMNTCASKANGGVCT NTMGSYTCSCLPGYTPSDDGRVCTDIDECATENG GCSEHSQCRNLPGSYECVCDAGYEKVEGSEHLCQ |
| 125. | Tgon\|TGME49_002400 Ortholog of EGF6_PfRipr short R6 | ECLTANGGCQHVCVNTPGTFFCDCAAGFVLGQD GRSCTDIDECALDENICEHKCENLPGAFQCRCNS GYKRSVDDPRKCV |
| 126. | Tgon\|TGME49_067680 Ortholog of EGF7_PfRipr short R7 | GYRGSGHTSKGAADGCVDIDECTEGVDTCPRQG GRCVNTPGSYRCECEEGYTYTTKEDGTVECVDIN ECG |
| 127. | Tgon\|TGME49_002400 Ortholog of EGF7_PfRipr short R7 | GFEGDGRTKGTGCSNIDECATGQAGCEQICKDFA PGYACSCYDGYMLKANGKDCQDINECL |
| 128. | Tgon\|TGME49_067680 Ortholog of EGF8_PfRipr short R8 | ECQSGDFECGPNSHCVDTEGSYKCDCNSGYKQD PENPDSCIDRDECEIEGACDENADCT |
| 129. | Tgon\|TGME49_002400 Ortholog of EGF8_PfRipr short R8 | GKLLPGRPALCDQQCLNLMGKYECGCYPGFVLQ PDGRCDDIDECIDPTLHGCDHICI |

TABLE 2-continued

Exemplary fragment sequences for the generation of novel Apicomplexa vaccine candidates.

| SEQ ID | Name | Sequence |
|---|---|---|
| 130. | Tgon\|TGME49_067680 Ortholog of EGF9_PfRipr short R9 | SCIDRDECEIEGACDENADCTNLPGSFSCTCRAG YRQEGELCVKMNLCADDENGGCSPHADCEHLDKI VCTCRPGYEGDGITCT |
| 131. | Tgon\|TGME49_002400 Ortholog of EGF9_PfRipr short R9 | RCDDIDECIDPTLHGCDHICINLPGTYSCQCRPGY RLSLEKKGACV |
| 132. | Tgon\|TGME49_067680 Ortholog of EGF10_PfRipr short R10 | ECATENGGCSEHSQCRNLPGSYECVCDAGYEKV EGSEHLCQ |
| 133. | Tgon\|TGME49_002400 Ortholog of EGF10_PfRipr short R10 | ECALDENICEHKCENLPGAFQCRCNSGYKRSVDD PRKCV |
| 134. | Tgon\|TGME49_043930 Ortholog of GAMA erythrocyte binding sequence | VPIKQKVQAIFSRLRMFKMNNETVLYEPDTEIIEKT VKAAYLDTTDRVFDVWGALLPQAATTTTAQLLTLL LPKPDVDLAEFYNKTMNSEGVISDGLQSQLPVNHT RLVERFALFLEEVYRDCWRNFFNVNDNFLSSSSS SETGEKATLSAASIPTVSAVQLSDAKVVDLADGVV RRGLEKAASMEAVVKGHSFVSLKSSTTEKGIDIAIV DSSDGVGVNELAKVFTDEKLIQE |
| 135. | Tgon\|TGME49_100100 Ortholog to Ron2L | ADIVQHMEDIGGAPPVSCVTNEILGVTCAPQAIAKA TTSAARVATQ |
| 136. | Ncan\|NCLIV_022530 Ortholog of EGF1_PfRipr short R1 | ECAENPALCEYGCTNLPGTYECTCPPDSKPRNDK RGCQ |
| 137. | Ncan\|NCLIV_069310 Ortholog of EGF1_PfRipr short R1 | ECTLNTDDCDSHATCENTEGSYTCACGSGYTGD GKTCE |
| 138. | Ncan\|NCLIV_022530 Ortholog of EGF2_PfRipr short R2 | VCVNTPGTFFCDCAAGFTLGEDGRSCTDVDECAL DENICEHRCENLPGAFQCHCNPGYKRGADDPRK CV |
| 139. | Ncan\|NCLIV_069310 Ortholog of EGF2_PfRipr short R2 | VCTNTVGSYVCSCLPGYTASDDGRTCTDIDECAT DNGGCSEHSQCQNLPGSYACVCDAGYQKVEGSN HLCQ |
| 140. | Ncan\|NCLIV_022530 Ortholog of EGF3_PfRipr short R3 | KCLNLVGKYECGCYPGFVLQPDGRCDDINECLDP SLHGCEQLCVNLPGTYSCQCRQGYRPSVEKRGA CVDIDECAENPALCEYGCTNLPGTYECTCPPDSK PRNDKRGCQPNLSCKEDASQCQGDHVCR |
| 141. | Ncan\|NCLIV_069310 Ortholog of EGF3_PfRipr short R3 | VCTNTVGSYVCSCLPGYTASDDGRTCTDIDECAT DNGGCSEHSQCQNLPGSYACVCDAGYQKVEGSN HLCQDIDECVANAPVPANSQCVNTAGSYDFACDA GFERKENACVKIDYCAQGGCSSLATCQENEQGTD YVCSCPSGYRTENEGRGTDGCIDIDECAENACAA YGSEGVVCQNTPGSFSCSCATGYVLNAGHCDEV DECAGS |
| 142. | Ncan\|NCLIV_022530 Ortholog of EGF4_PfRipr short R4 | DREGQGVTPAVRLQQQRELQGGRLLPGRPALCD QKCLNLVGKYECGCYPGFVLQPDGRCDDINECLD PSLHGCEQLCVNLPGTYSCQCRQGYRPSVEKRG ACV |
| 143. | Ncan\|NCLIV_069310 Ortholog of EGF4_PfRipr short R4 | NCENTSGSYICTCKNGFEMTENGCVDIDECADNN ANDCHNHRGRCINTAGSYTCECIAGFMGDGKECI NKNECESGDFHCPANSHCVDTEGSYKCDCNTGY ASDPENPESCV |

TABLE 2-continued

Exemplary fragment sequences for the generation of novel Apicomplexa vaccine candidates.

| SEQ ID | Name | Sequence |
|---|---|---|
| 144. | Ncan\|NCLIV_022530 Ortholog of EGF5_PfRipr short R5 | GRLLPGRPALCDQKCLNLVGKYECGCYPGFVLQP DGRCDDINECLDPSLHGCEQLCVNLPGTYSCQCR QGYRPSVEKRGACV |
| 145. | Ncan\|NCLIV_069310 Ortholog of EGF5_PfRipr short R5 | ECESGDFHCPANSHCVDTEGSYKCDCNTGYASD PENPESCVDVDECQIQGACDENADCTNMPGSYT CTCREGYRQEGELCVKMNLCTEAENPCSPNAFC ESLDKVVCTCKPGFEGDGITCA |
| 146. | Ncan\|NCLIV_022530 Ortholog of EGF6_PfRipr short R6 | ECLTANGGCQHVCVNTPGTFFCDCAAGFTLGED GRSCTDVDECALDENICEHRCENLPGAFQCHCNP GYKRGADDPRKCV |
| 147. | Ncan\|NCLIV_069310 Ortholog of EGF6_PfRipr short R6 | ECAEGVDTCPRQGGRCVNTPGSYKCECEAGYTY TTHADGSVECVDINECGVTELNTCASKANGGVCT NTVGSYVCSCLPGYTASDDGRTCTDIDECATDNG GCSEHSQCQNLPGSYACVCDAGYQKVEGSNHLCQ |
| 148. | Ncan\|NCLIV_022530 Ortholog of EGF7_PfRipr short R7 | GFEGDGRTKGTGCSNIDECATGQAGCEQICKDFA PGYACGCYDGYKLKANGKDCQDINECL |
| 149. | Ncan\|NCLIV_069310 Ortholog of EGF7_PfRipr short R7 | GYKGSGHTKKGAADGCVDIDECAEGVDTCPRQG GRCVNTPGSYKCECEAGYTYTTHADGSVECVDIN ECG |
| 150. | Ncan\|NCLIV_022530 Ortholog of EGF8_PfRipr short R8 | GRLLPGRPALCDQKCLNLVGKYECGCYPGFVLQP DGRCDDINECLDPSLHGCEQLCV |
| 151. | Ncan\|NCLIV_069310 Ortholog of EGF8_PfRipr short R8 | ECESGDFHCPANSHCVDTEGSYKCDCNTGYASD PENPESCVDVDECQIQGACDENADCT |
| 152. | Ncan\|NCLIV_022530 Ortholog of EGF9_PfRipr short R9 | RCDDINECLDPSLHGCEQLCVNLPGTYSCQCRQG YRPSVEKRGACV |
| 153. | Ncan\|NCLIV_069310 Ortholog of EGF9_PfRipr short R9 | SCVDVDECQIQGACDENADCTNMPGSYTCTCRE GYRQEGELCVKMNLCTEAENPCSPNAFCESLDKV VCTCKPGFEGDGITCA |
| 154. | Ncan\|NCLIV_022530 Ortholog of EGF10_PfRipr short R10 | ECALDENICEHRCENLPGAFQCHCNPGYKRGADD PRKCV |
| 155. | Ncan\|NCLIV_069310 Ortholog of EGF10_PfRipr short R10 | ECATDNGGCSEHSQCQNLPGSYACVCDAGYQKV EGSNHLCQ |
| 156. | Ncan\|NCLIV_018530 Ortholog of GAMA erythrocyte binding sequence | VPIKQKVMAVMSRLRMLQMHNDTVAFEVDSAGVE KIVKAAYLDVTDRVFGVWGGLLPQAAVTTTAQLLT LLLPKPDVDVAEFYNKTMNSEGAISDGVQDQLPV NHTRLVERFAIFVEEMYRDCWRKFFNTNDNFLAP ANDAETDAQDISSATSIPEVSAVQLNAGKVVDLLA NGVVERGLDHAASMEAVVKEHSFVSTASAAGER GIDMAIVDSSDGIGVADLAKVFTDEQAVRG |
| 157. | Ncan\|NCLIV_064620 Ortholog of Ron2L | TDIVQHMEDIGGAPPASCVTNEILGVTCAPQAIAKA TTSAAQVATQ |

TABLE 2-continued

Exemplary fragment sequences for the generation of novel Apicomplexa vaccine candidates.

| SEQ ID | Name | Sequence |
|---|---|---|
| 158. | Cpar\|cgd3_1860 Ortholog of EGF1_PfRipr short R1 | ECLESPELTGCSHGCINKRGGFQCTCPKGFQLGM DGKVCE |
| 159. | Cpar\|cgd3_1860 Ortholog of EGF2_PfRipr short R2 | ICVNTRGSFVCECPKGYTLDKNQQDCIDINECQEN SGLGPCEFGCKNLPGGFECQCPSGYKLDKKTQK CI |
| 160. | Cpar\|cgd3_1860 Ortholog of EGF3_PfRipr short R3 | VCFNKKGGFECKCGIGFQYDENENACKDINECVL NTHDCKKDSVCVNEDGGFSCKCLEKGFEFNKEKR ACEDIDECSNGDSKCDQLCFNTIGGYKCGCYKGF RLNLTGPEENRLDVQSRVCIDIDECLES |
| 161. | Cpar\|cgd3_1860 Ortholog of EGF4_PfRipr short R4 | NLCTGFGEVCFNKKGGFECKCGIGFQYDENENAC KDINECVLNTHDCKKDSVCVNEDGGFSCKCLEKG FEFNKEKRACE |
| 162. | Cpar\|cgd3_1860 Ortholog of EGF5_PfRipr short R5 | ECVLNTHDCKKDSVCVNEDGGFSCKCLEKGFEFN KEKRACEDIDECSNGDSKCDQLCFNTIGGYKCGC YKGFRLNLTGPEENRLDVQSRVCI |
| 163. | Cpar\|cgd3_1860 Ortholog of EGF6_PfRipr short R6 | ECMEGSHSCSHICVNTRGSFVCECPKGYTLDKNQ QDCIDINECQENSGLGPCEFGCKNLPGGFECQCP SGYKLDKKTQKCI |
| 164. | Cpar\|cgd3_1860 Ortholog of EGF7_PfRipr short R7 | GYIGDGRTKGTGCQNVNECLTGEARCEQLCTDYS PGYACSCNMGYRLNTKDMRSCIDIDECM |
| 165. | Cpar\|cgd3_1860 Ortholog of EGF8_PfRipr short R8 | ECVLNTHDCKKDSVCVNEDGGFSCKCLEKGFEFN KEKRACEDIDECSNGDSKCDQLCF |
| 166. | Cpar\|cgd3_1860 Ortholog of EGF9_PfRipr short R9 | ACEDIDECSNGDSKCDQLCFNTIGGYKCGCYKGF RLNLTGPEENRLDVQSRVCI |
| 167. | Cpar\|cgd3_1860 Ortholog of EGF10_PfRipr short R10 | ECQENSGLGPCEFGCKNLPGGFECQCPSGYKLD KKTQKCI |
| 168. | Cmur\|CMU_001710 Ortholog of EGF1_PfRipr short R1 | ECLETKELTGCSHGCENTYGSFKCTCPSGYELNS NGKICE |
| 169. | Cmur\|CMU_001710 Ortholog of EGF2_PfRipr short R2 | ICVNKPGSYTCECPTGYKLDIDKKNCIDIDECLEND GKGSCEYECRNLIGSYECICPSGYRLDKSNQKCK |
| 170. | Cmur\|CMU_001710 Ortholog of EGF3_PfRipr short R3 | ICENIIGSFKCVCGKGYTFHEEKGCLDVDECLNGT HDCPESTNCINIIGSFTCSCLKSGYRYNRNKKICED INECKNGEAHCEQICINTLGGYKCDCFPGFKYKVE RLDNELSSGTRGICIDINECLET |
| 171. | Cmur\|CMU_001710 Ortholog of EGF4_PfRipr short R4 | DICNQTGQICENIIGSFKCVCGKGYTFHEEKGCLD VDECLNGTHDCPESTNCINIIGSFTCSCLKSGYRY NRNKKICE |
| 172. | Cmur\|CMU_001710 Ortholog of EGF5_PfRipr short R5 | ECLNGTHDCPESTNCINIIGSFTCSCLKSGYRYNR NKKICEDINECKNGEAHCEQICINTLGGYKCDCFP GFKYKVERLDNELSSGTRGICI |

TABLE 2-continued

Exemplary fragment sequences for the generation of novel Apicomplexa vaccine candidates.

| SEQ ID | Name | Sequence |
|---|---|---|
| 173. | Cmur\|CMU_001710 Ortholog of EGF6_PfRipr short R6 | ECADGIHECSHICVNKPGSYTCECPTGYKLDIDKK NCIDIDECLENDGKGSCEYECRNLIGSYECICPSG YRLDKSNQKCK |
| 174. | Cmur\|CMU_001710 Ortholog of EGF7_PfRipr short R7 | GYYGDGRTKGTGCENINECTTGEARCEQMCTDY TPGYACSCLNGFKLNPKDLKGCLDIDECA |
| 175. | Cmur\|CMU_001710 Ortholog of EGF8_PfRipr short R8 | ECLNGTHDCPESTNCINIIGSFTCSCLKSGYRYNR NKKICEDINECKNGEAHCEQICI |
| 176. | Cmur\|CMU_001710 Ortholog of EGF9_PfRipr short R9 | ICEDINECKNGEAHCEQICINTLGGYKCDCFPGFK YKVERLDNELSSGTRGICI |
| 177. | Cmur\|CMU_001710 Ortholog of EGF10_PfRipr short R10 | ECLENDGKGSCEYECRNLIGSYECICPSGYRLDKS NQKCK |
| 178. | Chom\|Chro.30220 Ortholog of EGF1_PfRipr short R1 | ECLESPELTGCSHGCINKRGGFQCTCPKGFQLGM DGKVCE |
| 179. | Chom\|Chro.30220 Ortholog of EGF2_PfRipr short R2 | ICVNTRGSFVCECPKGYTLDKNQQDCIDINECQEN SGLGPCEFGCKNLPGGFECQCPSGYKLDKKTQK CI |
| 180. | Chom\|Chro.30220 Ortholog of EGF3_PfRipr short R3 | VCFNKKGGFECKCGTGFQYDENENACKDINECVL NTHDCKKDSVCVNEDGGFSCKCLEKGFEFNKEKR ACEDIDECSNGDSKCDQLCFNTIGGYRCGCYKGF RLNLTGPEENRLDVKSRVCIDIDECLES |
| 181. | Chom\|Chro.30220 Ortholog of EGF4_PfRipr short R4 | NLCTGFGEVCFNKKGGFECKCGTGFQYDENENA CKDINECVLNTHDCKKDSVCVNEDGGFSCKCLEK GFEFNKEKRACE |
| 182. | Chom\|Chro.30220 Ortholog of EGF5_PfRipr short R5 | ECVLNTHDCKKDSVCVNEDGGFSCKCLEKGFEFN KEKRACEDIDECSNGDSKCDQLCFNTIGGYRCGC YKGFRLNLTGPEENRLDVKSRVCI |
| 183. | ChomlChro.30220 Ortholog of EGF6_PfRipr short R6 | ECKEGSHSCSHICVNTRGSFVCECPKGYTLDKNQ QDCIDINECQENSGLGPCEFGCKNLPGGFECQCP SGYKLDKKTQKCI |
| 184. | Chom\|Chro.30220 Ortholog of EGF7_PfRipr short R7 | GYIGDGRTKGTGCQNVNECLTGEARCEQLCTDYS PGYACSCNMGYRLNTKDMRSCIDIDECK |
| 185. | Chom\|Chro.30220 Ortholog of EGF8_PfRipr short R8 | ECVLNTHDCKKDSVCVNEDGGFSCKCLEKGFEFN KEKRACEDIDECSNGDSKCDQLCF |
| 186. | Chom\|Chro.30220 Ortholog of EGF9_PfRipr short R9 | ACEDIDECSNGDSKCDQLCFNTIGGYRCGCYKGF RLNLTGPEENRLDVKSRVCI |
| 187. | Chom\|Chro.30220 Ortholog of EGF10_PfRipr short R10 | ECQENSGLGPCEFGCKNLPGGFECQCPSGYKLD KKTQKCI |

TABLE 2-continued

Exemplary fragment sequences for the generation of novel Apicomplexa vaccine candidates.

| SEQ ID | Name | Sequence |
|---|---|---|
| 188. | Bbov\|XP_001609788.1 Ortholog of TRAP_TSR | SSTTDMPSSTTDMSSSTTDMPSSPTDMPSSTTDM PSSPTHTRVEETDEEHNHRKDMDIKFPENMDDIPV EDIPMPIDPRHGVEPSASD |
| 189. | Bbov\|XP_001608815.1 Ortholog of Ron2L | ADIAQHAADVGVGPAESCFIMVKPPALHCVLKPVE TLMKSALTIGVQ |
| 190. | Tann\|TA07755 Ortholog of TRAP_TSR | PKDAVCKPIWSDWSKCDAKCGIGTRYQKLMGVTT ISEPTVGTNGKSGRTCEMIYENVEVPKEECSVECD EQGETEGSLDE |
| 191. | Tann\|TA19390 Ortholog of Ron2L | MDIAQHAVDVGHPPVETCWYLVKPPSMHCAIEPV SNLAISASSVAIR |
| 192. | Tpar\|XP_765541 Ortholog of Ron2L | MDIAQHAVDMGHPPVETCWYLVKPPSMHCAIEPI SNLAISASSVAIR |

FIG. 4 shows an exemplary sequence alignment of P. falciparum EGF9_Ripr (SEQ ID NO.16) and its orthologs in different Apicomplexa species (P. vivax, P. knowlesi, Toxoplasma gondii, Neospora caninum, Cryptosporidium parvum, Cryptosporidium muris, Cryptosporidium hominis).

Based on Apicomplexa heat stable fragment sequences from Table 2 advantageous embodiments of recombinant fusion proteins and/or fragments comprised in the compositions suitable as human and/or animal vaccines against apicomplexan pathogens are listed in the following Table 3.

TABLE 3

Examples of produced heat stable fusion proteins according to the present disclosure as basis for single-component or multi-component vaccine compositions against Apicomplexa.

| SEQ ID | Fragment Combination | Amino Acid Sequence |
|---|---|---|
| Single-stage, multi-fragment fusion proteins for P. falciparum vaccines ||| 
| 193. | 25FKO-230_C0 | MVTVDTVCKRGFLIQMSGHLECKCENDLVLVNEET CEEKVLKCDEKTVNKPCGDFSKCIKIDGNPVSYACK CNLGYDMVNNVCIPNECKNVACGNGKCILDTSNPV KTGVCSCNIGKVPNVQDQKCSKDGETKCSLKCLKE NEACKAVDGIYKCDCKDGFIIDNEASICTAAVEYVDE KERQGEIYPFGDEEEKDEGGESFTYEKSEVDKTDL FKFIEGGEGDDVYKVDGSKVLLDDDTISRVSKKHTA RDGEYGEYGEAVEDGENVIKIIRSVLQSGALPSVGV DELDKIDLSYETTES GDTAVSEDSYDKYASNN |
| 194. | CelTos-fCSP_TSR-TRAP_TSR | MAFRGNNGHDSSSSLYGGSQFIEQLDNSFTSAFLE SQSMNKIGDDLAETISNELVSVLQKNSPTFLESSFDI KSEVKKHAKSMLKELIKVGLPSFENLVAENVKPPKV DPATYGIIVPVLTSLFNKVETAVGAKVSDEIWNYNSP DVSESEESLSDDFFDAAGPSDKHIEQYLKKIQNSLS TEWSPCSVTCGNGIQVRIKPGSANKPKDELDYENDI EKKICKMEKCSSVFNVVNSAAVAMAEKTASCGVWD EWSPCSVTCGKGTRSRKREILHEGCTSELQEQCEE ERCLPK |
| 195. | 1_19-4-1_8-2_8-MSP3aGKO | MAISQHQCVKKQCPENSGCFRHLDEREECKCLLNY KQEGDKCVAAGLEDEDLCKHNNGGCGDDKLCEYV GNRRVKCKCKEGYKLEGIECVELLAAGNNKVCENT KCPLNSNCYVIDDEETCRCLPGFNNIKIDDEMNCVR DAAGDTLDCSRNNGGCDIHAKCSFINKQIVCECKDK FEGDGIYCSYSAAGKEIVKKYNLNLRNAILNNNAQIE NEENVNTAITGNDFSGGEFLWPGYTEELKAKKASE DAEKAANDAENAAKEAEEAAKEAVNLKESDKSYTK AKEAATAASKAKKAVETALKAKDDAEKSSKADSIST KTK |

TABLE 3-continued

Examples of produced heat stable fusion proteins according to the present disclosure as basis for single-component or multi-component vaccine compositions against Apicomplexa.

| SEQ ID | Fragment Combination | Amino Acid Sequence |
|---|---|---|
| | Multi-stage, multi-fragment fusion proteins for *P. falciparum* vaccines | |
| 196. | 1_19-1_8-2_8-4-25FKO | MAISQHQCVKKQCPENSGCFRHLDEREECKCLLNY KQEGDKCVAAGNNKVCENTKCPLNSNCYVIDDEET CRCLPGFNNIKIDDEMNCVRDAAGDTLDCSRNNGG CDIHAKCSFINKQIVCECKDKFEGDGIYCSYSAAGLE DEDLCKHNNGGCGDDKLCEYVGNRRVKCKCKEGY KLEGIECVELLAAVTVDTVCKRGFLIQMSGHLECKC ENDLVLVNEETCEEKVLKCDEKTVNKPCGDFSKCIK IDGNPVSYACKCNLGYDMVNNVCIPNECKNVACGN GKCILDTSNPVKTGVCSCNIGKVPNVQDQKCSKDG ETKCSLKCLKENEACKAVDGIYKCDCKDGFIIDNEA SICT |
| 197. | 1_19-1_8-2_8-4-25FKO-CSP_TSR | MAISQHQCVKKQCPENSGCFRHLDEREECKCLLNY KQEGDKCVAAGNNKVCENTKCPLNSNCYVIDDEET CRCLPGFNNIKIDDEMNCVRDAAGDTLDCSRNNGG CDIHAKCSFINKQIVCECKDKFEGDGIYCSYSAAGLE DEDLCKHNNGGCGDDKLCEYVGNRRVKCKCKEGY KLEGIECVELLAAVTVDTVCKRGFLIQMSGHLECKC ENDLVLVNEETCEEKVLKCDEKTVNKPCGDFSKCIK IDGNPVSYACKCNLGYDMVNNVCIPNECKNVACGN GKCILDTSNPVKTGVCSCNIGKVPNVQDQKCSKDG ETKCSLKCLKENEACKAVDGIYKCDCKDGFIIDNEA SICTAAGYLKKIQNSLSTEWSPCSVTCGNGIQVRIKP GSANKPKDELDYENDIEKKICKMEKCSSVFNVVNS |
| 198. | 1_19-1_8-2_8-4-1_10-2_10aglyc-25FKO-CSP_TSR | MAISQHQCVKKQCPENSGCFRHLDEREECKCLLNY KQEGDKCVAAGNNKVCENTKCPLNS NCYVIDDEETCRCLPGFNNIKIDDEMNCVRDAAGDT LDCSRNNGGCDIHAKCSFINKQIV CECKDKFEGDGIYCSYSAAGLEDEDLCKHNNGGC GDDKLCEYVGNRRVKCKCKEGYKLEG IECVELLAAGVNYICEYSKCGPNSRCYIVEKDKEQC RCQPNYIVDMSVNYFKCIPAAGKDMACSKNNGGCD VNAECTIVEGAVKCQCSHLYFGDGVFCVKAAVTVD TVCKRGFLIQMSGHLECKCENDLVLVNEETCEEKVL KCDEKTVNKPCGDFSKCIKIDGNPVSYACKCNLGY DMVNNVCIPNECKNVACGNGKCILDTSNPVKTGVC SCNIGKVPNVQDQKCSKDGETKCSLKCLKENEACK AVDGIYKCDCKDGFIIDNEASICTAAGYLKKIQNSLST EWSPCSVTCGNGIQVRIKPGSANKPKDELDYENDIE KKICKMEKCSSVFNVVNS |
| 199. | 1_19-1_8-2_8-4-R6-CelTos | MAISQHQCVKKQCPENSGCFRHLDEREECKCLLNY KQEGDKCVAAGNNKVCENTKCPLNSNCYVIDDEET CRCLPGFNNIKIDDEMNCVRDAAGDTLDCSRNNGG CDIHAKCSFINKQIVCECKDKFEGDGIYCSYSAAGLE DEDLCKHNNGGCGDDKLCEYVGNRRVKCKCKEGY KLEGIECVELLAAGKCKRKEYENICTNPNEMCAYNE ETDIVKCECKEHYYRSSRGECIAAVAMAFRGNNGH DSSSSLYGGSQFIEQLDNSFTSAFLESQSMNKIGDD LAETISNELVSVLQKNSPTFLESSFDIKSEVKKHAKS MLKELIKVGLPSFENLVAENVKPPKVDPATYGIIVPV LTSLFNKVETAVGAKVSDEIWNYNSPDVSESEESLS DDFFD |
| 200. | 1_19-1_8-2_8-4-R6-CelTos-25FKO-230_C0 | MAISQHQCVKKQCPENSGCFRHLDEREECKCLLNY KQEGDKCVAAGNNKVCENTKCPLNSNCYVIDDEET CRCLPGFNNIKIDDEMNCVRDAAGDTLDCSRNNGG CDIHAKCSFINKQIVCECKDKFEGDGIYCSYSAAGLE DEDLCKHNNGGCGDDKLCEYVGNRRVKCKCKEGY KLEGIECVELLAAGKCKRKEYENICTNPNEMCAYNE ETDIVKCECKEHYYRSSRGECIAAVAMAFRGNNGH DSSSSLYGGSQFIEQLDNSFTSAFLESQSMNKIGDD LAETISNELVSVLQKNSPTFLESSFDIKSEVKKHAKS MLKELIKVGLPSFENLVAENVKPPKVDPATYGIIVPV LTSLFNKVETAVGAKVSDEIWNYNSPDVSESEESLS DDFFDAAVTVDTVCKRGFLIQMSGHLECKCENDLV LVNEETCEEKVLKCDEKTVNKPCGDFSKCIKIDGNP VSYACKCNLGYDMVNNVCIPNECKNVACGNGKCIL DTSNPVKTGVCSCNIGKVPNVQDQKCSKDGETKCS LKCLKENEACKAVDGIYKCDCKDGFIIDNEASICTAA |

TABLE 3-continued

Examples of produced heat stable fusion proteins according to the present disclosure as basis for single-component or multi-component vaccine compositions against Apicomplexa.

| SEQ ID | Fragment Combination | Amino Acid Sequence |
|---|---|---|
| | | VEYVDEKERQGEIYPFGDEEEKDEGGESFTYEKSE VDKTDLFKFIEGGEGDDVYKVDGSKVLLDDDTISRV SKKHTARDGEYGEYGEAVEDGENVIKIIRSVLQSGA LPSVGVDELDKIDLSYETTESGDTAVSEDSYDKYAS NN |
| 201. | 1_19-1_8-2_8-4-R6-CelTos-25FKO-230_C0-fCSP_TSR-mTRAP_TSR-TRAP_TSR | MAISQHQCVKKQCPENSGCFRHLDEREECKCLLNY KQEGDKCVAAGNNKVCENTKCPLNS NCYVIDDEETCRCLPGFNNIKIDDEMNCVRDAAGDT LDCSRNNGGCDIHAKCSFINKQIV CECKDKFEGDGIYCSYSAAGLEDEDLCKHNNGGC GDDKLCEYVGNRRVKCKCKEGYKLEG IECVELLAAGKCKRKEYENICTNPNEMCAYNEETDI VKCECKEHYYRSSRGECIAAVAMAFRGNNGHDSS SSLYGGSQFIEQLDNSFTSAFLESQSMNKIGDDLAE TISNELVSVLQKNSPTFLESSFDIKSEVKKHAKSMLK ELIKVGLPSFENLVAENVKPPKVDPATYGIIVPVLTSL FNKVETAVGAKVSDEIWNYNSPDVSESEESLSDDF FDAAVTVDTVCKRGFLIQMSGHLECKCENDLVLVN EETCEEKVLKCDEKTVNKPCGDFSKCIKIDGNPVSY ACKCNLGYDMVNNVCIPNECKNVACGNGKCILDTS NPVKTGVCSCNIGKVPNVQDQKCSKDGETKCSLKC LKENEACKAVDGIYKCDCKDGFIIDNEASICTAAVEY VDEKERQGEIYPFGDEEEKDEGGESFTYEKSEVDK TDLFKFIEGGEGDDVYKVDGSKVLLDDDTISRVSKK HTARDGEYGEYGEAVEDGENVIKIIRSVLQSGALPS VGVDELDKIDLSYETTESGDTAVSEDSYDKYASNNA AGPSDKHIEQYLKKIQNSLSTEWSPCSVTCGNGIQV RIKPGSANKPKDELDYENDIEKKICKMEKCSSVFNV VNSAAVAMATHDTCDEWSEWSACTHGISTRKCLS DSSIKDETLVCTKCDKWGEWSECKDGRMHRKVLN CPFIKEEQECDVNNEAAVAMAEKTASCGVWDEWS PCSVTCGKGTRSRKREILHEGCTSELQEQCEEERC LPK |

Single-stage, multi-strain, multi-fragment fusion proteins for *P. falciparum* vaccines

| 202. | MSP1$_{19}$_3D7-MSP1$_{19}$_FUP-MSP1$_{19}$_Wellcome-MSP1$_{19}$_Type2 | MAISQHQCVKKQCPENSGCFRHLDEREECKCLLNY KQEGDKCVENPNPTCNENNGGCDADATCTEEDSG SSRKKITCECTKPDSYPLFDGIFCSSSNAAVAMAISQ HQCVKKQCPENSGCFRHLDEREECKCLLNYKQEG DKCVENPNPTCNENNGGCDADAKCTEEDSGSNGK KITCECTKPDSYPLFDGIFCSSSNAAVAMAISQHQC VKKQCPQNSGCFRHLDEREECKCLLNYKQEGDKC VENPNPTCNENNGGCDADAKCTEEDSGSNGKKITC ECTKPDSYPLFDGIFCSSSNAAVAMAISQHQCVKKQ CPQNSGCFRHLDEREECKCLLNYKQEGDKCVENP NPTCNENNGGCDADAKCTEEDSGSNGKKITCECTK PDSYPFFDGIFCSSSN |

Single-stage, multi-species, multi-fragment fusion proteins for apicomplexan vaccines

| 203. | PfTRAP_TSR-PvTRAP_TSR-PkHTRAP_TSR | MAEKTASCGVWDEWSPCSVTCGKGTRSRKREILH EGCTSELQEQCEEERCLPKAAVAMAERVANCGPW DPWTACSVTCGRGTHSRSRPSLHEKCTTHMVSEC EEGECPVEPEPLPVPAPLPTAAVAMAEVERIAKCGP TAATCGGCCGTGGCCATGGCTWDDWTPCSVTCG KGTHSRSRPLLHAGCTTHMVKECEMDECPVEP |
| 204. | PfTRAP_TSR-BbTRAP_TSR | EKTASCGVWDEWSPCSVTCGKGTRSRKREILHEG CTSELQEQCEEERCLPKRAAVAMAEPVWAEWSSC NGECGVPGKRTRALLDLRMIEKPVNGANGQPGKS CEDQKMNFLPQSETCTIE |
| 205. | PfTRAP_TSR-BbTRAP_TSR-CparTRAP_TSR | EKTASCGVWDEWSPCSVTCGKGTRSRKREILHEG CTSELQEQCEEERCLPKRAAVAMAEPVWAEWSSC NGECGVPGKRTRALLDLRMIEKPVNGANGQPGKS CEDQKMNFLPQSETCTIEAAVAMAATTCTVSTWSS WTTCSGVCGEMRSRTRSVLSFPRYDHEYCPHLIEY SNCVVENKCPEN |

Figure 5:
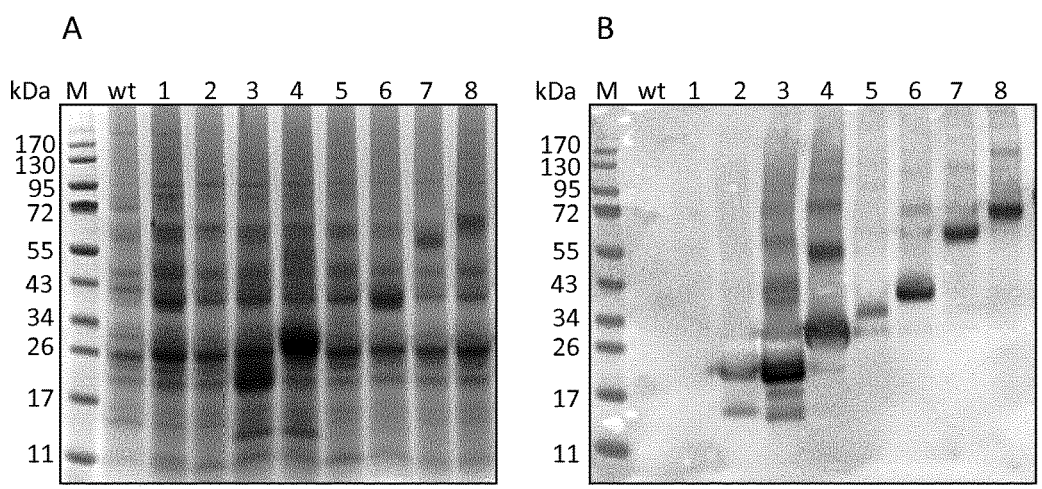
FIG. 5 is a Coomassie stained gel (A) and an Immunoblot analysis (B) showing the transient production of a multi-stage, multi-fragment malaria vaccine candidate (SEQ ID NO.198) and further fusion protein constructs according to the present disclosure based on heat stable fragments of different *P. falciparum* surface proteins in *Nicotiana benthamiana*.

Further, based on heat stable fragments of different apicomplexan surface proteins the transient production of a multi-stage, multi-fragment fusion protein (SEQ ID NO.198) and other different recombinant fusions proteins according to the present disclosure in *Nicotiana benthamiana* is shown in FIG. 5.

In an advantageous embodiment, the recombinant fusion protein comprises an 25FKO isolated EGF-like domain derived from MSP4, an isolated TSR domain derived from CSP, an isolated EGF-like domain derived from Pfs25, an isolated EGF-like domain derived from MSP1-19, two isolated EGF-like domains derived from MSP8 and two isolated EGF-like domains derived from MSP10.

In a further advantageous embodiment, the recombinant fusion protein comprises heat stable fragments derived from MSP 1_19, MSP 1_8, MSP 2_8, MSP-4, Pfs25FKO and CSP_TSR (see FIG. 8).

In further embodiments, the recombinant fusion proteins and/or vaccine compositions comprise a sequence selected from the group consisting of SEQ ID NO.193, SEQ ID NO.194, SEQ ID NO.195, SEQ ID NO.196, SEQ ID NO.197, SEQ ID NO.198, SEQ ID NO.199, SEQ ID NO.200, SEQ ID NO.201, SEQ ID NO.202 and SEQ ID NO. 205 including homologous polypeptides of these sequences, which are produced by recombinant or synthetic methods by substitution, insertion, addition or deletion of one or more amino acid residues.

In an advantageous embodiment, the isolated heat stable fragments comprised in the fusion proteins and/or vaccine compositions according to the present disclosure are selected from the group consisting of SEQ ID NO.1 to SEQ ID NO.192 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *P. falciparum* parasites are selected from the group consisting of SEQ ID NO.1 to SEQ ID NO.34 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or compositions according to the present disclosure and suitable as human and/or animal vaccines against *P. vivax* parasites are selected from the group consisting of SEQ ID NO.35 to SEQ ID NO.67 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *P. knowlesi* parasites are selected from the group consisting of SEQ ID NO.68 to SEQ ID NO.108 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *P. ovale* parasites are selected from the group consisting of SEQ ID NO.109 to SEQ ID NO.110 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *P. malariae* parasites are selected from the group consisting of SEQ ID NO.111 to SEQ ID NO.113 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Toxoplasma gondii* parasites are selected from the group consisting of SEQ ID NO.114 to SEQ ID NO.135 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Neospara caninum* parasites are selected from the group consisting of SEQ ID NO.136 to SEQ ID NO.157 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Cryptosporidium parvum* parasites are selected from the group consisting of SEQ ID NO.158 to SEQ ID NO.167 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Cryptosporidium muris* parasites are selected from the group consisting of SEQ ID NO.168 to SEQ ID NO.177 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Cryptosporidium hominis* parasites are selected from the group consisting of SEQ ID NO.178 to SEQ ID NO.187 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Babe-* sia bovis parasites are selected from the group consisting of SEQ ID NO.188 to SEQ ID NO.189 including homologous polypeptides of these sequences, which are produced by recombinant or synthetic methods by substitution, insertion, addition or deletion of one or more amino acid residues.

In another advantageous embodiment, the isolated heat stable fragments comprised in the fusion proteins and/or vaccine compositions according to the present disclosure and suitable as human and/or animal vaccines against *Theileria annulata* parasites are selected from the group consisting of SEQ ID NO.190 to SEQ ID NO.191 including homologous polypeptides of these sequences, which are produced by recombinant or synthetic methods by substitution, insertion, addition or deletion of one or more amino acid residues.

In another advantageous embodiment, the isolated heat stable fragment comprised in the fusion proteins or compositions according to the present disclosure and suitable as human and/or animal vaccines against *Theileria parva* parasites is the polypeptide with the amino acid sequence SEQ ID NO.192 including homologous polypeptides of this sequence, which are produced by recombinant or synthetic methods by substitution, insertion, addition or deletion of one or more amino acid residues.

In an advantageous embodiment, the recombinant fusion protein has the SEQ ID NO.197, or derivatives and variants thereof including homologous polypeptides of this sequence, which are produced by recombinant or synthetic methods by substitution, insertion, addition or deletion of one or more amino acid residues.

In an advantageous embodiment, the recombinant fusion protein has the SEQ ID NO.198, or derivatives and variants thereof including homologous polypeptides of this sequence, which are produced by recombinant or synthetic methods by substitution, insertion, addition or deletion of one or more amino acid residues.

The term “derivative” as used herein, refers to protein or polypeptide variants including fragments, chimeric proteins, fusion proteins, mutants, homologs, and peptidomimetics.

The term “modified form” or “variant” means that the fusion protein has been modified but retains the same functional characteristics, in particular heat stability and immunogenicity.

The term “homologous polypeptide” or “a homolog” according to the present disclosure comprises an amino acid sequence with a sequence identity of at least 70% or preferably at least 80%, 85%, 90%, 95%, 97% or 99% to a parent amino acid sequence.

Homology is defined as an analogue or variant of the fusion protein of the present disclosure. The fusion protein is characterised by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably “conservative”. Substitutions are preferably silent substitutions in the codon usage which will not lead to any change in the amino acid sequence, but may be introduced to enhance the expression of the protein. According to Table 4 amino acids in the same block of the second column and preferably in the same line of the fourth column may be substituted for each other. The amino acids in the second and fourth column are indicated in one-letter code.

In an advantageous embodiment, the treatment with fusion proteins and/or the compositions according to the present disclosure results in a cumulative inhibition in two apicomplexan life stages including the sexual stage of at least 70% (see table 6).

Further embodiments relates to methods for conjugating the recombinant fusion protein to itself or to other molecules, proteins or carriers, in particular by random ways or by using site-directed coupling methods. In particular, site directed coupling could be accommodated to N-glycosylation site specifically retained within or introduced into the recombinant fusion protein.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation or de-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

The term “modification” as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term “modifying”, as used herein, includes changing one or more amino acids in the antibodies or antigen-binding portions thereof. These changes can be produced by adding, substituting or deleting an amino acid at one or more positions. The change can be produced using known techniques, such as PCR mutagenesis.

In another aspect, the present disclosure pertains to isolated nucleic acid molecules, selected from the group consisting of a) nucleic acid molecules encoding a fusion proteins according to the present disclosure;
b) nucleic acid molecules encoding for a modified form of a fusion proteins according to the present disclosure, preferably in which one or more amino acid residues are conservatively substituted;
c) nucleic acid molecules that are capable of hybridizing to any of the nucleic acid molecules of a)-b) under stringent conditions
d) nucleic acid molecules that are capable of hybridizing to the complement of any of the nucleic acid molecules of a)-c) under stringent conditions
e) a nucleic acid molecule having a sequence identity of at least 85% with any of the nucleic acid molecules of a)-d) and encoding a heat stable fusion protein suitable as a human and/or animal vaccine against one or more parasites of the phylum Apicomplexa,
f) or complements of any of the nucleic acid molecules of a)-e).

The term “nucleic acid molecule” or “nucleic acid” is intended to indicate any single- or double stranded nucleic acid molecule of cDNA, genomic DNA, synthetic DNA or RNA, Peptide nucleic acid (PNA) or LNA origin.

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram. Conservative substitutions may be made, for example, according to Table 4 below which describes a generally accepted Venn diagram grouping of amino acids.

TABLE 4

Venn diagram grouping amino acids.

| | Set | | Sub-set | |
|---|---|---|---|---|
| Hydrophobic | F W Y H K M I L V A G C | Aromatic | F W Y H | |
| | | Aliphatic | I L V | |
| Polar | W Y H K R E D C S T N Q | Charged | H K R E D | |
| | | Positively charged | H K R | |
| | | Negatively charged | E D | |
| Small | V C A G S P T N D | Tiny | A G S | |

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN14, National Biomedical Research Foundation, Washington, D.C., which adapts the local homology algorithm of Smith and Waterman for peptide analysis. 15. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which was described before. 16 Software for performing BLAST analyses is publicly available through the National Center for Biotechnology Information (http://www.ncbi.nlm.nih.gov/). Likewise, computer programs for determining percent homology are also readily available.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes.

The present disclosure is also directed to vectors comprising a nucleotide molecule of the present disclosure. The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

In advantageous embodiments, the sequences of the isolated protein domains were inserted into the plant expression vector pTRAkc as NcoI and NotI fragments. pTRAkc is an example of a plant expression vector, which can be electroporated into agrobacteria and subsequently infiltrated into *Nicotiana* plants (Boes, A. et al. 2011). Other protein expression systems are also known in the art and are contemplated herein.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the invention may also be referred to as a "recombinant host cell".

The term "host cell(s)" refers to cell(s), which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archeobacteria, bacterial cells, insect cells, yeast, mammal cells, and/or plant cells. Bacteria envisioned as host cells can be either gram-negative or gram-positive, e.g. *Escherichia coli, Erwinia* sp., *Klebsellia* sp., *Lactobacillus* sp. or *Bacillus subtilis*. Typical yeast host cells are selected from the group consisting of *Saccharomyces cerevisiae, Hansenula polymorpha* and *Pichia pastoris*.

In advantageous embodiments, the host cell is a *Nicotiana benthamiana* plant cell or a *Nicotiana tabacum* plant cell. If mammalian, it is preferably a CHO, COS, NSO or 293 cell, if yeast, it is preferably *Pichia pastoris*.

Plants for use in accordance with the present disclosure include Angiosperms, Bryophytes (e.g., Hepaticae, Musci, etc), Ptepdophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae, e.g., pea, alfalfa, soybean), Gramineae (Poaceae, e.g., corn, wheat, nee), Solanaceae, particularly of the genus *Lycopersicon* (e.g., tomato), *Solarium* (e.g., potato, eggplant), *Capsium* (e.g., pepper), or *Nicotiana* (e.g., tobacco), Umbelhferae, particularly of the genus *Daucus* (e.g., carrot), *Apium* (e.g., celery), or Rutaceae (e.g., oranges), Compositae, particularly of the genus *Lactuca* (e.g., lettuce), Brassicaceae (Cruciferae), particularly of the genus *Brassica* or *Sinapis* In certain aspects, plants in accordance with the invention maybe species of *Brassica* or *Arabidopsis* Some exemplary Brassicaceae family members include *Brassica campestns, B cannata, B juncea, B napus, B nigra, B oleraceae, B tournifortu, Sinapis alba*, and *Raphanus sativus* Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc To express a fusion protein according to the present disclosure, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

In an advantageous embodiment, the expression vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virons may be prepared (e.g., from already infected plants), and may be applied to other plants according to known techniques. A wide variety of viruses are known that infect various plant species, and can be employed for polynucleotide expression according to the present invention (see, for example, in The Classification and Nomenclature of Viruses, "Sixth Report of the International Committee on Taxonomy of Viruses" (Ed Murphy et al), Springer Verlag New York, 1995, Grierson et al, Plant Molecular Biology, Blackie, London, pp 126-146, 1984, Gluzman er al, Communications in Molecular Biology Viral Vectors, Cold Spring Harbor Laboratory, Cold Spring Harbor, N.Y., pp 172-189, 1988, and Mathew, Plant Viruses Online, all of which are incorporated herein by reference) In certain embodiments, rather than delivering a single viral vector to a plant cell, multiple different vectors are delivered which, together, allow for replication (and, optionally cell-to-cell and/or long distance movement) of viral vector(s) Some or all of the proteins may be encoded by the genome of transgenic plants. In certain aspects, described in further detail herein, these systems include one or more viral vector components.

Further aspects of the disclosure relate to: a method of expressing in a host cell a recombinant fusion protein as described herein from a nucleic acid molecule described herein; a host cell capable of expressing a fusion protein as described herein in appropriate culture conditions for producing said fusion protein; a method of producing a fusion protein comprising culturing such a host cell under appropriate conditions, which method may further comprise isolating said fusion protein from the cell culture, and which method may further comprise admixing the isolated fusion protein with a suitable further component (which may, for example, be another protein or an excipient or carrier).

Therefore, some advantageous embodiments pertain to methods of producing recombinant fusion proteins according to the present disclosure; the methods comprise the steps of:
- a) providing a nucleic acid construct comprising a nucleic acid encoding the fusion protein,
- b) introducing the nucleic acid construct into a host cell, and
- c) maintaining the host cell under conditions permitting expression of the fusion protein,
- d) purifying the fusion protein from the host cell comprising a heat-treatment of the cell culture supernatant or extract, and
- e) optionally further processing of said fusion protein.

Further embodiments pertains to methods of preparing a biologically active, therapeutic agent which is substantially free of an active virus, wherein a source for a given fusion protein according to the present disclosure is subjected to a viral inactivation step under conditions sufficient to inactivate any virus present, in particular via a heat treatment and/or an acidic-treatment.

Further embodiments pertains to methods for purifying a recombinant fusion protein according to the present disclosure, comprising
- a) suspending host cells expressing said fusion protein at a pH<8 and incubating said suspension at a temperature of between 55-70. ° C.,
- b) separating, and
- c) collecting the soluble fraction of the suspension, containing the recombinant fusion protein, and
- d) purifying and optionally further processing said recombinant fusion protein.

Another embodiments relates to methods for purifying a recombinant fusion protein according to the present disclosure, comprising
- a) harvesting a cell culture of host cells expressing said fusion protein,
- b) resuspending said host cells at a pH<8 and incubating said suspension at a temperature of between 55-70. ° C.
- c) separating, and
- d) collecting the soluble fraction of the suspension, containing the recombinant protein,
- e) purifying and optionally further processing said recombinant fusion protein.

As discussed above, in accordance with the present disclosure, the recombinant fusion polypeptides may be produced in any desirable system. Vector constructs and expression systems are well known in the art and may be adapted to incorporate use of recombinant fusion polypeptides provided herein. For example, transgenic plant production is known and generation of constructs and plant production maybe adapted according to known techniques in the art. In some embodiments, transient expression systems in plants are desirable (see international patent application WO10037063A2).

In general, standard methods known in the art may be used for culturing or growing plants, plant cells, and/or plant tissues in accordance with the invention (e.g. clonal plants, clonal plant cells, clonal roots, clonal root lines, sprouts, sprouted seedlings, plants, etc) for production of recombinant polypeptides. A wide variety of culture media and bioreactors have been employed to culture hairy root cells, root cell lines, and plant cells (see for example Rao et al, 2002, Biotechnol Adv, 20 101).

In a certain embodiments, recombinant fusion polypeptides in accordance with the present description may be produced by any known method. In some embodiments, a fusion protein is expressed in a plant or portion thereof. Proteins may be isolated and purified in accordance with conventional conditions and techniques known in the art. These include methods such as extraction, precipitation, chromatography, affinity chromatography, electrophoresis, and the like. The present invention involves purification and affordable scaling up of production of recombinant fusion polypeptide(s) using any of a variety of plant expression systems known in the art and provided herein.

In some embodiments of the present disclosure, it will be desirable to isolate recombinant polypeptide(s) for vaccine products. Where a protein in accordance with the disclosure is produced from plant tissue(s) or a portion thereof, e.g., roots, root cells, plants, plant cells, that express them, methods known in the art may be used for any of partial or complete isolation from plant material. Where it is desirable to isolate the expression product from some or all of plant cells or tissues that express it, any available purification techniques maybe employed. Those of ordinary skill in the art are familiar with a wide range of fractionation and separation procedures (see, for example, Scopes et al, Protein Purification Principles and Practice, 3 rd Ed, Janson et al, 1993, Protein Purification Principles High Resolution Methods, and Applications, Wiley-VCH, 1998, Springer-Verlag, N Y, 1993, and Roe, Protein Purification Techniques, Oxford University Press, 2001, each of which is incorporated herein by reference). Those skilled in the art will appreciate that a method of obtaining desired recombinant fusion polypeptide(s) product(s) is by extraction. Plant material (e.g., roots, leaves, etc) may be extracted to remove desired products from residual biomass, thereby increasing the concentration and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. The plant material can be disrupted by vigorous blending or grinding while suspended in buffer solution and extracted biomass removed by filtration or centrifugation. The product earned in solution can be further purified by additional steps or converted to a dry powder by freeze-drying or precipitation. Extraction can be earned out by pressing plants or roots in a press or by being crushed as they are passed through closely spaced rollers. Fluids derived from crushed plants or roots are collected and processed according to methods well known in the art. Extraction by pressing allows release of products in a more concentrated form. In some embodiments, polypeptides can be further purified by chromatographic methods including, but not limited to anion exchange chromatography (Q Column) or ultrafiltration. Polypeptides that contain His-tags can be purified using nickel-exchange chromatography according to standard methods. In some embodiments, produced proteins or polypeptides are not isolated from plant tissue but rather are provided in the context of live plants (e.g., sprouted seedlings). In some embodiments, where the plant is edible, plant tissue containing expressed protein or polypeptide is provided directly for consumption. Thus, the present disclosure provides edible young plant biomass (e.g. edible sprouted seedlings) containing expressed protein or polypeptide.

As mentioned above, the heat-stability of the fragments and therefore the heat stability of the fusion proteins according to the present disclosure enable an efficient purification step by heating up the cell culture supernatant and/or cell extract. Many host cell proteins are denatured during that step and precipitate. They can thus be easily removed by centrifugation or filtration. Moreover, many host cell proteases are thermally inactivated, resulting in increased stability of the target recombinant fusion protein during downstream processing. The heat stability is moreover an extremely useful property for viral inactivation steps during downstream processing in vaccine manufacturing. Such steps are mandatory for ensuring product safety, but may not always be compatible with the activity of the target protein. In such cases expensive ultra/nano-filtration procedures have to be employed, including tedious and expensive process validation. By being able to employ simple heat treatment of the product, the overall process becomes cheaper and more efficient and results in a safer product. These properties are highly important for generating a vaccine that is particularly useful and applicable for developing countries.

According to one embodiment, the expressed product of interest may be obtained by disrupting the host cells. The fusion proteins are preferably expressed, e.g. secreted, into the culture medium and can be obtained therefrom. For this purpose, an appropriate leader peptide is provided in the polypeptide of interest. Leader sequences and expression cassette designs to achieve secretion are well known in the prior art. Also a combination of the respective methods is possible. Thereby, the fusion proteins can be produced and obtained/isolated efficiently with high yield.

The produced fusion proteins according to the present disclosure may be recovered, further purified, isolated, processed and/or modified by methods known in the art. For example, the polypeptide may be recovered from the nutrient medium by conventional procedures including, but not limited to, centrifugation, filtration, ultra-filtration, extraction or precipitation. Further processing steps such as purification steps may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

Furthermore, the isolated and purified polypeptide of interest may be further processed, such as e.g. formulated into a composition, e.g. a pharmaceutical composition.

Figure 6:
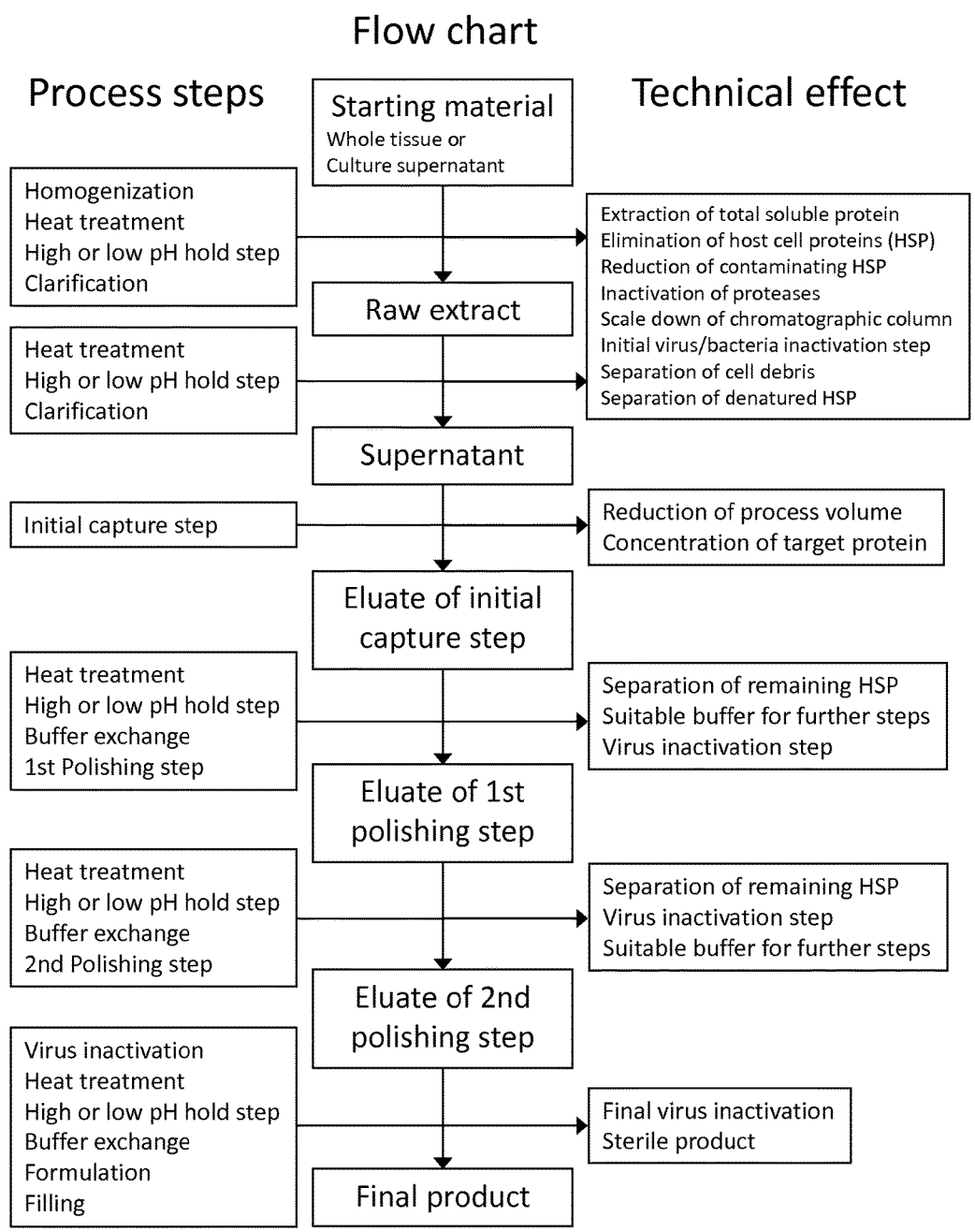
FIG. 6 shows a schematic flow chart of the protein purification processes according to the present disclosure.

According to the present disclosure a schematic flow chart of the protein purification process is illustrated in FIG. 6, wherein potential steps for a heat treatment and/or a high or low pH hold step are indicated on the right site. The technical effects as well as technical advantages are listed on the right site. Purification of the heat stable and/or acidic resistant recombinant fusion proteins according to the present disclosure can thus be carried out by a simple method comprising relatively few procedural steps, wherein the protein expressing cells (i.e. the host cells) are subjected to a heat treatment and/or in a low pH solution. This combined process in itself generates proteins practically free from contaminating host cell proteins and in particular of virus particles and/or viral proteins. The simplicity, ease and speed of this method should make it an attractive alternative in production of recombinant fusion proteins as basis for vaccines. Furthermore, it is not necessary to remove cell debris before the primary purification, and the whole process may be carried out in one vessel. Consequently, as mentioned above one aspect of the present disclosure lies in providing a cost-effective and simple process for harvesting the recombinant fusion proteins according to the present disclosure of high purity, including releasing a heterologous protein from a host cell, separating host cell proteins from the heterologous protein and removing contaminants from the protein solution. Such a method is characterised by comprising a novel combined cell disruption and purification step for fusion protein vaccine candidates as described herein.

Accordingly, the embodiments of the present disclosure relate to a process for purifying a recombinant fusion protein according to the present disclosure, which process comprises suspending host cells expressing said fusion protein e.g. in acetic acid and incubating said suspension at a temperature of between 50-90° C., separating and collecting the soluble fraction of the suspension containing the recombinant fusion protein.

In the present context, the term "process" may be used interchangeably with the terms "method" or "procedure" and refers in particular to any assembly and/or order of procedural steps for purifying a recombinantly produced fusion protein according to the present disclosure.

The term "multi-step" process is in the present context employed to describe a process for purifying a protein and/or a peptide, which comprises a series of costly and/or laborious and/or time-consuming and/or technically complicated purification steps. As a general rule, a multi-step process, in contrast to the process described in the methods of the present disclosure with one or only a few number of steps, comprises at least two distinctly separated procedural steps for the initial disruption of the host cell and for the first crude separation of the heterologous protein from host cell proteins and contaminants. Typically, these steps are again followed by at least one purification step. Although both the multi-step process and the process related to in the present disclosure may further comprise several additional purification steps, if need for even higher purity of the protein of interest arises, this is not essential for the process described in the present disclosure. The process of the present disclosure, generating substantially pure recombinant fusion proteins that are practically free from contaminating host cell proteins, can preferably be performed in essentially a single procedural step.

A suspension in which said host cells are suspended and/or resuspended in, according to the disclosure, may display a pH which is below or equal to 5, such as below or equal to 1, 2, 3, 4 or 5. Alternatively, a suspension according to the invention may display a pH below or equal to 3, such as about 0.5; 1.5; 1.75; 2.5; 2.75 or 3. Typically, the range of pH employed in said suspension is from 0.5 to 5, such as from 1 to 4.5; 1.5 to 3.5; 3 to 5, or 1 to 3.

In an embodiment the preferred acid for the process for purifying a recombination protein according to the disclosure is acetic acid. This is not to be understood to be limiting the method of protein purification to the specific use of acetic acid per se. As should be obvious to the person skilled in the art, the acid preferred to achieve a specific pH of the solution in which said host cells are suspended and/or re-suspended in will differ for different experimental set-ups and should be construed to comprise any sufficient acid.

Furthermore, a suspension for use in a process for purifying a recombination protein according to the disclosure will be incubated employing conditions with elevated temperatures, to allow for the initial purification to occur. An incubation period suitable for a process according to the invention may be a period of about 5-40 minutes, such as about 5 to 10, 10 to 20, 10 to 30, 5 to 35 or about 30 to 40 minutes, such as about 5, 10, 15, 18, 20, 25, 30, 35 or 40 minutes. Such an incubation period may also be longer, such as about 30 to 60 minutes. It will be clear to the skilled artisan, that said incubation time is chosen for achieving optimal results, and therefore may vary due to the other conditions (such as temperature variations) used during the process of purification. In one preferred embodiment of the invention, said incubation is performed for at least 5-35 minutes. In another, equally preferred embodiment of the invention, the incubation is performed for at least 20 minutes.

A suspension comprising host cells according to the present disclosure, may be incubated as a heat treatment step at a temperature of about 50 to 90° C., such as about 50 to 60° C., 60 to 70° C., 65 to 75° C., 70 to 80° C., 75 to 85° C. or 80 to 90° C., such as selected from about 65, 70, 75, 77, 79, 80, 82, 84, 86, 88, and/or 90° C. In one preferred embodiment of the disclosure, said incubation is performed at 70 to 90° C. In another, equally preferred embodiment of the disclosure, the incubation is performed at approximately 70° C. As will be obvious to the skilled person, the temperature might vary slightly due to the experimental set-up.

The term "cell disruption" is in the present context employed to describe the breaking apart of the cell wall and plasma membrane of the host cell to effect the release of intracellular products, thus allowing subsequent recovery. In general, the term is to be understood to include lysis, which is used in the field to describe the rupture of a cell by disrupting its plasma membrane, resulting in the loss of cell contents. The term can be used to relate to procedures resulting in either substantial and/or insubstantial amounts of cytoplasmic material being released. Occurrence of cell disruption can e.g. be shown by viable cell counts that measure bacterial action. With regards to cell disruption of gram-negative organism, this of course also includes the rupture of the outer membrane.

"Separation" of and/or "separating" the protein of interest from cell debris pertaining from the host cells, during a process of the present disclosure, may be performed by any suitable means, such as by centrifugation or filtration, and/or by using any other standard procedures such as, but not limited to, absorption of the protein of interest to immobilized immunoglobulin, as described by Sjoquist, U.S. Pat. No. 3,850,798 (1974), ion exchange, affinity or gel chromatography, precipitation (e.g. with ammonium sulphate), dialysis, filtration and/or by a combination of these methods.

"Collecting" the soluble fraction during a process of the present disclosure, may be performed by any suitable means, such as by using a pipette of a suitable size, to obtain the supernatant comprising the protein of interest from the vessel used in the process, or simply by decanting.

A "soluble fraction" according to the disclosure, refers to a fraction comprising the protein of interest, which protein is made soluble by the specific conditions employed during the process, such as the temperature and the pH chosen, to allow for direct separation of the protein of interest from the cell debris originating from the host cells in the vessel.

In an advantageous embodiment, the disclosure relates to a process for purifying a recombinant fusion protein according to the present disclosure, comprising harvesting a cell culture of host cells expressing said protein, re-suspending said host cells in acetic acid and incubating said suspension at 50-90° C., separating, and collecting the soluble fraction of the suspension, containing the recombinant fusion protein.

The term "harvesting" or to "harvest" (host) cells of interest in the present context, refers to a procedure of obtaining cells from a cell culture, which cells previously has been allowed to grow in or on a media, which media may have been provided with nutrients and/or other components to facilitate proliferation of the cells. Cells from the cell culture may be harvested by removing them from the media by any means of separation, such as by centrifugation, or by shaking and/or scraping, or by using a specific column, preferably wash the cells, and alternatively resuspending the cells in another solution suitable for the next procedural step.

Furthermore, the present disclosure is also directed to methods for viral inactivation of the recombinant protein product during downstream processing by heat-treatment by using the above-described methods comprising a heat-treatment.

The disclosure pertains also to vaccine compositions comprising a fusion protein according to the present disclosure. In order to ensure optimum performance of such a vaccine composition it is preferred that it comprises an immunologically and pharmaceutically acceptable carrier, vehicle or adjuvant. The vaccine compositions and the carrier may be in a physiologically acceptable medium.

Furthermore, the disclosure pertains to vaccine composition suitable as human and/or animal vaccine against one or more parasites of the phylum Apicomplexa comprising at least four isolated heat stable fragments from different Apicomplexa surface proteins, wherein each fragment contains at least one folded domain, wherein the isolated heat stable fragments are derived from Apicomplexa surface proteins presented on the surface of the parasite in at least two different stages in the life cycle of the parasite.

An effective vaccine, wherein a fusion protein of the disclosure is recognized by the animal, will in an animal model be able to decrease parasite load in blood and target organs, prolong survival times and/or diminish weight loss after challenge with a malarial parasite, compared to non-vaccinated animals.

Furthermore, the fusion protein of the invention may be coupled to a carbohydrate or a lipid moiety, e.g. a carrier, or a modified in other ways, e.g. being acetylated.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-gamma, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20% solution of a perfluorocarbon (Fluosol-DA) used as a block substitute may also be employed. Other possibilities involve the use of immune modulating substances such as cytokines or synthetic IFN-gamma inducers such as poly I:C in combination with the above-mentioned adjuvants.

Another possibility for achieving adjuvant effect is to employ the technique described in Gosselin et al, 1992. In brief, a relevant antigen such as an antigen of the present invention can be conjugated to an antibody (or antigen binding antibody fragment) against the Fc-receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 micro g to 1000 micro g, such as in the range from about 1 micro g to 300 micro g, and especially in the range from about 10 micro g to 50 micro g. Suitable regimens for initial administration and booster shots are also variable but are typified by an initial administration followed by subsequent inoculations or other administrations. The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5 percent to 10 percent, preferably 1-2 percent. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95 percent of active ingredient, preferably 25-70%.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Due to genetic variation, different individuals may react with immune responses of varying strength to the same protein. Therefore, the vaccine according to the disclosure may comprise several different fusion proteins according to the present disclosure in order to increase the immune response. The vaccine may comprise two or more fusion proteins or immunogenic portions, where all of the proteins are as defined above, or some but not all of the peptides may be derived from *P. falciparum* or other parasites from the genus *Plasmodium*, hi the latter example, the polypeptides not necessarily fulfilling the criteria set forth above for polypeptides may either act due to their own immunogenicity or merely act as adjuvants. The vaccine may comprise 1-20, such as 2-20 or even 3-20 different proteins or fusion proteins, such as 3-10 different proteins or fusion proteins.

In some embodiments, the fusion protein is adsorbed on or covalently bound to said carrier. In another embodiment, the carrier is a carrier protein.

The disclosure pertains also to antibody compositions comprising isolated antibodies or fragments thereof which bind to the recombinant fusion protein according to the present disclosure.

According to the present disclosure, the term "antibody" includes, but is not limited to recombinant antibodies, polyclonal antibodies, monoclonal antibodies, single chain antibodies, humanized antibodies, minibodies, diabodies, tribodies as well as antibody fragments, including antigen-binding portion of the antibodies according to the present disclosure, such as Fab', Fab, F(ab')$_2$ and single domain antibodies as mentioned above.

The disclosure further pertains to compositions comprising a recombinant fusion protein as described herein, wherein the composition is preferably a pharmaceutical and/or diagnostic composition. In some embodiments, the pharmaceutical compositions comprise a recombinant fusion protein and a pharmaceutically acceptable carrier.

The term "pharmaceutically acceptable carrier" includes any and all solvents, dispersion media, coatings, surfactants, antioxidants, preservatives (e.g. antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In advantageous embodiments, the fusion proteins according to the present disclosure are used for preparing a medicament for preventing or treating malaria, in particular malaria tropica.

In some embodiments, the pharmaceutical compositions further comprise an additional agent in particular a therapeutic agent.

The following methods and examples are offered for illustrative purposes only, and are not intended to limit the scope of the present disclosure in any way.

METHODS AND EXAMPLES

In the following examples, materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

1. Cloning of Expression Constructs

The antigen fragment sequences listed in Table 1 were analyzed for potential N-glycosylation sites (NetNGlyc 1.0). Potential N-gycosylation sites were eliminated by point mutations and optimized for plant expression (GeneArt). The optimized sequences were inserted into the plant expression vector pTRAkc as NcoI and NotI fragments. For the generation of antigen fusion proteins or DsRed fusions (a red fluorescent protein) the plant expression vector containing either the antigen or DsRed was linearized by NotI, 5' phosphate groups were removed by calf intestinal alkaline phosphatase (CIP) and the antigen domains were inserted as EagI fragments. All constructs carried a C-terminal $His_6$-tag for purification and a SEKDEL-tag for ER retrieval (Pelham, 1990). The fusion protein without any tag ($his_6$ and SEKDEL) was inserted as NcoI and XbaI fragment. A detailed description of the pTRAkc plasmid is reported in Boes et al (Boes et al. 2011). All recombinant genes were verified by sequencing and introduced into *Agrobacterium tumefaciens* strain GV3101 (pMP90RK) by electroporation. The recombinant *Agrobacterium tumefaciens* were cultivated as described previously (Sack et al. 2007; Vaquero et al. 1999). The optical density (OD) of the cultures was determined and expression strains were mixed with the *agrobacterium* strain carrying the silencing suppressor p19 (Plant Bioscience Limited, Norwich, England) at a 5:1 ratio to a final OD of 1.

Figure 8:
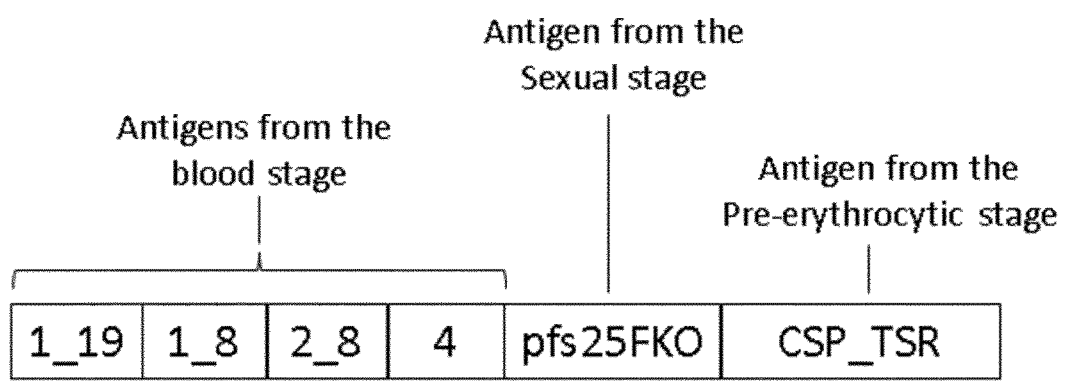
FIG. 8 is a schematic representation of an advantageous embodiment of a heat stable multi-stage multi-fragment fusion protein according to the present disclosure.

FIG. 8 shows a schematic representation of the multistage multi-domain fusion protein of SEQ ID NO: 197 comprising the following heat stable fragments:

1_19: EGF1 from the 19 kDa Fragment of MSP1 of *P. falciparum;* 1_8: EGF1 from MSP8 *P. falciparum;* 2_8: EGF2 from MSP8 of *P. falciparum;* 4: EGF from MSP4 of *P. falciparum;* pfs25FKO: Surface protein Pfs25. All potential N-glycan sites were eliminated by point mutations; CSP_TSR: TSR-domain from CSP of *P. falciparum.*

(EGF: Epidermal Growth Factor (EGF) like domain; TSR: Thrombospondin-related (TSR) like domain)

2. Transient Expression

The recombinant bacteria containing the expression cassettes were injected manually into 6-8 week old *Nicotiana benthamiana* plants grown in rockwool. Plant tissue samples were taken three-five days post infiltration (dpi) and the accumulation and integrity of target protein was determined. Large scale infiltration of proteins of interest was performed by vacuum infiltration. Infiltrated *Nicotiana benthamiana* plants were incubated for 3-5 days at 22° C. with a 16-h photoperiod.

3. Protein Extraction

Leaf disc samples were homogenized using an electropistill and soluble proteins were extracted with 2 ml PBS per gram of leaf material. Insoluble material was removed by centrifugation (16000×g, 20 min, 4° C.) and the clear supernatant was used directly for analysis. For purification, leaf material from fully infiltrated plants was homogenized in a blender with 3 ml PBS per gram of leaf material. After heat precipitation insoluble material was removed by a series of centrifugation and filtration steps. The cleared supernatant was used for the purification of the recombinant proteins.

4. Heat Precipitation

To evaluate the thermal stability of the fusion proteins an aliquot (100 μl-1 ml) of the clear supernatant was incubated at 70° C. for 5 min in a Thermoblock at 500 rpm. A detailed analysis of the fusion protein with the SEQ ID 197 was performed at different temperatures starting from 20° C. (reference) up to 90° C. in 10° C. steps (FIG. 3). After heat treatment samples were chilled on ice, insoluble material was removed by centrifugation (16000×g, 5 min) and the clear supernatant was used directly for analysis. The TSP content in the supernatant after heat treatment was determined by Bradford assay and the presence and integrity of the fusion protein was verified by sandwich ELISA or surface plasmon resonance spectroscopy using conformational specific antibodies. In case of purification the heat precipitation was conducted in a water bath set to 70° C. with the extract placed in a glass bottle inside. During heat treatment the glass bottle was shaken manually. The temperature was monitored and the heat precipitation was stopped after the temperature of the extract reached 65° C. Insoluble material was again removed by a series of centrifugation and filtration steps and used for further purification of the recombinant protein.

5. Determination of Total Soluble Protein (TSP) by Bradford

The concentration of total soluble protein was measured by a spectroscopic Bradford assay. Samples were used undiluted or in a serial dilution with PBS. 10 μl of sample was mixed with 200 μl 1× Roti-Quant (Carl Roth, K015.1), incubated for 5 min at room temperature and finally the OD at 595 nm was measured. The assay was performed in a 96 well format. The TSP was calculated using a standard curve generated by using BSA from New England Labs (NEB) as reference.

6. Murine Antibody Production for Immunoaffinity Chromatography

The hybridoma cells producing the antibody specific for EGF1 of MSP19 was ordered at the Malaria Research and Reference Reagent Resource Center MR4. The cells were adapted to a serum free and fully synthetic medium. For the antibody production the cells were cultivated in a Celline bio reactor (Sartorius) at 37° C. and 5% $CO_2$. In the celline bioreactor the cells were cultivated in a small cultivation compartment which is separated from the nutrient compartment by a dialysis membrane. The dialysis membrane allows the nutrients to get into the cultivation compartment but do not allow the antibody to escape from it. The hybridoma cells grow in serum free medium and were fed by the nutrition compartment filled with a complex medium. At the harvesting point the medium from the small cultivation compartment was taken, cells were removed by centrifugation and the supernatant was used for antibody purification by MEP HyperCel.

7. MEP HyperCel Purification of Murine Antibodies

The pH of cell culture supernatant containing the antibody was adjusted to pH 7.5-8.0 and $Na_4EDTA$ was added to a final concentration of 10 mM. The supernatant was centrifugated and 0.45 μm filtered prior purification by MEP HyperCel (Pall). The cell culture supernatant was loaded onto MEP HyderCel and unbound impurities were washed away in a first wash step at pH 7 followed by a step at pH 5. The bound antibody was eluted at pH 4 and antibody containing elution fraction were dialysed against either PBS or coupling buffer. All steps were performed with 50 mM citrate buffer at the described pH values.

8. Antibody Coupling to NHS Activated Sepharose for Immunoaffinity Chromatography NHS activated sepharose (GE healthcare, 17-0906-01) was washed with at least 10-15 matrix volumes (my) of ice cold 1 mM HCl. The matrix was settled by centrifugation, HCl was removed and the matrix was washed with coupling buffer. The coupling buffer was again removed by centrifugation and the matrix was mixed with the antibody previously dialysed against coupling buffer. The antibody was used at 4 mg/ml at an antibody solution/matrix ratio of 2:1. The coupling step was performed for 45 min at room temperature. After coupling the matrix was again settled by centrifugation and incubated over night in 3 my blocking solution. Finally, the blocking solution was removed and the matrix was washed with 1 my wash buffer 1 followed by 1 my wash buffer 2. These washing steps were repeated 3 times. The final matrix was stored in PBS at 4° C.

| Coupling buffer, pH 8.3 | 0.2M NaHCO3, 0.5M NaCl |
| Block and wash buffer 1, pH 8.5 | 0.1M Tris-HCl |
| Wash buffer 2, pH 4.0 | 0.1M Acetate, 0.5M NaCl |

9. Protein Purification

His-tagged recombinant proteins of interest were purified by immobilized metal ion chromatography (IMAC). Briefly, the pH of the extract was adjusted to pH 8.0 and NaCl was added to a final concentration of 500 mM. The target protein was captured on Chelating sepharose charged with Nickel. After a washing step with PBS adjusted to pH 8.0 the target protein was eluted in a step gradient at 15 mM, 50 mM and 250 mM imidazole dissolved in PBS at pH 8.0. The IMAC eluates were buffer exchanged by dialysis into a buffer suitable for further polishing the target protein by ion exchange chromatography (IEX) using MonoQ resin. The elution of the recombinant proteins was conducted with an increasing concentration of NaCl. Elution fractions containing the recombinant protein were dialysed against PBS.

Untagged recombinant proteins were purified by immunoaffinity chromatography (IAC). Briefly, the extract was adjusted to pH 7.5. The capture step is based on an immobilized antibody specific for the EGF1 of MSP19. After a washing step with PBS the target protein was eluted with 100 mM glycine at pH 2.5. The elution fractions were directly neutralized with 1M TRIS pH 8.8 and dialysed against PBS.

10. Immunization of Rabbits

The purified protein was sent to Biogenes (Berlin, Germany) for immunization of rabbits according to the "complete and Easy offer" and its corresponding immunization protocol.

11. Protein a Purification of Antibodies from Rabbit Sera

After immunization the antibodies from the rabbit antisera were purified by protein A chromatography. Briefly, serum samples were diluted 1:5 with PBS and filtered through 0.45 μm filter prior purification. The antibodies were bound onto Protein A resin and unbound impurities were removed by a washing step with PBS. The bound antibodies were eluted with 100 mM glycine pH 3.0 and directly neutralized with 1M TRIS pH 8.8. A buffer exchange against RPMI1640+ GlutaMax was performed using a HiPrep Desalting column and the antibodies were concentrated by centrifugal concentration devices to a concentration greater than 12 mg/ml and sterile filtered. Aliquots of 300 μl were stored at −20° C. For all subsequent functionality assays the antibodies were reconstituted with 300 μl sterile $H_2O$.

12. SDS-PAGE and Immunoblot Analysis

Proteins were separated on freshly-prepared 12% (w/v) polyacrylamide gels under reducing and non-reducing conditions or on commercial 4-12% (w/v) gradient gels (Invitrogen) and stained with Coomassie R-250 following the Fairbanks protocol (Wong et al. 2000). Separated proteins were blotted onto a nitrocellulose membrane (Whatman, Dassel, Germany) and blocked with 5% (w/v) skimmed milk dissolved in PBS. Proteins were probed with the following primary antibodies at a dilution of 1:5000: Rabbit anti-$His_6$-tag or mab 5.2 (monoclonal mouse antibody specific for EGF1 of MSP19). Secondary antibodies were Goat anti-Rabbit H+L alkaline phosphatase labeled or Goat anti-mouse IgG Fc alkaline phosphatase labeled. Bands were visualized with NBT/BCIP (1 mg·ml$^{-1}$ in substrate buffer: 150 mM NaCl, 2 mM $MgCl_2$, 50 mM Tris-HCl, pH 9.6). Between the incubation steps the membranes were washed three times with PBS supplemented with 0.05% (v/v) Tween-20.

FIG. 5 shows an accumulation analysis of different recombinant fusions proteins according to the present disclosure. Leaf disc samples were taken 5 dpi and proteins were extracted and heat precipitated as described above. Proteins were separated under reducing conditions. FIG. 5A shows a Coomassie stained gel; FIG. 5B is an Immunoblot analysis. Recombinant proteins were detected with Rabbit anti-His antibodies followed by goat anti-Rabbit H+L alkaline phosphatase labeled antibodies. Molecular weight standard is indicated at the left site. All of the recombinant fusion proteins could be detected except construct number 1 due to its small size and the selected transfer conditions.

The abbreviations in FIG. 5 are:
wt: extract of non-transformed wild-type *Nicotiana benthamiana* plant material
1-8: extract of transformed *Nicotiana benthamiana* plant material with malaria vaccine candidates of different complexity
1: 1_19
2: 1_19-1_8
3: 1_19-1_8-2_8
4: 1_19-1_8-2_8-4
5: 1_19-1_8-2_8-4-1_10
6: 1_19-1_8-2_8-4-1_10-2_10 aglyc
7: 1_19-1_8-2_8-4-1_10-2_10 aglyc-25FKO
8: 1_19-1_8-2_8-4-1_10-2_10 aglyc-25FKO-CSP_TSR (SEQ ID NO.198)
Immunoblot Detection:
rabbit anti-His antibodies followed by goat anti-rabbit H+L alkaline phosphatase labeled antibodies

13. ELISA

The thermal stabilities of the fusion proteins were analyzed by conventional sandwich ELISA. The rabbit serum specific for the fusion protein with the SEQ ID 198 was diluted 1:5000 dilution with PBS and coated for 1 h at room temperature. The wells were blocked with 5% (w/v) skimmed milk in PBS and incubated again for 1 h at room temperature. A serial dilution of the heat treated samples was applied and incubated for 1 h at room temperature followed by a conformational murine antibody specific for the fusion protein at a 1:5000 dilution. After incubation for 1 h at room temperature a HRPO labeled Goat anti-mouse Fc antibody was added. The recombinant fusion protein was detected with ABTS substrate at 405 nm. Between each step, the plates were washed three times with PBS supplemented with 0.05% (v/v) Tween-20. The amount of fusion protein was expressed as the percentage of the amount in the reference sample (20° C.) which was set to 100%.

The specific antibody (IgG) titer in the serum against the protein used for immunization as well as the reactivity against all subunits/domains was measured by ELISA using high-binding 96 well plates (Greiner bio-one, Frickenhausen, Germany) coated with the full-length protein as well as with single antigens as DsRed fusions at a concentration of 1 µg/ml After 1 h of incubation at room temperature. The wells were blocked with 5% (w/v) skimmed milk in PBS and incubated again for 1 h at room temperature. A serial dilution of the serum as well as the pre-immune serum was applied to the 96 well plate and incubated for 1 h at room temperature. The antigen-bound antibodies were probed with HRPO-labeled Goat anti-Rabbit IgG Fc and detected with ABTS substrate at 405 nm after 45 min. Between each step, the plates were washed three times with PBS supplemented with 0.05% (v/v) Tween-20. The specific IgG titer was defined as the dilution which results in an OD 405 nm twice the value of the pre-immune serum. The rabbit antibody titers induced against a multi-stage, multi-fragment vaccine candidate (SEQ ID No.197) according to the present disclosure is given below in Table 5.

TABLE 5

Rabbit antibody titers raised against a multi-stage, multi-fragment vaccine candidate (SEQ ID No. 197) according to the present disclosure.

| Pathogen stages covered by recombinant fusion protein | Assay | Minimal balanced antibody titer against every antigen fragment included in vaccine candidate SEQ ID NO. 197 |
|---|---|---|
| pre-erythrocytic stage asexual/blood stage sexual stage | ELISA | $1 \times 10^{-6}$ |

14. Immunofluorescence-Assay (IFA)

To visualize different stages of the P. falciparum parasite indirect IFA was performed in the main as described previously (Pradel et al, 2004). Cultivation of asexual stages and gametocytes of P. falciparum strain NF54 were performed as described previously (Ifediba and Vanderberg, 1981). Parasite preparations were air dried on 8-well diagnostic slides (Heat scientific) and fixed with −80° C. methanol for 10 min. To block nonspecific binding and to permeabilize membranes, fixed cells were incubated in 0.5% BSA, 0.01% saponin in PBS for 30 min at RT and subsequently in 0.5% BSA, 0.01% saponin, 1% neutral goat serum in PBS for 30 min at RT. Samples were incubated with the purified antibodies directed against the corresponding multi-stage, multi-fragment vaccine candidate, diluted in blocking solution without goat serum at 37° C. for 1 h. Purified antibodies were used at a final concentration of 15 µg/ml. For counterstaining of the different P. falciparum life cycle stages, mouse antisera directed against single P. falciparum antigen fragments from CSP (counterstaining of sporozoites), MSP1-19 (counterstaining of schizonts) or Pfs25 (counterstaining of macrogametes and zygotes) were generated by Fraunhofer IME and used in final concentrations of 1/200. Primary antibodies were visualized by incubation of cells with fluorescence-conjugated Alexa Fluor 488 goat-anti-mouse or Alexa Fluor 594 goat-anti-rabbit antibodies (Invitrogen) at a dilution of 1/1000 in blocking solution without goat serum. If no labeling of parasites with Alexa Fluor 594 coupled antibodies occurred, cells were counterstained with 0.05% Evans Blue in PBS. To highlight nuclei, samples were incubated with Hoechst in 0.01% saponin in PBS. Finally, cells were mounted with anti-fading solution AF2 (Citifluor Ltd.) and sealed with nail varnish. Examination of labeled cells and scanning of images was performed using a leica sp5 confocal microscope. Exemplary immunofluorescence assays of different Plasmodium falciparum stages with purified rabbit antibodies raised against a multi-stage, multi-fragment vaccine candidate (SEQ ID No.197) according to the present disclosure is illustrated in FIG. 7. In each section of the Figure (FIGS. 7A, 7B and 7C) a Hoechst nuclear staining is shown on the left, a positive control staining in the middle (murine control pAb, detection with anti-mouse pAb labeled with Alexa488) and a staining with purified rabbit pAb raised against a fusion protein having SEQ ID NO.197 on the right (detection with anti-rabbit pAb labeled with Alexa594).

15. Inhibition of Sporozoite Binding/Invasion (ISI)

To assess the ability of antisera directed against P. falciparum antigens to block the attachment and invasion of P. falciparum NF54 sporozoites to human liver cells, inhibition of sporozoite binding/invasion assays were performed following the protocols presented in Rathore et al. (2003) and McCormick et al. (2008). HepG2 cells were diluted in RPMI medium containing 10% FBS to a concentration of 60000/ml. 400 µl of this suspension were added to each well of E-C-L cell attachment matrix (Millipore) coated 8-well Lab-Tek permanox chamber slides (Heat Scientific). Cells were incubated for 48 h at 37° C. and 5% $CO_2$ to form a closed monolayer. On day 2 after seeding of HepG2 cells, Plasmodium falciparum NF54 sporozoites were isolated from Anopheles stephensi mosquitoes 19-21 days after an artificial infectious blood meal and collected in 0.0001% FBS in PBS. Sporozoites where counted using a neubauer hemocytometer and 20000 sporozoites in 300 µl RPMI/10% FBS where added to each well of HepG2 cells, washed 3 times with RPMI before. Purified polyclonal antibodies from rabbit antisera directed against P. falciparum antigens dissolved in RPMI where used at concentrations of 600 µg/ml and cells where subsequently incubated for 3 hours at 37° C. and 5% $CO_2$. To distinguish between extracellular and intracellular sporozoites a double labeling was performed following the protocols described previously (Hugel et al. 1996, Pradel and Frevert 2001) with some modifications. To label extracellular sporozoites, HepG2 cells were washed thrice with RPMI medium. Incubation with rabbit-anti-CSP (MRA-24, ATCC) diluted 1/200 in RPMI for 1 h at 37° C. was further followed by three washing steps with RPMI and incubation with alexa 488 conjugated goat-anti-rabbit antibodies (Invitrogen) diluted 1/1000 in RPMI at 37° C. for 1 h. Cells were washed thrice with PBS, air dried and fixed with methanol for 10 min at −80° C. Blocking and permeabilization of cell membranes was performed over night at 4° C. by incubation with 0.5% BSA, 0.01% saponin in PBS. To subsequently label all sporozoites, incubation with rabbit-anti-CSP (MRA-24, ATCC) diluted 1/200 in blocking solution for 1 h at 37° C. was followed by three washing steps with blocking solution and incubation with alexa 594 conjugated goat-anti-rabbit antibodies (Invitrogen) diluted 1/1000 in blocking solution at 37° C. for 1 h. To highlight nuclei, samples were incubated with Hoechst in PBS. Finally, cells were mounted with anti-fading solution AF2 (Citifluor Ltd.) and sealed with nail varnish. Counting of extracellular (red and green fluorescence) and intracellular (only red fluorescence) was performed using a Zeiss LSM510 confocal microscope. The ISI results of purified rabbit antibodies raised against a multi-stage, multi-fragment vaccine candidate (SEQ ID No.197) according to the present disclosure are listed below in Table 6.

TABLE 6

Exemplary inhibition results of purified rabbit antibodies raised against a multi-stage, multi-fragment vaccine candidate (SEQ ID No. 197) according to the present disclosure.

| Pathogen stage | Inhibition assay | Inhibition [%] |
| --- | --- | --- |
| pre-erythrocytic stage | inhibition of sporozoite binding/invasion | 40-55 |
| asexual/blood stage | growth inhibition assay | 30-50 |
| sexual stage | transmission blocking assay | 85-100 |

16. Growth Inhibition Assay (GIA)

The growth inhibitory potential against *Plasmodium* parasites was performed using a standardized protocol. The *P. falciparum* parasite strain 3D7A (provided by MR4) was maintained in culture at parasitemias below 5% at a haematocrit of 4% in RPMI medium supplemented with 10% Albumax II (Invitrogen), 25 mM Hepes, 12 µg/ml gentamicin and 100 µM hypoxanthine at 37° C. and 5% $CO_2$, 5% $O_2$ and 90% $N_2$. The cultures were maintained in a daily routine and parasitemia estimated by Giemsa staining. The erythrocyte used in the assay were mixed from 15 malaria-naïve blood donors and not older than 3 weeks. The erythrocytes were stored in SAG-Mannitol at 4° C. The parasites were synchronized by 10% Sorbitol treatment within a time window of 1-16 hours post invasion. For the assay, only highly synchronous cultures 36 to 40 hours post invasion were used.

Parasites and fresh RBCs and antibodies were mixed in a 96-well plate appropriately in order to have a final parasitemia of 0.1% and a final haematocrit of 2%. In case of having the purified rabbit antibodies dialysed against RPMI1640+GlutaMax HEPES was added to a final concentration of 25 mM. For the background control, only RBC without parasites were kept in culture under the same conditions as the parasites. A growth control for the monitoring the parasite growth was performed by culturing the *Plasmodium falciparum* parasite without additions. All samples were measured in triplicates. As negative control, malaria-naïve rabbit and human plasma were derived purified antibodies were tested. For positive control of complete invasion inhibition, EDTA (4 mM final concentration) and BG98 rabbit anti-AMA-1 polyclonal antibodies were used. The plates were incubated at 37° C., 95% humidity, 5% $CO_2$, 5% $O_2$, and 90% $N_2$ for 40 to 44 hours. At harvest, wells were washed once with cold PBS and frozen down. Parasite growth was estimated by a Malstat™ assay[32]. Absorbance was measured after 30 minutes at a wavelength of 655 nm using a spectrophotometer. Inhibitory capacity was estimated by the following formula:

$$\% \text{ inhibition} = 100\% - \frac{(A655 \text{ IgG sample} - A655 \text{ RBC control})}{(A655 \text{ Schizont control} - A655 \text{ RBC control})} * 100\%$$

As mentioned above, the growth inhibition assay is a standard in vitro assay to evaluate the inhibitory potential of antibodies. The assay simulates the asexual stage/blood stage. The GIA results of purified rabbit antibodies raised against a multi-stage, multi-fragment vaccine candidate (SEQ ID No.197) according to the present disclosure are listed in Table 6.

17. Transmission Blocking Assay (TBA)

To assess the ability of antisera directed against *P. falciparum* antigens to block the transmission of *P. falciparum* NF54 from the human to the mosquito, membrane feeding assays were performed (Bishop and Gilchrist, 1946). Briefly, mature stage V gametocytes were purified from cultures showing substantial exflagellation by percoll density gradient centrifugation (Kariuki et al, 1998) and mixed with an equal amount of fresh $A^+$-erythrocytes. Cells were then mixed with an equal amount of active human $A^+$-serum supplemented with the respective antiserum to test. Unpurified test sera where used up to a concentration of 1/10, purified test sera up to a concentration of 1 mg/ml. Samples were directly fed to 3-5 days old *A. stephensi* mosquitoes through a thin layer of parafilm stretched across the bottom of a glass feeder heated to 38° C. Mosquitoes used for infections were previously fed on a solution of 5% saccharose, 0.05% para-aminobenzoic acid, 40 µg/ml gentamicin soaked on cotton wool pads. Gentamicin was part of the diet to enhance overall infection rates (Beier M S et al, 1994). The mosquitoes were allowed to feed for 20 minutes on the blood meal and were afterwards kept in a secured insectary at 80% humidity and 26° C. On the following days, feeding was done using the above mentioned solution. To measure the infectivity of the different blood meals for each sample 20 midguts of blood fed mosquitoes were dissected 9-12 days after the infection and stained with 0.2% mercurochrome in PBS to facilitate counting of oocysts. Counting of oocysts was performed at a light microscope using a magnification of 100 fold. The TBA results of purified rabbit antibodies raised against a multi-stage, multi-fragment vaccine candidate (SEQ ID No.197) according to the present disclosure are listed in Table 6.

The results demonstrate the feasibility to produce a multi-stage, multi-fragment fusion protein according to the present disclosure based on heat stable fragments containing at least one folded domain from *Plasmodium falciparum* surface proteins of at least two different *Plasmodium* life cycle stages. The production was accomplished in different production systems. For the plant-based production more than 80% of the contaminating tobacco host cell proteins were eliminated without significant loss of the recombinant fusion protein by using a heat treatment step after extraction. The fusion protein retained its correct protein folding after heat treatment. The same is true after harsh acidic elution during immunoaffinity chromatography. The thermal stability as well as the pH stability is a favorable advantage of the present disclosure allowing for instance efficient removal of contaminating host cell proteins, inactivation of proteases, inactivation of pathogenic viruses and long-term storage. After purification the recombinant protein elicited a balanced antibody response in animals with a titer greater than $1 \times 10^{-6}$. Immune fluorescence assays confirmed that the induced antibodies specifically bind to the native *Plasmodium* antigens. Further, functional assays demonstrated specific parasite inhibition in every corresponding *Plasmodium* life cycle stage in a range from 30-100%.

REFERENCES

The contents of all cited references, including literature references, issued patents, and published patent applications, as cited throughout this application are hereby expressly incorporated by reference.

Altschul, S. F., Gish, W., Miller, W., Myers, E. W. & Lipman, D. J. Basic local alignment search tool. Journal of molecular biology 215, 403-10 (1990).

Ausubel, F. M. et al. Current protocols in molecular biology, edited by M. Ausubel, R. Brent, R. E. Kingston, D. D. Moore, J. G. Seidman, J. A. Smith, and K. Struhl. Volumes 1 and 2. John Wiley & Sons, Inc., Media, PA, 1988, 165.00. Molecular Reproduction and Development 1, 146-146 (1989).

Beier M S, Pumpuni C B, Beier J C, Davis J R. 1994. Effects of para-aminobenzoic acid, insulin, and gentamicin on *Plasmodium falciparum* development in anopheline mosquitoes (Diptera: Culicidae). J. Med. Entomol. 31(4): 561-565

Bergmann-Leitner E S, Mease R M, De La Vega P, Savranskaya T, Polhemus M, Ockenhouse C, Angov E. 2010. Immunization with pre-erythrocytic antigen CelTOS from *Plasmodium falciparum* elicits cross-species protection against heterologous challenge with *Plasmodium berghei*. PLoS One 5(8):e12294.

Bishop A and Gilchrist B M. 1946. Experiments upon the feeding of *Aedes aegypti* through animal membranes with a view to applying the method to the chemotherapy of malaria. Parasitology. 37: 85-100

Black C G, Wang L, Wu T, Coppel R L. 2003. Apical location of a novel EGF-like domain-containing protein of *Plasmodium falciparum*. Mol Biochem Parasitol 127 (1):59-68. Black C G, Wu T, Wang L, Hibbs A R, Coppel R L. 2001. Merozoite surface protein 8 of *Plasmodium falciparum* contains two epidermal growth factor-like domains. Mol Biochem Parasitol 114(2):217-26.

Black, C. G., Wang, L., Wu, T. & Coppel, R. L. Apical location of a novel EGF-like domain-containing protein of *Plasmodium falciparum*. Molecular and biochemical parasitology 127, 59-68 (2003).

Black C G, Wu T, Wang L, Hibbs A R, Coppel R L. Merozoite surface protein 8 of *Plasmodium falciparum* contains two epidermal growth factor-like domains. Mol Biochem Parasitol 2001; 114:217-26.

Blackman M J, Ling I T, Nicholls S C, Holder A A. 1991. Proteolytic processing of the *Plasmodium falciparum* merozoite surface protein-1 produces a membrane-bound fragment containing two epidermal growth factor-like domains. Mol Biochem Parasitol 49(1):29-33.

Boes A, Spiegel H, Delbruck H, Fischer R, Schillberg S, Sack M. 2011. Affinity purification of a framework 1 engineered mouse/human chimeric IgA2 antibody from tobacco. Biotechnol Bioeng 108(12):2804-14.

Brochet, X., Lefranc, M.-P. & Giudicelli, V. IMGT/V-QUEST: the highly customized and integrated system for IG and TR standardized V-J and V-D-J sequence analysis. Nucleic acids research 36, W503-8 (2008).

Chen L, Lopaticki S, Riglar D T, Dekiwadia C, Uboldi A D, Tham W H, O'Neill M T, Richard D, Baum J, Ralph S A and others. 2011. An EGF-like protein forms a complex with PfRh5 and is required for invasion of human erythrocytes by *Plasmodium falciparum*. PLoS Pathog 7(9): e1002199.

Dayhoff, M. O. Atlas of Protein Sequence and Structure (Vol 5, Supplement 3). 353-358 (Natl Biomedical Research: 1979).

Epping R J, Goldstone S D, Ingram L T et al. An epitope recognized by inhibitory monoclonal antibodies that react with a 51 kilodalton merozoite surface antigen in *Plasmodium falciparum*. Exp Parasitol 1988; 81:90-6.

García-Basteiro A L, Bassat Q and Alonso P L. 2012. Approaching the Target: the Path Towards an Effective Malaria Vaccine. Mediterr J Hematol Infect Dis. 4(1): e2012015

Geysen, H. M., Meloen, R. H. & Barteling, S. J. Use of peptide synthesis to probe viral antigens for epitopes to a resolution of a single amino acid. Proceedings of the National Academy of Sciences of the United States of America 81, 3998-4002 (1984).

Gosselin, E. J., K. Wardwell, D. R. Gosselin, N. Alter, J. L. Fisher, and P. M. Guyre. 1992. Enhanced antigen presentation using human Fc gamma receptor (monocyte/macrophage)-specific immunogens. J. Immunol. 149:3477-3481.

Hügel F U, Pradel G and Frevert U. 1996. Release of malaria circumsporozoite protein into the host cell cytoplasm and interaction with ribosomes. Mol Biochem Parasitol. 81(2): 151-170

Ifediba T, Vanderberg J P. 1981. Complete in vitro maturation of *Plasmodium falciparum* gametocytes. Nature. 294 (5839): 364-366

Kariuki M M, Kiaira J K, Mulaa F K, Mwangi J K, Wasunna M K and Martin S K. 1998. *Plasmodium falciparum*: Purification of the various gametocyte developmental stages from in vitro-cultivated parasites. Am. J. Trop. Med. Hyg. 59(4): 505-508

Kaslow D C, Quakyi I A, Syin C, Raum M G, Keister D B, Coligan J E, McCutchan T F, Miller L H. 1988. A vaccine candidate from the sexual stage of human malaria that contains EGF-like domains. Nature 333(6168):74-6.

Kusi, K. A. et al. Immunization with different PfAMA1 alleles in sequence induces clonal imprint humoral responses that are similar to responses induced by the same alleles as a vaccine cocktail in rabbits. Malaria journal 10, 40 (2011).

Livingstone, C. D. & Barton, G. J. Protein sequence alignments: a strategy for the hierarchical analysis of residue conservation. Computer applications in the biosciences: CABIOS 9, 745-56 (1993).

Mahajan, B., J. A. Berzofsky, et al. (2010). "Multiple antigen peptide vaccines against *Plasmodium falciparum* malaria." Infect Immun 78(11): 4613-4624.

Makler, M. T. et al. Parasite lactate dehydrogenase as an assay for *Plasmodium falciparum* drug sensitivity. The American journal of tropical medicine and hygiene 48, 739-41 (1993).

Marshall V M, Silva A, Foley M, Cranmer S, Wang L, McColl D J, Kemp D J, Coppel R L. 1997. A second merozoite surface protein (MSP-4) of *Plasmodium falciparum* that contains an epidermal growth factor-like domain. Infect Immun 65(11):4460-7.

Marshall V M, Tieqiao W, Coppel R L. 1998. Close linkage of three merozoite surface protein genes on chromosome 2 of *Plasmodium falciparum*. Mol Biochem Parasitol 94(1):13-25. Pelham H R. 1990. The retention signal for soluble proteins of the endoplasmic reticulum. Trends Biochem Sci 15(12):483-6.

Marshall V M, Silva A, Foley M et al. A second merozoite surface protein (MSP-4) of *Plasmodium falciparum* that contains an epidermal growth factor-like domain. Infect Immun 1997; 65:4460-7.

McCormick C J, Hollingdale M R and Taylor R. 2008. Sporozoite invasion assay. In: Methods in Malaria Research 5th Edition. K. Moll, I. Ljungström, H. Perlmann, A. Scherf and M. Wahlgren (Eds.). MR4/ATCC Manassas, Va. BioMalPar Paris, France. pp 138-140

Pachebat J A, Ling I T, Grainger M et al. The 22 kDa component of the protein complex on the surface of *Plasmodium falciparum* merozoites is derived from a larger precursor, merozoite surface protein 7. Mol Biochem Parasitol 2001; 117: 83-9.

Patarroyo M E, Amador R, Clavijo P, Moreno A, Guzman F, Romero P, et al. A synthetic vaccine protects humans against challenge with asexual blood stages of *Plasmodium falciparum* malaria. Nature. 1988; 332(6160):158-61

Pradel G, Hayton K, Aravind L, Iyer L M, Abrahamsen M S, Bonawitz A, Mejia C, Templeton T J. 2004. A multi-domain adhesion protein family expressed in *Plasmodium falciparum* is essential for transmission to the mosquito. J. Exp. Med. 199(11): 1533-1544

Pradel G and Frevert U. 2001. Malaria sporozoites actively enter and pass through rat Kupffer cells prior to hepatocyte invasion. Hepatology. 33(5): 1154-11654. Chothia, C. et al. Conformations of immunoglobulin hypervariable regions. *Nature* 342, 877-83

Plassmeyer M L, Reiter K, Shimp R L, Jr., Kotova S, Smith P D, Hurt D E, House B, Zou X, Zhang Y, Hickman M and others. 2009. Structure of the *Plasmodium falciparum* circumsporozoite protein, a leading malaria vaccine candidate. J Biol Chem 284(39):26951-63.

Rathore D, Hrstka S C, Sacci J B Jr, De la Vega P, Linhardt R J, Kumar S and McCutchan T F. 2003. Molecular mechanism of host specificity in *Plasmodium falciparum* infection: role of circumsporozoite protein. J Biol Chem. 278(42): 40905-40910

Richards, J. S. and J. G. Beeson (2009). "The future for blood-stage vaccines against malaria." Immunol Cell Biol 87(5): 377-390.

Roestenberg, M. et al. Safety and immunogenicity of a recombinant *Plasmodium falciparum AMA*1 malaria vaccine adjuvanted with Alhydrogel, Montanide ISA 720 or AS02. PloS one 3, e3960 (2008).

Sack M, Paetz A, Kunert R, Bomble M, Hesse F, Stiegler G, Fischer R, Katinger H, Stoeger E, Rademacher T. 2007. Functional analysis of the broadly neutralizing human anti-HIV-1 antibody 2F5 produced in transgenic BY-2 suspension cultures. FASEB J 21(8):1655-64.

Sambrook, J., Fritsch, E. F. & Maniatis, T. Molecular Cloning: A Laboratory Manual, Volume 1 to 3, 2nd edition. Sambrook J E F Fritsch and T Maniatis Molecular Cloning A Laboratory Manual Second Edition Vols 1 2 and 3 Cold Spring Harbor Laboratory Press Cold Spring Harbor N.Y. USA Illus Paper (1989).

Schwartz, L., G. V. Brown, et al. (2012). "A review of malaria vaccine clinical projects based on the WHO rainbow table." Malar J 11: 11.

Simmons, D., Woollett, G., Bergin-Cartwright, M., Kay, D., Scaife, J. 1987. A malaria protein exported into a new compartment within the host erythrocyte. EMBO J 6 (2): 485-91

Smith, T. F. & Waterman, M. S. Comparison of biosequences. Advances in Applied Mathematics 2, 482-489 (1981).

Srinivasan P, Beatty W L, Diouf A, Herrera R, Ambroggio X, Moch J K, Tyler J S, Narum D L, Pierce S K, Boothroyd J C and others. 2011. Binding of *Plasmodium* merozoite proteins RON2 and AMA1 triggers commitment to invasion. Proc Natl Acad Sci USA 108(32): 13275-80.

Tachibana M, Wu Y, Iriko H, Muratova O, MacDonald N J, Sattabongkot J, Takeo S, Otsuki H, Torii M, Tsuboi T. 2011. N-terminal prodomain of Pfs230 synthesized using a cell-free system is sufficient to induce complement-dependent malaria transmission-blocking activity. Clin Vacc Tan K., Duquette M., Liu J., Dong Y., Zhang R., Joachimiak A., Lawler J., Wang J. 2002. Crystal structure of the TSP-1 type 1 repeats: A novel layered fold and its biological implication. J. Cell Biol. 159: 373-382.

Taylor, W. R. The classification of amino acid conservation. Journal of theoretical biology 119, 205-18 (1986).

Tossavainen H, Pihlajamaa T, Huttunen T K, Raulo E, Rauvala H, Permi P, Kilpelainen I. 2006. The layered fold of the TSR domain of *P. falciparum* TRAP contains a heparin binding site. Protein Sci 15(7):1760-8.

Trucco C, Fernandez-Reyes D, Howell S et al. The merozoite surface protein 6 gene codes for a 36 kDa protein associated with the *Plasmodium falciparum* merozoite surface protein-1 complex. Mol Biochem Parasitol 2001; 112:91-101.

Tucker R. P. 2004. The thrombospondin type 1 repeat family. Int. J. Biochem. Cell Biol. 36: 969-974.

Uchime O, Herrera R, Reiter K, Kotova S, Shimp R L, Jr., Miura K, Jones D, Lebowitz J, Ambroggio X, Hurt D E and others. 2012. Analysis of the Conformation and Function of the *Plasmodium falciparum* Merozoite Proteins MTRAP and PTRAMP. Eukaryot Cell 11(5):615-25.

Vaquero C, Sack M, Chandler J, Drossard J, Schuster F, Monecke M, Schillberg S, Fischer R. 1999. Transient expression of a tumor-specific single-chain fragment and a chimeric antibody in tobacco leaves. Proc Natl Acad Sci USA 96(20):11128-33.

Wasmuth, J., Daub, J., Peregrin-Alvarez, J. M., Finney, C. A., Parkinson, J. (2009). "The origins of apicomplexan sequence innovation." Genome Res 19(7): 1202-1213.

Wong C, Sridhara S, Bardwell J C, Jakob U. 2000. Heating greatly speeds Coomassie blue staining and destaining. Biotechniques 28(3):426-8, 430, 432.

What is claimed is:

1. A recombinant fusion protein suitable as a human and/or animal vaccine against a parasite of the phylum Apicomplexa comprising a plurality of isolated heat stable fragments derived from at least two different Apicomplexa surface proteins presented on the surface of the parasite, wherein each fragment contains at least one folded domain, wherein the recombinant fusion protein comprises SEQ ID NO. 197, or a homologous polypeptide with at least 85% sequence identity to SEQ ID NO. 197 and comprising four blood stage antigens, a sexual stage antigen, and a pre-erythrocytic stage antigen.

2. The recombinant fusion protein according to claim 1, wherein the fusion protein comprises at least four different isolated heat stable fragments.

3. The recombinant fusion protein according to claim 1, wherein at least one of the folded domains is an EGF-like domain or a TSR domain.

4. The recombinant fusion protein according to claim 1, wherein the recombinant fusion protein further comprises at least one non-heat stable isolated fragment derived from an Apicomplexa surface protein, wherein the entire fusion protein is heat stable.

5. The recombinant fusion protein according to claim 1, wherein the fusion protein has a cysteine content of at least 5%.

6. The recombinant fusion protein according to claim 1, wherein the parasite of the phylum Apicomplexa is a parasite of the genus *Plasmodium*.

7. The recombinant fusion protein according to claim 1, wherein the isolated heat stable fragments are derived from Apicomplexa surface proteins selected from the group consisting of CelTos, CSP, EXP1, MSP1, MSP3, MSP4, MSP8, MSP10, mTRAP, Pfs230, Pfs25, Pfs45/48, Ripr, Ron2, TRAMP and TRAP.

8. The recombinant fusion protein according to claim 1, wherein one of the isolated heat stable fragments is SEQ ID NO:3 or a homologous peptide thereof comprising a substitution, insertion, addition or deletion of one or more amino acid residues.

9. The recombinant fusion protein according to claim 1, wherein the entire recombinant fusion protein is heat stable and/or pH stable.

10. The recombinant fusion protein according to claim 1, wherein the recombinant fusion protein comprises polypeptides of P. falciparum, characterized as PfMSP1, PfMSP8, PfMSP4, Pfs25, and a TSR domain from CSP.

11. The recombinant fusion protein according to claim 1, wherein the recombinant fusion protein comprises SEQ ID NO. 197.

12. The recombinant fusion protein according to claim 1, wherein the recombinant fusion protein comprises an EGF polypeptide of MSP1, an EGF polypeptide of MSP8, an EGF polypeptide of MSP4, a psf25FKO polypeptide, and a TSR polypeptide of CSP.

13. The recombinant fusion protein according to claim 1, wherein the blood stage antigens comprise one or more polypeptide sequences selected from the group consisting of SEQ NO. 1, SEQ ID NO. 2, SEQ ID NO. 3, and SEQ ID NO. 4.

14. The recombinant fusion protein according to claim 1, wherein the parasite of the phylum Apicomplexa is selected from the group consisting of P. falciparum, P. vivax, P. ovale, P. knowlesi and P. malariae.

15. A method of producing a recombinant fusion protein according to claim 1, the method comprising the steps of:
  a) providing a nucleic acid construct comprising a nucleic acid encoding the fusion protein of claim 1,
  b) introducing the nucleic acid construct into a host cell,
  c) maintaining the host cell under conditions permitting expression of the fusion protein, and
  d) purifying the fusion protein from the host cell comprising a heat-treatment of the cell culture supernatant or extract,
  e) optionally further processing of said fusion protein.

16. A pharmaceutical composition comprising the recombinant fusion protein according to claim 1, and a pharmaceutically acceptable carrier.

* * * * *

SEQUENCE LISTING

```
<160> NUMBER OF SEQ ID NOS: 205

<210> SEQ ID NO 1
<211> LENGTH: 41
<212> TYPE: PRT
<213> ORGANISM: Artificial Sequence
<220> FEATURE:
<223> OTHER INFORMATION: EGF1 of MSP119: short 1_19

<400> SEQUENCE: 1

Ile Ser Gln His Gln Cys Val Lys Lys Gln Cys Pro Glu Asn Ser Gly
1               5                   10                  15

Cys Phe Arg His Leu Asp Glu Arg Glu Cys Lys Cys Leu Leu Asn
            20                  25                  30
```

-continued

```
Tyr Lys Gln Glu Gly Asp Lys Cys Val
        35                  40

<210> SEQ ID NO 2
<211> LENGTH: 46
<212> TYPE: PRT
<213> ORGANISM: Artificial Sequence
<220> FEATURE:
<223> OTHER INFORMATION: f

<400> SEQUENCE: 2

Gly Asn Asn Lys Val Cys Glu Asn Thr Lys Cys Pro Leu Asn Ser Asn
1               5                   10                  15

Cys Tyr Val Ile Asp Asp Glu Glu Thr Cys Arg Cys Leu Pro Gly Phe
            20                  25                  30

Asn Asn Ile Lys Ile Asp Asp Glu Met Asn Cys Val Arg Asp
        35                  40                  45

<210> SEQ ID NO 3
<211> LENGTH: 44
<212> TYPE: PRT
<213> ORGANISM: Artificial Sequence
<220> FEATURE:
<223> OTHER INFORMATION: MSP-8

<400> SEQUENCE: 3

Gly Asp Thr Leu Asp Cys Ser Arg Asn Asn Gly Gly Cys Asp Ile His
1               5                   10                  15

Ala Lys Cys Ser Phe Ile Asn Lys Gln Ile Val Cys Glu Cys Lys Asp
            20                  25                  30

Lys Phe Glu Gly Asp Gly Ile Tyr Cys Ser Tyr Ser
        35                  40

<210> SEQ ID NO 4
<211> LENGTH: 48
<212> TYPE: PRT
<213> ORGANISM: Artificial Sequence
<220> FEATURE:
<223> OTHER INFORMATION: MSP-4

<400> SEQUENCE: 4

Gly Leu Glu Asp Glu Asp Leu Cys Lys His Asn Asn Gly Gly Cys Gly
1               5                   10                  15

Asp Asp Lys Leu Cys Glu Tyr Val Gly Asn Arg Arg Val Lys Cys Lys
            20                  25                  30

Cys Lys Glu Gly Tyr Lys Leu Glu Gly Ile Glu Cys Val Glu Leu Leu
        35                  40                  45

<210> SEQ ID NO 5
<211> LENGTH: 42
<212> TYPE: PRT
<213> ORGANISM: Artificial Sequence
<220> FEATURE:
<223> OTHER INFORMATION: MSP-5

<400> SEQUENCE: 5

Asn Arg Lys Ser Cys Ala Ile Asn Asn Gly Cys Ser Asp Asp Gln
1               5                   10                  15

Ile Cys Ile Asn Ile Asn Asn Ile Gly Val Lys Cys Ile Cys Lys Asp
            20                  25                  30

Gly Tyr Leu Leu Gly Thr Lys Cys Ile Ile
        35                  40
```

```
<210> SEQ ID NO 6
<211> LENGTH: 45
<212> TYPE: PRT
<213> ORGANISM: Artificial Sequence
<220> FEATURE:
<223> OTHER INFORMATION: MSP10

<400> SEQUENCE: 6

Val Asn Tyr Ile Cys Glu Tyr Ser Lys Cys Gly Pro Asn Ser Arg Cys
1               5                   10                  15

Tyr Ile Val Glu Lys Asp Lys Glu Gln Cys Arg Cys Gln Pro Asn Tyr
            20                  25                  30

Ile Val Asp Met Ser Val Asn Tyr Phe Lys Cys Ile Pro
        35                  40                  45

<210> SEQ ID NO 7
<211> LENGTH: 42
<212> TYPE: PRT
<213> ORGANISM: Artificial Sequence
<220> FEATURE:
<223> OTHER INFORMATION: MSP-10

<400> SEQUENCE: 7

Lys Asp Met Ala Cys Ser Lys Asn Asn Gly Gly Cys Asp Val Asn Ala
1               5                   10                  15

Glu Cys Thr Ile Val Glu Gly Ala Val Lys Cys Gln Cys Ser His Leu
            20                  25                  30

Tyr Phe Gly Asp Gly Val Phe Cys Val Lys
        35                  40

<210> SEQ ID NO 8
<211> LENGTH: 35
<212> TYPE: PRT
<213> ORGANISM: Artificial Sequence
<220> FEATURE:
<223> OTHER INFORMATION: PfRipr

<400> SEQUENCE: 8

Arg Cys Thr Gln Asp Ile Cys Ser Val Asn Gln Phe Cys Asp Gly Glu
1               5                   10                  15

Asn Glu Ala Cys Thr Cys Lys Thr Ser Leu Leu Pro Ser Ala Lys Asn
            20                  25                  30

Asn Cys Glu
        35

<210> SEQ ID NO 9
<211> LENGTH: 38
<212> TYPE: PRT
<213> ORGANISM: Artificial Sequence
<220> FEATURE:
<223> OTHER INFORMATION: PfRipr

<400> SEQUENCE: 9

Leu Cys Thr Val Leu Asn Cys Pro Glu Asn Ser Ala Cys Glu Gln Ile
1               5                   10                  15

Gly Asn Gly Lys Lys Ala Glu Cys Lys Cys Glu Asn Gly Lys Tyr Tyr
            20                  25                  30

His Asn Asn Lys Cys Tyr
        35

<210> SEQ ID NO 10
```

```
<211> LENGTH: 39
<212> TYPE: PRT
<213> ORGANISM: Artificial Sequence
<220> FEATURE:
<223> OTHER INFORMATION: PfRipr

<400> SEQUENCE: 10

Ser Cys Ser Asn Leu Asn Lys Cys His Asn Ala Ala Cys Tyr Gly
1               5                   10                  15

Asn Arg Phe Asn Tyr Asp Cys Phe Cys Asp Asn Pro Tyr Ile Ser Lys
            20                  25                  30

Tyr Gly Asn Lys Leu Cys Glu
        35

<210> SEQ ID NO 11
<211> LENGTH: 37
<212> TYPE: PRT
<213> ORGANISM: Artificial Sequence
<220> FEATURE:
<223> OTHER INFORMATION: PfRipr

<400> SEQUENCE: 11

Asp Cys Glu Ser Val Leu Cys Ser Gln Asn Gln Val Cys Gln Ile Leu
1               5                   10                  15

Pro Asn Asp Lys Leu Ile Cys Gln Cys Glu Glu Gly Tyr Lys Asn Val
            20                  25                  30

Lys Gly Lys Cys Val
        35

<210> SEQ ID NO 12
<211> LENGTH: 35
<212> TYPE: PRT
<213> ORGANISM: Artificial Sequence
<220> FEATURE:
<223> OTHER INFORMATION: PfRipr

<400> SEQUENCE: 12

Lys Cys Asp Leu Ser Cys Pro Ser Asn Lys Val Cys Val Ile Glu Asn
1               5                   10                  15

Gly Lys Gln Thr Cys Lys Cys Ser Glu Arg Phe Val Leu Glu Asn Gly
            20                  25                  30

Val Cys Ile
        35

<210> SEQ ID NO 13
<211> LENGTH: 44
<212> TYPE: PRT
<213> ORGANISM: Artificial Sequence
<220> FEATURE:
<223> OTHER INFORMATION: PfRipr

<400> SEQUENCE: 13

Lys Cys Lys Arg Lys Glu Tyr Glu Asn Ile Cys Thr Asn Pro Asn Glu
1               5                   10                  15

Met Cys Ala Tyr Asn Glu Glu Thr Asp Ile Val Lys Cys Glu Cys Lys
            20                  25                  30

Glu His Tyr Tyr Arg Ser Ser Arg Gly Glu Cys Ile
        35                  40

<210> SEQ ID NO 14
<211> LENGTH: 38
<212> TYPE: PRT
<213> ORGANISM: Artificial Sequence
```

```
<220> FEATURE:
<223> OTHER INFORMATION: PfRipr

<400> SEQUENCE: 14

Gly Tyr Cys Lys Asp Ile Asn Cys Lys Glu Asn Glu Cys Ser Ile
1               5                   10                  15

Val Asn Phe Lys Pro Glu Cys Val Cys Lys Glu Asn Leu Lys Lys Asn
            20                  25                  30

Asn Lys Gly Glu Cys Ile
        35

<210> SEQ ID NO 15
<211> LENGTH: 40
<212> TYPE: PRT
<213> ORGANISM: Artificial Sequence
<220> FEATURE:
<223> OTHER INFORMATION: PfRipr

<400> SEQUENCE: 15

Ser Cys Leu Ile Asn Glu Gly Asn Cys Pro Lys Asp Ser Lys Cys Ile
1               5                   10                  15

Tyr Arg Glu Tyr Lys Pro His Glu Cys Val Cys Asn Lys Gln Gly His
            20                  25                  30

Val Ala Val Asn Gly Lys Cys Val
        35                  40

<210> SEQ ID NO 16
<211> LENGTH: 37
<212> TYPE: PRT
<213> ORGANISM: Artificial Sequence
<220> FEATURE:
<223> OTHER INFORMATION: PfRipr

<400> SEQUENCE: 16

Lys Cys Val His Asn Lys Lys Cys Ser Glu Asn Ser Ile Cys Val Asn
1               5                   10                  15

Val Met Lys Glu Pro Ile Cys Val Cys Thr Tyr Asn Tyr Tyr Lys Lys
            20                  25                  30

Asp Gly Val Cys Leu
        35

<210> SEQ ID NO 17
<211> LENGTH: 38
<212> TYPE: PRT
<213> ORGANISM: Artificial Sequence
<220> FEATURE:
<223> OTHER INFORMATION: PfRipr

<400> SEQUENCE: 17

Pro Cys Leu Lys Asp Asn Gly Gly Cys Ser Arg Asn Ser Glu Cys Thr
1               5                   10                  15

Phe Lys Tyr Ser Lys Ile Asn Cys Ala Cys Lys Glu Asn Tyr Lys Asn
            20                  25                  30

Lys Asp Asp Ser Cys Val
        35

<210> SEQ ID NO 18
<211> LENGTH: 171
<212> TYPE: PRT
<213> ORGANISM: Artificial Sequence
<220> FEATURE:
<223> OTHER INFORMATION: Pfs25
```

<400> SEQUENCE: 18

Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
        35                  40                  45

Lys Pro Cys Gly Asp Phe Ser Lys Cys Ile Lys Ile Asp Gly Asn Pro
    50                  55                  60

Val Ser Tyr Ala Cys Lys Cys Asn Leu Gly Tyr Asp Met Val Asn Asn
65                  70                  75                  80

Val Cys Ile Pro Asn Glu Cys Lys Asn Val Thr Cys Gly Asn Gly Lys
                85                  90                  95

Cys Ile Leu Asp Thr Ser Asn Pro Val Lys Thr Gly Val Cys Ser Cys
            100                 105                 110

Asn Ile Gly Lys Val Pro Asn Val Gln Asp Gln Asn Lys Cys Ser Lys
        115                 120                 125

Asp Gly Glu Thr Lys Cys Ser Leu Lys Cys Leu Lys Glu Asn Glu Thr
    130                 135                 140

Cys Lys Ala Val Asp Gly Ile Tyr Lys Cys Asp Cys Lys Asp Gly Phe
145                 150                 155                 160

Ile Ile Asp Asn Glu Ser Ser Ile Cys Thr Ala
                165                 170

<210> SEQ ID NO 19
<211> LENGTH: 73
<212> TYPE: PRT
<213> ORGANISM: Artificial Sequence
<220> FEATURE:
<223> OTHER INFORMATION: fullCSP

<400> SEQUENCE: 19

Pro Ser Asp Lys His Ile Glu Gly Tyr Leu Lys Lys Ile Gln Asn Ser
1               5                   10                  15

Leu Ser Thr Glu Trp Ser Pro Cys Ser Val Thr Cys Gly Asn Gly Ile
            20                  25                  30

Gln Val Arg Ile Lys Pro Gly Ser Ala Asn Lys Pro Lys Asp Glu Leu
        35                  40                  45

Asp Tyr Glu Asn Asp Ile Glu Lys Lys Ile Cys Lys Met Glu Lys Cys
    50                  55                  60

Ser Ser Val Phe Asn Val Val Asn Ser
65                  70

<210> SEQ ID NO 20
<211> LENGTH: 66
<212> TYPE: PRT
<213> ORGANISM: Artificial Sequence
<220> FEATURE:
<223> OTHER INFORMATION: CSP

<400> SEQUENCE: 20

Tyr Leu Lys Lys Ile Gln Asn Ser Leu Ser Thr Glu Trp Ser Pro Cys
1               5                   10                  15

Ser Val Thr Cys Gly Asn Gly Ile Gln Val Arg Ile Lys Pro Gly Ser
            20                  25                  30

Ala Asn Lys Pro Lys Asp Glu Leu Asp Tyr Glu Asn Asp Ile Glu Lys
        35                  40                  45

```
Lys Ile Cys Lys Met Glu Lys Cys Ser Ser Val Phe Asn Val Val Asn
            50                  55                  60

Ser Ser
65

<210> SEQ ID NO 21
<211> LENGTH: 74
<212> TYPE: PRT
<213> ORGANISM: Artificial Sequence
<220> FEATURE:
<223> OTHER INFORMATION: mTRAP

<400> SEQUENCE: 21

Thr His Asp Thr Cys Asp Glu Trp Ser Glu Trp Ser Ala Cys Thr His
1               5                   10                  15

Gly Ile Ser Thr Arg Lys Cys Leu Ser Asp Ser Ser Ile Lys Asp Glu
            20                  25                  30

Thr Leu Val Cys Thr Lys Cys Asp Lys Trp Gly Glu Trp Ser Glu Cys
        35                  40                  45

Lys Asp Gly Arg Met His Arg Lys Val Leu Asn Cys Pro Phe Ile Lys
    50                  55                  60

Glu Glu Gln Glu Cys Asp Val Asn Asn Glu
65                  70

<210> SEQ ID NO 22
<211> LENGTH: 51
<212> TYPE: PRT
<213> ORGANISM: Artificial Sequence
<220> FEATURE:
<223> OTHER INFORMATION: TRAP

<400> SEQUENCE: 22

Glu Lys Thr Ala Ser Cys Gly Val Trp Asp Glu Trp Ser Pro Cys Ser
1               5                   10                  15

Val Thr Cys Gly Lys Gly Thr Arg Ser Arg Lys Arg Glu Ile Leu His
            20                  25                  30

Glu Gly Cys Thr Ser Glu Leu Gln Glu Gln Cys Glu Glu Glu Arg Cys
        35                  40                  45

Leu Pro Lys
    50

<210> SEQ ID NO 23
<211> LENGTH: 66
<212> TYPE: PRT
<213> ORGANISM: Artificial Sequence
<220> FEATURE:
<223> OTHER INFORMATION: TRAMP

<400> SEQUENCE: 23

Phe Tyr Ser Glu Trp Gly Glu Trp Ser Asn Cys Ala Met Asp Cys Asp
1               5                   10                  15

His Pro Asp Asn Val Gln Ile Arg Glu Arg Glu Cys Ile His Pro Ser
            20                  25                  30

Gly Asp Cys Phe Lys Gly Asp Leu Lys Glu Ser Arg Pro Cys Ile Ile
        35                  40                  45

Pro Leu Pro Pro Cys Asn Glu Leu Phe Ser His Lys Asp Asn Ser Ala
    50                  55                  60

Phe Lys
65
```

```
<210> SEQ ID NO 24
<211> LENGTH: 285
<212> TYPE: PRT
<213> ORGANISM: Artificial Sequence
<220> FEATURE:
<223> OTHER INFORMATION: EBA175

<400> SEQUENCE: 24
```

Met Ala Asp Lys Asn Ser Val Asp Thr Asn Thr Lys Val Trp Glu Cys
1               5                   10                  15

Lys Lys Pro Tyr Lys Leu Ser Thr Lys Asp Val Cys Val Pro Pro Arg
            20                  25                  30

Arg Gln Glu Leu Cys Leu Gly Asn Ile Asp Arg Ile Tyr Asp Lys Asn
        35                  40                  45

Leu Leu Met Ile Lys Glu His Ile Leu Ala Ile Ala Ile Tyr Glu Ser
50                  55                  60

Arg Ile Leu Lys Arg Lys Tyr Lys Asn Lys Asp Asp Lys Glu Val Cys
65                  70                  75                  80

Lys Ile Ile Asn Lys Ala Phe Ala Asp Ile Arg Asp Ile Ile Gly Gly
                85                  90                  95

Thr Asp Tyr Trp Asn Asp Leu Ser Asn Arg Lys Leu Val Gly Lys Ile
            100                 105                 110

Asn Thr Asn Ser Asn Tyr Val His Arg Asn Lys Gln Asn Asp Lys Leu
        115                 120                 125

Phe Arg Asp Glu Trp Trp Lys Val Ile Lys Lys Asp Val Trp Asn Val
130                 135                 140

Ile Ser Trp Val Phe Lys Asp Lys Thr Val Cys Lys Glu Asp Asp Ile
145                 150                 155                 160

Glu Asn Ile Pro Gln Phe Phe Arg Trp Phe Ser Glu Trp Gly Asp Asp
                165                 170                 175

Tyr Cys Gln Asp Lys Thr Lys Met Ile Glu Thr Leu Lys Val Glu Cys
            180                 185                 190

Lys Glu Lys Pro Cys Glu Asp Asp Asn Cys Lys Arg Lys Cys Asn Ser
        195                 200                 205

Tyr Lys Glu Trp Ile Ser Lys Lys Glu Glu Tyr Asn Lys Gln Ala
210                 215                 220

Lys Gln Tyr Gln Glu Tyr Gln Lys Gly Asn Asn Tyr Lys Met Tyr Ser
225                 230                 235                 240

Glu Phe Lys Ser Ile Lys Pro Glu Val Tyr Leu Lys Lys Tyr Ser Glu
                245                 250                 255

Lys Cys Ser Asn Leu Asn Phe Glu Asp Glu Phe Lys Glu Glu Leu His
            260                 265                 270

Ser Asp Tyr Lys Asn Lys Cys Thr Met Cys Pro Glu Val
        275                 280                 285

```
<210> SEQ ID NO 25
<211> LENGTH: 120
<212> TYPE: PRT
<213> ORGANISM: Artificial Sequence
<220> FEATURE:
<223> OTHER INFORMATION: EBA140

<400> SEQUENCE: 25
```

Met Ala Arg Gln Asp Glu Ser Ser Asp Ile Ser Arg Val Asn Ser Pro
1               5                   10                  15

Glu Leu Asn Asn Asn His Lys Thr Asn Ile Tyr Asp Ser Asp Tyr Glu
            20                  25                  30

```
Asp Val Asn Asn Lys Leu Ile Asn Ser Phe Val Glu Asn Lys Ser Val
            35                  40                  45

Lys Lys Lys Arg Ser Leu Ser Phe Ile Asn Asn Lys Thr Lys Ser Tyr
 50                  55                  60

Asp Ile Ile Pro Pro Ser Tyr Ser Tyr Arg Asn Asp Lys Phe Asn Ser
 65                  70                  75                  80

Leu Ser Glu Asn Glu Asp Asn Ser Gly Asn Thr Asn Ser Asn Asn Phe
                 85                  90                  95

Ala Asn Thr Ser Glu Ile Ser Ile Gly Lys Asp Asn Lys Gln Tyr Thr
            100                 105                 110

Phe Ile Gln Lys Arg Thr His Leu
        115                 120
```

<210> SEQ ID NO 26
<211> LENGTH: 136
<212> TYPE: PRT
<213> ORGANISM: Artificial Sequence
<220> FEATURE:
<223> OTHER INFORMATION: EBA 140

<400> SEQUENCE: 26

```
Met Lys Lys Ser Lys Thr Gln Met Glu Val Leu Thr Asn Leu Tyr Lys
 1               5                  10                  15

Lys Lys Asn Ser Gly Val Asp Lys Asn Asn Phe Leu Asn Asp Leu Phe
            20                  25                  30

Lys Lys Asn Asn Lys Asn Asp Leu Asp Asp Phe Lys Asn Glu Lys
            35                  40                  45

Glu Tyr Asp Asp Leu Cys Asp Cys Arg Tyr Thr Ala Thr Ile Ile Lys
 50                  55                  60

Ser Phe Leu Asn Gly Pro Ala Lys Asn Asp Val Asp Ile Ala Ser Gln
 65                  70                  75                  80

Ile Asn Val Asn Asp Leu Arg Gly Phe Gly Cys Asn Tyr Lys Ser Asn
                 85                  90                  95

Asn Glu Lys Ser Trp Asn Cys Thr Gly Thr Phe Thr Asn Lys Phe Pro
            100                 105                 110

Gly Thr Cys Glu Pro Pro Arg Arg Gln Thr Leu Cys Leu Gly Arg Thr
            115                 120                 125

Tyr Leu Leu His Arg Gly His Glu
130                 135
```

<210> SEQ ID NO 27
<211> LENGTH: 71
<212> TYPE: PRT
<213> ORGANISM: Artificial Sequence
<220> FEATURE:
<223> OTHER INFORMATION: EBL1

<400> SEQUENCE: 27

```
Met Ala Cys Asn Ala Ile Leu Gly Ser Tyr Ala Asp Ile Gly Asp Ile
 1               5                  10                  15

Val Arg Gly Leu Asp Val Trp Arg Asp Ile Asn Thr Asn Lys Leu Ser
            20                  25                  30

Glu Lys Phe Gln Lys Ile Phe Met Gly Gly Asn Ser Arg Lys Lys
            35                  40                  45

Gln Asn Asp Asn Asn Glu Arg Asn Lys Trp Trp Glu Lys Gln Arg Asn
 50                  55                  60

Leu Ile Trp Ser Ser Met Val
 65                  70
```

<210> SEQ ID NO 28
<211> LENGTH: 192
<212> TYPE: PRT
<213> ORGANISM: Artificial Sequence
<220> FEATURE:
<223> OTHER INFORMATION: GAMA EBS

<400> SEQUENCE: 28

```
Lys Asp Ile Ile Lys Leu Leu Lys Asp Leu Ile Lys Tyr Leu His Ile
1               5                   10                  15

Val Lys Phe Glu Asn Asn Glu Pro Thr Thr Asn Ile Asp Glu Glu Gly
            20                  25                  30

Ile Arg Lys Leu Leu Glu Asn Ser Phe Phe Asp Leu Asn Asp Asp Ile
        35                  40                  45

Leu Ile Val Arg Leu Leu Leu Lys Pro Gln Thr Val Ile Leu Thr Val
    50                  55                  60

Ile Gln Ser Phe Met Leu Met Thr Pro Ser Pro Ser Arg Asp Ala Lys
65                  70                  75                  80

Ala Tyr Cys Lys Lys Ala Leu Ile Asn Asp Gln Leu Val Pro Thr Asn
                85                  90                  95

Asp Ala Asn Ile Leu Ser Glu Glu Asn Glu Leu Val Asn Asn Phe Ala
            100                 105                 110

Thr Lys Tyr Val Leu Ile Tyr Glu Lys Met Lys Leu Gln Glu Leu Lys
        115                 120                 125

Glu Met Glu Glu Ser Lys Leu Lys Met Lys Tyr Ser Lys Thr Asn Leu
    130                 135                 140

Ala Ala Leu Gln Val Thr Asn Pro Gln Asn Asn Lys Asp Lys Asn Asp
145                 150                 155                 160

Ala Ser Asn Lys Asn Asn Asn Pro Asn Asn Ala Ala Thr Pro Leu Ile
                165                 170                 175

Ala Val Val Thr Asp Leu Ser Gly Glu Lys Thr Glu Asp Ile Ile Asn
            180                 185                 190
```

<210> SEQ ID NO 29
<211> LENGTH: 146
<212> TYPE: PRT
<213> ORGANISM: Artificial Sequence
<220> FEATURE:
<223> OTHER INFORMATION: Pfs230

<400> SEQUENCE: 29

```
Met Ala Glu Tyr Val Asp Glu Lys Glu Arg Gln Gly Glu Ile Tyr Pro
1               5                   10                  15

Phe Gly Asp Glu Glu Lys Asp Glu Gly Gly Glu Ser Phe Thr Tyr
            20                  25                  30

Glu Lys Ser Glu Val Asp Lys Thr Asp Leu Phe Lys Phe Ile Glu Gly
        35                  40                  45

Gly Glu Gly Asp Asp Val Tyr Lys Val Asp Gly Ser Lys Val Leu Leu
    50                  55                  60

Asp Asp Asp Thr Ile Ser Arg Val Ser Lys Lys His Thr Ala Arg Asp
65                  70                  75                  80

Gly Glu Tyr Gly Glu Tyr Gly Glu Ala Val Glu Asp Gly Glu Asn Val
                85                  90                  95

Ile Lys Ile Ile Arg Ser Val Leu Gln Ser Gly Ala Leu Pro Ser Val
            100                 105                 110

Gly Val Asp Glu Leu Asp Lys Ile Asp Leu Ser Tyr Glu Thr Thr Glu
```

```
                 115                 120                 125
Ser Gly Asp Thr Ala Val Ser Glu Asp Ser Tyr Asp Lys Tyr Ala Ser
        130                 135                 140

Asn Asn
145

<210> SEQ ID NO 30
<211> LENGTH: 158
<212> TYPE: PRT
<213> ORGANISM: Artificial Sequence
<220> FEATURE:
<223> OTHER INFORMATION: CelTos

<400> SEQUENCE: 30

Phe Arg Gly Asn Asn Gly His Asp Ser Ser Ser Leu Tyr Gly Gly
1               5                   10                  15

Ser Gln Phe Ile Glu Gln Leu Asp Asn Ser Phe Thr Ser Ala Phe Leu
            20                  25                  30

Glu Ser Gln Ser Met Asn Lys Ile Gly Asp Asp Leu Ala Glu Thr Ile
        35                  40                  45

Ser Asn Glu Leu Val Ser Val Leu Gln Lys Asn Ser Pro Thr Phe Leu
    50                  55                  60

Glu Ser Ser Phe Asp Ile Lys Ser Glu Val Lys Lys His Ala Lys Ser
65                  70                  75                  80

Met Leu Lys Glu Leu Ile Lys Val Gly Leu Pro Ser Phe Glu Asn Leu
                85                  90                  95

Val Ala Glu Asn Val Lys Pro Pro Lys Val Asp Pro Ala Thr Tyr Gly
            100                 105                 110

Ile Ile Val Pro Val Leu Thr Ser Leu Phe Asn Lys Val Glu Thr Ala
        115                 120                 125

Val Gly Ala Lys Val Ser Asp Glu Ile Trp Asn Tyr Asn Ser Pro Asp
    130                 135                 140

Val Ser Glu Ser Glu Glu Ser Leu Ser Asp Asp Phe Phe Asp
145                 150                 155

<210> SEQ ID NO 31
<211> LENGTH: 48
<212> TYPE: PRT
<213> ORGANISM: Artificial Sequence
<220> FEATURE:
<223> OTHER INFORMATION: Ron2L

<400> SEQUENCE: 31

Met Asp Ile Thr Gln Gln Ala Lys Asp Ile Gly Ala Gly Pro Val Ala
1               5                   10                  15

Ser Cys Phe Thr Thr Arg Met Ser Pro Pro Gln Gln Ile Cys Leu Asn
            20                  25                  30

Ser Val Val Asn Thr Ala Leu Ser Thr Ser Thr Gln Ser Ala Met Lys
        35                  40                  45

<210> SEQ ID NO 32
<211> LENGTH: 118
<212> TYPE: PRT
<213> ORGANISM: Artificial Sequence
<220> FEATURE:
<223> OTHER INFORMATION: EXP1

<400> SEQUENCE: 32

Glu Lys Thr Asn Lys Gly Thr Gly Ser Gly Val Ser Ser Lys Lys Lys
1               5                   10                  15
```

-continued

Asn Lys Lys Gly Ser Gly Glu Pro Leu Ile Asp Val His Asp Leu Ile
            20                  25                  30

Ser Asp Met Ile Lys Lys Glu Glu Leu Val Glu Val Asn Lys Arg
            35                  40                  45

Lys Ser Lys Tyr Lys Leu Ala Thr Ser Asn Thr Glu Lys Gly Arg His
 50                  55                  60

Pro Phe Lys Ile Gly Ser Ser Asp Pro Ala Asp Asn Ala Asn Pro Asp
65                  70                  75                  80

Ala Asp Ser Glu Ser Asn Gly Glu Pro Asn Ala Gly Pro Gln Val Thr
                85                  90                  95

Ala Gln Asp Val Thr Pro Glu Gln Pro Gln Gly Asp Asp Asn Asn Leu
            100                 105                 110

Val Ser Gly Thr Glu His
            115

<210> SEQ ID NO 33
<211> LENGTH: 132
<212> TYPE: PRT
<213> ORGANISM: Artificial Sequence
<220> FEATURE:
<223> OTHER INFORMATION: MSP3a

<400> SEQUENCE: 33

Lys Glu Ile Val Lys Lys Tyr Asn Leu Asn Leu Arg Asn Ala Ile Leu
1               5                   10                  15

Asn Asn Asn Ala Gln Ile Glu Asn Glu Asn Val Asn Thr Ala Ile
            20                  25                  30

Thr Gly Asn Asp Phe Ser Gly Gly Glu Phe Leu Trp Pro Gly Tyr Thr
            35                  40                  45

Glu Glu Leu Lys Ala Lys Lys Ala Ser Glu Asp Ala Glu Lys Ala Ala
 50                  55                  60

Asn Asp Ala Glu Asn Ala Ala Lys Glu Ala Glu Ala Ala Lys Glu
65                  70                  75                  80

Ala Val Asn Leu Lys Glu Ser Asp Lys Ser Tyr Thr Lys Ala Lys Glu
                85                  90                  95

Ala Ala Thr Ala Ala Ser Lys Ala Lys Lys Ala Val Glu Thr Ala Leu
            100                 105                 110

Lys Ala Lys Asp Asp Ala Glu Lys Ser Ser Lys Ala Asp Ser Ile Ser
            115                 120                 125

Thr Lys Thr Lys
     130

<210> SEQ ID NO 34
<211> LENGTH: 400
<212> TYPE: PRT
<213> ORGANISM: Artificial Sequence
<220> FEATURE:
<223> OTHER INFORMATION: Pfs4845

<400> SEQUENCE: 34

Asn Asn Asp Phe Cys Lys Pro Ser Ser Leu Asn Ser Glu Ile Ser Gly
1               5                   10                  15

Phe Ile Gly Tyr Lys Cys Asn Phe Ser Asn Glu Gly Val His Asn Leu
            20                  25                  30

Lys Pro Asp Met Arg Glu Arg Arg Ser Ile Phe Cys Thr Ile His Ser
            35                  40                  45

Tyr Phe Ile Tyr Asp Lys Ile Arg Leu Ile Ile Pro Lys Lys Ser Ser

```
            50                  55                  60
Ser Pro Glu Phe Lys Ile Leu Pro Glu Lys Cys Phe Gln Lys Val Tyr
 65                  70                  75                  80

Thr Asp Tyr Glu Asn Arg Val Glu Thr Asp Ile Ser Glu Leu Gly Leu
                 85                  90                  95

Ile Glu Tyr Glu Ile Glu Asn Asp Thr Asn Pro Asn Tyr Asn Glu
                100                 105                 110

Arg Thr Ile Thr Ile Ser Pro Phe Ser Pro Lys Asp Ile Glu Phe Phe
                115                 120                 125

Cys Phe Cys Asp Asn Thr Glu Lys Val Ile Ser Ser Ile Gly Arg
                130                 135                 140

Ser Ala Met Val His Val Arg Val Leu Lys Tyr Pro His Asn Ile Leu
145                 150                 155                 160

Phe Thr Asn Leu Thr Asn Asp Leu Phe Thr Tyr Leu Pro Lys Thr Tyr
                165                 170                 175

Asn Glu Ser Asn Phe Val Ser Asn Val Leu Glu Val Glu Leu Asn Asp
                180                 185                 190

Gly Glu Leu Phe Val Leu Ala Cys Glu Leu Ile Asn Lys Lys Cys Phe
                195                 200                 205

Gln Glu Gly Lys Glu Lys Ala Leu Tyr Lys Ser Asn Lys Ile Ile Tyr
210                 215                 220

His Lys Asn Leu Thr Ile Phe Lys Ala Pro Phe Tyr Val Thr Ser Lys
225                 230                 235                 240

Asp Val Asn Thr Glu Cys Thr Cys Lys Phe Lys Asn Asn Tyr Lys
                245                 250                 255

Ile Val Leu Lys Pro Lys Tyr Glu Lys Lys Val Ile His Gly Cys Asn
                260                 265                 270

Phe Ser Ser Asn Val Ser Ser Lys His Thr Phe Thr Asp Ser Leu Asp
                275                 280                 285

Ile Ser Leu Val Asp Asp Ser Ala His Ile Ser Cys Asn Val His Leu
                290                 295                 300

Ser Glu Pro Lys Tyr Asn His Leu Val Gly Leu Asn Cys Pro Gly Asp
305                 310                 315                 320

Ile Ile Pro Asp Cys Phe Phe Gln Val Tyr Gln Pro Glu Ser Glu Glu
                325                 330                 335

Leu Glu Pro Ser Asn Ile Val Tyr Leu Asp Ser Gln Ile Asn Ile Gly
                340                 345                 350

Asp Ile Glu Tyr Tyr Glu Asp Ala Glu Gly Asp Asp Lys Ile Lys Leu
                355                 360                 365

Phe Gly Ile Val Gly Ser Ile Pro Lys Thr Thr Ser Phe Thr Cys Ile
                370                 375                 380

Cys Lys Lys Asp Lys Lys Ser Ala Tyr Met Thr Val Thr Ile Asp Ser
385                 390                 395                 400

<210> SEQ ID NO 35
<211> LENGTH: 41
<212> TYPE: PRT
<213> ORGANISM: Artificial Sequence
<220> FEATURE:
<223> OTHER INFORMATION: MSP1-19

<400> SEQUENCE: 35

Ser Ser Glu His Thr Cys Ile Asp Thr Asn Val Pro Asp Asn Ala Ala
 1               5                  10                  15

Cys Tyr Arg Tyr Leu Asp Gly Thr Glu Glu Trp Arg Cys Leu Leu Thr
```

```
                    20                  25                  30

Phe Lys Glu Glu Gly Gly Lys Cys Val
        35                  40

<210> SEQ ID NO 36
<211> LENGTH: 46
<212> TYPE: PRT
<213> ORGANISM: Artificial Sequence
<220> FEATURE:
<223> OTHER INFORMATION: MSP-8

<400> SEQUENCE: 36

Gln Lys Asn Asn Val Cys Glu His Lys Lys Cys Pro Leu Asn Ser Asn
1               5                   10                  15

Cys Tyr Val Ile Asn Gly Glu Glu Val Cys Arg Cys Leu Pro Gly Phe
            20                  25                  30

Ser Asp Val Lys Ile Asp Asn Val Met Asn Cys Val Arg Asp
        35                  40                  45

<210> SEQ ID NO 37
<211> LENGTH: 44
<212> TYPE: PRT
<213> ORGANISM: Artificial Sequence
<220> FEATURE:
<223> OTHER INFORMATION: MSP-8

<400> SEQUENCE: 37

Asp Asp Thr Leu Asp Cys Ser Asn Asn Gly Gly Cys Asp Val Asn
1               5                   10                  15

Ala Thr Cys Thr Leu Ile Asp Lys Lys Ile Val Cys Glu Cys Lys Asp
            20                  25                  30

Asn Phe Glu Gly Asp Gly Ile Tyr Cys Ser Tyr Ser
        35                  40

<210> SEQ ID NO 38
<211> LENGTH: 48
<212> TYPE: PRT
<213> ORGANISM: Artificial Sequence
<220> FEATURE:
<223> OTHER INFORMATION: MSP-4

<400> SEQUENCE: 38

Val Asp Glu Asn Ala Asn Leu Cys Leu Asp Asn Asn Gly Gly Cys Gly
1               5                   10                  15

Asp Asp Lys Ile Cys Glu Asn Leu Gly Lys Gly Ile Val Lys Cys Leu
            20                  25                  30

Cys Lys Pro Gly Tyr Lys Leu Val Gly Thr Glu Cys Val Glu Ser Ser
        35                  40                  45

<210> SEQ ID NO 39
<211> LENGTH: 42
<212> TYPE: PRT
<213> ORGANISM: Artificial Sequence
<220> FEATURE:
<223> OTHER INFORMATION: MSP-5

<400> SEQUENCE: 39

Asn Ala Lys Ser Cys Ser Val Asp Asn Gly Gly Cys Ala Asp Asp Gln
1               5                   10                  15

Ile Cys Ile Arg Ile Asp Asn Ile Gly Ile Lys Cys Ile Cys Lys Glu
            20                  25                  30

Gly His Leu Phe Gly Asp Lys Cys Ile Leu
```

<210> SEQ ID NO 40
<211> LENGTH: 45
<212> TYPE: PRT
<213> ORGANISM: Artificial Sequence
<220> FEATURE:
<223> OTHER INFORMATION: MSP-10

<400> SEQUENCE: 40

Val Asn His Ile Cys Glu Tyr Ser Lys Cys Gly Ala Asn Ala Arg Cys
1               5                   10                  15

Tyr Ile Val Glu Lys Asp Lys Glu Cys Arg Cys Arg Ala Asn Tyr
            20                  25                  30

Met Pro Asp Asp Ser Val Asp Tyr Phe Lys Cys Ile Pro
        35                  40                  45

<210> SEQ ID NO 41
<211> LENGTH: 43
<212> TYPE: PRT
<213> ORGANISM: Artificial Sequence
<220> FEATURE:
<223> OTHER INFORMATION: MSP-10

<400> SEQUENCE: 41

Val Glu Lys Asp Cys Ser Lys Glu Asn Gly Asn Cys Asp Val Asn Ala
1               5                   10                  15

Glu Cys Ser Ile Asp Lys Asn Lys Asp Ile Lys Cys Gln Cys Lys Phe
            20                  25                  30

Asn Tyr Ile Gly Asp Gly Ile Phe Cys Val Met
        35                  40

<210> SEQ ID NO 42
<211> LENGTH: 35
<212> TYPE: PRT
<213> ORGANISM: Artificial Sequence
<220> FEATURE:
<223> OTHER INFORMATION: PfRipr

<400> SEQUENCE: 42

Thr Cys Asn Ser Arg Val Cys Ser Val Asn Gln Phe Cys Asp Glu Ala
1               5                   10                  15

Thr Glu Ser Cys Val Cys Lys Thr Ser Leu Leu Pro Val Glu Lys Thr
            20                  25                  30

His Cys Leu
        35

<210> SEQ ID NO 43
<211> LENGTH: 38
<212> TYPE: PRT
<213> ORGANISM: Artificial Sequence
<220> FEATURE:
<223> OTHER INFORMATION: PfRipr

<400> SEQUENCE: 43

Val Cys Asp Ala Ile Lys Cys Pro Glu Asp Ala Thr Cys Val Val Glu
1               5                   10                  15

Arg Asn Ser Lys Lys Ala Glu Cys Arg Cys Asp Glu Gly Lys Tyr Leu
            20                  25                  30

His Lys Asn Glu Cys Tyr
        35

<210> SEQ ID NO 44
<211> LENGTH: 40
<212> TYPE: PRT
<213> ORGANISM: Artificial Sequence
<220> FEATURE:
<223> OTHER INFORMATION: PfRipr

<400> SEQUENCE: 44

```
Thr Cys Glu Asp Leu Cys Lys Thr Cys Gly Pro Asn Ser Ser Cys Tyr
1               5                   10                  15

Gly Asn Lys Tyr Lys His Lys Cys Leu Cys Asn Ser Pro Phe Glu Ser
            20                  25                  30

Lys Lys Asn His Ser Ile Cys Glu
        35                  40
```

<210> SEQ ID NO 45
<211> LENGTH: 36
<212> TYPE: PRT
<213> ORGANISM: Artificial Sequence
<220> FEATURE:
<223> OTHER INFORMATION: PfRipr

<400> SEQUENCE: 45

```
Ser Cys Asp Ala Gln Val Cys Gly Lys Asn Gln Ile Cys Lys Met Val
1               5                   10                  15

Asp Ala Lys Ala Thr Cys Thr Cys Ala Asp Lys Tyr Gln Asn Val Asn
            20                  25                  30

Gly Val Cys Leu
        35
```

<210> SEQ ID NO 46
<211> LENGTH: 35
<212> TYPE: PRT
<213> ORGANISM: Artificial Sequence
<220> FEATURE:
<223> OTHER INFORMATION: PfRipr

<400> SEQUENCE: 46

```
Lys Cys Asp Leu Leu Cys Pro Ser Asn Lys Ser Cys Leu Leu Glu Asn
1               5                   10                  15

Gly Lys Lys Ile Cys Lys Cys Ile Asn Gly Leu Thr Leu Gln Asn Gly
            20                  25                  30

Glu Cys Val
        35
```

<210> SEQ ID NO 47
<211> LENGTH: 44
<212> TYPE: PRT
<213> ORGANISM: Artificial Sequence
<220> FEATURE:
<223> OTHER INFORMATION: PfRipr

<400> SEQUENCE: 47

```
Lys Cys Lys Arg Lys Glu Tyr Gln Gln Leu Cys Thr Asn Glu Lys Glu
1               5                   10                  15

His Cys Val Tyr Asp Glu Gln Thr Asp Ile Val Arg Cys Asp Cys Val
            20                  25                  30

Asp His Phe Lys Arg Asn Glu Arg Gly Ile Cys Ile
        35                  40
```

<210> SEQ ID NO 48
<211> LENGTH: 44
<212> TYPE: PRT

<213> ORGANISM: Artificial Sequence
<220> FEATURE:
<223> OTHER INFORMATION: PfRipr

<400> SEQUENCE: 48

Gly Ile Cys Ile Pro Val Asp Tyr Cys Lys Asn Val Thr Cys Lys Glu
1               5                   10                  15

Asn Glu Ile Cys Lys Val Val Asn Asn Thr Pro Thr Cys Glu Cys Lys
            20                  25                  30

Glu Asn Leu Lys Arg Asn Ser Asn Glu Cys Val
        35                  40

<210> SEQ ID NO 49
<211> LENGTH: 40
<212> TYPE: PRT
<213> ORGANISM: Artificial Sequence
<220> FEATURE:
<223> OTHER INFORMATION: PfRipr

<400> SEQUENCE: 49

Met Cys Leu Val Asn Lys Gly Asn Cys Pro Ile Asp Ser Glu Cys Ile
1               5                   10                  15

Tyr His Glu Lys Lys Arg His Gln Cys Leu Cys His Lys Lys Gly Leu
            20                  25                  30

Val Ala Ile Asn Gly Lys Cys Val
        35                  40

<210> SEQ ID NO 50
<211> LENGTH: 47
<212> TYPE: PRT
<213> ORGANISM: Artificial Sequence
<220> FEATURE:
<223> OTHER INFORMATION: PfRipr

<400> SEQUENCE: 50

Met Cys Arg Ser Asp Gln Asn Lys Cys Ser Glu Asn Ser Ile Cys Val
1               5                   10                  15

Asn Gln Val Asn Lys Glu Pro Leu Cys Ile Cys Leu Phe Asn Tyr Val
            20                  25                  30

Lys Ser Arg Ser Gly Asp Ser Pro Glu Gly Gly Gln Thr Cys Val
        35                  40                  45

<210> SEQ ID NO 51
<211> LENGTH: 69
<212> TYPE: PRT
<213> ORGANISM: Artificial Sequence
<220> FEATURE:
<223> OTHER INFORMATION: PfRipr

<400> SEQUENCE: 51

Pro Cys Leu Ala His Asn Gly Gly Cys Ser Pro Asn Glu Val Cys Thr
1               5                   10                  15

Phe Lys Asn Gly Lys Val Ser Cys Ala Cys Gly Glu Asn Tyr Arg Pro
            20                  25                  30

Arg Gly Lys Asp Ser Pro Thr Gly Gln Ala Val Lys Arg Gly Glu Ala
        35                  40                  45

Thr Lys Arg Gly Asp Ala Gly Gln Pro Gly Gln Ala His Ser Ala Asn
    50                  55                  60

Glu Asn Ala Cys Leu
65

<210> SEQ ID NO 52
<211> LENGTH: 173
<212> TYPE: PRT
<213> ORGANISM: Artificial Sequence
<220> FEATURE:
<223> OTHER INFORMATION: Pvs25

<400> SEQUENCE: 52

```
Val Thr Val Asp Thr Ile Cys Lys Asn Gly Gln Leu Val Gln Met Ser
1               5                   10                  15

Asn His Phe Lys Cys Met Cys Asn Glu Gly Leu Val His Leu Ser Glu
            20                  25                  30

Asn Thr Cys Glu Glu Lys Asn Glu Cys Lys Lys Glu Thr Leu Gly Lys
        35                  40                  45

Ala Cys Gly Glu Phe Gly Gln Cys Ile Glu Asn Pro Asp Pro Ala Gln
    50                  55                  60

Val Asn Met Tyr Lys Cys Gly Cys Ile Glu Gly Tyr Thr Leu Lys Glu
65                  70                  75                  80

Asp Thr Cys Val Leu Asp Val Cys Gln Tyr Lys Asn Cys Gly Glu Ser
                85                  90                  95

Gly Glu Cys Ile Val Glu Tyr Leu Ser Glu Ile Gln Ser Ala Gly Cys
            100                 105                 110

Ser Cys Ala Ile Gly Lys Val Pro Asn Pro Glu Asp Glu Lys Lys Cys
        115                 120                 125

Thr Lys Thr Gly Glu Thr Ala Cys Gln Leu Lys Cys Asn Thr Asp Asn
    130                 135                 140

Glu Val Cys Lys Asn Val Glu Gly Val Tyr Lys Cys Gln Cys Met Glu
145                 150                 155                 160

Gly Phe Thr Phe Asp Lys Glu Lys Asn Val Cys Leu Ser
                165                 170
```

<210> SEQ ID NO 53
<211> LENGTH: 72
<212> TYPE: PRT
<213> ORGANISM: Artificial Sequence
<220> FEATURE:
<223> OTHER INFORMATION: fullCSP

<400> SEQUENCE: 53

```
Pro Asn Glu Lys Ser Val Lys Glu Tyr Leu Asp Lys Val Arg Ala Thr
1               5                   10                  15

Val Gly Thr Glu Trp Thr Pro Cys Ser Val Thr Cys Gly Val Gly Val
            20                  25                  30

Arg Val Arg Arg Arg Val Asn Ala Ala Asn Lys Lys Pro Glu Asp Leu
        35                  40                  45

Thr Leu Asn Asp Leu Glu Thr Asp Val Cys Thr Met Asp Lys Cys Ala
    50                  55                  60

Gly Ile Phe Asn Val Val Ser Asn
65                  70
```

<210> SEQ ID NO 54
<211> LENGTH: 65
<212> TYPE: PRT
<213> ORGANISM: Artificial Sequence
<220> FEATURE:
<223> OTHER INFORMATION: shortCSP

<400> SEQUENCE: 54

```
Tyr Leu Asp Lys Val Arg Ala Thr Val Gly Thr Glu Trp Thr Pro Cys
1               5                   10                  15
```

```
Ser Val Thr Cys Gly Val Gly Val Arg Val Arg Arg Val Asn Ala
            20                  25                  30

Ala Asn Lys Lys Pro Glu Asp Leu Thr Leu Asn Asp Leu Glu Thr Asp
         35                  40                  45

Val Cys Thr Met Asp Lys Cys Ala Gly Ile Phe Asn Val Val Ser Asn
 50                  55                  60

Ser
65

<210> SEQ ID NO 55
<211> LENGTH: 74
<212> TYPE: PRT
<213> ORGANISM: Artificial Sequence
<220> FEATURE:
<223> OTHER INFORMATION: mTRAP

<400> SEQUENCE: 55

Ile Gly Lys Arg Lys Cys Glu Gln Trp Asp Ser Trp Ser Ala Cys Lys
 1               5                  10                  15

Asp Gly Ile Ser Thr Arg Val Cys Leu Thr Asn Lys Ser Val Thr Asp
            20                  25                  30

Lys Met Thr Cys Lys Ala Cys Asn Ile Trp Gly Asp Trp Ser Ala Cys
         35                  40                  45

Lys Asn Gly Lys Arg His Arg Lys Val Val Asn Cys Pro Phe Ile Arg
 50                  55                  60

Glu Glu Gln Asp Cys Asp Pro Asn Lys Ser
65                  70

<210> SEQ ID NO 56
<211> LENGTH: 51
<212> TYPE: PRT
<213> ORGANISM: Artificial Sequence
<220> FEATURE:
<223> OTHER INFORMATION: TRAP

<400> SEQUENCE: 56

Glu Arg Val Ala Asn Cys Gly Pro Trp Asp Pro Trp Thr Ala Cys Ser
 1               5                  10                  15

Val Thr Cys Gly Arg Gly Thr His Ser Arg Ser Arg Pro Ser Leu His
            20                  25                  30

Glu Lys Cys Thr Thr His Met Val Ser Glu Cys Glu Gly Glu Cys
         35                  40                  45

Pro Val Glu
    50

<210> SEQ ID NO 57
<211> LENGTH: 66
<212> TYPE: PRT
<213> ORGANISM: Artificial Sequence
<220> FEATURE:
<223> OTHER INFORMATION: TRAMP

<400> SEQUENCE: 57

Phe Tyr Thr Glu Trp Gly Glu Trp Ser Gln Cys Ser Met Glu Cys Asp
 1               5                  10                  15

His Pro Asp Asn Val Gln Ile Arg Glu Arg Lys Cys Ala Asp Pro Ser
            20                  25                  30

Gly Asn Cys Phe Lys Gly Asp Leu Lys Glu Thr Arg Pro Cys Gln Val
         35                  40                  45
```

Pro Leu Pro Pro Cys Asn Ser Leu Phe Glu His Lys Glu Ser Ser Thr
            50                  55                  60

Phe Lys
65

<210> SEQ ID NO 58
<211> LENGTH: 297
<212> TYPE: PRT
<213> ORGANISM: Artificial Sequence
<220> FEATURE:
<223> OTHER INFORMATION: EBA175

<400> SEQUENCE: 58

Lys Asn Cys Asn Tyr Lys Arg Lys Arg Glu Arg Asp Trp Asp Cys
1               5                   10                  15

Asn Thr Lys Lys Asp Val Cys Ile Pro Asp Arg Arg Tyr Gln Leu Cys
            20                  25                  30

Met Lys Glu Leu Thr Asn Leu Val Asn Asn Thr Asp Thr Asn Phe His
            35                  40                  45

Arg Asp Ile Thr Phe Arg Lys Leu Tyr Leu Lys Arg Lys Leu Ile Tyr
    50                  55                  60

Asp Ala Ala Val Glu Gly Asp Leu Leu Leu Lys Leu Asn Asn Tyr Arg
65                  70                  75                  80

Tyr Asn Lys Asp Phe Cys Lys Asp Ile Arg Trp Ser Leu Gly Asp Phe
                85                  90                  95

Gly Asp Ile Ile Met Gly Thr Asp Met Glu Gly Ile Gly Tyr Ser Lys
                100                 105                 110

Val Val Glu Asn Asn Leu Arg Ser Ile Phe Gly Thr Asp Glu Lys Ala
            115                 120                 125

Gln Gln Arg Arg Lys Gln Trp Trp Asn Glu Ser Lys Ala Gln Ile Trp
    130                 135                 140

Thr Ala Met Met Tyr Ser Val Lys Lys Arg Leu Lys Gly Asn Phe Ile
145                 150                 155                 160

Trp Ile Cys Lys Leu Asn Val Ala Val Asn Ile Glu Pro Gln Ile Tyr
                165                 170                 175

Arg Trp Ile Arg Glu Trp Gly Arg Asp Tyr Val Ser Glu Leu Pro Thr
            180                 185                 190

Glu Val Gln Lys Leu Lys Glu Lys Cys Asp Gly Lys Ile Asn Tyr Thr
        195                 200                 205

Asp Lys Lys Val Cys Lys Val Pro Pro Cys Gln Asn Ala Cys Lys Ser
    210                 215                 220

Tyr Asp Gln Trp Ile Thr Arg Lys Lys Asn Gln Trp Asp Val Leu Ser
225                 230                 235                 240

Asn Lys Phe Ile Ser Val Lys Asn Ala Glu Lys Val Gln Thr Ala Gly
                245                 250                 255

Ile Val Thr Pro Tyr Asp Ile Leu Lys Gln Glu Leu Asp Glu Phe Asn
            260                 265                 270

Glu Val Ala Phe Glu Asn Glu Ile Asn Lys Arg Asp Gly Ala Tyr Ile
        275                 280                 285

Glu Leu Cys Val Cys Ser Val Glu Glu
    290                 295

<210> SEQ ID NO 59
<211> LENGTH: 96
<212> TYPE: PRT
<213> ORGANISM: Artificial Sequence
<220> FEATURE:

<223> OTHER INFORMATION: EBA140

<400> SEQUENCE: 59

Glu Arg Trp Leu Gln Gly Thr Asn Glu Arg Ser Glu Glu Asn Ile
1               5                   10                  15

Lys Tyr Lys Tyr Val Thr Glu Leu Lys Ile Lys Tyr Ala Gln Met Asn
            20                  25                  30

Gly Lys Arg Ser Ser Arg Ile Leu Lys Glu Ser Ile Tyr Gly Ala His
        35                  40                  45

Asn Phe Gly Gly Asn Ser Tyr Met Glu Gly Lys Asp Gly Asp Lys
    50                  55                  60

Thr Gly Glu Glu Lys Asp Gly Gly Glu His Lys Thr Asp Ser Lys Thr
65                  70                  75                  80

Asp Asn Gly Lys Gly Ala Asn Asn Leu Val Met Leu Asp Tyr Glu Thr
                85                  90                  95

<210> SEQ ID NO 60
<211> LENGTH: 135
<212> TYPE: PRT
<213> ORGANISM: Artificial Sequence
<220> FEATURE:
<223> OTHER INFORMATION: EBA140

<400> SEQUENCE: 60

Met Tyr Ser Val Lys Lys Arg Leu Lys Gly Asn Phe Ile Trp Ile Cys
1               5                   10                  15

Lys Leu Asn Val Ala Val Asn Ile Glu Pro Gln Ile Tyr Arg Trp Ile
            20                  25                  30

Arg Glu Trp Gly Arg Asp Tyr Val Ser Glu Leu Pro Thr Glu Val Gln
        35                  40                  45

Lys Leu Lys Glu Lys Cys Asp Gly Lys Ile Asn Tyr Thr Asp Lys Lys
    50                  55                  60

Val Cys Lys Val Pro Pro Cys Gln Asn Ala Cys Lys Ser Tyr Asp Gln
65                  70                  75                  80

Trp Ile Thr Arg Lys Lys Asn Gln Trp Asp Val Leu Ser Asn Lys Phe
                85                  90                  95

Ile Ser Val Lys Asn Ala Glu Lys Val Gln Thr Ala Gly Ile Val Thr
            100                 105                 110

Pro Tyr Asp Ile Leu Lys Gln Glu Leu Asp Glu Phe Asn Glu Val Ala
        115                 120                 125

Phe Glu Asn Glu Ile Asn Lys
    130                 135

<210> SEQ ID NO 61
<211> LENGTH: 65
<212> TYPE: PRT
<213> ORGANISM: Artificial Sequence
<220> FEATURE:
<223> OTHER INFORMATION: EBL1

<400> SEQUENCE: 61

Asp Phe Cys Lys Asp Ile Arg Trp Ser Leu Gly Asp Phe Gly Asp Ile
1               5                   10                  15

Ile Met Gly Thr Asp Met Glu Gly Ile Gly Tyr Ser Lys Val Val Glu
            20                  25                  30

Asn Asn Leu Arg Ser Ile Phe Gly Thr Asp Glu Lys Ala Gln Gln Arg
        35                  40                  45

Arg Lys Gln Trp Trp Asn Glu Ser Lys Ala Gln Ile Trp Thr Ala Met

Met
65

<210> SEQ ID NO 62
<211> LENGTH: 324
<212> TYPE: PRT
<213> ORGANISM: Artificial Sequence
<220> FEATURE:
<223> OTHER INFORMATION: GAMA

<400> SEQUENCE: 62

Lys Asp Val Ala Val Leu Val Arg Asp Leu Leu Lys Asn Thr Asn Ile
1               5                   10                  15

Ile Lys Phe Glu Asn Asn Glu Pro Thr Ser Gln Met Asp Asp Glu Glu
            20                  25                  30

Ile Lys Lys Leu Ile Glu Ser Ser Phe Phe Asp Leu Ser Asp Asn Thr
        35                  40                  45

Met Leu Met Arg Leu Leu Ile Lys Pro Gln Ala Ala Ile Leu Leu Ile
50                  55                  60

Ile Glu Ser Phe Ile Met Met Thr Pro Ser Pro Thr Arg Asp Ala Lys
65                  70                  75                  80

Thr Tyr Cys Lys Lys Ala Leu Val Asn Gly Gln Leu Ile Glu Thr Ser
                85                  90                  95

Asp Leu Asn Ala Ala Thr Glu Glu Asp Asp Leu Ile Asn Glu Phe Ser
            100                 105                 110

Ser Arg Tyr Asn Leu Phe Tyr Glu Arg Leu Lys Leu Glu Glu Leu Arg
        115                 120                 125

Glu Ile Glu Gln Asn Arg Lys Ala Leu Lys Asn Ser Lys Gly Thr Leu
130                 135                 140

Ser Val Leu Glu Val Ala Asn Ser Gln Asn Ala Pro Asp Gly Lys Gly
145                 150                 155                 160

Val Asn Gly Ser Gly Asn Ala Ala Asn Ala Ala Asn Ala Asn Ala Asn
                165                 170                 175

Ala Ala Asn Ala Asn Ala Asn Ala Asn Ala Asn Gly Asn Leu
            180                 185                 190

Ala Asn Ala Asn Leu Ala Asn Ala Asn Ala Asn Ala Asp Ala Ala
        195                 200                 205

Asn Ala Asn Ala Asn Ala Asn Ala Asn Ala Asn Ala Ala Asn
210                 215                 220

Ala Asn Leu Ala Asn Ala Asn Leu Ala Asn Ala Asn Leu Ala Asn Ala
225                 230                 235                 240

Asn Leu Ala Asn Ala Asn Leu Ala Asn Ala Asn Leu Ala Asn Ala Asn
                245                 250                 255

Ala Ala Asn Ala Asn Ala Asn Ala Asn Ala Asn Gly Asn Ala
            260                 265                 270

Pro Asn Ser Asn Asn Gly Ser Gly Ser Pro Leu Ile Val Val Gly
        275                 280                 285

Ala Asp Leu Gly Glu Lys Thr Glu Asp Ile Ile Lys Asn Asn Val Asp
290                 295                 300

Val Ala Ala Leu Thr Ala Asp Val Glu Gln Ala Phe Lys Asn Leu Glu
305                 310                 315                 320

Leu Gln Ser Gly

<210> SEQ ID NO 63

```
<211> LENGTH: 150
<212> TYPE: PRT
<213> ORGANISM: Artificial Sequence
<220> FEATURE:
<223> OTHER INFORMATION: Pvs230

<400> SEQUENCE: 63

Leu Ala Glu Glu Asp Asp Gly Asp Asp Glu Asp Gly Asp Val Asp Asp
1               5                   10                  15

Asp Asp Gly Asn Asp Asp Gly Glu Gly Thr His Thr Gln Pro Gln Val
                20                  25                  30

Lys Gly Met Asp Asp Glu Asp Leu Glu Gly Pro Pro Gly Glu Asp Asp
            35                  40                  45

Cys Phe Val Leu Pro Glu Ala Gly Ala Ser Asp Gly Val Phe Asp Lys
        50                  55                  60

Val Asp Glu Ala Phe Glu Thr Thr Ile Lys Gly Asp Gly Asn Val Leu
65                  70                  75                  80

Gln Ala Ser Asp Pro Glu Val Glu Thr Phe Ala Ser Ser Asn Thr Asn
                85                  90                  95

Lys Glu Tyr Val Cys Asp Phe Val Lys His Ile Thr Met Lys Glu Ala
            100                 105                 110

Ser Lys Lys Val Val Ile Cys Glu Met Lys Ile Gln Glu Pro Leu Val
        115                 120                 125

Lys Val Lys Ile Leu Cys Pro Thr Lys Tyr Ala Asp Val Ile Lys Tyr
130                 135                 140

Gly Ser Met Glu Phe Phe
145                 150

<210> SEQ ID NO 64
<211> LENGTH: 161
<212> TYPE: PRT
<213> ORGANISM: Artificial Sequence
<220> FEATURE:
<223> OTHER INFORMATION: CelTos

<400> SEQUENCE: 64

Leu Arg Gly Lys Ser Gly Ser Thr Ala Ser Ser Ser Leu Glu Gly Gly
1               5                   10                  15

Ser Glu Phe Ser Glu Arg Ile Gly Asn Ser Leu Ser Ser Phe Leu Ser
                20                  25                  30

Glu Ser Ala Ser Leu Glu Val Ile Gly Asn Glu Leu Ala Asp Asn Ile
            35                  40                  45

Ala Asn Glu Ile Val Ser Ser Leu Gln Lys Asp Ser Ala Ser Phe Leu
        50                  55                  60

Gln Ser Gly Phe Asp Val Lys Thr Gln Leu Lys Ala Thr Ala Lys Lys
65                  70                  75                  80

Val Leu Val Glu Ala Leu Lys Ala Ala Leu Glu Pro Thr Glu Lys Ile
                85                  90                  95

Val Ala Ser Thr Ile Lys Pro Pro Arg Val Ser Glu Ala Tyr Phe
            100                 105                 110

Leu Leu Gly Pro Val Val Lys Thr Leu Phe Asn Lys Val Glu Asp Val
        115                 120                 125

Leu His Lys Pro Ile Pro Asp Thr Ile Trp Glu Tyr Glu Ser Lys Gly
        130                 135                 140

Ser Leu Glu Glu Glu Glu Ala Glu Asp Glu Phe Ser Asp Glu Leu Leu
145                 150                 155                 160

Asp
```

-continued

```
<210> SEQ ID NO 65
<211> LENGTH: 48
<212> TYPE: PRT
<213> ORGANISM: Artificial Sequence
<220> FEATURE:
<223> OTHER INFORMATION: Exp1

<400> SEQUENCE: 65

Met Asp Ile Ser Gln His Ala Thr Asp Ile Gly Met Gly Pro Ala Thr
1               5                   10                  15

Ser Cys Tyr Thr Ser Thr Ile Pro Pro Lys Gln Val Cys Ile Gln
            20                  25                  30

Gln Ala Val Lys Ala Thr Leu Thr Ser Ser Thr Gln Ala Cys Met Lys
        35                  40                  45

<210> SEQ ID NO 66
<211> LENGTH: 118
<212> TYPE: PRT
<213> ORGANISM: Artificial Sequence
<220> FEATURE:
<223> OTHER INFORMATION: Exp1

<400> SEQUENCE: 66

Gly Asp Asn Val Asn Gly Leu Gly Ala Gly Asn Pro Lys Lys Lys Ser
1               5                   10                  15

Pro Lys Ser Lys Ser Pro Glu Pro Leu Ile Asp Val His Glu Leu Ile
            20                  25                  30

Ser Glu Ile Val Arg Lys Glu Glu Leu Val Asn Met Thr Lys Lys
        35                  40                  45

Lys Ser Asn Tyr Lys Leu Ala Thr Thr Val Leu Ala Ser Ala Leu Ser
    50                  55                  60

Ala Val Leu Leu Gly Gly Ala Asn Ala Gly Asn Gly Arg His Pro Phe
65                  70                  75                  80

Ser Leu Gly Gly Gly Lys Gly Gly Asp Ala Ala Pro Thr Glu Pro Thr
                85                  90                  95

Pro Ala Pro Thr Ala Pro Ser Ala Thr Gly Leu Asn Asp Asp Gly Ser
            100                 105                 110

Ser Ser Gly Thr Glu Ser
        115

<210> SEQ ID NO 67
<211> LENGTH: 409
<212> TYPE: PRT
<213> ORGANISM: Artificial Sequence
<220> FEATURE:
<223> OTHER INFORMATION: Pvs4845

<400> SEQUENCE: 67

His Thr Gln Met Ala Lys Gly Glu Val Lys Tyr Val Pro Pro Glu Glu
1               5                   10                  15

Leu Asn Lys Asp Val Ser Gly Phe Phe Gly Phe Lys Cys Asn Phe Ser
            20                  25                  30

Ser Lys Gly Val His Asn Leu Glu Pro Ile Leu Thr Glu Lys Arg Ser
        35                  40                  45

Leu Val Cys Ser Ile Tyr Ser Tyr Phe Ile Tyr Asp Lys Ile Lys Leu
    50                  55                  60

Thr Ile Pro Lys Lys Ile Pro Gly Ser Lys Phe Lys Met Leu Pro Glu
65                  70                  75                  80
```

Lys Cys Phe Gln Thr Val Tyr Thr Asn Tyr Glu Lys Arg Thr Glu Glu
                85                  90                  95

Lys Ile Glu Asn Met Gly Leu Val Glu Tyr Glu Val Lys Glu Asp Asp
            100                 105                 110

Ser Asn Ser Glu Tyr Thr Glu Lys Ile Leu Thr Ile Ser Pro Phe Asn
            115                 120                 125

Thr Lys Asp Val Glu Phe Phe Cys Ile Cys Asp Asn Ser Glu Asn Val
        130                 135                 140

Ile Ser Asn Val Lys Gly Arg Val Ala Leu Val Gln Val Asn Val Leu
145                 150                 155                 160

Lys Tyr Pro His Lys Ile Thr Ser Ile Asn Leu Thr Lys Glu Pro Tyr
                165                 170                 175

Ser Tyr Leu Pro Asn Gln Val Asp Lys Thr Ser Phe Lys Ser His Lys
            180                 185                 190

Leu Asp Leu Glu Leu Gln Asp Gly Glu Leu Val Val Leu Ala Cys Glu
        195                 200                 205

Lys Val Asp Asp Lys Cys Phe Lys Lys Gly Lys Asp Thr Ser Pro Leu
        210                 215                 220

Ser Leu Tyr Lys Ser Lys Lys Ile Val Tyr His Lys Asn Leu Ser Ile
225                 230                 235                 240

Phe Lys Ala Pro Val Tyr Val Lys Ser Ala Asp Val Thr Ala Glu Cys
                245                 250                 255

Ser Cys Asn Val Asp Ser Thr Ile Tyr Thr Leu Ser Leu Lys Pro Val
            260                 265                 270

Tyr Thr Lys Lys Leu Ile His Gly Cys Asn Phe Ser Ser Asp Lys Ser
        275                 280                 285

Thr His Asn Phe Thr Asn His Val Asp Met Ala Glu Leu Gly Glu Asn
        290                 295                 300

Ala Gln Ile Thr Cys Ser Ile Glu Leu Val Asp Thr Ser Tyr Asn His
305                 310                 315                 320

Leu Ile Gly Met Ser Cys Pro Gly Glu Val Leu Pro Glu Cys Phe Phe
                325                 330                 335

Gln Val Tyr Gln Arg Glu Ser Pro Glu Leu Glu Pro Ser Lys Ile Val
            340                 345                 350

Tyr Leu Asp Ala Gln Leu Asn Ile Gly Asn Val Glu Tyr Phe Glu Asp
        355                 360                 365

Ser Lys Gly Glu Asn Ile Val Lys Ile Phe Gly Leu Val Gly Ser Ile
        370                 375                 380

Pro Lys Thr Thr Ser Phe Thr Cys Ile Cys Arg Lys Gly Lys Lys Ile
385                 390                 395                 400

Gly Tyr Met Ser Val Lys Ile Ala Ala
                405

<210> SEQ ID NO 68
<211> LENGTH: 41
<212> TYPE: PRT
<213> ORGANISM: Artificial Sequence
<220> FEATURE:
<223> OTHER INFORMATION: MSP1-19

<400> SEQUENCE: 68

Ser Ser Ala His Lys Cys Ile Asp Thr Asn Val Pro Glu Asn Ala Ala
1               5                   10                  15

Cys Tyr Arg Tyr Leu Asp Gly Thr Glu Glu Trp Arg Cys Leu Leu Gly
            20                  25                  30

Phe Lys Glu Val Gly Gly Lys Cys Val
            35                  40

<210> SEQ ID NO 69
<211> LENGTH: 46
<212> TYPE: PRT
<213> ORGANISM: Artificial Sequence
<220> FEATURE:
<223> OTHER INFORMATION: MSP-8

<400> SEQUENCE: 69

Glu Lys Asn Asn Val Cys Glu His Lys Lys Cys Pro Leu Asn Ser Asn
1               5                   10                  15

Cys Tyr Val Ile Asp Gly Glu Glu Val Cys Arg Cys Leu Pro Gly Phe
                20                  25                  30

Ser Asp Val Lys Ile Asp Asn Val Met Asn Cys Val Arg Asp
            35                  40                  45

<210> SEQ ID NO 70
<211> LENGTH: 44
<212> TYPE: PRT
<213> ORGANISM: Artificial Sequence
<220> FEATURE:
<223> OTHER INFORMATION: MSP-8

<400> SEQUENCE: 70

Asp Asp Thr Val Asp Cys Asn Asn Asn Gly Gly Cys Asp Val Asn
1               5                   10                  15

Ala Thr Cys Thr Leu Ile Asp Lys Lys Ile Val Cys Glu Cys Lys Asp
                20                  25                  30

Asn Phe Gln Gly Asp Gly Ile Tyr Cys Ser Tyr Ser
            35                  40

<210> SEQ ID NO 71
<211> LENGTH: 48
<212> TYPE: PRT
<213> ORGANISM: Artificial Sequence
<220> FEATURE:
<223> OTHER INFORMATION: MSP-4

<400> SEQUENCE: 71

Lys Asp His Asn Glu Asn Leu Cys Ser Glu Asn Asn Gly Gly Cys Gly
1               5                   10                  15

Asn Asp Lys Ile Cys Glu Asn Ile Gly Asp Gly Ile Val Lys Cys Leu
                20                  25                  30

Cys Lys Pro Gly Tyr Lys Leu Val Gly Thr Glu Cys Val Glu Ala Ser
            35                  40                  45

<210> SEQ ID NO 72
<211> LENGTH: 42
<212> TYPE: PRT
<213> ORGANISM: Artificial Sequence
<220> FEATURE:
<223> OTHER INFORMATION: MSP-5

<400> SEQUENCE: 72

Asn Thr Lys Ser Cys Ser Val Asn Asn Gly Gly Cys Ala Asp Gln
1               5                   10                  15

Ile Cys Ile Arg Ile Asn Asn Met Gly Ile Lys Cys Ile Cys Lys Glu
                20                  25                  30

Gly His Leu Phe Gly Gly Lys Cys Ile Leu
            35                  40

<210> SEQ ID NO 73
<211> LENGTH: 45
<212> TYPE: PRT
<213> ORGANISM: Artificial Sequence
<220> FEATURE:
<223> OTHER INFORMATION: MSP10

<400> SEQUENCE: 73

Val Asn His Ile Cys Glu Tyr Ser Lys Cys Gly Pro Asn Ala Arg Cys
1               5                   10                  15

Tyr Ile Val Glu Lys Asp Lys Glu Glu Cys Arg Cys Ile Ala Asn Tyr
            20                  25                  30

Met Pro Asp Asn Ser Val Asp Tyr Phe Lys Cys Ile Pro
        35                  40                  45

<210> SEQ ID NO 74
<211> LENGTH: 43
<212> TYPE: PRT
<213> ORGANISM: Artificial Sequence
<220> FEATURE:
<223> OTHER INFORMATION: MSP-10

<400> SEQUENCE: 74

Thr Val Lys Asp Cys Ser Lys Glu Asn Gly Asn Cys Asp Val Asn Ala
1               5                   10                  15

Glu Cys Ser Ile Asp Lys Lys Glu Asn Ile Lys Cys Gln Cys Asn His
            20                  25                  30

Gly Tyr Ile Gly Asp Gly Ile Phe Cys Val Leu
        35                  40

<210> SEQ ID NO 75
<211> LENGTH: 35
<212> TYPE: PRT
<213> ORGANISM: Artificial Sequence
<220> FEATURE:
<223> OTHER INFORMATION: PfRipr

<400> SEQUENCE: 75

Lys Cys Lys Ser Arg Ile Cys Ser Val Asn Glu Phe Cys Asp Glu Leu
1               5                   10                  15

Thr Glu Ser Cys Val Cys Lys Thr Ser Leu Leu Pro Val Glu Lys Thr
            20                  25                  30

Gln Cys Ser
        35

<210> SEQ ID NO 76
<211> LENGTH: 38
<212> TYPE: PRT
<213> ORGANISM: Artificial Sequence
<220> FEATURE:
<223> OTHER INFORMATION: PfRipr

<400> SEQUENCE: 76

Val Cys Asp Ala Ile Lys Cys Pro Thr Asn Ser Thr Cys Val Val Asp
1               5                   10                  15

Glu Asn Thr Lys Lys Gly Glu Cys Arg Cys Glu Asp Asp Lys Tyr Leu
            20                  25                  30

Tyr Lys Asn Lys Cys Tyr
        35

<210> SEQ ID NO 77
<211> LENGTH: 40

```
<212> TYPE: PRT
<213> ORGANISM: Artificial Sequence
<220> FEATURE:
<223> OTHER INFORMATION: PfRipr

<400> SEQUENCE: 77

Thr Cys Val Asp Leu Cys Thr Arg Cys Gly Pro Asn Ser Ser Cys Tyr
1               5                   10                  15

Gly Asn Lys His Lys Tyr Lys Cys Phe Cys Asn Ser Pro Tyr Val Asn
            20                  25                  30

Lys Asn Asn Ser Asn Cys Glu
        35                  40

<210> SEQ ID NO 78
<211> LENGTH: 36
<212> TYPE: PRT
<213> ORGANISM: Artificial Sequence
<220> FEATURE:
<223> OTHER INFORMATION: PfRipr

<400> SEQUENCE: 78

Thr Cys Asn Ser Gln Val Cys Gly Lys Asn Gln Thr Cys Lys Met Ile
1               5                   10                  15

Asn Asn Lys Pro Thr Cys Ile Cys Ala Asp Lys Tyr Gln Asp Val Asn
            20                  25                  30

Gly Val Cys Val
        35

<210> SEQ ID NO 79
<211> LENGTH: 35
<212> TYPE: PRT
<213> ORGANISM: Artificial Sequence
<220> FEATURE:
<223> OTHER INFORMATION: PfRipr

<400> SEQUENCE: 79

Lys Cys Asp Leu Leu Cys Pro Ser Asn Lys Ser Cys Leu Ile Glu Asn
1               5                   10                  15

Gly Lys Lys Ile Cys Lys Cys Ile Asn Gly Leu Thr Leu Glu Asn Gly
            20                  25                  30

Val Cys Ile
        35

<210> SEQ ID NO 80
<211> LENGTH: 44
<212> TYPE: PRT
<213> ORGANISM: Artificial Sequence
<220> FEATURE:
<223> OTHER INFORMATION: PfRipr

<400> SEQUENCE: 80

Lys Cys Lys Arg Lys Glu Tyr Gln Asn Ala Cys Thr Asn Glu Lys Glu
1               5                   10                  15

Gln Cys Val Tyr Asp Glu Gln Lys Asp Ile Val Arg Cys Asp Cys Val
            20                  25                  30

Asp His Phe Gln Arg Asn Asp Arg Gly Ile Cys Val
        35                  40

<210> SEQ ID NO 81
<211> LENGTH: 44
<212> TYPE: PRT
<213> ORGANISM: Artificial Sequence
<220> FEATURE:
```

<223> OTHER INFORMATION: PfRipr

<400> SEQUENCE: 81

Gly Ile Cys Val Pro Val Glu Tyr Cys Lys Asn Val Thr Cys Lys Glu
1               5                   10                  15

Asn Glu Ile Cys Lys Val Ile Asn Asn Thr Pro Thr Cys Glu Cys Lys
            20                  25                  30

Glu Asn Leu Lys Arg Asn Asn Lys Asn Glu Cys Ile
        35                  40

<210> SEQ ID NO 82
<211> LENGTH: 40
<212> TYPE: PRT
<213> ORGANISM: Artificial Sequence
<220> FEATURE:
<223> OTHER INFORMATION: PfRipr

<400> SEQUENCE: 82

Met Cys Leu Val Asn Lys Gly Asn Cys Pro Pro Asp Ser Glu Cys Ile
1               5                   10                  15

Tyr His Glu Lys Lys His Glu Cys Leu Cys His Lys Lys Gly Leu
            20                  25                  30

Val Ala Ile Asn Gly Lys Cys Val
        35                  40

<210> SEQ ID NO 83
<211> LENGTH: 47
<212> TYPE: PRT
<213> ORGANISM: Artificial Sequence
<220> FEATURE:
<223> OTHER INFORMATION: PfRipr

<400> SEQUENCE: 83

Met Cys Arg Thr Asp Gln Asn Lys Cys Ser Glu Asn Ser Ile Cys Val
1               5                   10                  15

Asn Gln Val Asn Lys Glu Pro Leu Cys Ile Cys Leu Phe Asn Tyr Glu
            20                  25                  30

Lys Ser Ile Ala Gly Leu Ser Thr Gln Gly Ala His Thr Cys Val
        35                  40                  45

<210> SEQ ID NO 84
<211> LENGTH: 87
<212> TYPE: PRT
<213> ORGANISM: Artificial Sequence
<220> FEATURE:
<223> OTHER INFORMATION: Pks25

<400> SEQUENCE: 84

Pro Cys Leu Thr Asn Asn Gly Gly Cys Ser Pro Asn Glu Ile Cys Thr
1               5                   10                  15

Leu Lys Asn Arg Lys Val Val Cys Ser Cys Gly Glu Asn Tyr Arg Pro
            20                  25                  30

Lys Gly Lys Glu Ser Gln Leu Gly Pro Met Ala Gln Arg Gly Gln Leu
        35                  40                  45

Gly Lys Leu Gly Gln Leu Gly Gln Leu Gly Gln Leu Gly Gln Leu Gly
    50                  55                  60

Gln Leu Gly Lys Arg Gly Lys Leu Gly Gln Leu Gly Asn Pro Pro Thr
65                  70                  75                  80

Pro Glu Asp Asn Ala Cys Ile
                85

<210> SEQ ID NO 85
<211> LENGTH: 173
<212> TYPE: PRT
<213> ORGANISM: Artificial Sequence
<220> FEATURE:
<223> OTHER INFORMATION: Pks25

<400> SEQUENCE: 85

```
Val Thr Val Asp Thr Leu Cys Lys Asn Gly His Leu Ala Gln Met Ser
  1               5                  10                  15

His His Phe Lys Cys Ile Cys Asn Asp Gly Leu Val His Ile Ser Glu
             20                  25                  30

Asn Glu Cys Gly Glu Lys Thr Glu Cys Lys Glu Asn Leu Gly Lys
         35                  40                  45

Thr Cys Gly Asp Phe Gly Ile Cys Arg Lys Gly Pro Asp Ala Ala Gln
     50                  55                  60

Gln Ser Thr Tyr Lys Cys Asp Cys Ile Lys Glu Tyr Thr Leu Lys Asp
 65                  70                  75                  80

Gly Thr Cys Val Val Asp Val Cys Leu Tyr Lys Asp Cys Gly Gln Ser
                 85                  90                  95

Gly Glu Cys Ile Gly Glu Phe Leu Thr Glu Val Lys Ser Ala Ala Cys
            100                 105                 110

Ser Cys Ser Ile Gly Lys Val Pro Asn Pro Glu Asp Glu Lys Lys Cys
        115                 120                 125

Thr Lys Asp Gly Glu Thr Thr Cys Gln Leu Lys Cys Asn Thr Glu Asn
    130                 135                 140

Glu Val Cys Lys Ala Val Gln Gly Val Tyr Lys Cys Gln Cys Met Glu
145                 150                 155                 160

Gly Phe Lys Phe Asp Lys Glu Lys Lys Glu Cys Ile Ser
                165                 170
```

<210> SEQ ID NO 86
<211> LENGTH: 72
<212> TYPE: PRT
<213> ORGANISM: Artificial Sequence
<220> FEATURE:
<223> OTHER INFORMATION: fullCSP

<400> SEQUENCE: 86

```
Pro Asn Glu Lys Val Val Asn Asp Tyr Leu His Lys Ile Arg Ser Ser
  1               5                  10                  15

Val Thr Thr Glu Trp Thr Pro Cys Ser Val Thr Cys Gly Asn Gly Val
             20                  25                  30

Arg Ile Arg Arg Lys Ala His Ala Gly Asn Lys Lys Ala Glu Asp Leu
         35                  40                  45

Thr Met Asp Asp Leu Glu Val Glu Ala Cys Val Met Asp Lys Cys Ala
     50                  55                  60

Gly Ile Phe Asn Val Val Ser Asn
 65                  70
```

<210> SEQ ID NO 87
<211> LENGTH: 65
<212> TYPE: PRT
<213> ORGANISM: Artificial Sequence
<220> FEATURE:
<223> OTHER INFORMATION: shortCSP

<400> SEQUENCE: 87

```
Tyr Leu His Lys Ile Arg Ser Ser Val Thr Thr Glu Trp Thr Pro Cys
```

```
                 1               5                  10                 15
             Ser Val Thr Cys Gly Asn Gly Val Arg Ile Arg Arg Lys Ala His Ala
                         20                  25                 30

Gly Asn Lys Lys Ala Glu Asp Leu Thr Met Asp Asp Leu Glu Val Glu
                     35                  40                 45

Ala Cys Val Met Asp Lys Cys Ala Gly Ile Phe Asn Val Val Ser Asn
                 50                  55                  60

Ser
             65

<210> SEQ ID NO 88
<211> LENGTH: 74
<212> TYPE: PRT
<213> ORGANISM: Artificial Sequence
<220> FEATURE:
<223> OTHER INFORMATION: mTRAP

<400> SEQUENCE: 88

Ile Arg Asp Lys Arg Cys Glu Gln Trp Asp Ser Trp Ser Pro Cys Lys
1               5                  10                  15

Asn Gly Ile Ser Thr Arg Ile Cys Leu Thr Asp Lys Ser Val Thr Asp
            20                  25                  30

Lys Met Thr Cys Thr Met Cys Asn Ile Trp Gly Glu Trp Ser Ala Cys
        35                  40                  45

Gln Asn Gly Lys Arg His Arg Lys Ile Val Asn Cys Pro Phe Ile Arg
    50                  55                  60

Glu Asp Gln Asp Cys Asp Pro Asn Asn Ser
65                  70

<210> SEQ ID NO 89
<211> LENGTH: 51
<212> TYPE: PRT
<213> ORGANISM: Artificial Sequence
<220> FEATURE:
<223> OTHER INFORMATION: TRAP

<400> SEQUENCE: 89

Glu Arg Ile Ala Lys Cys Gly Pro Trp Asp Asp Trp Thr Pro Cys Ser
1               5                  10                  15

Val Thr Cys Gly Lys Gly Thr His Ser Arg Ser Arg Pro Leu Leu His
            20                  25                  30

Ala Gly Cys Thr Thr His Met Val Lys Glu Cys Glu Met Asp Glu Cys
        35                  40                  45

Pro Val Glu
    50

<210> SEQ ID NO 90
<211> LENGTH: 66
<212> TYPE: PRT
<213> ORGANISM: Artificial Sequence
<220> FEATURE:
<223> OTHER INFORMATION: TRAMP

<400> SEQUENCE: 90

Phe Tyr Thr Glu Trp Gly Glu Trp Ser Lys Cys Ser Met Glu Cys Asp
1               5                  10                  15

His Pro Asp Asn Val Gln Ile Arg Glu Arg Lys Cys Ala Asn Thr Ser
            20                  25                  30

Gly Asp Cys Phe Lys Gly Asp Leu Lys Glu Thr Arg Pro Cys Gln Val
        35                  40                  45
```

```
Pro Leu Pro Pro Cys Asn Ser Leu Phe Glu Leu Lys Glu Ser Ser Thr
        50                  55                  60

Phe Lys
65

<210> SEQ ID NO 91
<211> LENGTH: 297
<212> TYPE: PRT
<213> ORGANISM: Artificial Sequence
<220> FEATURE:
<223> OTHER INFORMATION: EBA175

<400> SEQUENCE: 91

Arg Arg Cys Asn Asn Lys Arg Lys Arg Gly Ala Arg Asp Trp Asp Cys
1               5                   10                  15

Pro Thr Lys Lys Asp Val Cys Ile Pro Asp Arg Arg Tyr Gln Leu Cys
            20                  25                  30

Met Lys Glu Leu Thr Asn Leu Val Asn Asn Thr Lys Thr His Ser His
        35                  40                  45

Asn Asp Ile Thr Phe Leu Lys Leu Asn Leu Lys Glu Lys Leu Thr Tyr
    50                  55                  60

Asp Ala Ala Val Glu Gly Asp Leu Leu Leu Lys Lys Tyr Asn Asn Val
65                  70                  75                  80

Tyr Ser Glu Asp Leu Cys Lys Asp Ile Lys Trp Ser Leu Glu Asp Phe
                85                  90                  95

Gly Asp Ile Ile Met Gly Thr Asp Met Glu Gly Ile Gly Tyr Ser Gln
            100                 105                 110

Val Val Glu Asn Asn Leu Arg Ser Ile Phe Gly Thr Gly Thr Ser Ala
        115                 120                 125

Gln Leu Asp Arg Lys Lys Trp Trp Asn Asp His Lys Lys Tyr Ile Trp
    130                 135                 140

Glu Ala Thr Ile Leu Ser Val Lys Lys Leu Asn Gly Tyr Ser Ala
145                 150                 155                 160

Trp Asn Cys Lys Glu Asp Val Gln Ile Asn Val Glu Pro Gln Ile Tyr
                165                 170                 175

Arg Trp Ile Arg Glu Trp Gly Met Asp Tyr Met Ser Glu Leu Pro Lys
            180                 185                 190

Glu Gln Arg Lys Ile Lys Glu Lys Cys Asp Arg Lys Leu Tyr Tyr Thr
        195                 200                 205

Asn Leu Arg Ile Cys Thr Met Ser Pro Cys Asn Asp Ser Cys Lys Leu
    210                 215                 220

Tyr Asp Gln Trp Ile Thr Arg Lys Lys Gln Trp Asp Val Leu Ser
225                 230                 235                 240

Thr Lys Phe Ser Ser Val Lys Lys Gly Gln Ile Ile Glu Thr Glu Asn
                245                 250                 255

Ile Thr Thr Ala Tyr Asp Ile Leu Lys Gln Glu Leu Asn Gly Phe Asn
            260                 265                 270

Glu Val Met Phe Glu Asn Glu Ile Asn Lys Arg Asp Asn Val Tyr Ile
        275                 280                 285

Asp Ile Cys Leu Cys Ala Ala Asp Glu
    290                 295

<210> SEQ ID NO 92
<211> LENGTH: 297
<212> TYPE: PRT
<213> ORGANISM: Artificial Sequence
```

<220> FEATURE:
<223> OTHER INFORMATION: EBA175

<400> SEQUENCE: 92

Asp Lys Cys Asn Asp Lys Arg Lys Arg Gly Glu Arg Asp Trp Asp Cys
1               5                   10                  15

Pro Ala Glu Lys Asp Ile Cys Ile Ser Asp Arg Arg Tyr Gln Leu Cys
                20                  25                  30

Met Lys Glu Leu Thr Asn Leu Val Asn Asn Thr Arg Thr His Ser His
            35                  40                  45

Asn Asp Ile Thr Phe Leu Lys Leu Asn Leu Lys Arg Lys Leu Met Tyr
        50                  55                  60

Asp Ala Ala Val Glu Gly Asp Leu Leu Leu Lys Lys Asn Asn Tyr Gln
65                  70                  75                  80

Tyr Asn Lys Glu Phe Cys Lys Asp Ile Arg Trp Gly Leu Gly Asp Phe
                85                  90                  95

Gly Asp Ile Ile Met Gly Thr Asn Met Glu Gly Ile Gly Tyr Ser Gln
            100                 105                 110

Val Val Glu Asn Asn Leu Arg Ser Ile Phe Gly Thr Asp Glu Lys Ala
        115                 120                 125

Lys Gln Asp Arg Lys Gln Trp Trp Asn Glu Ser Lys Glu His Ile Trp
130                 135                 140

Arg Ala Met Met Phe Ser Ile Arg Ser Arg Leu Lys Glu Lys Phe Val
145                 150                 155                 160

Trp Ile Cys Lys Lys Asp Val Thr Leu Lys Val Glu Pro Gln Ile Tyr
                165                 170                 175

Arg Trp Ile Arg Glu Trp Gly Arg Asp Tyr Met Ser Glu Leu Pro Lys
            180                 185                 190

Glu Gln Gly Lys Leu Asn Glu Lys Cys Ala Ser Lys Leu Tyr Tyr Asn
        195                 200                 205

Asn Met Ala Ile Cys Met Leu Pro Leu Cys His Asp Ala Cys Lys Ser
210                 215                 220

Tyr Asp Gln Trp Ile Thr Arg Lys Lys Gln Trp Asp Val Leu Ser
225                 230                 235                 240

Thr Lys Phe Ser Ser Val Lys Lys Thr Gln Lys Ile Gly Thr Glu Asn
                245                 250                 255

Ile Ala Thr Ala Tyr Asp Ile Leu Lys Gln Glu Leu Asn Gly Phe Lys
            260                 265                 270

Glu Ala Thr Phe Glu Asn Glu Ile Asn Lys Arg Asp Asn Leu Tyr Asn
        275                 280                 285

His Leu Cys Pro Cys Val Val Glu Glu
290                 295

<210> SEQ ID NO 93
<211> LENGTH: 296
<212> TYPE: PRT
<213> ORGANISM: Artificial Sequence
<220> FEATURE:
<223> OTHER INFORMATION: EBA175

<400> SEQUENCE: 93

Asp Lys Cys Asn Asp Lys Arg Lys Arg Gly Glu Arg Asp Trp Asp Cys
1               5                   10                  15

Pro Thr Glu Lys Asp Val Cys Ile Pro Asp Arg Arg Tyr Gln Leu Cys
                20                  25                  30

Met Met Glu Ile Thr Asn Leu Val Asp Asn Thr Asn Thr His Phe His

```
                35                  40                  45
Ser Asp Ile Ile Phe Arg Lys Ser Tyr Phe Glu Arg Arg Leu Ile Tyr
 50                  55                  60

Asp Val Gly Ala Glu Gly Asp Leu Leu Leu Lys Lys Tyr Asn Asn Val
 65                  70                  75                  80

Tyr Ser Glu Asp Leu Cys Lys Asp Ile Lys Trp Ser Leu Gln Asp Phe
                 85                  90                  95

Gly Asp Ile Ile Met Gly Thr Asp Met Glu Gly Ile Gly Tyr Ser Leu
                100                 105                 110

Val Val Glu Asn Asn Leu Arg Ser Ile Phe Gly Thr Gly Thr Ser Ala
            115                 120                 125

Glu Leu Asp Arg Lys Lys Trp Trp Asn Asp His Lys Lys Asp Ile Trp
130                 135                 140

Lys Ala Met Ile Leu Ser Val Lys Glu Lys Asn Arg Tyr Ser Ala Trp
145                 150                 155                 160

Asn Cys Lys Glu Asp Val Gln Ile Asn Val Glu Pro Gln Ile Tyr Arg
                165                 170                 175

Trp Ile Arg Glu Trp Gly Arg Asp Tyr Met Ser Glu Phe Arg Glu Gln
                180                 185                 190

Arg Arg Lys Leu Asn Glu Lys Cys Glu Asp Lys Leu Tyr Tyr Ser Thr
            195                 200                 205

Met Leu Ile Cys Thr Leu Pro Pro Cys Asn Asn Ala Cys Lys Ser Tyr
210                 215                 220

Asp Glu Trp Ile Thr Gly Lys Lys Gln Trp Asp Val Leu Ser Thr
225                 230                 235                 240

Lys Phe Ser Ser Val Lys Lys Ala Gln Lys Ile Glu Thr Glu Asn Ile
                245                 250                 255

Ala Arg Ala Tyr Asp Ile Leu Lys Gln Glu Leu Asn Gly Phe Asn Glu
                260                 265                 270

Val Thr Phe Glu Asn Glu Ile Asn Lys Arg Asp Lys Leu Tyr Asn Tyr
            275                 280                 285

Phe Cys Val Cys Ile Val Gln Glu
            290                 295

<210> SEQ ID NO 94
<211> LENGTH: 119
<212> TYPE: PRT
<213> ORGANISM: Artificial Sequence
<220> FEATURE:
<223> OTHER INFORMATION: EBA140

<400> SEQUENCE: 94

Leu Leu Glu Cys Glu Asn Glu Tyr Val Lys Asn Glu Asn Gly Tyr Lys
 1               5                  10                  15

Leu Ala Thr Gly His His Tyr Met Asp Asn Asp Gln Ile Glu Arg Trp
                20                  25                  30

Leu Gln Gly Thr Asp Arg Ser Arg Arg Val Lys Ile Glu Glu Asn Val
            35                  40                  45

Lys Tyr Lys Tyr Asn Val Glu Glu Leu Asn Thr Lys Tyr Glu Gln Thr
 50                  55                  60

Lys Gly Lys Arg Ile Asn Arg Ile Leu Lys Glu Ser Thr Tyr Glu Ala
 65                  70                  75                  80

Gln Asn Val Ala Asp Asn Asn Tyr Ile Asp Asp Lys Ala Asn Gly Glu
                85                  90                  95

Tyr Lys Thr Asp Asn Lys Thr Asn Lys Gly Glu Gly Ala Arg Asn Met
```

Val Met Leu Asp Tyr Asp Ile
    115

<210> SEQ ID NO 95
<211> LENGTH: 119
<212> TYPE: PRT
<213> ORGANISM: Artificial Sequence
<220> FEATURE:
<223> OTHER INFORMATION: EBA140

<400> SEQUENCE: 95

Leu Leu Glu Cys Glu Asn Glu Tyr Val Lys Asn Glu Asn Gly Tyr Lys
1               5                   10                  15

Leu Ala Thr Gly His His Tyr Met Asp Asn Asp Gln Ile Glu Gln Trp
            20                  25                  30

Leu Gln Gly Thr Asp Arg Ser Arg Val Lys Ile Glu Glu Asn Val
        35                  40                  45

Lys Tyr Lys Tyr Asn Val Glu Glu Leu Asn Thr Lys Tyr Glu Gln Met
    50                  55                  60

Lys Gly Lys Arg Ile Asn Arg Ile Leu Lys Glu Ser Thr Tyr Glu Ala
65                  70                  75                  80

Gln Asn Val Ala Asp Asn Asn Tyr Ile Asp Asp Lys Ala Asn Gly Glu
                85                  90                  95

His Lys Thr Asp Asn Lys Thr Asn Lys Gly Glu Gly Ala Arg Asn Met
            100                 105                 110

Val Met Leu Asp Tyr Asp Ile
    115

<210> SEQ ID NO 96
<211> LENGTH: 119
<212> TYPE: PRT
<213> ORGANISM: Artificial Sequence
<220> FEATURE:
<223> OTHER INFORMATION: EBA140

<400> SEQUENCE: 96

Leu Leu Glu Cys Glu Asn Glu Tyr Val Lys Asn Glu Asn Gly Tyr Lys
1               5                   10                  15

Leu Ala Thr Gly His His Tyr Met Asp Asn Asp Gln Ile Glu Arg Trp
            20                  25                  30

Leu Gln Gly Thr Asp Arg Ser Arg Val Lys Ile Glu Glu Asn Val
        35                  40                  45

Lys Tyr Lys Tyr Asn Val Glu Glu Leu Asn Thr Lys Tyr Glu Gln Met
    50                  55                  60

Lys Gly Lys Arg Ile Asn Arg Ile Leu Lys Glu Ser Thr Tyr Glu Ala
65                  70                  75                  80

Gln Asn Val Ala Asp Asn Asn Tyr Ile Asp Asp Lys Ala Asn Gly Glu
                85                  90                  95

Tyr Lys Thr Asp Asn Lys Thr Asn Lys Gly Glu Gly Ala Arg Asn Met
            100                 105                 110

Val Met Leu Asp Tyr Asp Ile
    115

<210> SEQ ID NO 97
<211> LENGTH: 135
<212> TYPE: PRT
<213> ORGANISM: Artificial Sequence
<220> FEATURE:

<223> OTHER INFORMATION: EBA140

<400> SEQUENCE: 97

Ile Leu Ser Val Lys Lys Leu Asn Gly Tyr Ser Ala Trp Asn Cys
1               5                   10                  15

Lys Glu Asp Val Gln Ile Asn Val Glu Pro Gln Ile Tyr Arg Trp Ile
            20                  25                  30

Arg Glu Trp Gly Met Asp Tyr Met Ser Glu Leu Pro Lys Glu Gln Arg
        35                  40                  45

Lys Ile Lys Glu Lys Cys Asp Arg Lys Leu Tyr Tyr Thr Asn Leu Arg
    50                  55                  60

Ile Cys Thr Met Ser Pro Cys Asn Asp Ser Cys Lys Leu Tyr Asp Gln
65                  70                  75                  80

Trp Ile Thr Arg Lys Lys Gln Trp Asp Val Leu Ser Thr Lys Phe
                85                  90                  95

Ser Ser Val Lys Lys Gly Gln Ile Ile Glu Thr Glu Asn Ile Thr Thr
                100                 105                 110

Ala Tyr Asp Ile Leu Lys Gln Glu Leu Asn Gly Phe Asn Glu Val Met
            115                 120                 125

Phe Glu Asn Glu Ile Asn Lys
        130                 135

<210> SEQ ID NO 98
<211> LENGTH: 135
<212> TYPE: PRT
<213> ORGANISM: Artificial Sequence
<220> FEATURE:
<223> OTHER INFORMATION: EBA140

<400> SEQUENCE: 98

Met Phe Ser Ile Arg Ser Arg Leu Lys Glu Lys Phe Val Trp Ile Cys
1               5                   10                  15

Lys Lys Asp Val Thr Leu Lys Val Glu Pro Gln Ile Tyr Arg Trp Ile
            20                  25                  30

Arg Glu Trp Gly Arg Asp Tyr Met Ser Glu Leu Pro Lys Glu Gln Gly
        35                  40                  45

Lys Leu Asn Glu Lys Cys Ala Ser Lys Leu Tyr Tyr Asn Asn Met Ala
    50                  55                  60

Ile Cys Met Leu Pro Leu Cys His Asp Ala Cys Lys Ser Tyr Asp Gln
65                  70                  75                  80

Trp Ile Thr Arg Lys Lys Gln Trp Asp Val Leu Ser Thr Lys Phe
                85                  90                  95

Ser Ser Val Lys Lys Thr Gln Lys Ile Gly Thr Glu Asn Ile Ala Thr
                100                 105                 110

Ala Tyr Asp Ile Leu Lys Gln Glu Leu Asn Gly Phe Lys Glu Ala Thr
            115                 120                 125

Phe Glu Asn Glu Ile Asn Lys
        130                 135

<210> SEQ ID NO 99
<211> LENGTH: 134
<212> TYPE: PRT
<213> ORGANISM: Artificial Sequence
<220> FEATURE:
<223> OTHER INFORMATION: EBA140

<400> SEQUENCE: 99

Ile Leu Ser Val Lys Glu Lys Asn Arg Tyr Ser Ala Trp Asn Cys Lys

```
  1               5                  10                 15
Glu Asp Val Gln Ile Asn Val Glu Pro Gln Ile Tyr Arg Trp Ile Arg
            20                 25                 30
Glu Trp Gly Arg Asp Tyr Met Ser Glu Phe Arg Glu Gln Arg Arg Lys
            35                 40                 45
Leu Asn Glu Lys Cys Glu Asp Lys Leu Tyr Tyr Ser Thr Met Leu Ile
 50                 55                 60
Cys Thr Leu Pro Pro Cys Asn Asn Ala Cys Lys Ser Tyr Asp Glu Trp
 65                 70                 75                 80
Ile Thr Gly Lys Lys Gln Trp Asp Val Leu Ser Thr Lys Phe Ser
            85                 90                 95
Ser Val Lys Lys Ala Gln Lys Ile Glu Thr Glu Asn Ile Ala Arg Ala
            100                105                110
Tyr Asp Ile Leu Lys Gln Glu Leu Asn Gly Phe Asn Glu Val Thr Phe
            115                120                125
Glu Asn Glu Ile Asn Lys
            130
```

<210> SEQ ID NO 100
<211> LENGTH: 65
<212> TYPE: PRT
<213> ORGANISM: Artificial Sequence
<220> FEATURE:
<223> OTHER INFORMATION: EBL1

<400> SEQUENCE: 100

```
Asp Leu Cys Lys Asp Ile Lys Trp Ser Leu Glu Asp Phe Gly Asp Ile
 1               5                  10                 15
Ile Met Gly Thr Asp Met Glu Gly Ile Gly Tyr Ser Gln Val Val Glu
            20                 25                 30
Asn Asn Leu Arg Ser Ile Phe Gly Thr Gly Thr Ser Ala Gln Leu Asp
            35                 40                 45
Arg Lys Lys Trp Trp Asn Asp His Lys Lys Tyr Ile Trp Glu Ala Thr
 50                 55                 60
Ile
65
```

<210> SEQ ID NO 101
<211> LENGTH: 65
<212> TYPE: PRT
<213> ORGANISM: Artificial Sequence
<220> FEATURE:
<223> OTHER INFORMATION: EBL1

<400> SEQUENCE: 101

```
Glu Phe Cys Lys Asp Ile Arg Trp Gly Leu Gly Asp Phe Gly Asp Ile
 1               5                  10                 15
Ile Met Gly Thr Asn Met Glu Gly Ile Gly Tyr Ser Gln Val Val Glu
            20                 25                 30
Asn Asn Leu Arg Ser Ile Phe Gly Thr Asp Glu Lys Ala Lys Gln Asp
            35                 40                 45
Arg Lys Gln Trp Trp Asn Glu Ser Lys Glu His Ile Trp Arg Ala Met
 50                 55                 60
Met
65
```

<210> SEQ ID NO 102
<211> LENGTH: 65

```
<212> TYPE: PRT
<213> ORGANISM: Artificial Sequence
<220> FEATURE:
<223> OTHER INFORMATION: EBL1

<400> SEQUENCE: 102

Asp Leu Cys Lys Asp Ile Lys Trp Ser Leu Gln Asp Phe Gly Asp Ile
1               5                   10                  15

Ile Met Gly Thr Asp Met Glu Gly Ile Gly Tyr Ser Leu Val Val Glu
            20                  25                  30

Asn Asn Leu Arg Ser Ile Phe Gly Thr Gly Thr Ser Ala Glu Leu Asp
                35                  40                  45

Arg Lys Lys Trp Trp Asn Asp His Lys Lys Asp Ile Trp Lys Ala Met
    50                  55                  60

Ile
65

<210> SEQ ID NO 103
<211> LENGTH: 225
<212> TYPE: PRT
<213> ORGANISM: Artificial Sequence
<220> FEATURE:
<223> OTHER INFORMATION: GAMA

<400> SEQUENCE: 103

Lys Asp Val Val Leu Val Arg Asp Leu Leu Lys Asp Thr Asn Ile
1               5                   10                  15

Ile Lys Phe Glu Lys Asn Glu Pro Thr Ser Gln Ile Asp Asp Glu Gly
            20                  25                  30

Ile Lys Lys Leu Ile Glu Ser Ser Phe Phe Asp Leu Ser Asp Asn Thr
                35                  40                  45

Met Leu Met Arg Leu Ile Ile Lys Pro Gln Ala Ser Ile Leu Phe Ile
    50                  55                  60

Ile Gln Ser Phe Ile Met Met Thr Pro Ser Pro Thr Arg Asp Ala Arg
65                  70                  75                  80

Met Tyr Cys Lys Lys Lys Leu Val Asn Gly Gln Leu Ile Glu Asn Asn
                85                  90                  95

Asp Leu Lys Ala Glu Thr Glu Glu Glu Asp Met Ile Asn Glu Phe Ser
            100                 105                 110

Ser Lys Tyr Asn Leu Phe Tyr Glu Arg Leu Lys Met Glu Glu Leu Arg
        115                 120                 125

Glu Ile Glu Gln Asp Arg Lys Ser Leu Lys Asn Ser Lys Gly Asn Leu
    130                 135                 140

Ser Val Leu Glu Val Arg Asn Ser Gln Asn Gly Pro Asp Gly Lys Glu
145                 150                 155                 160

Val Asn Gly Ser Gly Asp Ala Ala Asn Gly Asn Met Asn Gly Gly
                165                 170                 175

Asn Asn Gly Ser Ala Ser Ser Leu Ile Val Val Arg Asp Asp Leu
            180                 185                 190

Ala Glu Lys Thr Asp Asp Ile Ile Lys Asn Asn Val Asp Leu Glu Ser
    195                 200                 205

Leu Lys Ala Asp Val Glu Gln Ala Phe Arg Asn Phe Glu Tyr Gln Ser
        210                 215                 220

Gly
225

<210> SEQ ID NO 104
```

<211> LENGTH: 149
<212> TYPE: PRT
<213> ORGANISM: Artificial Sequence
<220> FEATURE:
<223> OTHER INFORMATION: Pks230

<400> SEQUENCE: 104

```
Asp Glu Glu Glu Glu Asp Asn Asp Gly Glu Ser Ile Ser Tyr Gly
1               5                   10                  15

Asp Met Asp Gln Asp Glu Gln Asp Glu Asn Tyr Gln Met Lys Gly
            20                  25                  30

Met Asp Leu Glu Glu Asp Glu Asp Val Leu Asp Ser Asp Val Phe
        35                  40                  45

Leu Pro Leu Val Asp Ser Asp Ala Ser Asp Gly Thr Phe Asp Ala Val
    50                  55                  60

Asp Asp Asp Phe Gln Thr Thr Ile Lys Lys Asp Gly Glu Glu Leu Glu
65                  70                  75                  80

Gln Ser Asp Ser Thr Val Glu Ile Phe Ala Ser Ser Asn Thr Asn Lys
                85                  90                  95

Glu Tyr Val Cys Asp Phe Glu Lys Gly Lys Ile Leu Lys Glu Thr Thr
            100                 105                 110

Lys Lys Thr Lys Ile Cys Glu Met Lys Ile Gln Glu Pro Leu Val Lys
        115                 120                 125

Val Lys Ile Val Cys Pro Thr Lys Tyr Ser Asp Val Ser Ala Asp Gly
    130                 135                 140

Ser Met Gly Phe Ile
145
```

<210> SEQ ID NO 105
<211> LENGTH: 161
<212> TYPE: PRT
<213> ORGANISM: Artificial Sequence
<220> FEATURE:
<223> OTHER INFORMATION: CelTos

<400> SEQUENCE: 105

```
Leu Arg Gly Lys Ser Gly Leu Thr Ala Ser Ser Leu Glu Gly Gly
1               5                   10                  15

Ser Glu Phe Ser Glu Arg Ile Gly Asn Thr Leu Ser Ser Phe Leu Ser
            20                  25                  30

Glu Ser Ala Ser Leu Glu Val Ile Gly Asn Glu Leu Ala Asp Asn Ile
        35                  40                  45

Ala Asn Glu Ile Val Gly Ser Leu Gln Asn Asp Ser Ala Ser Phe Leu
    50                  55                  60

Gln Ser Glu Phe Asp Val Lys Ala Gln Leu Lys Ala Thr Ala Lys Lys
65                  70                  75                  80

Val Leu Thr Glu Ala Leu Lys Ala Ala Leu Glu Pro Thr Glu Lys Ile
                85                  90                  95

Val Ala Ser Thr Ile Lys Pro Pro Arg Ile Lys Glu Asp Ile Tyr Phe
            100                 105                 110

Leu Leu Ser Pro Val Val Arg Ser Leu Phe Asn Lys Val Glu Asp Val
        115                 120                 125

Leu His Lys Pro Val Ser Asp Asp Ile Trp Asn Tyr Glu Ser Arg Gly
    130                 135                 140

Ser Ser Ser Glu Glu Glu Asp Glu Val Asp Ser Asp Glu Asp Phe Leu
145                 150                 155                 160

Asp
```

-continued

```
<210> SEQ ID NO 106
<211> LENGTH: 48
<212> TYPE: PRT
<213> ORGANISM: Artificial Sequence
<220> FEATURE:
<223> OTHER INFORMATION: Ron2L

<400> SEQUENCE: 106

Met Asp Ile Thr Gln His Ala Ser Asp Ile Gly Met Gly Pro Val Thr
1               5                   10                  15

Ser Cys Tyr Thr Ser Thr Ile Pro Pro Lys Gln Val Cys Ile Gln
            20                  25                  30

Gln Ala Val Lys Val Thr Leu Thr Asn Ser Thr Gln Ala Cys Met Lys
        35                  40                  45

<210> SEQ ID NO 107
<211> LENGTH: 105
<212> TYPE: PRT
<213> ORGANISM: Artificial Sequence
<220> FEATURE:
<223> OTHER INFORMATION: EXP1

<400> SEQUENCE: 107

Gly Asn Asn Ile Asn His Ser Gly Pro His His Pro Lys Lys Lys Thr
1               5                   10                  15

Pro Lys Ser Lys Ala Pro Glu Pro Leu Ile Asp Val His Glu Leu Ile
            20                  25                  30

Gly Glu Met Val Arg Lys Glu Glu Leu Ile Asn Val Thr Lys Lys
        35                  40                  45

Lys Ser Lys Tyr Lys Leu Ala Thr Thr Val Leu Ala Ser Ala Leu Ser
    50                  55                  60

Ala Val Leu Leu Gly Gly Ala Asn Ala Gly Asn Gly Arg His Pro Phe
65                  70                  75                  80

Ser Leu Gly Gly Gly Lys Gly Gly Glu Ala Ala Pro Ala Glu Ser Ala
                85                  90                  95

Pro Thr Val Asp Glu Pro Ala Thr Lys
            100                 105

<210> SEQ ID NO 108
<211> LENGTH: 409
<212> TYPE: PRT
<213> ORGANISM: Artificial Sequence
<220> FEATURE:
<223> OTHER INFORMATION: Pks4845

<400> SEQUENCE: 108

His Thr Gln Met Ala Lys Gly Glu Val Lys Tyr Val Pro Pro Glu Glu
1               5                   10                  15

Leu Asn Lys Asp Val Ser Gly Phe Phe Gly Phe Lys Cys Asn Phe Ser
            20                  25                  30

Ser Lys Gly Val His Asn Leu Glu Pro Ile Leu Thr Glu Lys Arg Ser
        35                  40                  45

Leu Val Cys Ser Ile Tyr Ser Tyr Phe Ile Tyr Asp Lys Ile Lys Leu
    50                  55                  60

Thr Ile Pro Lys Lys Ile Pro Gly Ser Lys Phe Lys Met Leu Pro Glu
65                  70                  75                  80

Lys Cys Phe Gln Thr Val Tyr Thr Asn Tyr Glu Lys Arg Thr Glu Glu
                85                  90                  95
```

```
Lys Ile Glu Asn Met Gly Leu Val Glu Tyr Val Lys Glu Asp Asp
            100                 105                 110

Ser Asn Ser Glu Tyr Thr Glu Lys Ile Leu Thr Ile Ser Pro Phe Asn
        115                 120                 125

Thr Lys Asp Val Glu Phe Phe Cys Ile Cys Asp Asn Ser Glu Asn Val
    130                 135                 140

Ile Ser Asn Val Lys Gly Arg Val Ala Leu Val Gln Val Asn Val Leu
145                 150                 155                 160

Lys Tyr Pro His Lys Ile Thr Ser Ile Asn Leu Thr Lys Glu Pro Tyr
                165                 170                 175

Ser Tyr Leu Pro Asn Gln Val Asp Lys Thr Ser Phe Lys Ser His Lys
            180                 185                 190

Leu Asp Leu Glu Leu Gln Asp Gly Glu Leu Val Val Leu Ala Cys Glu
        195                 200                 205

Lys Val Asp Asp Lys Cys Phe Lys Lys Gly Lys Asp Thr Ser Pro Leu
    210                 215                 220

Ser Leu Tyr Lys Ser Lys Lys Ile Val Tyr His Lys Asn Leu Ser Ile
225                 230                 235                 240

Phe Lys Ala Pro Val Tyr Val Lys Ser Ala Asp Val Thr Ala Glu Cys
                245                 250                 255

Ser Cys Asn Val Asp Ser Thr Ile Tyr Thr Leu Ser Leu Lys Pro Val
            260                 265                 270

Tyr Thr Lys Lys Leu Ile His Gly Cys Asn Phe Ser Ser Asp Lys Ser
        275                 280                 285

Thr His Asn Phe Thr Asn His Val Asp Met Ala Glu Leu Gly Glu Asn
    290                 295                 300

Ala Gln Ile Thr Cys Ser Ile Glu Leu Val Asp Thr Ser Tyr Asn His
305                 310                 315                 320

Leu Ile Gly Met Ser Cys Pro Gly Glu Val Leu Pro Glu Cys Phe Phe
                325                 330                 335

Gln Val Tyr Gln Arg Glu Ser Pro Glu Leu Glu Pro Ser Lys Ile Val
            340                 345                 350

Tyr Leu Asp Ala Gln Leu Asn Ile Gly Asn Val Glu Tyr Phe Glu Asp
        355                 360                 365

Ser Lys Gly Glu Asn Ile Val Lys Ile Phe Gly Leu Val Gly Ser Ile
    370                 375                 380

Pro Lys Thr Thr Ser Phe Thr Cys Ile Cys Arg Lys Gly Lys Lys Ile
385                 390                 395                 400

Gly Tyr Met Ser Val Lys Ile Ala Ala
                405

<210> SEQ ID NO 109
<211> LENGTH: 41
<212> TYPE: PRT
<213> ORGANISM: Artificial Sequence
<220> FEATURE:
<223> OTHER INFORMATION: MSP1-19

<400> SEQUENCE: 109

Gly Ser Lys His Lys Cys Ile Asp Ile Thr Tyr Pro Asp Asn Ala Gly
1               5                   10                  15

Cys Tyr Arg Phe Ser Asp Gly Arg Glu Glu Trp Arg Cys Leu Leu Asn
            20                  25                  30

Phe Lys Lys Val Gly Glu Thr Cys Val
        35                  40
```

-continued

<210> SEQ ID NO 110
<211> LENGTH: 171
<212> TYPE: PRT
<213> ORGANISM: Artificial Sequence
<220> FEATURE:
<223> OTHER INFORMATION: Pos25

<400> SEQUENCE: 110

Val Thr Val Asp Thr Asn Cys Lys Asn Gly Thr Leu Val Gln Met Ser
1               5                   10                  15

Asn His Leu Glu Cys Lys Cys Asn Glu Asn Phe Val His Val Ser Glu
            20                  25                  30

Asp Ile Cys Glu Glu Lys Phe Glu Cys Asn Asp Lys Met Val Asn Asn
        35                  40                  45

Pro Cys Gly Asp Tyr Ser Thr Cys Ile Lys Asn Val Asp Gln Glu Ile
    50                  55                  60

Glu Lys Tyr Ile Cys Thr Cys Ile Ser Gly Phe Glu Tyr Asp Asn Lys
65                  70                  75                  80

Val Cys Val Pro Ala Glu Cys Lys Gly Ile Ser Cys Val Asn Gly Lys
                85                  90                  95

Cys Ile Val Asn Pro Ser Pro Asp Asn Lys Glu Gly Arg Cys Ser Cys
            100                 105                 110

Asn Ile Gly Lys Val Pro Asn Pro Glu Asp Asn Asn Asn Cys Thr Lys
        115                 120                 125

Asp Gly Asp Thr Glu Cys Lys Leu Lys Cys Thr Lys Glu Asn Glu Ile
    130                 135                 140

Cys Lys Asn Val Glu Gly Leu Phe Glu Cys Asn Cys Gln Asp Gly Phe
145                 150                 155                 160

Ile Met Asp Leu Glu Gln Asn Leu Cys Lys Ala
                165                 170

<210> SEQ ID NO 111
<211> LENGTH: 41
<212> TYPE: PRT
<213> ORGANISM: Artificial Sequence
<220> FEATURE:
<223> OTHER INFORMATION: MSP19

<400> SEQUENCE: 111

Ser Ala Lys His Ala Cys Thr Glu Thr Lys Tyr Pro Glu Asn Ala Gly
1               5                   10                  15

Cys Tyr Arg Tyr Glu Asp Gly Lys Glu Val Trp Arg Cys Leu Leu Asn
            20                  25                  30

Tyr Lys Leu Val Asp Gly Gly Cys Val
        35                  40

<210> SEQ ID NO 112
<211> LENGTH: 72
<212> TYPE: PRT
<213> ORGANISM: Artificial Sequence
<220> FEATURE:
<223> OTHER INFORMATION: fullCSP

<400> SEQUENCE: 112

Pro Ser Glu Glu His Ile Lys Asn Tyr Leu Glu Ser Ile Arg Asn Ser
1               5                   10                  15

Ile Thr Glu Glu Trp Ser Pro Cys Ser Val Thr Cys Gly Ser Gly Ile
            20                  25                  30

Arg Ala Arg Arg Lys Val Gly Ala Lys Asn Lys Lys Pro Ala Glu Leu

```
                 35                  40                  45
Val Leu Ser Asp Leu Glu Thr Glu Ile Cys Ser Leu Asp Lys Cys Ser
     50                  55                  60

Ser Ile Phe Asn Val Val Ser Asn
 65                  70
```

<210> SEQ ID NO 113
<211> LENGTH: 65
<212> TYPE: PRT
<213> ORGANISM: Artificial Sequence
<220> FEATURE:
<223> OTHER INFORMATION: shortCSP

<400> SEQUENCE: 113

```
Tyr Leu Glu Ser Ile Arg Asn Ser Ile Thr Glu Glu Trp Ser Pro Cys
 1               5                  10                  15

Ser Val Thr Cys Gly Ser Gly Ile Arg Ala Arg Arg Lys Val Gly Ala
             20                  25                  30

Lys Asn Lys Lys Pro Ala Glu Leu Val Leu Ser Asp Leu Glu Thr Glu
         35                  40                  45

Ile Cys Ser Leu Asp Lys Cys Ser Ser Ile Phe Asn Val Val Ser Asn
     50                  55                  60

Ser
 65
```

<210> SEQ ID NO 114
<211> LENGTH: 38
<212> TYPE: PRT
<213> ORGANISM: Artificial Sequence
<220> FEATURE:
<223> OTHER INFORMATION: Ortholog

<400> SEQUENCE: 114

```
Glu Cys Ala Leu Asn Thr Asp Asn Cys Asp Ser His Ala Thr Cys Glu
 1               5                  10                  15

Asn Thr Asp Gly Ser Tyr His Cys Ala Cys Gly Ser Gly Phe Thr Gly
             20                  25                  30

Asp Gly Phe Thr Cys Glu
         35
```

<210> SEQ ID NO 115
<211> LENGTH: 38
<212> TYPE: PRT
<213> ORGANISM: Artificial Sequence
<220> FEATURE:
<223> OTHER INFORMATION: Ortholog

<400> SEQUENCE: 115

```
Glu Cys Ala Glu Asn Pro Glu Leu Cys Glu Phe Gly Cys Lys Asn Leu
 1               5                  10                  15

Pro Gly Ala Tyr Glu Cys Thr Cys Pro Pro Asp Ser Lys Gln Arg Ala
             20                  25                  30

Asp Lys Arg Gly Cys Glu
         35
```

<210> SEQ ID NO 116
<211> LENGTH: 71
<212> TYPE: PRT
<213> ORGANISM: Artificial Sequence
<220> FEATURE:
<223> OTHER INFORMATION: Ortholog

```
<400> SEQUENCE: 116

Val Cys Thr Asn Thr Met Gly Ser Tyr Thr Cys Ser Cys Leu Pro Gly
1               5                   10                  15

Tyr Thr Pro Ser Asp Asp Gly Arg Val Cys Thr Asp Ile Asp Glu Cys
            20                  25                  30

Ala Thr Glu Asn Gly Gly Cys Ser Glu His Ser Gln Cys Arg Asn Leu
        35                  40                  45

Pro Gly Ser Tyr Glu Cys Val Cys Asp Ala Gly Tyr Glu Lys Val Glu
    50                  55                  60

Gly Ser Glu His Leu Cys Gln
65                  70

<210> SEQ ID NO 117
<211> LENGTH: 69
<212> TYPE: PRT
<213> ORGANISM: Artificial Sequence
<220> FEATURE:
<223> OTHER INFORMATION: Ortholog

<400> SEQUENCE: 117

Val Cys Val Asn Thr Pro Gly Thr Phe Phe Cys Asp Cys Ala Ala Gly
1               5                   10                  15

Phe Val Leu Gly Gln Asp Gly Arg Ser Cys Thr Asp Ile Asp Glu Cys
            20                  25                  30

Ala Leu Asp Glu Asn Ile Cys Glu His Lys Cys Glu Asn Leu Pro Gly
        35                  40                  45

Ala Phe Gln Cys Arg Cys Asn Ser Gly Tyr Lys Arg Ser Val Asp Asp
    50                  55                  60

Pro Arg Lys Cys Val
65

<210> SEQ ID NO 118
<211> LENGTH: 209
<212> TYPE: PRT
<213> ORGANISM: Artificial Sequence
<220> FEATURE:
<223> OTHER INFORMATION: Ortholog

<400> SEQUENCE: 118

Val Cys Thr Asn Thr Met Gly Ser Tyr Thr Cys Ser Cys Leu Pro Gly
1               5                   10                  15

Tyr Thr Pro Ser Asp Asp Gly Arg Val Cys Thr Asp Ile Asp Glu Cys
            20                  25                  30

Ala Thr Glu Asn Gly Gly Cys Ser Glu His Ser Gln Cys Arg Asn Leu
        35                  40                  45

Pro Gly Ser Tyr Glu Cys Val Cys Asp Ala Gly Tyr Glu Lys Val Glu
    50                  55                  60

Gly Ser Glu His Leu Cys Gln Asp Ile Asp Glu Cys Ala Ala Gly Thr
65                  70                  75                  80

Ala Thr Ile Pro Asn Asn Ser Asn Cys Val Asn Thr Ala Gly Ser Tyr
                85                  90                  95

Glu Phe Ala Cys Lys Pro Gly Phe Glu His Lys Asp Asn Ala Cys Ser
                100                 105                 110

Lys Ile Asp Tyr Cys Gly Arg Gly Cys Asn Ser Leu Ala Thr Cys
            115                 120                 125

Glu Glu Thr Ala Asp Gly Thr Asp Tyr Val Cys Thr Cys Pro Lys Gly
        130                 135                 140
```

```
Phe Val Thr Gln Asn Glu Gly Arg Gly Ala Asp Gly Cys Thr Asp Val
145                 150                 155                 160

Asp Glu Cys Ala Glu Asn Gly Cys Ala Ala Tyr Gly Ser Glu Gly Val
            165                 170                 175

Ile Cys Glu Asn Thr Pro Gly Ser Phe Asn Cys Ser Cys Ala Asn Gly
        180                 185                 190

Tyr Leu Leu Asn Asn Gly Val Cys Glu Glu Ile Asp Glu Cys Ala Gly
        195                 200                 205

Ser
```

<210> SEQ ID NO 119
<211> LENGTH: 129
<212> TYPE: PRT
<213> ORGANISM: Artificial Sequence
<220> FEATURE:
<223> OTHER INFORMATION: Ortholog

<400> SEQUENCE: 119

```
Gln Cys Leu Asn Leu Met Gly Lys Tyr Glu Cys Gly Cys Tyr Pro Gly
1               5                   10                  15

Phe Val Leu Gln Pro Asp Gly Arg Cys Asp Asp Ile Asp Glu Cys Ile
            20                  25                  30

Asp Pro Thr Leu His Gly Cys Asp His Ile Cys Ile Asn Leu Pro Gly
        35                  40                  45

Thr Tyr Ser Cys Gln Cys Arg Pro Gly Tyr Arg Leu Ser Leu Glu Lys
    50                  55                  60

Lys Gly Ala Cys Val Asp Ile Asp Glu Cys Ala Glu Asn Pro Glu Leu
65                  70                  75                  80

Cys Glu Phe Gly Cys Lys Asn Leu Pro Gly Ala Tyr Glu Cys Thr Cys
                85                  90                  95

Pro Pro Asp Ser Lys Gln Arg Ala Asp Lys Arg Gly Cys Glu Pro Asn
            100                 105                 110

Leu Ser Cys Lys Glu Asp Pro Ser Gln Cys Gln Gly Asp His Val Cys
        115                 120                 125

Arg
```

<210> SEQ ID NO 120
<211> LENGTH: 111
<212> TYPE: PRT
<213> ORGANISM: Artificial Sequence
<220> FEATURE:
<223> OTHER INFORMATION: Ortholog

<400> SEQUENCE: 120

```
Asp Cys Glu Asn Thr Ser Gly Ser Tyr Ile Cys Lys Cys Lys Ala Gly
1               5                   10                  15

Phe Glu Met Arg Asp Asn Gln Cys Val Asp Ile Asp Glu Cys Ala Thr
            20                  25                  30

Asn Thr Asn Glu Cys His Asn His Arg Gly Arg Cys Ile Asn Thr His
        35                  40                  45

Gly Ser Tyr Thr Cys Glu Cys Ile Ala Gly Phe Ile Gly Asp Gly Lys
    50                  55                  60

Ile Cys Ile Asn Lys Asn Glu Cys Gln Ser Gly Asp Phe Glu Cys Gly
65                  70                  75                  80

Pro Asn Ser His Cys Val Asp Thr Glu Gly Ser Tyr Lys Cys Asp Cys
                85                  90                  95

Asn Ser Gly Tyr Lys Gln Asp Pro Glu Asn Pro Asp Ser Cys Ile
```

<210> SEQ ID NO 121
<211> LENGTH: 103
<212> TYPE: PRT
<213> ORGANISM: Artificial Sequence
<220> FEATURE:
<223> OTHER INFORMATION: Ortholog

<400> SEQUENCE: 121

Asn Ser Glu Gly Gln Gly Val Thr Pro Ala Val Arg Ile Gln Gln Gln
1               5                   10                  15

Arg Glu Leu Gln Gly Gly Lys Leu Leu Pro Gly Arg Pro Ala Leu Cys
            20                  25                  30

Asp Gln Gln Cys Leu Asn Leu Met Gly Lys Tyr Glu Cys Gly Cys Tyr
        35                  40                  45

Pro Gly Phe Val Leu Gln Pro Asp Gly Arg Cys Asp Asp Ile Asp Glu
    50                  55                  60

Cys Ile Asp Pro Thr Leu His Gly Cys Asp His Ile Cys Ile Asn Leu
65                  70                  75                  80

Pro Gly Thr Tyr Ser Cys Gln Cys Arg Pro Gly Tyr Arg Leu Ser Leu
                85                  90                  95

Glu Lys Lys Gly Ala Cys Val
            100

<210> SEQ ID NO 122
<211> LENGTH: 122
<212> TYPE: PRT
<213> ORGANISM: Artificial Sequence
<220> FEATURE:
<223> OTHER INFORMATION: Ortholog

<400> SEQUENCE: 122

Glu Cys Gln Ser Gly Asp Phe Glu Cys Gly Pro Asn Ser His Cys Val
1               5                   10                  15

Asp Thr Glu Gly Ser Tyr Lys Cys Asp Cys Asn Ser Gly Tyr Lys Gln
            20                  25                  30

Asp Pro Glu Asn Pro Asp Ser Cys Ile Asp Arg Asp Glu Cys Glu Ile
        35                  40                  45

Glu Gly Ala Cys Asp Glu Asn Ala Asp Cys Thr Asn Leu Pro Gly Ser
    50                  55                  60

Phe Ser Cys Thr Cys Arg Ala Gly Tyr Arg Gln Gly Glu Leu Cys
65                  70                  75                  80

Val Lys Met Asn Leu Cys Ala Asp Glu Asn Gly Cys Ser Pro
                85                  90                  95

His Ala Asp Cys Glu His Leu Asp Lys Ile Val Cys Thr Cys Arg Pro
            100                 105                 110

Gly Tyr Glu Gly Asp Gly Ile Thr Cys Thr
        115                 120

<210> SEQ ID NO 123
<211> LENGTH: 82
<212> TYPE: PRT
<213> ORGANISM: Artificial Sequence
<220> FEATURE:
<223> OTHER INFORMATION: PfRipr

<400> SEQUENCE: 123

Gly Lys Leu Leu Pro Gly Arg Pro Ala Leu Cys Asp Gln Gln Cys Leu
1               5                   10                  15

```
Asn Leu Met Gly Lys Tyr Glu Cys Gly Cys Tyr Pro Gly Phe Val Leu
            20                  25                  30

Gln Pro Asp Gly Arg Cys Asp Ile Asp Glu Cys Ile Asp Pro Thr
        35                  40                  45

Leu His Gly Cys Asp His Ile Cys Ile Asn Leu Pro Gly Thr Tyr Ser
    50                  55                  60

Cys Gln Cys Arg Pro Gly Tyr Arg Leu Ser Leu Glu Lys Lys Gly Ala
65                  70                  75                  80

Cys Val
```

<210> SEQ ID NO 124
<211> LENGTH: 135
<212> TYPE: PRT
<213> ORGANISM: Artificial Sequence
<220> FEATURE:
<223> OTHER INFORMATION: PfRipr

<400> SEQUENCE: 124

```
Glu Cys Thr Glu Gly Val Asp Thr Cys Pro Arg Gln Gly Gly Arg Cys
1               5                   10                  15

Val Asn Thr Pro Gly Ser Tyr Arg Cys Glu Cys Glu Glu Gly Tyr Thr
            20                  25                  30

Tyr Thr Thr Lys Glu Asp Gly Thr Val Glu Cys Val Asp Ile Asn Glu
        35                  40                  45

Cys Gly Val Ser Glu Met Asn Thr Cys Ala Ser Lys Ala Asn Gly Gly
    50                  55                  60

Val Cys Thr Asn Thr Met Gly Ser Tyr Thr Cys Ser Cys Leu Pro Gly
65                  70                  75                  80

Tyr Thr Pro Ser Asp Asp Gly Arg Val Cys Thr Asp Ile Asp Glu Cys
            85                  90                  95

Ala Thr Glu Asn Gly Gly Cys Ser Glu His Ser Gln Cys Arg Asn Leu
        100                 105                 110

Pro Gly Ser Tyr Glu Cys Val Cys Asp Ala Gly Tyr Glu Lys Val Glu
    115                 120                 125

Gly Ser Glu His Leu Cys Gln
    130                 135
```

<210> SEQ ID NO 125
<211> LENGTH: 80
<212> TYPE: PRT
<213> ORGANISM: Artificial Sequence
<220> FEATURE:
<223> OTHER INFORMATION: PfRipr

<400> SEQUENCE: 125

```
Glu Cys Leu Thr Ala Asn Gly Gly Cys Gln His Val Cys Val Asn Thr
1               5                   10                  15

Pro Gly Thr Phe Phe Cys Asp Cys Ala Ala Gly Phe Val Leu Gly Gln
            20                  25                  30

Asp Gly Arg Ser Cys Thr Asp Ile Asp Glu Cys Ala Leu Asp Glu Asn
        35                  40                  45

Ile Cys Glu His Lys Cys Glu Asn Leu Pro Gly Ala Phe Gln Cys Arg
    50                  55                  60

Cys Asn Ser Gly Tyr Lys Arg Ser Val Asp Asp Pro Arg Lys Cys Val
65                  70                  75                  80
```

<210> SEQ ID NO 126

```
<211> LENGTH: 70
<212> TYPE: PRT
<213> ORGANISM: Artificial Sequence
<220> FEATURE:
<223> OTHER INFORMATION: PfRipr

<400> SEQUENCE: 126

Gly Tyr Arg Gly Ser Gly His Thr Ser Lys Gly Ala Ala Asp Gly Cys
1               5                   10                  15

Val Asp Ile Asp Glu Cys Thr Glu Gly Val Asp Thr Cys Pro Arg Gln
            20                  25                  30

Gly Gly Arg Cys Val Asn Thr Pro Gly Ser Tyr Arg Cys Glu Cys Glu
        35                  40                  45

Glu Gly Tyr Thr Tyr Thr Thr Lys Glu Asp Gly Thr Val Glu Cys Val
    50                  55                  60

Asp Ile Asn Glu Cys Gly
65                  70

<210> SEQ ID NO 127
<211> LENGTH: 61
<212> TYPE: PRT
<213> ORGANISM: Artificial Sequence
<220> FEATURE:
<223> OTHER INFORMATION: PfRipr

<400> SEQUENCE: 127

Gly Phe Glu Gly Asp Gly Arg Thr Lys Gly Thr Gly Cys Ser Asn Ile
1               5                   10                  15

Asp Glu Cys Ala Thr Gly Gln Ala Gly Cys Glu Gln Ile Cys Lys Asp
            20                  25                  30

Phe Ala Pro Gly Tyr Ala Cys Ser Cys Tyr Asp Gly Tyr Met Leu Lys
        35                  40                  45

Ala Asn Gly Lys Asp Cys Gln Asp Ile Asn Glu Cys Leu
    50                  55                  60

<210> SEQ ID NO 128
<211> LENGTH: 59
<212> TYPE: PRT
<213> ORGANISM: Artificial Sequence
<220> FEATURE:
<223> OTHER INFORMATION: PfRipr

<400> SEQUENCE: 128

Glu Cys Gln Ser Gly Asp Phe Glu Cys Gly Pro Asn Ser His Cys Val
1               5                   10                  15

Asp Thr Glu Gly Ser Tyr Lys Cys Asp Cys Asn Ser Gly Tyr Lys Gln
            20                  25                  30

Asp Pro Glu Asn Pro Asp Ser Cys Ile Asp Arg Asp Glu Cys Glu Ile
        35                  40                  45

Glu Gly Ala Cys Asp Glu Asn Ala Asp Cys Thr
    50                  55

<210> SEQ ID NO 129
<211> LENGTH: 57
<212> TYPE: PRT
<213> ORGANISM: Artificial Sequence
<220> FEATURE:
<223> OTHER INFORMATION: PfRipr

<400> SEQUENCE: 129

Gly Lys Leu Leu Pro Gly Arg Pro Ala Leu Cys Asp Gln Gln Cys Leu
1               5                   10                  15
```

-continued

```
Asn Leu Met Gly Lys Tyr Glu Cys Gly Cys Tyr Pro Gly Phe Val Leu
            20                  25                  30

Gln Pro Asp Gly Arg Cys Asp Asp Ile Asp Glu Cys Ile Asp Pro Thr
        35                  40                  45

Leu His Gly Cys Asp His Ile Cys Ile
    50                  55

<210> SEQ ID NO 130
<211> LENGTH: 84
<212> TYPE: PRT
<213> ORGANISM: Artificial Sequence
<220> FEATURE:
<223> OTHER INFORMATION: PfRipr

<400> SEQUENCE: 130

Ser Cys Ile Asp Arg Asp Glu Cys Glu Ile Glu Gly Ala Cys Asp Glu
1               5                   10                  15

Asn Ala Asp Cys Thr Asn Leu Pro Gly Ser Phe Ser Cys Thr Cys Arg
            20                  25                  30

Ala Gly Tyr Arg Gln Glu Gly Glu Leu Cys Val Lys Met Asn Leu Cys
        35                  40                  45

Ala Asp Asp Glu Asn Gly Gly Cys Ser Pro His Ala Asp Cys Glu His
    50                  55                  60

Leu Asp Lys Ile Val Cys Thr Cys Arg Pro Gly Tyr Glu Gly Asp Gly
65                  70                  75                  80

Ile Thr Cys Thr

<210> SEQ ID NO 131
<211> LENGTH: 46
<212> TYPE: PRT
<213> ORGANISM: Artificial Sequence
<220> FEATURE:
<223> OTHER INFORMATION: PfRipr

<400> SEQUENCE: 131

Arg Cys Asp Asp Ile Asp Glu Cys Ile Asp Pro Thr Leu His Gly Cys
1               5                   10                  15

Asp His Ile Cys Ile Asn Leu Pro Gly Thr Tyr Ser Cys Gln Cys Arg
            20                  25                  30

Pro Gly Tyr Arg Leu Ser Leu Glu Lys Lys Gly Ala Cys Val
        35                  40                  45

<210> SEQ ID NO 132
<211> LENGTH: 41
<212> TYPE: PRT
<213> ORGANISM: Artificial Sequence
<220> FEATURE:
<223> OTHER INFORMATION: PfRipr

<400> SEQUENCE: 132

Glu Cys Ala Thr Glu Asn Gly Gly Cys Ser His Ser Gln Cys Arg
1               5                   10                  15

Asn Leu Pro Gly Ser Tyr Glu Cys Val Cys Asp Ala Gly Tyr Glu Lys
            20                  25                  30

Val Glu Gly Ser Glu His Leu Cys Gln
        35                  40

<210> SEQ ID NO 133
<211> LENGTH: 39
<212> TYPE: PRT
```

<213> ORGANISM: Artificial Sequence
<220> FEATURE:
<223> OTHER INFORMATION: PfRipr

<400> SEQUENCE: 133

| | | | | | | | | | | | | | | |
|---|---|---|---|---|---|---|---|---|---|---|---|---|---|---|
| Glu | Cys | Ala | Leu | Asp | Glu | Asn | Ile | Cys | Glu | His | Lys | Cys | Glu | Asn | Leu |
| 1 | | | | 5 | | | | | 10 | | | | | 15 | |
| Pro | Gly | Ala | Phe | Gln | Cys | Arg | Cys | Asn | Ser | Gly | Tyr | Lys | Arg | Ser | Val |
| | | | 20 | | | | | 25 | | | | | 30 | | |
| Asp | Asp | Pro | Arg | Lys | Cys | Val | | | | | | | | | |
| | | | | 35 | | | | | | | | | | | |

<210> SEQ ID NO 134
<211> LENGTH: 234
<212> TYPE: PRT
<213> ORGANISM: Artificial Sequence
<220> FEATURE:
<223> OTHER INFORMATION: GAMA

<400> SEQUENCE: 134

Val Pro Ile Lys Gln Lys Val Gln Ala Ile Phe Ser Arg Leu Arg Met
1               5                   10                  15

Phe Lys Met Asn Asn Glu Thr Val Leu Tyr Glu Pro Asp Thr Glu Ile
            20                  25                  30

Ile Glu Lys Thr Val Lys Ala Ala Tyr Leu Asp Thr Thr Asp Arg Val
        35                  40                  45

Phe Asp Val Trp Gly Ala Leu Leu Pro Gln Ala Ala Thr Thr Thr Thr
    50                  55                  60

Ala Gln Leu Leu Thr Leu Leu Pro Lys Pro Asp Val Asp Leu Ala
65                  70                  75                  80

Glu Phe Tyr Asn Lys Thr Met Asn Ser Glu Gly Val Ile Ser Asp Gly
                85                  90                  95

Leu Gln Ser Gln Leu Pro Val Asn His Thr Arg Leu Val Glu Arg Phe
            100                 105                 110

Ala Leu Phe Leu Glu Glu Val Tyr Arg Asp Cys Trp Arg Asn Phe Phe
        115                 120                 125

Asn Val Asn Asp Asn Phe Leu Ser Ser Ser Ser Ser Glu Thr Gly
    130                 135                 140

Glu Lys Ala Thr Leu Ser Ala Ala Ser Ile Pro Thr Val Ser Ala Val
145                 150                 155                 160

Gln Leu Ser Asp Ala Lys Val Val Asp Leu Ala Asp Gly Val Val Arg
                165                 170                 175

Arg Gly Leu Glu Lys Ala Ala Ser Met Glu Ala Val Val Lys Gly His
            180                 185                 190

Ser Phe Val Ser Leu Lys Ser Ser Thr Thr Glu Lys Gly Ile Asp Ile
        195                 200                 205

Ala Ile Val Asp Ser Ser Asp Gly Val Gly Val Asn Glu Leu Ala Lys
    210                 215                 220

Val Phe Thr Asp Glu Lys Leu Ile Gln Glu
225                 230

<210> SEQ ID NO 135
<211> LENGTH: 46
<212> TYPE: PRT
<213> ORGANISM: Artificial Sequence
<220> FEATURE:
<223> OTHER INFORMATION: Ron2L

<400> SEQUENCE: 135

```
Ala Asp Ile Val Gln His Met Glu Asp Ile Gly Gly Ala Pro Pro Val
1               5                   10                  15

Ser Cys Val Thr Asn Glu Ile Leu Gly Val Thr Cys Ala Pro Gln Ala
                20                  25                  30

Ile Ala Lys Ala Thr Thr Ser Ala Ala Arg Val Ala Thr Gln
            35                  40                  45

<210> SEQ ID NO 136
<211> LENGTH: 38
<212> TYPE: PRT
<213> ORGANISM: Artificial Sequence
<220> FEATURE:
<223> OTHER INFORMATION: PfRipr

<400> SEQUENCE: 136

Glu Cys Ala Glu Asn Pro Ala Leu Cys Glu Tyr Gly Cys Thr Asn Leu
1               5                   10                  15

Pro Gly Thr Tyr Glu Cys Thr Cys Pro Pro Asp Ser Lys Pro Arg Asn
                20                  25                  30

Asp Lys Arg Gly Cys Gln
            35

<210> SEQ ID NO 137
<211> LENGTH: 38
<212> TYPE: PRT
<213> ORGANISM: Artificial Sequence
<220> FEATURE:
<223> OTHER INFORMATION: PfRipr

<400> SEQUENCE: 137

Glu Cys Thr Leu Asn Thr Asp Asp Cys Asp Ser His Ala Thr Cys Glu
1               5                   10                  15

Asn Thr Glu Gly Ser Tyr Thr Cys Ala Cys Gly Ser Gly Tyr Thr Gly
                20                  25                  30

Asp Gly Lys Thr Cys Glu
            35

<210> SEQ ID NO 138
<211> LENGTH: 69
<212> TYPE: PRT
<213> ORGANISM: Artificial Sequence
<220> FEATURE:
<223> OTHER INFORMATION: PfRipr

<400> SEQUENCE: 138

Val Cys Val Asn Thr Pro Gly Thr Phe Phe Cys Asp Cys Ala Ala Gly
1               5                   10                  15

Phe Thr Leu Gly Glu Asp Gly Arg Ser Cys Thr Asp Val Asp Glu Cys
                20                  25                  30

Ala Leu Asp Glu Asn Ile Cys Glu His Arg Cys Glu Asn Leu Pro Gly
            35                  40                  45

Ala Phe Gln Cys His Cys Asn Pro Gly Tyr Lys Arg Gly Ala Asp Asp
        50                  55                  60

Pro Arg Lys Cys Val
65

<210> SEQ ID NO 139
<211> LENGTH: 71
<212> TYPE: PRT
<213> ORGANISM: Artificial Sequence
<220> FEATURE:
```

<223> OTHER INFORMATION: PfRipr

<400> SEQUENCE: 139

Val Cys Thr Asn Thr Val Gly Ser Tyr Val Cys Ser Cys Leu Pro Gly
1               5                   10                  15

Tyr Thr Ala Ser Asp Asp Gly Arg Thr Cys Thr Asp Ile Asp Glu Cys
            20                  25                  30

Ala Thr Asp Asn Gly Gly Cys Ser Glu His Ser Gln Cys Gln Asn Leu
        35                  40                  45

Pro Gly Ser Tyr Ala Cys Val Cys Asp Ala Gly Tyr Gln Lys Val Glu
    50                  55                  60

Gly Ser Asn His Leu Cys Gln
65                  70

<210> SEQ ID NO 140
<211> LENGTH: 129
<212> TYPE: PRT
<213> ORGANISM: Artificial Sequence
<220> FEATURE:
<223> OTHER INFORMATION: PfRipr

<400> SEQUENCE: 140

Lys Cys Leu Asn Leu Val Gly Lys Tyr Glu Cys Gly Cys Tyr Pro Gly
1               5                   10                  15

Phe Val Leu Gln Pro Asp Gly Arg Cys Asp Asp Ile Asn Glu Cys Leu
            20                  25                  30

Asp Pro Ser Leu His Gly Cys Glu Gln Leu Cys Val Asn Leu Pro Gly
        35                  40                  45

Thr Tyr Ser Cys Gln Cys Arg Gln Gly Tyr Arg Pro Ser Val Glu Lys
    50                  55                  60

Arg Gly Ala Cys Val Asp Ile Asp Glu Cys Ala Glu Asn Pro Ala Leu
65                  70                  75                  80

Cys Glu Tyr Gly Cys Thr Asn Leu Pro Gly Thr Tyr Glu Cys Thr Cys
                85                  90                  95

Pro Pro Asp Ser Lys Pro Arg Asn Asp Lys Arg Gly Cys Gln Pro Asn
            100                 105                 110

Leu Ser Cys Lys Glu Asp Ala Ser Gln Cys Gln Gly Asp His Val Cys
        115                 120                 125

Arg

<210> SEQ ID NO 141
<211> LENGTH: 208
<212> TYPE: PRT
<213> ORGANISM: Artificial Sequence
<220> FEATURE:
<223> OTHER INFORMATION: PfRipr

<400> SEQUENCE: 141

Val Cys Thr Asn Thr Val Gly Ser Tyr Val Cys Ser Cys Leu Pro Gly
1               5                   10                  15

Tyr Thr Ala Ser Asp Asp Gly Arg Thr Cys Thr Asp Ile Asp Glu Cys
            20                  25                  30

Ala Thr Asp Asn Gly Gly Cys Ser Glu His Ser Gln Cys Gln Asn Leu
        35                  40                  45

Pro Gly Ser Tyr Ala Cys Val Cys Asp Ala Gly Tyr Gln Lys Val Glu
    50                  55                  60

Gly Ser Asn His Leu Cys Gln Asp Ile Asp Glu Cys Val Ala Asn Ala
65                  70                  75                  80

```
Pro Val Pro Ala Asn Ser Gln Cys Val Asn Thr Ala Gly Ser Tyr Asp
                85                  90                  95

Phe Ala Cys Asp Ala Gly Phe Glu Arg Lys Glu Asn Ala Cys Val Lys
            100                 105                 110

Ile Asp Tyr Cys Ala Gln Gly Gly Cys Ser Ser Leu Ala Thr Cys Gln
            115                 120                 125

Glu Asn Glu Gln Gly Thr Asp Tyr Val Cys Ser Cys Pro Ser Gly Tyr
            130                 135                 140

Arg Thr Glu Asn Glu Gly Arg Gly Thr Asp Gly Cys Ile Asp Ile Asp
145                 150                 155                 160

Glu Cys Ala Glu Asn Ala Cys Ala Ala Tyr Gly Ser Glu Gly Val Val
                165                 170                 175

Cys Gln Asn Thr Pro Gly Ser Phe Ser Cys Ser Cys Ala Thr Gly Tyr
            180                 185                 190

Val Leu Asn Ala Gly His Cys Asp Glu Val Asp Glu Cys Ala Gly Ser
            195                 200                 205

<210> SEQ ID NO 142
<211> LENGTH: 103
<212> TYPE: PRT
<213> ORGANISM: Artificial Sequence
<220> FEATURE:
<223> OTHER INFORMATION: PfRipr

<400> SEQUENCE: 142

Asp Arg Glu Gly Gln Gly Val Thr Pro Ala Val Arg Leu Gln Gln Gln
1               5                   10                  15

Arg Glu Leu Gln Gly Gly Arg Leu Leu Pro Gly Arg Pro Ala Leu Cys
                20                  25                  30

Asp Gln Lys Cys Leu Asn Leu Val Gly Lys Tyr Glu Cys Gly Cys Tyr
            35                  40                  45

Pro Gly Phe Val Leu Gln Pro Asp Gly Arg Cys Asp Asp Ile Asn Glu
        50                  55                  60

Cys Leu Asp Pro Ser Leu His Gly Cys Glu Gln Leu Cys Val Asn Leu
65                  70                  75                  80

Pro Gly Thr Tyr Ser Cys Gln Cys Arg Gln Gly Tyr Arg Pro Ser Val
                85                  90                  95

Glu Lys Arg Gly Ala Cys Val
            100

<210> SEQ ID NO 143
<211> LENGTH: 112
<212> TYPE: PRT
<213> ORGANISM: Artificial Sequence
<220> FEATURE:
<223> OTHER INFORMATION: PfRipr

<400> SEQUENCE: 143

Asn Cys Glu Asn Thr Ser Gly Ser Tyr Ile Cys Thr Cys Lys Asn Gly
1               5                   10                  15

Phe Glu Met Thr Glu Asn Gly Cys Val Asp Ile Asp Glu Cys Ala Asp
                20                  25                  30

Asn Asn Ala Asn Asp Cys His Asn His Arg Gly Arg Cys Ile Asn Thr
            35                  40                  45

Ala Gly Ser Tyr Thr Cys Glu Cys Ile Ala Gly Phe Met Gly Asp Gly
        50                  55                  60

Lys Glu Cys Ile Asn Lys Asn Glu Cys Glu Ser Gly Asp Phe His Cys
```

```
65                  70                  75                  80
Pro Ala Asn Ser His Cys Val Asp Thr Glu Gly Ser Tyr Lys Cys Asp
                85                  90                  95
Cys Asn Thr Gly Tyr Ala Ser Asp Pro Glu Asn Pro Glu Ser Cys Val
            100                 105                 110
```

<210> SEQ ID NO 144
<211> LENGTH: 82
<212> TYPE: PRT
<213> ORGANISM: Artificial Sequence
<220> FEATURE:
<223> OTHER INFORMATION: PfRipr

<400> SEQUENCE: 144

```
Gly Arg Leu Leu Pro Gly Arg Pro Ala Leu Cys Asp Gln Lys Cys Leu
1               5                   10                  15
Asn Leu Val Gly Lys Tyr Glu Cys Gly Cys Tyr Pro Gly Phe Val Leu
                20                  25                  30
Gln Pro Asp Gly Arg Cys Asp Asp Ile Asn Glu Cys Leu Asp Pro Ser
            35                  40                  45
Leu His Gly Cys Glu Gln Leu Cys Val Asn Leu Pro Gly Thr Tyr Ser
        50                  55                  60
Cys Gln Cys Arg Gln Gly Tyr Arg Pro Ser Val Glu Lys Arg Gly Ala
65                  70                  75                  80
Cys Val
```

<210> SEQ ID NO 145
<211> LENGTH: 121
<212> TYPE: PRT
<213> ORGANISM: Artificial Sequence
<220> FEATURE:
<223> OTHER INFORMATION: PfRipr

<400> SEQUENCE: 145

```
Glu Cys Glu Ser Gly Asp Phe His Cys Pro Ala Asn Ser His Cys Val
1               5                   10                  15
Asp Thr Glu Gly Ser Tyr Lys Cys Asp Cys Asn Thr Gly Tyr Ala Ser
                20                  25                  30
Asp Pro Glu Asn Pro Glu Ser Cys Val Asp Val Asp Glu Cys Gln Ile
            35                  40                  45
Gln Gly Ala Cys Asp Glu Asn Ala Asp Cys Thr Asn Met Pro Gly Ser
        50                  55                  60
Tyr Thr Cys Thr Cys Arg Glu Gly Tyr Arg Gln Glu Gly Glu Leu Cys
65                  70                  75                  80
Val Lys Met Asn Leu Cys Thr Glu Ala Glu Asn Pro Cys Ser Pro Asn
                85                  90                  95
Ala Phe Cys Glu Ser Leu Asp Lys Val Val Cys Thr Cys Lys Pro Gly
            100                 105                 110
Phe Glu Gly Asp Gly Ile Thr Cys Ala
        115                 120
```

<210> SEQ ID NO 146
<211> LENGTH: 80
<212> TYPE: PRT
<213> ORGANISM: Artificial Sequence
<220> FEATURE:
<223> OTHER INFORMATION: PfRipr

<400> SEQUENCE: 146

-continued

Glu Cys Leu Thr Ala Asn Gly Gly Cys Gln His Val Cys Val Asn Thr
1               5                   10                  15

Pro Gly Thr Phe Phe Cys Asp Cys Ala Ala Gly Phe Thr Leu Gly Glu
            20                  25                  30

Asp Gly Arg Ser Cys Thr Asp Val Asp Glu Cys Ala Leu Asp Glu Asn
            35                  40                  45

Ile Cys Glu His Arg Cys Glu Asn Leu Pro Gly Ala Phe Gln Cys His
50                  55                  60

Cys Asn Pro Gly Tyr Lys Arg Gly Ala Asp Asp Pro Arg Lys Cys Val
65                  70                  75                  80

<210> SEQ ID NO 147
<211> LENGTH: 135
<212> TYPE: PRT
<213> ORGANISM: Artificial Sequence
<220> FEATURE:
<223> OTHER INFORMATION: PfRipr

<400> SEQUENCE: 147

Glu Cys Ala Glu Gly Val Asp Thr Cys Pro Arg Gln Gly Gly Arg Cys
1               5                   10                  15

Val Asn Thr Pro Gly Ser Tyr Lys Cys Glu Cys Glu Ala Gly Tyr Thr
            20                  25                  30

Tyr Thr Thr His Ala Asp Gly Ser Val Glu Cys Val Asp Ile Asn Glu
            35                  40                  45

Cys Gly Val Thr Glu Leu Asn Thr Cys Ala Ser Lys Ala Asn Gly Gly
50                  55                  60

Val Cys Thr Asn Thr Val Gly Ser Tyr Val Cys Ser Cys Leu Pro Gly
65                  70                  75                  80

Tyr Thr Ala Ser Asp Asp Gly Arg Thr Cys Thr Asp Ile Asp Glu Cys
            85                  90                  95

Ala Thr Asp Asn Gly Gly Cys Ser Glu His Ser Gln Cys Gln Asn Leu
            100                 105                 110

Pro Gly Ser Tyr Ala Cys Val Cys Asp Ala Gly Tyr Gln Lys Val Glu
        115                 120                 125

Gly Ser Asn His Leu Cys Gln
        130                 135

<210> SEQ ID NO 148
<211> LENGTH: 61
<212> TYPE: PRT
<213> ORGANISM: Artificial Sequence
<220> FEATURE:
<223> OTHER INFORMATION: PfRipr

<400> SEQUENCE: 148

Gly Phe Glu Gly Asp Gly Arg Thr Lys Gly Thr Gly Cys Ser Asn Ile
1               5                   10                  15

Asp Glu Cys Ala Thr Gly Gln Ala Gly Cys Glu Gln Ile Cys Lys Asp
            20                  25                  30

Phe Ala Pro Gly Tyr Ala Cys Gly Cys Tyr Asp Gly Tyr Lys Leu Lys
        35                  40                  45

Ala Asn Gly Lys Asp Cys Gln Asp Ile Asn Glu Cys Leu
50                  55                  60

<210> SEQ ID NO 149
<211> LENGTH: 70
<212> TYPE: PRT
<213> ORGANISM: Artificial Sequence

```
<220> FEATURE:
<223> OTHER INFORMATION: PfRipr

<400> SEQUENCE: 149

Gly Tyr Lys Gly Ser Gly His Thr Lys Lys Gly Ala Ala Asp Gly Cys
1               5                   10                  15

Val Asp Ile Asp Glu Cys Ala Glu Gly Val Asp Thr Cys Pro Arg Gln
            20                  25                  30

Gly Gly Arg Cys Val Asn Thr Pro Gly Ser Tyr Lys Cys Glu Cys Glu
        35                  40                  45

Ala Gly Tyr Thr Tyr Thr Thr His Ala Asp Gly Ser Val Glu Cys Val
    50                  55                  60

Asp Ile Asn Glu Cys Gly
65                  70

<210> SEQ ID NO 150
<211> LENGTH: 57
<212> TYPE: PRT
<213> ORGANISM: Artificial Sequence
<220> FEATURE:
<223> OTHER INFORMATION: PfRipr

<400> SEQUENCE: 150

Gly Arg Leu Leu Pro Gly Arg Pro Ala Leu Cys Asp Gln Lys Cys Leu
1               5                   10                  15

Asn Leu Val Gly Lys Tyr Glu Cys Gly Cys Tyr Pro Gly Phe Val Leu
            20                  25                  30

Gln Pro Asp Gly Arg Cys Asp Asp Ile Asn Glu Cys Leu Asp Pro Ser
        35                  40                  45

Leu His Gly Cys Glu Gln Leu Cys Val
    50                  55

<210> SEQ ID NO 151
<211> LENGTH: 59
<212> TYPE: PRT
<213> ORGANISM: Artificial Sequence
<220> FEATURE:
<223> OTHER INFORMATION: PfRipr

<400> SEQUENCE: 151

Glu Cys Glu Ser Gly Asp Phe His Cys Pro Ala Asn Ser His Cys Val
1               5                   10                  15

Asp Thr Glu Gly Ser Tyr Lys Cys Asp Cys Asn Thr Gly Tyr Ala Ser
            20                  25                  30

Asp Pro Glu Asn Pro Glu Ser Cys Val Asp Val Asp Glu Cys Gln Ile
        35                  40                  45

Gln Gly Ala Cys Asp Glu Asn Ala Asp Cys Thr
    50                  55

<210> SEQ ID NO 152
<211> LENGTH: 46
<212> TYPE: PRT
<213> ORGANISM: Artificial Sequence
<220> FEATURE:
<223> OTHER INFORMATION: PfRipr

<400> SEQUENCE: 152

Arg Cys Asp Asp Ile Asn Glu Cys Leu Asp Pro Ser Leu His Gly Cys
1               5                   10                  15

Glu Gln Leu Cys Val Asn Leu Pro Gly Thr Tyr Ser Cys Gln Cys Arg
            20                  25                  30
```

-continued

Gln Gly Tyr Arg Pro Ser Val Glu Lys Arg Gly Ala Cys Val
                35                  40                  45

<210> SEQ ID NO 153
<211> LENGTH: 83
<212> TYPE: PRT
<213> ORGANISM: Artificial Sequence
<220> FEATURE:
<223> OTHER INFORMATION: PfRipr

<400> SEQUENCE: 153

Ser Cys Val Asp Val Asp Glu Cys Gln Ile Gln Gly Ala Cys Asp Glu
1               5                   10                  15

Asn Ala Asp Cys Thr Asn Met Pro Gly Ser Tyr Thr Cys Thr Cys Arg
            20                  25                  30

Glu Gly Tyr Arg Gln Glu Gly Glu Leu Cys Val Lys Met Asn Leu Cys
        35                  40                  45

Thr Glu Ala Glu Asn Pro Cys Ser Pro Asn Ala Phe Cys Glu Ser Leu
    50                  55                  60

Asp Lys Val Val Cys Thr Cys Lys Pro Gly Phe Glu Gly Asp Gly Ile
65                  70                  75                  80

Thr Cys Ala

<210> SEQ ID NO 154
<211> LENGTH: 39
<212> TYPE: PRT
<213> ORGANISM: Artificial Sequence
<220> FEATURE:
<223> OTHER INFORMATION: PfRipr

<400> SEQUENCE: 154

Glu Cys Ala Leu Asp Glu Asn Ile Cys Glu His Arg Cys Glu Asn Leu
1               5                   10                  15

Pro Gly Ala Phe Gln Cys His Cys Asn Pro Gly Tyr Lys Arg Gly Ala
            20                  25                  30

Asp Asp Pro Arg Lys Cys Val
        35

<210> SEQ ID NO 155
<211> LENGTH: 41
<212> TYPE: PRT
<213> ORGANISM: Artificial Sequence
<220> FEATURE:
<223> OTHER INFORMATION: PfRipr

<400> SEQUENCE: 155

Glu Cys Ala Thr Asp Asn Gly Gly Cys Ser Glu His Ser Gln Cys Gln
1               5                   10                  15

Asn Leu Pro Gly Ser Tyr Ala Cys Val Cys Asp Ala Gly Tyr Gln Lys
            20                  25                  30

Val Glu Gly Ser Asn His Leu Cys Gln
        35                  40

<210> SEQ ID NO 156
<211> LENGTH: 235
<212> TYPE: PRT
<213> ORGANISM: Artificial Sequence
<220> FEATURE:
<223> OTHER INFORMATION: GAMA

<400> SEQUENCE: 156

```
Val Pro Ile Lys Gln Lys Val Met Ala Val Met Ser Arg Leu Arg Met
1               5                   10                  15

Leu Gln Met His Asn Asp Thr Val Ala Phe Glu Val Asp Ser Ala Gly
                20                  25                  30

Val Glu Lys Ile Val Lys Ala Ala Tyr Leu Asp Val Thr Asp Arg Val
            35                  40                  45

Phe Gly Val Trp Gly Gly Leu Leu Pro Gln Ala Ala Val Thr Thr Thr
        50                  55                  60

Ala Gln Leu Leu Thr Leu Leu Pro Lys Pro Asp Val Asp Val Ala
65                  70                  75                  80

Glu Phe Tyr Asn Lys Thr Met Asn Ser Glu Gly Ala Ile Ser Asp Gly
                85                  90                  95

Val Gln Asp Gln Leu Pro Val Asn His Thr Arg Leu Val Glu Arg Phe
                100                 105                 110

Ala Ile Phe Val Glu Glu Met Tyr Arg Asp Cys Trp Arg Lys Phe Phe
                115                 120                 125

Asn Thr Asn Asp Asn Phe Leu Ala Pro Ala Asn Asp Ala Glu Thr Asp
                130                 135                 140

Ala Gln Asp Ile Ser Ser Ala Thr Ser Ile Pro Glu Val Ser Ala Val
145                 150                 155                 160

Gln Leu Asn Ala Gly Lys Val Val Asp Leu Leu Ala Asn Gly Val Val
                165                 170                 175

Glu Arg Gly Leu Asp His Ala Ala Ser Met Glu Ala Val Val Lys Glu
                180                 185                 190

His Ser Phe Val Ser Thr Ala Ser Ala Ala Gly Glu Arg Gly Ile Asp
                195                 200                 205

Met Ala Ile Val Asp Ser Ser Asp Gly Ile Gly Val Ala Asp Leu Ala
                210                 215                 220

Lys Val Phe Thr Asp Glu Gln Ala Val Arg Gly
225                 230                 235

<210> SEQ ID NO 157
<211> LENGTH: 46
<212> TYPE: PRT
<213> ORGANISM: Artificial Sequence
<220> FEATURE:
<223> OTHER INFORMATION: Ron2L

<400> SEQUENCE: 157

Thr Asp Ile Val Gln His Met Glu Asp Ile Gly Gly Ala Pro Pro Ala
1               5                   10                  15

Ser Cys Val Thr Asn Glu Ile Leu Gly Val Thr Cys Ala Pro Gln Ala
                20                  25                  30

Ile Ala Lys Ala Thr Thr Ser Ala Ala Gln Val Ala Thr Gln
            35                  40                  45

<210> SEQ ID NO 158
<211> LENGTH: 40
<212> TYPE: PRT
<213> ORGANISM: Artificial Sequence
<220> FEATURE:
<223> OTHER INFORMATION: PfRipr

<400> SEQUENCE: 158

Glu Cys Leu Glu Ser Pro Glu Leu Thr Gly Cys Ser His Gly Cys Ile
1               5                   10                  15

Asn Lys Arg Gly Gly Phe Gln Cys Thr Cys Pro Lys Gly Phe Gln Leu
                20                  25                  30
```

```
Gly Met Asp Gly Lys Val Cys Glu
        35              40

<210> SEQ ID NO 159
<211> LENGTH: 70
<212> TYPE: PRT
<213> ORGANISM: Artificial Sequence
<220> FEATURE:
<223> OTHER INFORMATION: PfRipr

<400> SEQUENCE: 159

Ile Cys Val Asn Thr Arg Gly Ser Phe Val Cys Glu Cys Pro Lys Gly
1               5                   10                  15

Tyr Thr Leu Asp Lys Asn Gln Gln Asp Cys Ile Asp Ile Asn Glu Cys
            20                  25                  30

Gln Glu Asn Ser Gly Leu Gly Pro Cys Glu Phe Gly Cys Lys Asn Leu
        35                  40                  45

Pro Gly Gly Phe Glu Cys Gln Cys Pro Ser Gly Tyr Lys Leu Asp Lys
    50                  55                  60

Lys Thr Gln Lys Cys Ile
65                  70

<210> SEQ ID NO 160
<211> LENGTH: 130
<212> TYPE: PRT
<213> ORGANISM: Artificial Sequence
<220> FEATURE:
<223> OTHER INFORMATION: PfRipr

<400> SEQUENCE: 160

Val Cys Phe Asn Lys Lys Gly Gly Phe Glu Cys Lys Cys Gly Ile Gly
1               5                   10                  15

Phe Gln Tyr Asp Glu Asn Glu Asn Ala Cys Lys Asp Ile Asn Glu Cys
            20                  25                  30

Val Leu Asn Thr His Asp Cys Lys Lys Asp Ser Val Cys Val Asn Glu
        35                  40                  45

Asp Gly Gly Phe Ser Cys Lys Cys Leu Glu Lys Gly Phe Glu Phe Asn
    50                  55                  60

Lys Glu Lys Arg Ala Cys Glu Asp Ile Asp Glu Cys Ser Asn Gly Asp
65                  70                  75                  80

Ser Lys Cys Asp Gln Leu Cys Phe Asn Thr Ile Gly Gly Tyr Lys Cys
                85                  90                  95

Gly Cys Tyr Lys Gly Phe Arg Leu Asn Leu Thr Gly Pro Glu Glu Asn
            100                 105                 110

Arg Leu Asp Val Gln Ser Arg Val Cys Ile Asp Ile Asp Glu Cys Leu
        115                 120                 125

Glu Ser
    130

<210> SEQ ID NO 161
<211> LENGTH: 79
<212> TYPE: PRT
<213> ORGANISM: Artificial Sequence
<220> FEATURE:
<223> OTHER INFORMATION: PfRipr

<400> SEQUENCE: 161

Asn Leu Cys Thr Gly Phe Gly Glu Val Cys Phe Asn Lys Lys Gly Gly
1               5                   10                  15
```

Phe Glu Cys Lys Cys Gly Ile Gly Phe Gln Tyr Asp Glu Asn Glu Asn
                20                  25                  30

Ala Cys Lys Asp Ile Asn Glu Cys Val Leu Asn Thr His Asp Cys Lys
            35                  40                  45

Lys Asp Ser Val Cys Val Asn Glu Asp Gly Gly Phe Ser Cys Lys Cys
 50                  55                  60

Leu Glu Lys Gly Phe Glu Phe Asn Lys Glu Lys Arg Ala Cys Glu
 65                  70                  75

<210> SEQ ID NO 162
<211> LENGTH: 92
<212> TYPE: PRT
<213> ORGANISM: Artificial Sequence
<220> FEATURE:
<223> OTHER INFORMATION: PfRipr

<400> SEQUENCE: 162

Glu Cys Val Leu Asn Thr His Asp Cys Lys Lys Asp Ser Val Cys Val
1               5                   10                  15

Asn Glu Asp Gly Gly Phe Ser Cys Lys Cys Leu Glu Lys Gly Phe Glu
                20                  25                  30

Phe Asn Lys Glu Lys Arg Ala Cys Glu Asp Ile Asp Glu Cys Ser Asn
            35                  40                  45

Gly Asp Ser Lys Cys Asp Gln Leu Cys Phe Asn Thr Ile Gly Gly Tyr
 50                  55                  60

Lys Cys Gly Cys Tyr Lys Gly Phe Arg Leu Asn Leu Thr Gly Pro Glu
 65                  70                  75                  80

Glu Asn Arg Leu Asp Val Gln Ser Arg Val Cys Ile
                85                  90

<210> SEQ ID NO 163
<211> LENGTH: 81
<212> TYPE: PRT
<213> ORGANISM: Artificial Sequence
<220> FEATURE:
<223> OTHER INFORMATION: PfRipr

<400> SEQUENCE: 163

Glu Cys Met Glu Gly Ser His Ser Cys Ser His Ile Cys Val Asn Thr
1               5                   10                  15

Arg Gly Ser Phe Val Cys Glu Cys Pro Lys Gly Tyr Thr Leu Asp Lys
                20                  25                  30

Asn Gln Gln Asp Cys Ile Asp Ile Asn Glu Cys Gln Glu Asn Ser Gly
            35                  40                  45

Leu Gly Pro Cys Glu Phe Gly Cys Lys Asn Leu Pro Gly Gly Phe Glu
 50                  55                  60

Cys Gln Cys Pro Ser Gly Tyr Lys Leu Asp Lys Lys Thr Gln Lys Cys
 65                  70                  75                  80

Ile

<210> SEQ ID NO 164
<211> LENGTH: 62
<212> TYPE: PRT
<213> ORGANISM: Artificial Sequence
<220> FEATURE:
<223> OTHER INFORMATION: PfRipr

<400> SEQUENCE: 164

Gly Tyr Ile Gly Asp Gly Arg Thr Lys Gly Thr Gly Cys Gln Asn Val
1               5                   10                  15

```
Asn Glu Cys Leu Thr Gly Glu Ala Arg Cys Glu Gln Leu Cys Thr Asp
         20                  25                  30

Tyr Ser Pro Gly Tyr Ala Cys Ser Cys Asn Met Gly Tyr Arg Leu Asn
         35                  40                  45

Thr Lys Asp Met Arg Ser Cys Ile Asp Ile Asp Glu Cys Met
         50                  55                  60

<210> SEQ ID NO 165
<211> LENGTH: 58
<212> TYPE: PRT
<213> ORGANISM: Artificial Sequence
<220> FEATURE:
<223> OTHER INFORMATION: PfRipr

<400> SEQUENCE: 165

Glu Cys Val Leu Asn Thr His Asp Cys Lys Lys Asp Ser Val Cys Val
1               5                   10                  15

Asn Glu Asp Gly Gly Phe Ser Cys Lys Cys Leu Glu Lys Gly Phe Glu
         20                  25                  30

Phe Asn Lys Glu Lys Arg Ala Cys Glu Asp Ile Asp Glu Cys Ser Asn
         35                  40                  45

Gly Asp Ser Lys Cys Asp Gln Leu Cys Phe
         50                  55

<210> SEQ ID NO 166
<211> LENGTH: 54
<212> TYPE: PRT
<213> ORGANISM: Artificial Sequence
<220> FEATURE:
<223> OTHER INFORMATION: PfRipr

<400> SEQUENCE: 166

Ala Cys Glu Asp Ile Asp Glu Cys Ser Asn Gly Asp Ser Lys Cys Asp
1               5                   10                  15

Gln Leu Cys Phe Asn Thr Ile Gly Gly Tyr Lys Cys Gly Cys Tyr Lys
         20                  25                  30

Gly Phe Arg Leu Asn Leu Thr Gly Pro Glu Glu Asn Arg Leu Asp Val
         35                  40                  45

Gln Ser Arg Val Cys Ile
         50

<210> SEQ ID NO 167
<211> LENGTH: 40
<212> TYPE: PRT
<213> ORGANISM: Artificial Sequence
<220> FEATURE:
<223> OTHER INFORMATION: PfRipr

<400> SEQUENCE: 167

Glu Cys Gln Glu Asn Ser Gly Leu Gly Pro Cys Glu Phe Gly Cys Lys
1               5                   10                  15

Asn Leu Pro Gly Gly Phe Glu Cys Gln Cys Pro Ser Gly Tyr Lys Leu
         20                  25                  30

Asp Lys Lys Thr Gln Lys Cys Ile
         35                  40

<210> SEQ ID NO 168
<211> LENGTH: 40
<212> TYPE: PRT
<213> ORGANISM: Artificial Sequence
<220> FEATURE:
```

<223> OTHER INFORMATION: PfRipr

<400> SEQUENCE: 168

Glu Cys Leu Glu Thr Lys Glu Leu Thr Gly Cys Ser His Gly Cys Glu
1               5                   10                  15

Asn Thr Tyr Gly Ser Phe Lys Cys Thr Cys Pro Ser Gly Tyr Glu Leu
            20                  25                  30

Asn Ser Asn Gly Lys Ile Cys Glu
        35                  40

<210> SEQ ID NO 169
<211> LENGTH: 70
<212> TYPE: PRT
<213> ORGANISM: Artificial Sequence
<220> FEATURE:
<223> OTHER INFORMATION: PfRipr

<400> SEQUENCE: 169

Ile Cys Val Asn Lys Pro Gly Ser Tyr Thr Cys Glu Cys Pro Thr Gly
1               5                   10                  15

Tyr Lys Leu Asp Ile Asp Lys Lys Asn Cys Ile Asp Ile Asp Glu Cys
            20                  25                  30

Leu Glu Asn Asp Gly Lys Gly Ser Cys Glu Tyr Cys Arg Asn Leu
        35                  40                  45

Ile Gly Ser Tyr Glu Cys Ile Cys Pro Ser Gly Tyr Arg Leu Asp Lys
    50                  55                  60

Ser Asn Gln Lys Cys Lys
65                  70

<210> SEQ ID NO 170
<211> LENGTH: 129
<212> TYPE: PRT
<213> ORGANISM: Artificial Sequence
<220> FEATURE:
<223> OTHER INFORMATION: PfRipr

<400> SEQUENCE: 170

Ile Cys Glu Asn Ile Ile Gly Ser Phe Lys Cys Val Cys Gly Lys Gly
1               5                   10                  15

Tyr Thr Phe His Glu Glu Lys Gly Cys Leu Asp Val Asp Glu Cys Leu
            20                  25                  30

Asn Gly Thr His Asp Cys Pro Glu Ser Thr Asn Cys Ile Asn Ile Ile
        35                  40                  45

Gly Ser Phe Thr Cys Ser Cys Leu Lys Ser Gly Tyr Arg Tyr Asn Arg
    50                  55                  60

Asn Lys Lys Ile Cys Glu Asp Ile Asn Glu Cys Lys Asn Gly Glu Ala
65                  70                  75                  80

His Cys Glu Gln Ile Cys Ile Asn Thr Leu Gly Gly Tyr Lys Cys Asp
                85                  90                  95

Cys Phe Pro Gly Phe Lys Tyr Lys Val Glu Arg Leu Asn Glu Leu
            100                 105                 110

Ser Ser Gly Thr Arg Gly Ile Cys Ile Asp Ile Asn Glu Cys Leu Glu
        115                 120                 125

Thr

<210> SEQ ID NO 171
<211> LENGTH: 78
<212> TYPE: PRT
<213> ORGANISM: Artificial Sequence
<220> FEATURE:
<223> OTHER INFORMATION: PfRipr

<400> SEQUENCE: 171

Asp Ile Cys Asn Gln Thr Gly Gln Ile Cys Glu Asn Ile Ile Gly Ser
1               5                   10                  15

Phe Lys Cys Val Cys Gly Lys Gly Tyr Thr Phe His Glu Glu Lys Gly
            20                  25                  30

Cys Leu Asp Val Asp Glu Cys Leu Asn Gly Thr His Asp Cys Pro Glu
        35                  40                  45

Ser Thr Asn Cys Ile Asn Ile Ile Gly Ser Phe Thr Cys Ser Cys Leu
    50                  55                  60

Lys Ser Gly Tyr Arg Tyr Asn Arg Asn Lys Lys Ile Cys Glu
65                  70                  75

<210> SEQ ID NO 172
<211> LENGTH: 92
<212> TYPE: PRT
<213> ORGANISM: Artificial Sequence
<220> FEATURE:
<223> OTHER INFORMATION: PfRipr

<400> SEQUENCE: 172

Glu Cys Leu Asn Gly Thr His Asp Cys Pro Glu Ser Thr Asn Cys Ile
1               5                   10                  15

Asn Ile Ile Gly Ser Phe Thr Cys Ser Cys Leu Lys Ser Gly Tyr Arg
            20                  25                  30

Tyr Asn Arg Asn Lys Lys Ile Cys Glu Asp Ile Asn Glu Cys Lys Asn
        35                  40                  45

Gly Glu Ala His Cys Glu Gln Ile Cys Ile Asn Thr Leu Gly Gly Tyr
    50                  55                  60

Lys Cys Asp Cys Phe Pro Gly Phe Lys Tyr Lys Val Glu Arg Leu Asp
65                  70                  75                  80

Asn Glu Leu Ser Ser Gly Thr Arg Gly Ile Cys Ile
            85                  90

<210> SEQ ID NO 173
<211> LENGTH: 81
<212> TYPE: PRT
<213> ORGANISM: Artificial Sequence
<220> FEATURE:
<223> OTHER INFORMATION: PfRipr

<400> SEQUENCE: 173

Glu Cys Ala Asp Gly Ile His Glu Cys Ser His Ile Cys Val Asn Lys
1               5                   10                  15

Pro Gly Ser Tyr Thr Cys Glu Cys Pro Thr Gly Tyr Lys Leu Asp Ile
            20                  25                  30

Asp Lys Lys Asn Cys Ile Asp Ile Asp Glu Cys Leu Glu Asn Asp Gly
        35                  40                  45

Lys Gly Ser Cys Glu Tyr Glu Cys Arg Asn Leu Ile Gly Ser Tyr Glu
    50                  55                  60

Cys Ile Cys Pro Ser Gly Tyr Arg Leu Asp Lys Ser Asn Gln Lys Cys
65                  70                  75                  80

Lys

<210> SEQ ID NO 174
<211> LENGTH: 62
<212> TYPE: PRT

<213> ORGANISM: Artificial Sequence
<220> FEATURE:
<223> OTHER INFORMATION: PfRipr

<400> SEQUENCE: 174

Gly Tyr Tyr Gly Asp Gly Arg Thr Lys Gly Thr Gly Cys Glu Asn Ile
1               5                   10                  15

Asn Glu Cys Thr Thr Gly Glu Ala Arg Cys Glu Gln Met Cys Thr Asp
            20                  25                  30

Tyr Thr Pro Gly Tyr Ala Cys Ser Cys Leu Asn Gly Phe Lys Leu Asn
        35                  40                  45

Pro Lys Asp Leu Lys Gly Cys Leu Asp Ile Asp Glu Cys Ala
    50                  55                  60

<210> SEQ ID NO 175
<211> LENGTH: 54
<212> TYPE: PRT
<213> ORGANISM: Artificial Sequence
<220> FEATURE:
<223> OTHER INFORMATION: PfRipr

<400> SEQUENCE: 175

Ile Cys Glu Asp Ile Asn Glu Cys Lys Asn Gly Glu Ala His Cys Glu
1               5                   10                  15

Gln Ile Cys Ile Asn Thr Leu Gly Gly Tyr Lys Cys Asp Cys Phe Pro
            20                  25                  30

Gly Phe Lys Tyr Lys Val Glu Arg Leu Asp Asn Glu Leu Ser Ser Gly
        35                  40                  45

Thr Arg Gly Ile Cys Ile
    50

<210> SEQ ID NO 176
<211> LENGTH: 54
<212> TYPE: PRT
<213> ORGANISM: Artificial Sequence
<220> FEATURE:
<223> OTHER INFORMATION: PfRipr

<400> SEQUENCE: 176

Ile Cys Glu Asp Ile Asn Glu Cys Lys Asn Gly Glu Ala His Cys Glu
1               5                   10                  15

Gln Ile Cys Ile Asn Thr Leu Gly Gly Tyr Lys Cys Asp Cys Phe Pro
            20                  25                  30

Gly Phe Lys Tyr Lys Val Glu Arg Leu Asp Asn Glu Leu Ser Ser Gly
        35                  40                  45

Thr Arg Gly Ile Cys Ile
    50

<210> SEQ ID NO 177
<211> LENGTH: 40
<212> TYPE: PRT
<213> ORGANISM: Artificial Sequence
<220> FEATURE:
<223> OTHER INFORMATION: PfRipr

<400> SEQUENCE: 177

Glu Cys Leu Glu Asn Asp Gly Lys Gly Ser Cys Glu Tyr Glu Cys Arg
1               5                   10                  15

Asn Leu Ile Gly Ser Tyr Glu Cys Ile Cys Pro Ser Gly Tyr Arg Leu
            20                  25                  30

Asp Lys Ser Asn Gln Lys Cys Lys

<210> SEQ ID NO 178
<211> LENGTH: 40
<212> TYPE: PRT
<213> ORGANISM: Artificial Sequence
<220> FEATURE:
<223> OTHER INFORMATION: PfRipr

<400> SEQUENCE: 178

Glu Cys Leu Glu Ser Pro Glu Leu Thr Gly Cys Ser His Gly Cys Ile
1               5                   10                  15

Asn Lys Arg Gly Gly Phe Gln Cys Thr Cys Pro Lys Gly Phe Gln Leu
            20                  25                  30

Gly Met Asp Gly Lys Val Cys Glu
        35                  40

<210> SEQ ID NO 179
<211> LENGTH: 70
<212> TYPE: PRT
<213> ORGANISM: Artificial Sequence
<220> FEATURE:
<223> OTHER INFORMATION: PfRipr

<400> SEQUENCE: 179

Ile Cys Val Asn Thr Arg Gly Ser Phe Val Cys Glu Cys Pro Lys Gly
1               5                   10                  15

Tyr Thr Leu Asp Lys Asn Gln Gln Asp Cys Ile Asp Ile Asn Glu Cys
            20                  25                  30

Gln Glu Asn Ser Gly Leu Gly Pro Cys Glu Phe Gly Cys Lys Asn Leu
        35                  40                  45

Pro Gly Gly Phe Glu Cys Gln Cys Pro Ser Gly Tyr Lys Leu Asp Lys
    50                  55                  60

Lys Thr Gln Lys Cys Ile
65                  70

<210> SEQ ID NO 180
<211> LENGTH: 130
<212> TYPE: PRT
<213> ORGANISM: Artificial Sequence
<220> FEATURE:
<223> OTHER INFORMATION: PfRipr

<400> SEQUENCE: 180

Val Cys Phe Asn Lys Lys Gly Gly Phe Glu Cys Lys Cys Gly Thr Gly
1               5                   10                  15

Phe Gln Tyr Asp Glu Asn Glu Asn Ala Cys Lys Asp Ile Asn Glu Cys
            20                  25                  30

Val Leu Asn Thr His Asp Cys Lys Lys Asp Ser Val Cys Val Asn Glu
        35                  40                  45

Asp Gly Gly Phe Ser Cys Lys Cys Leu Glu Lys Gly Phe Glu Phe Asn
    50                  55                  60

Lys Glu Lys Arg Ala Cys Glu Asp Ile Asp Glu Cys Ser Asn Gly Asp
65                  70                  75                  80

Ser Lys Cys Asp Gln Leu Cys Phe Asn Thr Ile Gly Gly Tyr Arg Cys
            85                  90                  95

Gly Cys Tyr Lys Gly Phe Arg Leu Asn Leu Thr Gly Pro Glu Glu Asn
        100                 105                 110

Arg Leu Asp Val Lys Ser Arg Val Cys Ile Asp Ile Asp Glu Cys Leu
    115                 120                 125

```
Glu Ser
    130

<210> SEQ ID NO 181
<211> LENGTH: 79
<212> TYPE: PRT
<213> ORGANISM: Artificial Sequence
<220> FEATURE:
<223> OTHER INFORMATION: PfRipr

<400> SEQUENCE: 181

Asn Leu Cys Thr Gly Phe Gly Glu Val Cys Phe Asn Lys Lys Gly Gly
1               5                   10                  15

Phe Glu Cys Lys Cys Gly Thr Gly Phe Gln Tyr Asp Glu Asn Glu Asn
                20                  25                  30

Ala Cys Lys Asp Ile Asn Glu Cys Val Leu Asn Thr His Asp Cys Lys
            35                  40                  45

Lys Asp Ser Val Cys Val Asn Glu Asp Gly Gly Phe Ser Cys Lys Cys
        50                  55                  60

Leu Glu Lys Gly Phe Glu Phe Asn Lys Glu Lys Arg Ala Cys Glu
65                  70                  75

<210> SEQ ID NO 182
<211> LENGTH: 92
<212> TYPE: PRT
<213> ORGANISM: Artificial Sequence
<220> FEATURE:
<223> OTHER INFORMATION: PfRipr

<400> SEQUENCE: 182

Glu Cys Val Leu Asn Thr His Asp Cys Lys Lys Asp Ser Val Cys Val
1               5                   10                  15

Asn Glu Asp Gly Gly Phe Ser Cys Lys Cys Leu Glu Lys Gly Phe Glu
                20                  25                  30

Phe Asn Lys Glu Lys Arg Ala Cys Glu Asp Ile Asp Glu Cys Ser Asn
            35                  40                  45

Gly Asp Ser Lys Cys Asp Gln Leu Cys Phe Asn Thr Ile Gly Gly Tyr
        50                  55                  60

Arg Cys Gly Cys Tyr Lys Gly Phe Arg Leu Asn Leu Thr Gly Pro Glu
65                  70                  75                  80

Glu Asn Arg Leu Asp Val Lys Ser Arg Val Cys Ile
                85                  90

<210> SEQ ID NO 183
<211> LENGTH: 81
<212> TYPE: PRT
<213> ORGANISM: Artificial Sequence
<220> FEATURE:
<223> OTHER INFORMATION: PfRipr

<400> SEQUENCE: 183

Glu Cys Lys Glu Gly Ser His Ser Cys Ser His Ile Cys Val Asn Thr
1               5                   10                  15

Arg Gly Ser Phe Val Cys Glu Cys Pro Lys Gly Tyr Thr Leu Asp Lys
                20                  25                  30

Asn Gln Gln Asp Cys Ile Asp Ile Asn Glu Cys Gln Glu Asn Ser Gly
            35                  40                  45

Leu Gly Pro Cys Glu Phe Gly Cys Lys Asn Leu Pro Gly Gly Phe Glu
        50                  55                  60
```

-continued

Cys Gln Cys Pro Ser Gly Tyr Lys Leu Asp Lys Thr Gln Lys Cys
65                  70                  75                  80

Ile

<210> SEQ ID NO 184
<211> LENGTH: 62
<212> TYPE: PRT
<213> ORGANISM: Artificial Sequence
<220> FEATURE:
<223> OTHER INFORMATION: PfRipr

<400> SEQUENCE: 184

Gly Tyr Ile Gly Asp Gly Arg Thr Lys Gly Thr Gly Cys Gln Asn Val
1               5                   10                  15

Asn Glu Cys Leu Thr Gly Glu Ala Arg Cys Glu Gln Leu Cys Thr Asp
                20                  25                  30

Tyr Ser Pro Gly Tyr Ala Cys Ser Cys Asn Met Gly Tyr Arg Leu Asn
            35                  40                  45

Thr Lys Asp Met Arg Ser Cys Ile Asp Ile Asp Glu Cys Lys
        50                  55                  60

<210> SEQ ID NO 185
<211> LENGTH: 58
<212> TYPE: PRT
<213> ORGANISM: Artificial Sequence
<220> FEATURE:
<223> OTHER INFORMATION: PfRipr

<400> SEQUENCE: 185

Glu Cys Val Leu Asn Thr His Asp Cys Lys Lys Asp Ser Val Cys Val
1               5                   10                  15

Asn Glu Asp Gly Gly Phe Ser Cys Lys Cys Leu Glu Lys Gly Phe Glu
                20                  25                  30

Phe Asn Lys Glu Lys Arg Ala Cys Glu Asp Ile Asp Glu Cys Ser Asn
            35                  40                  45

Gly Asp Ser Lys Cys Asp Gln Leu Cys Phe
        50                  55

<210> SEQ ID NO 186
<211> LENGTH: 54
<212> TYPE: PRT
<213> ORGANISM: Artificial Sequence
<220> FEATURE:
<223> OTHER INFORMATION: PfRipr

<400> SEQUENCE: 186

Ala Cys Glu Asp Ile Asp Glu Cys Ser Asn Gly Asp Ser Lys Cys Asp
1               5                   10                  15

Gln Leu Cys Phe Asn Thr Ile Gly Gly Tyr Arg Cys Gly Cys Tyr Lys
                20                  25                  30

Gly Phe Arg Leu Asn Leu Thr Gly Pro Glu Glu Asn Arg Leu Asp Val
            35                  40                  45

Lys Ser Arg Val Cys Ile
        50

<210> SEQ ID NO 187
<211> LENGTH: 40
<212> TYPE: PRT
<213> ORGANISM: Artificial Sequence
<220> FEATURE:
<223> OTHER INFORMATION: PfRipr

```
<400> SEQUENCE: 187

Glu Cys Gln Glu Asn Ser Gly Leu Gly Pro Cys Glu Phe Gly Cys Lys
1               5                   10                  15

Asn Leu Pro Gly Gly Phe Glu Cys Gln Cys Pro Ser Gly Tyr Lys Leu
            20                  25                  30

Asp Lys Lys Thr Gln Lys Cys Ile
            35                  40

<210> SEQ ID NO 188
<211> LENGTH: 88
<212> TYPE: PRT
<213> ORGANISM: Artificial Sequence
<220> FEATURE:
<223> OTHER INFORMATION: TRAP

<400> SEQUENCE: 188

Ser Ser Thr Thr Asp Met Pro Ser Ser Thr Thr Asp Met Ser Ser Ser
1               5                   10                  15

Thr Thr Asp Met Pro Ser Ser Pro Thr Asp Met Pro Ser Ser Thr Thr
            20                  25                  30

Asp Met Pro Ser Ser Pro Thr His Thr Arg Val Glu Glu Thr Asp Glu
            35                  40                  45

Glu His Asn His Arg Lys Asp Met Asp Ile Lys Phe Pro Glu Asn Met
        50                  55                  60

Asp Asp Ile Pro Val Glu Asp Ile Pro Met Pro Ile Asp Pro Arg His
65                  70                  75                  80

Gly Val Glu Pro Ser Ala Ser Asp
                85

<210> SEQ ID NO 189
<211> LENGTH: 47
<212> TYPE: PRT
<213> ORGANISM: Artificial Sequence
<220> FEATURE:
<223> OTHER INFORMATION: Ron2L

<400> SEQUENCE: 189

Ala Asp Ile Ala Gln His Ala Ala Asp Val Gly Val Gly Pro Ala Glu
1               5                   10                  15

Ser Cys Phe Ile Met Val Lys Pro Pro Ala Leu His Cys Val Leu Lys
            20                  25                  30

Pro Val Glu Thr Leu Met Lys Ser Ala Leu Thr Ile Gly Val Gln
            35                  40                  45

<210> SEQ ID NO 190
<211> LENGTH: 80
<212> TYPE: PRT
<213> ORGANISM: Artificial Sequence
<220> FEATURE:
<223> OTHER INFORMATION: TRAP

<400> SEQUENCE: 190

Pro Lys Asp Ala Val Cys Lys Pro Ile Trp Ser Asp Trp Ser Lys Cys
1               5                   10                  15

Asp Ala Lys Cys Gly Ile Gly Thr Arg Tyr Gln Lys Leu Met Gly Val
            20                  25                  30

Thr Thr Ile Ser Glu Pro Thr Val Gly Thr Asn Gly Lys Ser Gly Arg
            35                  40                  45

Thr Cys Glu Met Ile Tyr Glu Asn Val Glu Val Pro Lys Glu Glu Cys
        50                  55                  60
```

```
Ser Val Glu Cys Asp Glu Gln Gly Glu Thr Glu Gly Ser Leu Asp Glu
 65                  70                  75                  80
```

<210> SEQ ID NO 191
<211> LENGTH: 47
<212> TYPE: PRT
<213> ORGANISM: Artificial Sequence
<220> FEATURE:
<223> OTHER INFORMATION: Ron2L

<400> SEQUENCE: 191

```
Met Asp Ile Ala Gln His Ala Val Asp Val Gly His Pro Pro Val Glu
 1               5                  10                  15

Thr Cys Trp Tyr Leu Val Lys Pro Pro Ser Met His Cys Ala Ile Glu
             20                  25                  30

Pro Val Ser Asn Leu Ala Ile Ser Ala Ser Ser Val Ala Ile Arg
         35                  40                  45
```

<210> SEQ ID NO 192
<211> LENGTH: 47
<212> TYPE: PRT
<213> ORGANISM: Artificial Sequence
<220> FEATURE:
<223> OTHER INFORMATION: Ron2L

<400> SEQUENCE: 192

```
Met Asp Ile Ala Gln His Ala Val Asp Met Gly His Pro Pro Val Glu
 1               5                  10                  15

Thr Cys Trp Tyr Leu Val Lys Pro Pro Ser Met His Cys Ala Ile Glu
             20                  25                  30

Pro Ile Ser Asn Leu Ala Ile Ser Ala Ser Ser Val Ala Ile Arg
         35                  40                  45
```

<210> SEQ ID NO 193
<211> LENGTH: 317
<212> TYPE: PRT
<213> ORGANISM: Artificial Sequence
<220> FEATURE:
<223> OTHER INFORMATION: 25FKO-230_C0

<400> SEQUENCE: 193

```
Met Val Thr Val Asp Thr Val Cys Lys Arg Gly Phe Leu Ile Gln Met
 1               5                  10                  15

Ser Gly His Leu Glu Cys Lys Cys Glu Asn Asp Leu Val Leu Val Asn
             20                  25                  30

Glu Glu Thr Cys Glu Glu Lys Val Leu Lys Cys Asp Glu Lys Thr Val
         35                  40                  45

Asn Lys Pro Cys Gly Asp Phe Ser Lys Cys Ile Lys Ile Asp Gly Asn
 50                  55                  60

Pro Val Ser Tyr Ala Cys Lys Cys Asn Leu Gly Tyr Asp Met Val Asn
 65                  70                  75                  80

Asn Val Cys Ile Pro Asn Glu Cys Lys Asn Val Ala Cys Gly Asn Gly
             85                  90                  95

Lys Cys Ile Leu Asp Thr Ser Asn Pro Val Lys Thr Gly Val Cys Ser
            100                 105                 110

Cys Asn Ile Gly Lys Val Pro Asn Val Gln Asp Gln Lys Cys Ser Lys
            115                 120                 125

Asp Gly Glu Thr Lys Cys Ser Leu Lys Cys Leu Lys Glu Asn Glu Ala
        130                 135                 140
```

```
Cys Lys Ala Val Asp Gly Ile Tyr Lys Cys Asp Cys Lys Asp Gly Phe
145                 150                 155                 160

Ile Ile Asp Asn Glu Ala Ser Ile Cys Thr Ala Ala Val Glu Tyr Val
                165                 170                 175

Asp Glu Lys Glu Arg Gln Gly Glu Ile Tyr Pro Phe Gly Asp Glu Glu
            180                 185                 190

Glu Lys Asp Glu Gly Gly Glu Ser Phe Thr Tyr Glu Lys Ser Glu Val
            195                 200                 205

Asp Lys Thr Asp Leu Phe Lys Phe Ile Glu Gly Glu Gly Asp Asp
        210                 215                 220

Val Tyr Lys Val Asp Gly Ser Lys Val Leu Leu Asp Asp Thr Ile
225                 230                 235                 240

Ser Arg Val Ser Lys Lys His Thr Ala Arg Asp Gly Glu Tyr Gly Glu
                245                 250                 255

Tyr Gly Glu Ala Val Glu Asp Gly Glu Asn Val Ile Lys Ile Ile Arg
            260                 265                 270

Ser Val Leu Gln Ser Gly Ala Leu Pro Ser Val Gly Val Asp Glu Leu
            275                 280                 285

Asp Lys Ile Asp Leu Ser Tyr Glu Thr Thr Glu Ser Gly Asp Thr Ala
        290                 295                 300

Val Ser Glu Asp Ser Tyr Asp Lys Tyr Ala Ser Asn Asn
305                 310                 315

<210> SEQ ID NO 194
<211> LENGTH: 293
<212> TYPE: PRT
<213> ORGANISM: Artificial Sequence
<220> FEATURE:
<223> OTHER INFORMATION: CelTos-fCSP_TSR-TRAP_TSR

<400> SEQUENCE: 194

Met Ala Phe Arg Gly Asn Asn Gly His Asp Ser Ser Ser Ser Leu Tyr
1               5                   10                  15

Gly Gly Ser Gln Phe Ile Glu Gln Leu Asp Asn Ser Phe Thr Ser Ala
            20                  25                  30

Phe Leu Glu Ser Gln Ser Met Asn Lys Ile Gly Asp Asp Leu Ala Glu
        35                  40                  45

Thr Ile Ser Asn Glu Leu Val Ser Val Leu Gln Lys Asn Ser Pro Thr
    50                  55                  60

Phe Leu Glu Ser Ser Phe Asp Ile Lys Ser Glu Val Lys Lys His Ala
65                  70                  75                  80

Lys Ser Met Leu Lys Glu Leu Ile Lys Val Gly Leu Pro Ser Phe Glu
                85                  90                  95

Asn Leu Val Ala Glu Asn Val Lys Pro Pro Lys Val Asp Pro Ala Thr
            100                 105                 110

Tyr Gly Ile Ile Val Pro Val Leu Thr Ser Leu Phe Asn Lys Val Glu
        115                 120                 125

Thr Ala Val Gly Ala Lys Val Ser Asp Glu Ile Trp Asn Tyr Asn Ser
    130                 135                 140

Pro Asp Val Ser Glu Ser Glu Glu Ser Leu Ser Asp Asp Phe Phe Asp
145                 150                 155                 160

Ala Ala Gly Pro Ser Asp Lys His Ile Glu Gln Tyr Leu Lys Lys Ile
                165                 170                 175

Gln Asn Ser Leu Ser Thr Glu Trp Ser Pro Cys Ser Val Thr Cys Gly
            180                 185                 190
```

```
Asn Gly Ile Gln Val Arg Ile Lys Pro Gly Ser Ala Asn Lys Pro Lys
            195                 200                 205

Asp Glu Leu Asp Tyr Glu Asn Asp Ile Glu Lys Lys Ile Cys Lys Met
        210                 215                 220

Glu Lys Cys Ser Ser Val Phe Asn Val Val Asn Ser Ala Ala Val Ala
225                 230                 235                 240

Met Ala Glu Lys Thr Ala Ser Cys Gly Val Trp Asp Glu Trp Ser Pro
                245                 250                 255

Cys Ser Val Thr Cys Gly Lys Gly Thr Arg Ser Arg Lys Arg Glu Ile
                260                 265                 270

Leu His Glu Gly Cys Thr Ser Glu Leu Gln Glu Gln Cys Glu Glu Glu
            275                 280                 285

Arg Cys Leu Pro Lys
    290

<210> SEQ ID NO 195
<211> LENGTH: 322
<212> TYPE: PRT
<213> ORGANISM: Artificial Sequence
<220> FEATURE:
<223> OTHER INFORMATION: 1_19-4-1_8-2_8-MSP3aGKO

<400> SEQUENCE: 195

Met Ala Ile Ser Gln His Gln Cys Val Lys Gln Cys Pro Glu Asn
1               5                   10                  15

Ser Gly Cys Phe Arg His Leu Asp Glu Arg Glu Cys Lys Cys Leu
                20                  25                  30

Leu Asn Tyr Lys Gln Glu Gly Asp Lys Cys Val Ala Ala Gly Leu Glu
            35                  40                  45

Asp Glu Asp Leu Cys Lys His Asn Asn Gly Cys Gly Asp Asp Lys
    50                  55                  60

Leu Cys Glu Tyr Val Gly Asn Arg Arg Val Cys Lys Cys Lys Glu
65                  70                  75                  80

Gly Tyr Lys Leu Glu Gly Ile Glu Cys Val Glu Leu Leu Ala Ala Gly
                85                  90                  95

Asn Asn Lys Val Cys Glu Asn Thr Lys Cys Pro Leu Asn Ser Asn Cys
                100                 105                 110

Tyr Val Ile Asp Asp Glu Glu Thr Cys Arg Cys Leu Pro Gly Phe Asn
                115                 120                 125

Asn Ile Lys Ile Asp Asp Glu Met Asn Cys Val Arg Asp Ala Ala Gly
130                 135                 140

Asp Thr Leu Asp Cys Ser Arg Asn Asn Gly Cys Asp Ile His Ala
145                 150                 155                 160

Lys Cys Ser Phe Ile Asn Lys Gln Ile Val Cys Glu Cys Lys Asp Lys
                165                 170                 175

Phe Glu Gly Asp Gly Ile Tyr Cys Ser Tyr Ser Ala Ala Gly Lys Glu
                180                 185                 190

Ile Val Lys Lys Tyr Asn Leu Asn Leu Arg Asn Ala Ile Leu Asn Asn
            195                 200                 205

Asn Ala Gln Ile Glu Asn Glu Glu Asn Val Asn Thr Ala Ile Thr Gly
        210                 215                 220

Asn Asp Phe Ser Gly Gly Glu Phe Leu Trp Pro Gly Tyr Thr Glu Glu
225                 230                 235                 240

Leu Lys Ala Lys Lys Ala Ser Glu Asp Ala Glu Lys Ala Ala Asn Asp
                245                 250                 255
```

```
Ala Glu Asn Ala Ala Lys Glu Ala Glu Ala Ala Lys Glu Ala Val
            260                 265                 270

Asn Leu Lys Glu Ser Asp Lys Ser Tyr Thr Lys Ala Lys Glu Ala Ala
            275                 280                 285

Thr Ala Ala Ser Lys Ala Lys Lys Ala Val Glu Thr Ala Leu Lys Ala
        290                 295                 300

Lys Asp Asp Ala Glu Lys Ser Ser Lys Ala Asp Ser Ile Ser Thr Lys
305                 310                 315                 320

Thr Lys

<210> SEQ ID NO 196
<211> LENGTH: 358
<212> TYPE: PRT
<213> ORGANISM: Artificial Sequence
<220> FEATURE:
<223> OTHER INFORMATION: 1_19-1_8-2_8-4-25FKO

<400> SEQUENCE: 196

Met Ala Ile Ser Gln His Gln Cys Val Lys Lys Gln Cys Pro Glu Asn
1               5                   10                  15

Ser Gly Cys Phe Arg His Leu Asp Glu Arg Glu Glu Cys Lys Cys Leu
            20                  25                  30

Leu Asn Tyr Lys Gln Glu Gly Asp Lys Cys Val Ala Ala Gly Asn Asn
        35                  40                  45

Lys Val Cys Glu Asn Thr Lys Cys Pro Leu Asn Ser Asn Cys Tyr Val
    50                  55                  60

Ile Asp Asp Glu Glu Thr Cys Arg Cys Leu Pro Gly Phe Asn Asn Ile
65                  70                  75                  80

Lys Ile Asp Asp Glu Met Asn Cys Val Arg Asp Ala Ala Gly Asp Thr
                85                  90                  95

Leu Asp Cys Ser Arg Asn Asn Gly Gly Cys Asp Ile His Ala Lys Cys
            100                 105                 110

Ser Phe Ile Asn Lys Gln Ile Val Cys Glu Cys Lys Asp Lys Phe Glu
        115                 120                 125

Gly Asp Gly Ile Tyr Cys Ser Tyr Ser Ala Ala Gly Leu Glu Asp Glu
    130                 135                 140

Asp Leu Cys Lys His Asn Asn Gly Gly Cys Gly Asp Asp Lys Leu Cys
145                 150                 155                 160

Glu Tyr Val Gly Asn Arg Arg Val Lys Cys Lys Cys Lys Glu Gly Tyr
                165                 170                 175

Lys Leu Glu Gly Ile Glu Cys Val Glu Leu Leu Ala Ala Val Thr Val
            180                 185                 190

Asp Thr Val Cys Lys Arg Gly Phe Leu Ile Gln Met Ser Gly His Leu
        195                 200                 205

Glu Cys Lys Cys Glu Asn Asp Leu Val Leu Asn Glu Glu Thr Cys
    210                 215                 220

Glu Glu Lys Val Leu Lys Cys Asp Glu Lys Thr Val Asn Lys Pro Cys
225                 230                 235                 240

Gly Asp Phe Ser Lys Cys Ile Lys Ile Asp Gly Asn Pro Val Ser Tyr
                245                 250                 255

Ala Cys Lys Cys Asn Leu Gly Tyr Asp Met Val Asn Asn Val Cys Ile
            260                 265                 270

Pro Asn Glu Cys Lys Asn Val Ala Cys Gly Asn Gly Lys Cys Ile Leu
        275                 280                 285

Asp Thr Ser Asn Pro Val Lys Thr Gly Val Cys Ser Cys Asn Ile Gly
```

```
            290                 295                 300
Lys Val Pro Asn Val Gln Asp Gln Lys Cys Ser Lys Asp Gly Glu Thr
305                 310                 315                 320

Lys Cys Ser Leu Lys Cys Leu Lys Glu Asn Glu Ala Cys Lys Ala Val
                325                 330                 335

Asp Gly Ile Tyr Lys Cys Asp Cys Lys Asp Gly Phe Ile Ile Asp Asn
                340                 345                 350

Glu Ala Ser Ile Cys Thr
                355

<210> SEQ ID NO 197
<211> LENGTH: 426
<212> TYPE: PRT
<213> ORGANISM: Artificial Sequence
<220> FEATURE:
<223> OTHER INFORMATION: 1_19-1_8-2_8-4-25FKO-CSP_TSR

<400> SEQUENCE: 197

Met Ala Ile Ser Gln His Gln Cys Val Lys Gln Cys Pro Glu Asn
1               5                   10                  15

Ser Gly Cys Phe Arg His Leu Asp Glu Arg Glu Cys Lys Cys Leu
                20                  25                  30

Leu Asn Tyr Lys Gln Glu Gly Asp Lys Cys Val Ala Ala Gly Asn Asn
                35                  40                  45

Lys Val Cys Glu Asn Thr Lys Cys Pro Leu Asn Ser Asn Cys Tyr Val
50                  55                  60

Ile Asp Asp Glu Glu Thr Cys Arg Cys Leu Pro Gly Phe Asn Asn Ile
65                  70                  75                  80

Lys Ile Asp Asp Glu Met Asn Cys Val Arg Asp Ala Ala Gly Asp Thr
                85                  90                  95

Leu Asp Cys Ser Arg Asn Asn Gly Gly Cys Asp Ile His Ala Lys Cys
                100                 105                 110

Ser Phe Ile Asn Lys Gln Ile Val Cys Glu Cys Lys Asp Lys Phe Glu
                115                 120                 125

Gly Asp Gly Ile Tyr Cys Ser Tyr Ser Ala Ala Gly Leu Glu Asp Glu
130                 135                 140

Asp Leu Cys Lys His Asn Asn Gly Gly Cys Gly Asp Asp Lys Leu Cys
145                 150                 155                 160

Glu Tyr Val Gly Asn Arg Arg Val Lys Cys Lys Cys Lys Glu Gly Tyr
                165                 170                 175

Lys Leu Glu Gly Ile Glu Cys Val Glu Leu Leu Ala Ala Val Thr Val
                180                 185                 190

Asp Thr Val Cys Lys Arg Gly Phe Leu Ile Gln Met Ser Gly His Leu
                195                 200                 205

Glu Cys Lys Cys Glu Asn Asp Leu Val Leu Val Asn Glu Glu Thr Cys
210                 215                 220

Glu Glu Lys Val Leu Lys Cys Asp Glu Lys Thr Val Asn Lys Pro Cys
225                 230                 235                 240

Gly Asp Phe Ser Lys Cys Ile Lys Ile Asp Gly Asn Pro Val Ser Tyr
                245                 250                 255

Ala Cys Lys Cys Asn Leu Gly Tyr Asp Met Val Asn Asn Val Cys Ile
                260                 265                 270

Pro Asn Glu Cys Lys Asn Val Ala Cys Gly Asn Gly Lys Cys Ile Leu
                275                 280                 285

Asp Thr Ser Asn Pro Val Lys Thr Gly Val Cys Ser Cys Asn Ile Gly
```

```
              290                 295                 300
Lys Val Pro Asn Val Gln Asp Gln Lys Cys Ser Lys Asp Gly Glu Thr
305                 310                 315                 320

Lys Cys Ser Leu Lys Cys Leu Lys Glu Asn Glu Ala Cys Lys Ala Val
                325                 330                 335

Asp Gly Ile Tyr Lys Cys Asp Cys Lys Asp Gly Phe Ile Ile Asp Asn
            340                 345                 350

Glu Ala Ser Ile Cys Thr Ala Ala Gly Tyr Leu Lys Lys Ile Gln Asn
        355                 360                 365

Ser Leu Ser Thr Glu Trp Ser Pro Cys Ser Val Thr Cys Gly Asn Gly
    370                 375                 380

Ile Gln Val Arg Ile Lys Pro Gly Ser Ala Asn Lys Pro Lys Asp Glu
385                 390                 395                 400

Leu Asp Tyr Glu Asn Asp Ile Glu Lys Lys Ile Cys Lys Met Glu Lys
                405                 410                 415

Cys Ser Ser Val Phe Asn Val Val Asn Ser
            420                 425

<210> SEQ ID NO 198
<211> LENGTH: 519
<212> TYPE: PRT
<213> ORGANISM: Artificial Sequence
<220> FEATURE:
<223> OTHER INFORMATION: 1_19-1_8-2_8-4-1_10-2_10aglyc-25FKO-CSP_TSR

<400> SEQUENCE: 198

Met Ala Ile Ser Gln His Gln Cys Val Lys Lys Gln Cys Pro Glu Asn
1               5                   10                  15

Ser Gly Cys Phe Arg His Leu Asp Glu Arg Glu Glu Cys Lys Cys Leu
            20                  25                  30

Leu Asn Tyr Lys Gln Glu Gly Asp Lys Cys Val Ala Ala Gly Asn Asn
        35                  40                  45

Lys Val Cys Glu Asn Thr Lys Cys Pro Leu Asn Ser Asn Cys Tyr Val
    50                  55                  60

Ile Asp Asp Glu Glu Thr Cys Arg Cys Leu Pro Gly Phe Asn Asn Ile
65                  70                  75                  80

Lys Ile Asp Asp Glu Met Asn Cys Val Arg Asp Ala Ala Gly Asp Thr
                85                  90                  95

Leu Asp Cys Ser Arg Asn Asn Gly Gly Cys Asp Ile His Ala Lys Cys
            100                 105                 110

Ser Phe Ile Asn Lys Gln Ile Val Cys Glu Cys Lys Asp Lys Phe Glu
        115                 120                 125

Gly Asp Gly Ile Tyr Cys Ser Tyr Ser Ala Ala Gly Leu Glu Asp Glu
    130                 135                 140

Asp Leu Cys Lys His Asn Asn Gly Cys Gly Asp Asp Lys Leu Cys
145                 150                 155                 160

Glu Tyr Val Gly Asn Arg Arg Val Lys Cys Lys Cys Lys Glu Gly Tyr
                165                 170                 175

Lys Leu Glu Gly Ile Glu Cys Val Glu Leu Leu Ala Ala Gly Val Asn
            180                 185                 190

Tyr Ile Cys Glu Tyr Ser Lys Cys Gly Pro Asn Ser Arg Cys Tyr Ile
        195                 200                 205

Val Glu Lys Asp Lys Glu Gln Cys Arg Cys Gln Pro Asn Tyr Ile Val
    210                 215                 220

Asp Met Ser Val Asn Tyr Phe Lys Cys Ile Pro Ala Ala Gly Lys Asp
```

```
                225                 230                 235                 240
        Met Ala Cys Ser Lys Asn Asn Gly Gly Cys Asp Val Asn Ala Glu Cys
                        245                 250                 255

Thr Ile Val Glu Gly Ala Val Lys Cys Gln Cys Ser His Leu Tyr Phe
                        260                 265                 270

Gly Asp Gly Val Phe Cys Val Lys Ala Ala Val Thr Val Asp Thr Val
                        275                 280                 285

Cys Lys Arg Gly Phe Leu Ile Gln Met Ser Gly His Leu Glu Cys Lys
                        290                 295                 300

Cys Glu Asn Asp Leu Val Leu Val Asn Glu Glu Thr Cys Glu Lys
        305                 310                 315                 320

Val Leu Lys Cys Asp Glu Lys Thr Val Asn Lys Pro Cys Gly Asp Phe
                        325                 330                 335

Ser Lys Cys Ile Lys Ile Asp Gly Asn Pro Val Ser Tyr Ala Cys Lys
                        340                 345                 350

Cys Asn Leu Gly Tyr Asp Met Val Asn Asn Val Cys Ile Pro Asn Glu
                        355                 360                 365

Cys Lys Asn Val Ala Cys Gly Asn Gly Lys Cys Ile Leu Asp Thr Ser
                        370                 375                 380

Asn Pro Val Lys Thr Gly Val Cys Ser Cys Asn Ile Gly Lys Val Pro
        385                 390                 395                 400

Asn Val Gln Asp Gln Lys Cys Ser Lys Asp Gly Glu Thr Lys Cys Ser
                        405                 410                 415

Leu Lys Cys Leu Lys Glu Asn Glu Ala Cys Lys Ala Val Asp Gly Ile
                        420                 425                 430

Tyr Lys Cys Asp Cys Lys Asp Gly Phe Ile Ile Asp Asn Glu Ala Ser
                        435                 440                 445

Ile Cys Thr Ala Ala Gly Tyr Leu Lys Lys Ile Gln Asn Ser Leu Ser
                        450                 455                 460

Thr Glu Trp Ser Pro Cys Ser Val Thr Cys Gly Asn Gly Ile Gln Val
        465                 470                 475                 480

Arg Ile Lys Pro Gly Ser Ala Asn Lys Pro Leu Asp Glu Leu Asp Tyr
                        485                 490                 495

Glu Asn Asp Ile Glu Lys Lys Ile Cys Lys Met Glu Lys Cys Ser Ser
                        500                 505                 510

Val Phe Asn Val Val Asn Ser
                        515

<210> SEQ ID NO 199
<211> LENGTH: 398
<212> TYPE: PRT
<213> ORGANISM: Artificial Sequence
<220> FEATURE:
<223> OTHER INFORMATION: 1_19-1_8-2_8-4-R6-CelTos

<400> SEQUENCE: 199

Met Ala Ile Ser Gln His Gln Cys Val Lys Lys Gln Cys Pro Glu Asn
        1               5                   10                  15

Ser Gly Cys Phe Arg His Leu Asp Glu Arg Glu Glu Cys Lys Cys Leu
                        20                  25                  30

Leu Asn Tyr Lys Gln Glu Gly Asp Lys Cys Val Ala Ala Gly Asn Asn
                        35                  40                  45

Lys Val Cys Glu Asn Thr Lys Cys Pro Leu Asn Ser Asn Cys Tyr Val
                        50                  55                  60

Ile Asp Asp Glu Glu Thr Cys Arg Cys Leu Pro Gly Phe Asn Asn Ile
```

```
                65                  70                  75                  80
Lys Ile Asp Asp Glu Met Asn Cys Val Arg Asp Ala Ala Gly Asp Thr
                    85                  90                  95

Leu Asp Cys Ser Arg Asn Asn Gly Gly Cys Asp Ile His Ala Lys Cys
                100                 105                 110

Ser Phe Ile Asn Lys Gln Ile Val Cys Glu Cys Lys Asp Lys Phe Glu
                115                 120                 125

Gly Asp Gly Ile Tyr Cys Ser Tyr Ser Ala Ala Gly Leu Glu Asp Glu
            130                 135                 140

Asp Leu Cys Lys His Asn Asn Gly Gly Cys Gly Asp Asp Lys Leu Cys
145                 150                 155                 160

Glu Tyr Val Gly Asn Arg Arg Val Lys Cys Lys Cys Lys Glu Gly Tyr
                165                 170                 175

Lys Leu Glu Gly Ile Glu Cys Val Glu Leu Leu Ala Ala Gly Lys Cys
            180                 185                 190

Lys Arg Lys Glu Tyr Glu Asn Ile Cys Thr Asn Pro Asn Glu Met Cys
        195                 200                 205

Ala Tyr Asn Glu Glu Thr Asp Ile Val Lys Cys Glu Cys Lys Glu His
        210                 215                 220

Tyr Tyr Arg Ser Ser Arg Gly Glu Cys Ile Ala Ala Val Ala Met Ala
225                 230                 235                 240

Phe Arg Gly Asn Asn Gly His Asp Ser Ser Ser Leu Tyr Gly Gly
                245                 250                 255

Ser Gln Phe Ile Glu Gln Leu Asp Asn Ser Phe Thr Ser Ala Phe Leu
                260                 265                 270

Glu Ser Gln Ser Met Asn Lys Ile Gly Asp Asp Leu Ala Glu Thr Ile
            275                 280                 285

Ser Asn Glu Leu Val Ser Val Leu Gln Lys Asn Ser Pro Thr Phe Leu
        290                 295                 300

Glu Ser Ser Phe Asp Ile Lys Ser Glu Val Lys Lys His Ala Lys Ser
305                 310                 315                 320

Met Leu Lys Glu Leu Ile Lys Val Gly Leu Pro Ser Phe Glu Asn Leu
                325                 330                 335

Val Ala Glu Asn Val Lys Pro Pro Lys Val Asp Pro Ala Thr Tyr Gly
                340                 345                 350

Ile Ile Val Pro Val Leu Thr Ser Leu Phe Asn Lys Val Glu Thr Ala
            355                 360                 365

Val Gly Ala Lys Val Ser Asp Glu Ile Trp Asn Tyr Asn Ser Pro Asp
        370                 375                 380

Val Ser Glu Ser Glu Glu Ser Leu Ser Asp Asp Phe Phe Asp
385                 390                 395

<210> SEQ ID NO 200
<211> LENGTH: 716
<212> TYPE: PRT
<213> ORGANISM: Artificial Sequence
<220> FEATURE:
<223> OTHER INFORMATION: 1_19-1_8-2_8-4-R6-CelTos-25FKO-230_C0

<400> SEQUENCE: 200

Met Ala Ile Ser Gln His Gln Cys Val Lys Lys Gln Cys Pro Glu Asn
1               5                   10                  15

Ser Gly Cys Phe Arg His Leu Asp Glu Arg Glu Glu Cys Lys Cys Leu
                20                  25                  30

Leu Asn Tyr Lys Gln Glu Gly Asp Lys Cys Val Ala Ala Gly Asn Asn
```

```
            35                  40                  45
Lys Val Cys Glu Asn Thr Lys Cys Pro Leu Asn Ser Asn Cys Tyr Val
 50                  55                  60

Ile Asp Asp Glu Glu Thr Cys Arg Cys Leu Pro Gly Phe Asn Asn Ile
65                   70                  75                  80

Lys Ile Asp Asp Glu Met Asn Cys Val Arg Asp Ala Ala Gly Asp Thr
                 85                  90                  95

Leu Asp Cys Ser Arg Asn Asn Gly Gly Cys Asp Ile His Ala Lys Cys
                100                 105                 110

Ser Phe Ile Asn Lys Gln Ile Val Cys Glu Cys Lys Asp Lys Phe Glu
            115                 120                 125

Gly Asp Gly Ile Tyr Cys Ser Tyr Ser Ala Ala Gly Leu Glu Asp Glu
        130                 135                 140

Asp Leu Cys Lys His Asn Asn Gly Gly Cys Gly Asp Asp Lys Leu Cys
145                 150                 155                 160

Glu Tyr Val Gly Asn Arg Arg Val Lys Cys Lys Cys Lys Glu Gly Tyr
                165                 170                 175

Lys Leu Glu Gly Ile Glu Cys Val Glu Leu Leu Ala Ala Gly Lys Cys
            180                 185                 190

Lys Arg Lys Glu Tyr Glu Asn Ile Cys Thr Asn Pro Asn Glu Met Cys
        195                 200                 205

Ala Tyr Asn Glu Glu Thr Asp Ile Val Lys Cys Glu Cys Lys Glu His
    210                 215                 220

Tyr Tyr Arg Ser Ser Arg Gly Glu Cys Ile Ala Ala Val Ala Met Ala
225                 230                 235                 240

Phe Arg Gly Asn Asn Gly His Asp Ser Ser Ser Leu Tyr Gly Gly
                245                 250                 255

Ser Gln Phe Ile Glu Gln Leu Asp Asn Ser Phe Thr Ser Ala Phe Leu
            260                 265                 270

Glu Ser Gln Ser Met Asn Lys Ile Gly Asp Asp Leu Ala Glu Thr Ile
        275                 280                 285

Ser Asn Glu Leu Val Ser Val Leu Gln Lys Asn Ser Pro Thr Phe Leu
    290                 295                 300

Glu Ser Ser Phe Asp Ile Lys Ser Glu Val Lys Lys His Ala Lys Ser
305                 310                 315                 320

Met Leu Lys Glu Leu Ile Lys Val Gly Leu Pro Ser Phe Glu Asn Leu
                325                 330                 335

Val Ala Glu Asn Val Lys Pro Pro Lys Val Asp Pro Ala Thr Tyr Gly
            340                 345                 350

Ile Ile Val Pro Val Leu Thr Ser Leu Phe Asn Lys Val Glu Thr Ala
        355                 360                 365

Val Gly Ala Lys Val Ser Asp Glu Ile Trp Asn Tyr Asn Ser Pro Asp
    370                 375                 380

Val Ser Glu Ser Glu Glu Ser Leu Ser Asp Asp Phe Phe Asp Ala Ala
385                 390                 395                 400

Val Thr Val Asp Thr Val Cys Lys Arg Gly Phe Leu Ile Gln Met Ser
                405                 410                 415

Gly His Leu Glu Cys Lys Cys Glu Asn Asp Leu Val Leu Val Asn Glu
            420                 425                 430

Glu Thr Cys Glu Glu Lys Val Leu Lys Cys Asp Glu Lys Thr Val Asn
        435                 440                 445

Lys Pro Cys Gly Asp Phe Ser Lys Cys Ile Lys Ile Asp Gly Asn Pro
    450                 455                 460
```

Val Ser Tyr Ala Cys Lys Cys Asn Leu Gly Tyr Asp Met Val Asn Asn
465                 470                 475                 480

Val Cys Ile Pro Asn Glu Cys Lys Asn Val Ala Cys Gly Asn Gly Lys
                485                 490                 495

Cys Ile Leu Asp Thr Ser Asn Pro Val Lys Thr Gly Val Cys Ser Cys
            500                 505                 510

Asn Ile Gly Lys Val Pro Asn Val Gln Asp Gln Lys Cys Ser Lys Asp
            515                 520                 525

Gly Glu Thr Lys Cys Ser Leu Lys Cys Leu Lys Glu Asn Glu Ala Cys
            530                 535                 540

Lys Ala Val Asp Gly Ile Tyr Lys Cys Asp Cys Lys Asp Gly Phe Ile
545                 550                 555                 560

Ile Asp Asn Glu Ala Ser Ile Cys Thr Ala Ala Val Glu Tyr Val Asp
                565                 570                 575

Glu Lys Glu Arg Gln Gly Glu Ile Tyr Pro Phe Gly Asp Glu Glu
            580                 585                 590

Lys Asp Glu Gly Gly Glu Ser Phe Thr Tyr Glu Lys Ser Glu Val Asp
            595                 600                 605

Lys Thr Asp Leu Phe Lys Phe Ile Glu Gly Gly Glu Gly Asp Val
            610                 615                 620

Tyr Lys Val Asp Gly Ser Lys Val Leu Leu Asp Asp Asp Thr Ile Ser
625                 630                 635                 640

Arg Val Ser Lys Lys His Thr Ala Arg Asp Gly Glu Tyr Gly Glu Tyr
                645                 650                 655

Gly Glu Ala Val Glu Asp Gly Glu Asn Val Ile Lys Ile Ile Arg Ser
            660                 665                 670

Val Leu Gln Ser Gly Ala Leu Pro Ser Val Gly Val Asp Glu Leu Asp
            675                 680                 685

Lys Ile Asp Leu Ser Tyr Glu Thr Thr Glu Ser Gly Asp Thr Ala Val
            690                 695                 700

Ser Glu Asp Ser Tyr Asp Lys Tyr Ala Ser Asn Asn
705                 710                 715

<210> SEQ ID NO 201
<211> LENGTH: 929
<212> TYPE: PRT
<213> ORGANISM: Artificial Sequence
<220> FEATURE:
<223> OTHER INFORMATION: 1_19-1_8-2_8-4-R6-CelTos-25FKO-230_C0-
      fCSP_TSR-mTRAP_TSR-TRAP_TSR

<400> SEQUENCE: 201

Met Ala Ile Ser Gln His Gln Cys Val Lys Lys Gln Cys Pro Glu Asn
1               5                   10                  15

Ser Gly Cys Phe Arg His Leu Asp Glu Arg Glu Cys Lys Cys Leu
            20                  25                  30

Leu Asn Tyr Lys Gln Glu Gly Asp Lys Cys Val Ala Ala Gly Asn Asn
                35                  40                  45

Lys Val Cys Glu Asn Thr Lys Cys Pro Leu Asn Ser Asn Cys Tyr Val
            50                  55                  60

Ile Asp Asp Glu Glu Thr Cys Arg Cys Leu Pro Gly Phe Asn Asn Ile
65                  70                  75                  80

Lys Ile Asp Asp Glu Met Asn Cys Val Arg Asp Ala Ala Gly Asp Thr
                85                  90                  95

Leu Asp Cys Ser Arg Asn Asn Gly Gly Cys Asp Ile His Ala Lys Cys

```
              100                 105                 110
Ser Phe Ile Asn Lys Gln Ile Val Cys Glu Cys Lys Asp Lys Phe Glu
              115                 120                 125

Gly Asp Gly Ile Tyr Cys Ser Tyr Ser Ala Ala Gly Leu Glu Asp Glu
        130                 135                 140

Asp Leu Cys Lys His Asn Asn Gly Gly Cys Gly Asp Asp Lys Leu Cys
145                 150                 155                 160

Glu Tyr Val Gly Asn Arg Arg Val Lys Cys Lys Cys Lys Glu Gly Tyr
                    165                 170                 175

Lys Leu Glu Gly Ile Glu Cys Val Glu Leu Leu Ala Ala Gly Lys Cys
                180                 185                 190

Lys Arg Lys Glu Tyr Glu Asn Ile Cys Thr Asn Pro Asn Glu Met Cys
            195                 200                 205

Ala Tyr Asn Glu Glu Thr Asp Ile Val Lys Cys Glu Cys Lys Glu His
        210                 215                 220

Tyr Tyr Arg Ser Ser Arg Gly Glu Cys Ile Ala Ala Val Ala Met Ala
225                 230                 235                 240

Phe Arg Gly Asn Asn Gly His Asp Ser Ser Ser Leu Tyr Gly Gly
                    245                 250                 255

Ser Gln Phe Ile Glu Gln Leu Asp Asn Ser Phe Thr Ser Ala Phe Leu
                260                 265                 270

Glu Ser Gln Ser Met Asn Lys Ile Gly Asp Asp Leu Ala Glu Thr Ile
            275                 280                 285

Ser Asn Glu Leu Val Ser Val Leu Gln Lys Asn Ser Pro Thr Phe Leu
        290                 295                 300

Glu Ser Ser Phe Asp Ile Lys Ser Glu Val Lys Lys His Ala Lys Ser
305                 310                 315                 320

Met Leu Lys Glu Leu Ile Lys Val Gly Leu Pro Ser Phe Glu Asn Leu
                    325                 330                 335

Val Ala Glu Asn Val Lys Pro Pro Lys Val Asp Pro Ala Thr Tyr Gly
                340                 345                 350

Ile Ile Val Pro Val Leu Thr Ser Leu Phe Asn Lys Val Glu Thr Ala
            355                 360                 365

Val Gly Ala Lys Val Ser Asp Glu Ile Trp Asn Tyr Asn Ser Pro Asp
        370                 375                 380

Val Ser Glu Ser Glu Glu Ser Leu Ser Asp Asp Phe Phe Asp Ala Ala
385                 390                 395                 400

Val Thr Val Asp Thr Val Cys Lys Arg Gly Phe Leu Ile Gln Met Ser
                    405                 410                 415

Gly His Leu Glu Cys Lys Cys Glu Asn Asp Leu Val Leu Val Asn Glu
                420                 425                 430

Glu Thr Cys Glu Glu Lys Val Leu Lys Cys Asp Glu Lys Thr Val Asn
            435                 440                 445

Lys Pro Cys Gly Asp Phe Ser Lys Cys Ile Lys Ile Asp Gly Asn Pro
        450                 455                 460

Val Ser Tyr Ala Cys Lys Cys Asn Leu Gly Tyr Asp Met Val Asn Asn
465                 470                 475                 480

Val Cys Ile Pro Asn Glu Cys Lys Asn Val Ala Cys Gly Asn Gly Lys
                    485                 490                 495

Cys Ile Leu Asp Thr Ser Asn Pro Val Lys Thr Gly Val Cys Ser Cys
                500                 505                 510

Asn Ile Gly Lys Val Pro Asn Val Gln Asp Gln Lys Cys Ser Lys Asp
            515                 520                 525
```

```
Gly Glu Thr Lys Cys Ser Leu Lys Cys Leu Lys Glu Asn Glu Ala Cys
            530                 535                 540

Lys Ala Val Asp Gly Ile Tyr Lys Cys Asp Cys Lys Asp Gly Phe Ile
545                 550                 555                 560

Ile Asp Asn Glu Ala Ser Ile Cys Thr Ala Val Glu Tyr Val Asp
                565                 570                 575

Glu Lys Glu Arg Gln Gly Glu Ile Tyr Pro Phe Gly Asp Glu Glu
            580                 585                 590

Lys Asp Glu Gly Gly Glu Ser Phe Thr Tyr Glu Lys Ser Glu Val Asp
            595                 600                 605

Lys Thr Asp Leu Phe Lys Phe Ile Glu Gly Gly Glu Gly Asp Asp Val
            610                 615                 620

Tyr Lys Val Asp Gly Ser Lys Val Leu Leu Asp Asp Asp Thr Ile Ser
625                 630                 635                 640

Arg Val Ser Lys Lys His Thr Ala Arg Asp Gly Glu Tyr Gly Glu Tyr
                645                 650                 655

Gly Glu Ala Val Glu Asp Gly Glu Asn Val Ile Lys Ile Ile Arg Ser
            660                 665                 670

Val Leu Gln Ser Gly Ala Leu Pro Ser Val Gly Val Asp Glu Leu Asp
            675                 680                 685

Lys Ile Asp Leu Ser Tyr Glu Thr Thr Glu Ser Gly Asp Thr Ala Val
690                 695                 700

Ser Glu Asp Ser Tyr Asp Lys Tyr Ala Ser Asn Asn Ala Ala Gly Pro
705                 710                 715                 720

Ser Asp Lys His Ile Glu Gln Tyr Leu Lys Lys Ile Gln Asn Ser Leu
            725                 730                 735

Ser Thr Glu Trp Ser Pro Cys Ser Val Thr Cys Gly Asn Gly Ile Gln
            740                 745                 750

Val Arg Ile Lys Pro Gly Ser Ala Asn Lys Pro Lys Asp Glu Leu Asp
            755                 760                 765

Tyr Glu Asn Asp Ile Glu Lys Lys Ile Cys Lys Met Glu Lys Cys Ser
            770                 775                 780

Ser Val Phe Asn Val Val Asn Ser Ala Ala Val Ala Met Ala Thr His
785                 790                 795                 800

Asp Thr Cys Asp Glu Trp Ser Glu Trp Ser Ala Cys Thr His Gly Ile
                805                 810                 815

Ser Thr Arg Lys Cys Leu Ser Asp Ser Ser Ile Lys Asp Glu Thr Leu
            820                 825                 830

Val Cys Thr Lys Cys Asp Lys Trp Gly Glu Trp Ser Glu Cys Lys Asp
            835                 840                 845

Gly Arg Met His Arg Lys Val Leu Asn Cys Pro Phe Ile Lys Glu Glu
850                 855                 860

Gln Glu Cys Asp Val Asn Asn Glu Ala Val Ala Met Ala Glu Lys
865                 870                 875                 880

Thr Ala Ser Cys Gly Val Trp Asp Glu Trp Ser Pro Cys Ser Val Thr
                885                 890                 895

Cys Gly Lys Gly Thr Arg Ser Arg Lys Arg Glu Ile Leu His Glu Gly
            900                 905                 910

Cys Thr Ser Glu Leu Gln Glu Gln Cys Glu Glu Glu Arg Cys Leu Pro
            915                 920                 925

Lys
```

-continued

```
<210> SEQ ID NO 202
<211> LENGTH: 400
<212> TYPE: PRT
<213> ORGANISM: Artificial Sequence
<220> FEATURE:
<223> OTHER INFORMATION: MSP119_3D7-MSP119_FUP-MSP119_Wellcome-
      MSP119A_Type2

<400> SEQUENCE: 202

Met Ala Ile Ser Gln His Gln Cys Val Lys Lys Gln Cys Pro Glu Asn
1               5                   10                  15

Ser Gly Cys Phe Arg His Leu Asp Glu Arg Glu Cys Lys Cys Leu
            20                  25                  30

Leu Asn Tyr Lys Gln Glu Gly Asp Lys Cys Val Glu Asn Pro Asn Pro
            35                  40                  45

Thr Cys Asn Glu Asn Asn Gly Gly Cys Asp Ala Asp Ala Thr Cys Thr
    50                  55                  60

Glu Glu Asp Ser Gly Ser Ser Arg Lys Lys Ile Thr Cys Glu Cys Thr
65                  70                  75                  80

Lys Pro Asp Ser Tyr Pro Leu Phe Asp Gly Ile Phe Cys Ser Ser Ser
                85                  90                  95

Asn Ala Ala Val Ala Met Ala Ile Ser Gln His Gln Cys Val Lys Lys
                100                 105                 110

Gln Cys Pro Glu Asn Ser Gly Cys Phe Arg His Leu Asp Glu Arg Glu
            115                 120                 125

Glu Cys Lys Cys Leu Leu Asn Tyr Lys Gln Glu Gly Asp Lys Cys Val
    130                 135                 140

Glu Asn Pro Asn Pro Thr Cys Asn Glu Asn Asn Gly Gly Cys Asp Ala
145                 150                 155                 160

Asp Ala Lys Cys Thr Glu Glu Asp Ser Gly Ser Asn Gly Lys Lys Ile
                165                 170                 175

Thr Cys Glu Cys Thr Lys Pro Asp Ser Tyr Pro Leu Phe Asp Gly Ile
                180                 185                 190

Phe Cys Ser Ser Ser Asn Ala Ala Val Ala Met Ala Ile Ser Gln His
        195                 200                 205

Gln Cys Val Lys Lys Gln Cys Pro Gln Asn Ser Gly Cys Phe Arg His
    210                 215                 220

Leu Asp Glu Arg Glu Glu Cys Lys Cys Leu Leu Asn Tyr Lys Gln Glu
225                 230                 235                 240

Gly Asp Lys Cys Val Glu Asn Pro Asn Pro Thr Cys Asn Glu Asn Asn
                245                 250                 255

Gly Gly Cys Asp Ala Asp Ala Lys Cys Thr Glu Glu Asp Ser Gly Ser
            260                 265                 270

Asn Gly Lys Lys Ile Thr Cys Glu Cys Thr Lys Pro Asp Ser Tyr Pro
        275                 280                 285

Leu Phe Asp Gly Ile Phe Cys Ser Ser Ser Asn Ala Ala Val Ala Met
    290                 295                 300

Ala Ile Ser Gln His Gln Cys Val Lys Lys Gln Cys Pro Gln Asn Ser
305                 310                 315                 320

Gly Cys Phe Arg His Leu Asp Glu Arg Glu Glu Cys Lys Cys Leu Leu
                325                 330                 335

Asn Tyr Lys Gln Glu Gly Asp Lys Cys Val Glu Asn Pro Asn Pro Thr
            340                 345                 350

Cys Asn Glu Asn Asn Gly Gly Cys Asp Ala Asp Ala Lys Cys Thr Glu
        355                 360                 365
```

```
Glu Asp Ser Gly Ser Asn Gly Lys Lys Ile Thr Cys Glu Cys Thr Lys
    370                 375                 380

Pro Asp Ser Tyr Pro Phe Phe Asp Gly Ile Phe Cys Ser Ser Ser Asn
385                 390                 395                 400

<210> SEQ ID NO 203
<211> LENGTH: 203
<212> TYPE: PRT
<213> ORGANISM: Artificial Sequence
<220> FEATURE:
<223> OTHER INFORMATION: PfTRAP_TSR-PvTRAP_TSR-PkHTRAP_TSR

<400> SEQUENCE: 203

Met Ala Glu Lys Thr Ala Ser Cys Gly Val Trp Asp Glu Trp Ser Pro
1               5                   10                  15

Cys Ser Val Thr Cys Gly Lys Gly Thr Arg Ser Arg Lys Arg Glu Ile
                20                  25                  30

Leu His Glu Gly Cys Thr Ser Glu Leu Gln Glu Gln Cys Glu Glu Glu
            35                  40                  45

Arg Cys Leu Pro Lys Ala Ala Val Ala Met Ala Glu Arg Val Ala Asn
        50                  55                  60

Cys Gly Pro Trp Asp Pro Trp Thr Ala Cys Ser Val Thr Cys Gly Arg
65                  70                  75                  80

Gly Thr His Ser Arg Ser Arg Pro Ser Leu His Glu Lys Cys Thr Thr
                85                  90                  95

His Met Val Ser Glu Cys Glu Gly Glu Cys Pro Val Glu Pro Glu
            100                 105                 110

Pro Leu Pro Val Pro Ala Pro Leu Pro Thr Ala Ala Val Ala Met Ala
        115                 120                 125

Glu Val Glu Arg Ile Ala Lys Cys Gly Pro Thr Ala Ala Thr Cys Gly
130                 135                 140

Gly Cys Cys Gly Thr Gly Gly Cys Cys Ala Thr Gly Gly Cys Thr Trp
145                 150                 155                 160

Asp Asp Trp Thr Pro Cys Ser Val Thr Cys Gly Lys Gly Thr His Ser
                165                 170                 175

Arg Ser Arg Pro Leu Leu His Ala Gly Cys Thr Thr His Met Val Lys
            180                 185                 190

Glu Cys Glu Met Asp Glu Cys Pro Val Glu Pro
        195                 200

<210> SEQ ID NO 204
<211> LENGTH: 120
<212> TYPE: PRT
<213> ORGANISM: Artificial Sequence
<220> FEATURE:
<223> OTHER INFORMATION: PfTRAP_TSR-BbTRAP_TSR

<400> SEQUENCE: 204

Glu Lys Thr Ala Ser Cys Gly Val Trp Asp Glu Trp Ser Pro Cys Ser
1               5                   10                  15

Val Thr Cys Gly Lys Gly Thr Arg Ser Arg Lys Arg Glu Ile Leu His
                20                  25                  30

Glu Gly Cys Thr Ser Glu Leu Gln Glu Gln Cys Glu Glu Glu Arg Cys
            35                  40                  45

Leu Pro Lys Arg Ala Ala Val Ala Met Ala Glu Pro Val Trp Ala Glu
        50                  55                  60

Trp Ser Ser Cys Asn Gly Glu Cys Gly Val Pro Gly Lys Arg Thr Arg
65                  70                  75                  80
```

```
Ala Leu Leu Asp Leu Arg Met Ile Glu Lys Pro Val Asn Gly Ala Asn
                85                  90                  95

Gly Gln Pro Gly Lys Ser Cys Glu Asp Gln Lys Met Asn Phe Leu Pro
            100                 105                 110

Gln Ser Glu Thr Cys Thr Ile Glu
        115                 120

<210> SEQ ID NO 205
<211> LENGTH: 184
<212> TYPE: PRT
<213> ORGANISM: Artificial Sequence
<220> FEATURE:
<223> OTHER INFORMATION: PfTRAP_TSR-BbTRAP_TSR-CparTRAP_TSR

<400> SEQUENCE: 205

Glu Lys Thr Ala Ser Cys Gly Val Trp Asp Glu Trp Ser Pro Cys Ser
1               5                   10                  15

Val Thr Cys Gly Lys Gly Thr Arg Ser Arg Lys Arg Glu Ile Leu His
            20                  25                  30

Glu Gly Cys Thr Ser Glu Leu Gln Glu Gln Cys Glu Glu Glu Arg Cys
        35                  40                  45

Leu Pro Lys Arg Ala Ala Val Ala Met Ala Glu Pro Val Trp Ala Glu
    50                  55                  60

Trp Ser Ser Cys Asn Gly Glu Cys Gly Val Pro Gly Lys Arg Thr Arg
65                  70                  75                  80

Ala Leu Leu Asp Leu Arg Met Ile Glu Lys Pro Val Asn Gly Ala Asn
                85                  90                  95

Gly Gln Pro Gly Lys Ser Cys Glu Asp Gln Lys Met Asn Phe Leu Pro
            100                 105                 110

Gln Ser Glu Thr Cys Thr Ile Glu Ala Ala Val Ala Met Ala Ala Thr
        115                 120                 125

Thr Cys Thr Val Ser Thr Trp Ser Ser Trp Thr Cys Ser Gly Val
    130                 135                 140

Cys Gly Glu Met Arg Ser Arg Thr Arg Ser Val Leu Ser Phe Pro Arg
145                 150                 155                 160

Tyr Asp His Glu Tyr Cys Pro His Leu Ile Glu Tyr Ser Asn Cys Val
                165                 170                 175

Val Glu Asn Lys Cys Pro Glu Asn
            180
```